US012103976B2

(12) United States Patent
Lakins et al.

(10) Patent No.: US 12,103,976 B2
(45) Date of Patent: Oct. 1, 2024

(54) FC BINDING FRAGMENTS COMPRISING A CD137 ANTIGEN-BINDING SITE

(71) Applicant: F-star Therapeutics Limited, Cambridge (GB)

(72) Inventors: Matthew Lakins, Cambridge (GB); Jose Munoz-Olaya, Cambridge (GB); Sarka Pechouckova, Cambridge (GB); Mihriban Tuna, Cambridge (GB)

(73) Assignee: invoX Pharma Limited, London (GB)

( * ) Notice: Subject to any disclaimer, the term of this patent is extended or adjusted under 35 U.S.C. 154(b) by 935 days.

(21) Appl. No.: 17/259,754

(22) PCT Filed: Jul. 12, 2019

(86) PCT No.: PCT/EP2019/068803

§ 371 (c)(1),
(2) Date: Jan. 12, 2021

(87) PCT Pub. No.: WO2020/011972

PCT Pub. Date: Jan. 16, 2020

(65) Prior Publication Data

US 2021/0277134 A1 Sep. 9, 2021
US 2022/0119539 A9 Apr. 21, 2022

(30) Foreign Application Priority Data

Jul. 12, 2018 (GB) ...................................... 1811408

(51) Int. Cl.

| | |
|---|---|
| ***C07K 16/00*** | (2006.01) |
| ***A61P 35/00*** | (2006.01) |
| ***C07K 16/28*** | (2006.01) |
| *A61K 39/00* | (2006.01) |

(52) U.S. Cl.

CPC .......... *C07K 16/2878* (2013.01); *A61P 35/00* (2018.01); *A61K 2039/505* (2013.01); *C07K 2317/31* (2013.01); *C07K 2317/526* (2013.01); *C07K 2317/565* (2013.01); *C07K 2317/71* (2013.01)

(58) Field of Classification Search

None
See application file for complete search history.

(56) References Cited

U.S. PATENT DOCUMENTS

| | | | |
|---|---|---|---|
| 3,909,459 | A | 9/1975 | Friese et al. |
| 3,967,230 | A | 6/1976 | Kamigaito et al. |
| 4,004,183 | A | 1/1977 | Oki et al. |
| 6,380,664 | B1 | 4/2002 | Pollner |
| 7,288,638 | B2 | 10/2007 | Jure-Kunkel et al. |
| 7,592,426 | B2 | 9/2009 | Ebel et al. |
| 8,217,149 | B2 | 7/2012 | Irving et al. |
| 8,383,796 | B2 | 2/2013 | Korman et al. |
| 8,911,732 | B2 | 12/2014 | Dennis et al. |
| 9,567,399 | B1 | 2/2017 | Campbell et al. |
| 9,617,338 | B1 | 4/2017 | Campbell et al. |
| 10,090,646 | B2 | 10/2018 | Takaoka et al. |
| 10,205,305 | B2 | 2/2019 | Uegaki et al. |
| 10,233,258 | B2 | 3/2019 | Akamatsu et al. |
| 10,604,576 | B2 | 3/2020 | Campbell et al. |
| 11,214,618 | B2 | 1/2022 | Tuna et al. |
| 11,214,620 | B2 | 1/2022 | Campbell et al. |
| 11,548,948 | B2 | 1/2023 | Tuna et al. |
| 11,629,193 | B2 | 4/2023 | Tuna et al. |
| 2003/0030355 | A1 | 2/2003 | Honda |
| 2009/0055944 | A1 | 2/2009 | Korman et al. |
| 2012/0237498 | A1 | 9/2012 | Ahrens et al. |
| 2012/0276104 | A1 | 11/2012 | Woisetschlager |
| 2013/0034559 | A1 | 2/2013 | Queva et al. |
| 2014/0004121 | A1 | 1/2014 | Fanslow, III et al. |
| 2014/0341917 | A1 | 11/2014 | Nastri et al. |
| 2015/0214697 | A1 | 7/2015 | Yoshida et al. |
| 2015/0259420 | A1 | 9/2015 | Triebel et al. |
| 2016/0043531 | A1 | 2/2016 | Firstenberg et al. |
| 2016/0137740 | A1 | 5/2016 | Hammond et al. |
| 2016/0244528 | A1 | 8/2016 | Gray et al. |
| 2017/0198050 | A1 | 7/2017 | Eckelman et al. |
| 2017/0355756 | A1 | 12/2017 | Julien et al. |
| 2017/0362321 | A1 | 12/2017 | Campbell et al. |
| 2018/0118841 | A1 | 5/2018 | Ellmark et al. |
| 2018/0175592 | A1 | 6/2018 | Uegaki et al. |
| 2018/0194862 | A1 | 7/2018 | Akamatsu et al. |
| 2018/0339031 | A1 | 11/2018 | Masternak et al. |

(Continued)

FOREIGN PATENT DOCUMENTS

| | | |
|---|---|---|
| CN | 101802006 A | 8/2010 |
| CN | 104955845 A | 9/2015 |

(Continued)

OTHER PUBLICATIONS

Lin et al. Fc-dependent expression of CD137 on human NK cells: insights into "agonistic" effects of anti-CD137 monoclonal antibodies. Blood. Aug. 1, 2008.*
Wang et al. "Retargeting T Cells for HER2-Positive Tumor Killing by a Bispecific Fv-Fc Antibody." PloS one 8.9 (2013).*
Segal et al. Results from an Integrated Safety Analysis of Urelumab, an Agonist Anti-CD137 Monoclonal Antibody. Clin Cancer Res Apr. 15, 2017.*

(Continued)

*Primary Examiner* — Kevin S Orwig
*Assistant Examiner* — Estella M. Gustilo
(74) *Attorney, Agent, or Firm* — Wolf, Greenfield & Sacks, P.C.

(57) ABSTRACT

The invention relates to specific binding members that bind CD137. The specific binding members comprise a CD137 antigen-binding site located in a constant domain of the specific binding member and find application in the treatment of cancer and infectious diseases, for example.

22 Claims, 19 Drawing Sheets

Specification includes a Sequence Listing.

(56) References Cited

U.S. PATENT DOCUMENTS

| | | | |
|---|---|---|---|
| 2019/0106494 | A1 | 4/2019 | Wang et al. |
| 2019/0202920 | A1 | 7/2019 | Tuna et al. |
| 2019/0256602 | A1 | 8/2019 | Campbell et al. |
| 2019/0330344 | A1 | 10/2019 | Tuna et al. |
| 2019/0330351 | A1 | 10/2019 | Campbell et al. |
| 2019/0338032 | A1 | 11/2019 | Campbell et al. |
| 2019/0338049 | A1 | 11/2019 | Tuna et al. |
| 2020/0407446 | A1 | 12/2020 | McCourt et al. |
| 2021/0139590 | A1 | 5/2021 | Tuna et al. |
| 2021/0237498 | A1 | 8/2021 | Yoda et al. |
| 2021/0238299 | A1 | 8/2021 | Pechouckova et al. |
| 2021/0301022 | A1 | 9/2021 | Wollerton et al. |
| 2021/0309753 | A1 | 10/2021 | Tuna et al. |
| 2021/0355228 | A1 | 11/2021 | Lakins et al. |
| 2022/0048996 | A1 | 2/2022 | Tuna et al. |
| 2022/0049007 | A1 | 2/2022 | Lakins et al. |
| 2022/0185890 | A1 | 6/2022 | Tuna et al. |
| 2022/0185894 | A1 | 6/2022 | Campbell et al. |
| 2022/0267421 | A1 | 8/2022 | Munoz-Olaya et al. |
| 2022/0275092 | A1 | 9/2022 | Morrow et al. |
| 2023/0357413 | A1 | 11/2023 | Tuna et al. |
| 2023/0406935 | A1 | 12/2023 | Tuna et al. |

FOREIGN PATENT DOCUMENTS

| | | | |
|---|---|---|---|
| CN | 104968364 | A | 10/2015 |
| CN | 107523546 | A | 12/2017 |
| EP | 1025230 | B1 | 2/2006 |
| EP | 1180123 | B1 | 7/2008 |
| EP | 2407487 | A1 | 1/2012 |
| EP | 2546268 | A1 | 1/2013 |
| EP | 2242771 | B1 | 7/2013 |
| EP | 2905030 | A1 | 8/2015 |
| EP | 2215121 | B1 | 2/2016 |
| EP | 3354661 | A1 | 8/2018 |
| EP | 3470426 | A1 | 4/2019 |
| JP | S51-046628 | A | 4/1976 |
| JP | 2003-022886 | A | 1/2003 |
| JP | 2011-521905 | A | 7/2011 |
| JP | 2012-500006 | A | 1/2012 |
| JP | 2016-513467 | A | 5/2016 |
| JP | 2016-533395 | A | 10/2016 |
| JP | 2017-010741 | A | 1/2017 |
| JP | 2018-508475 | A | 3/2018 |
| RU | 2017112379 | A | 10/2018 |
| TW | 201642897 | A | 12/2016 |
| WO | WO 2005/035584 | A1 | 4/2005 |
| WO | WO 2006/072620 | A1 | 7/2006 |
| WO | WO 2006/088447 | A1 | 8/2006 |
| WO | WO 2006/099141 | A2 | 9/2006 |
| WO | WO 2008/003103 | A2 | 1/2008 |
| WO | WO 2008/068048 | A2 | 6/2008 |
| WO | WO 2009/000006 | A1 | 12/2008 |
| WO | WO 2009/068204 | A1 | 6/2009 |
| WO | WO 2009/126944 | A1 | 10/2009 |
| WO | WO 2009/132876 | A1 | 11/2009 |
| WO | WO 2010/019570 | A2 | 2/2010 |
| WO | WO 2010/057047 | A1 | 5/2010 |
| WO | WO 2010/111282 | A1 | 9/2010 |
| WO | WO 2010/124797 | A1 | 11/2010 |
| WO | WO 2012/130831 | A1 | 10/2012 |
| WO | WO 2013/181634 | A2 | 12/2013 |
| WO | WO 2014/004549 | A2 | 1/2014 |
| WO | WO 2014/008218 | A1 | 1/2014 |
| WO | WO 2014/052064 | A1 | 4/2014 |
| WO | WO 2014/089113 | A1 | 6/2014 |
| WO | WO 2014/140180 | A1 | 9/2014 |
| WO | WO 2014/151910 | A1 | 9/2014 |
| WO | WO 2015/048312 | A1 | 4/2015 |
| WO | WO 2015/049537 | A1 | 4/2015 |
| WO | WO 2015/119923 | A1 | 8/2015 |
| WO | WO 2015/138920 | A1 | 9/2015 |
| WO | WO 2015/198312 | A1 | 12/2015 |
| WO | WO 2015/200119 | A1 | 12/2015 |
| WO | WO 2016/028672 | A1 | 2/2016 |
| WO | WO 2016/040880 | A1 | 3/2016 |
| WO | WO 2016/111645 | A1 | 7/2016 |
| WO | WO 2016/162505 | A1 | 10/2016 |
| WO | WO 2016/177802 | A1 | 11/2016 |
| WO | WO 2016/185016 | A1 | 11/2016 |
| WO | WO 2016/200782 | A1 | 12/2016 |
| WO | WO 2017/009456 | A1 | 1/2017 |
| WO | WO 2017/015560 | A2 | 1/2017 |
| WO | WO 2017/025498 | A1 | 2/2017 |
| WO | WO 2017/049452 | A1 | 3/2017 |
| WO | WO 2017/052241 | A1 | 3/2017 |
| WO | WO 2017/055398 | A2 | 4/2017 |
| WO | WO 2017/062888 | A1 | 4/2017 |
| WO | WO 2017/077085 | A2 | 5/2017 |
| WO | WO 2017/087589 | A2 | 5/2017 |
| WO | WO 2017/087901 | A2 | 5/2017 |
| WO | WO 2017/123650 | A2 | 7/2017 |
| WO | WO 2017/182672 | A1 | 10/2017 |
| WO | WO 2017/193032 | A2 | 11/2017 |
| WO | WO 2017/205738 | A1 | 11/2017 |
| WO | WO 2017/220555 | A1 | 12/2017 |
| WO | WO 2017/220569 | A1 | 12/2017 |
| WO | WO 2017/019846 | A8 | 1/2018 |
| WO | WO 2018/017673 | A1 | 1/2018 |
| WO | WO 2017/220990 | A9 | 3/2018 |
| WO | WO 2018/056821 | A1 | 3/2018 |
| WO | WO 2018/060480 | A1 | 4/2018 |
| WO | WO 2018/091740 | A2 | 5/2018 |
| WO | WO 2018/115859 | A1 | 6/2018 |
| WO | WO 2018/127610 | A1 | 7/2018 |
| WO | WO 2018/222711 | A2 | 12/2018 |
| WO | WO 2019/025545 | A1 | 2/2019 |

OTHER PUBLICATIONS

[No Author Listed] F-star Alpha: A new asset centric company. Retrieved from http://www.onenucleus.com/media/Events/LSLS/11%20feb%202014/Jane%20Dancer.pdf on Jan. 8, 2015. 15 pages.

Asgarov et al., A new anti-mesothelin antibody targets selectively the membrane-associated form. MAbs. Apr. 2017;9(3):567-577. doi: 10.1080/19420862.2017.1288770.

Bacac et al., Abstract 1494: CEA TCB: A novel head-to-tail 2:1 T cell bispecific antibody for treatment of CEA-positive solid tumors. Oncoimmunology. Aug. 2016; 5(Abstract): e1203498. Epub Jun. 24, 2016. doi: 10.1080/2162402X.2016.1203498.

Chester et al., 4-1BB agonism: adding the accelerator to cancer immunotherapy. Cancer Immunol Immunother. Oct. 2016;65(10):1243-8. doi: 10.1007/s00262-016-1829-2. Epub Mar. 31, 2016.

Chester et al., Dual antibody therapy to harness the innate anti-tumor immune response to enhance antibody targeting of tumors. Curr Opin Immunol. Apr. 2015;33:1-8. doi: 10.1016/j.coi.2014.12.010. Epub Jan. 7, 2015.

Goding et al., Combination of adoptive cell transfer, anti-PD-L1 and anti-LAG-3 antibodies for the treatment of recurrent tumors: better with more. OncoImmunology. Oct. 22, 2013;2(8):e25050-1-e25050-3.

Hasenhindl et al., Creating stable stem regions for loop elongation in Fcabs—insights from combining yeast surface display, in silico loop reconstruction and molecular dynamics simulations. Biochim Biophys Acta. 2014;1844(9):1530-1540. doi:10.1016/j.bbapap.2014.04.020.

Hasenhindl et al., Stability assessment on a library scale: a rapid method for the evaluation of the commutability and insertion of residues in C-terminal loops of the CH3 domains of IgG1-Fc. Protein Eng Des Sel. 2013;26(10):675-682.

Jing et al., Combined immune checkpoint protein blockade and low dose whole body irradiation as immunotherapy for myeloma. Journal of Immunotherapy of Cancer. doi: 10.1186/S40425-014-0043-Z. Jan. 20, 2015. 15 pages.

Kraman et al., A LAG-3/PD-L1 bispecific antibody inhibits tumor growth in two syngeneic colon carcinoma models. Journal of ImmunoTherapy of Cancer. 2016;4(Suppl 1):82(abstract P124).

Kraman et al., A LAG-3/PD-L1 bispecific antibody inhibits tumor growth in two syngeneic colon carcinoma models. Retrieved from http://www.f-star.com/media/73722/A-LAG-3-PD-L1-bispecific-

(56) References Cited

OTHER PUBLICATIONS antibody-inhibits-tumour-growth-in-two-syngeneic-colon-carcinoma-models.pdf. Nov. 9-13, 2016. 1 page.
Lakins et al., A Novel CD137/PD-L1 Bispecific Antibody Modulates the Tumour Microenvironmentby Activating CD8+ T cells and Results in Tumour Growth Inhibition. F-Star Poster. Nov. 7, 2018. 1 page. Retrieved from https://www.f-star.com/media/87488/201811-SITC-2018-F-star-FS222-Poster-ONLINE.pdf.
Lee et al., 4-1BB and OX40 dual costimulation synergistically stimulate primary specific CD8 T cells for robust effector function. J Immunol. Sep. 1, 2004;173(5):3002-12. doi: 10.4049/jimmunol.173.5.3002.
Leung et al., A HER2-specific Modified Fc Fragment (Fcab) Induces Antitumor Effects Through Degradation of HER2 and Apoptosis. Mol Ther. Nov. 2015;23(11):1722-1733. doi: 10.1038/mt.2015.127. Epub Aug. 3, 2015. Erratum in: Mol Ther. Nov. 2015;23(11):1794.
Lobner et al., Engineered IgG1-Fc—one fragment to bind them all. Immunol Rev. Mar. 2016;270(1):113-31. doi: 10.1111/imr.12385.
Lobner et al., Two-faced Fcab prevents polymerization with VEGF and reveals thermodynamics and the 2.15 Å crystal structure of the complex. MAbs. Oct. 2017;9(7):1088-1104. doi: 10.1080/19420862.2017.1364825. Epub Aug. 17, 2017.
Lundqvist et al., 31st Annual Meeting and Associated Programs of the Society for Immunotherapy of Cancer (SITC 2016): Part One. Journal for Immunotherapy of Cancer. Nov. 16, 2016;4(1):74(abstract P124).
Qui et al., CD134 plus CD137 dual costimulation induces Eomesodermin in CD4 T cells to program cytotoxic Th1 differentiation. J Immunol. Oct. 1, 2011;187(7):3555-64. doi: 10.4049/jimmunol.1101244. Epub Aug. 31, 2011.
Ramelet et al., Beneficial outcome of combination therapy with 4-1BB targeting antibody. Eur J Cancer. Nov. 29, 2016;69(Suppl 1):S96-S97.
Sallin et al., The anti-lymphoma activities of anti-CD137 monoclonal antibodies are enhanced in Fc?RIII(-/-) mice. Cancer Immunol Immunother. Sep. 2014;63(9):947-58. doi: 10.1007/s00262-014-1567-2. Epub Jun. 14, 2014.
Schlothauer et al., Novel human IgG1 and IgG4 Fc-engineered antibodies with completely abolished immune effector functions. Protein Eng Des Sel. Oct. 2016;29(10):457-466. doi: 10.1093/protein/gzw040. Epub Aug. 29, 2016.
Shindo et al., Combination immunotherapy with 4-1BB activation and PD-1 blockade enhances antitumor efficacy in a mouse model of subcutaneous tumor. Anticancer Res. Jan. 2015;35(1):129-36.
Vilgelm et al., Combinatorial approach to cancer immunotherapy: strength in numbers. Journal of Leukocyte Biology. 2016;100(2):275-90. Epub Jun. 2, 2016.
Wozniak-Knopp et al., Designing Fcabs: well-expressed and stable high affinity antigen-binding Fc fragments. Protein Eng Des Sel. Sep. 1, 2017;30(9):657-671. doi: 10.1093/protein/gzx042.
Wozniak-Knopp et al., Introducing antigen-binding sites in structural loops of immunoglobulin constant domains: Fc fragments with engineered HER2/neu-binding sites and antibody properties. Protein Eng Des Sel. 2010;23(4):289-297. doi:10.1093/protein/gzq005.
Xu et al, In vitro characterization of five humanized OKT3 effector function variant antibodies. Cell Immunol. Feb. 25, 2000;200(1):16-26.
[No Author Listed] Abstract for CHI Immuno-Oncology Summit Europe. Mar. 18-22, 2019. 1 page. PDR303.
[No Author Listed] First-in-Class bispecific antibodies for cancer immunotherapy. Presentation at Takeda. Dec. 13, 2016. 24 pages. PDR160.
[No Author Listed] F-Star Modular Bispecific Antibodies. Summary for ATLAS deck. Presented at JP Morgan. Jan. 2017. 1 page. PDR159.
[No Author Listed], FS118 First in Human Study in Patients With Advanced Malignancies. Sponsored by F-star Therapeutics Limited. Clinical Trial. Retrieved from https://clinicaltrials.gov/ct2/show/NCT03440437. Feb. 22, 2018. 7 pages.
[No Author Listed], Molecular biological basis of immunotherapy. New and Orphan Drugs for Leukemia Therapeutics. Sep. 30, 2016. 387-390. Retrieved on Dec. 18, 2023. 7 pages.
[No Author Listed], Pipeline Overview: F-star is developing a pipeline of bispecific antibodies focused on oncology and immuno-oncology. F-Start website update. Sep. 2016. 2 pages. PDR126.
Ascierto et al., Initial efficacy of anti-lymphocyte activation gene-3 (anti-LAG-3:BMS-986016) in combination with nivolumab (nivo) in pts with melanoma (MEL) previously treated with anti-PD-1/PD-L1 therapy. J Clin Oncology. May 20, 2017;35(15):9520-9520. Abstract only. doi: 10.1200/JCO.2017.35.15_suppl.9520. EPub May 30, 2017.
Asgarov et al., A new anti-mesothelin antibody targets selectively the membrane-associated form. MAbs. Apr. 2017;9(3):Supplementary Data. doi: 10.1080/19420862.2017.1288770. 6 pages.
Awuah et al., Reduced Shedding of Surface Mesothelin Improves Efficacy of Mesothelin-Targeting Recombinant Immunotoxins. Mol Cancer Ther. Jul. 2016;15(7):1648-55. doi: 10.1158/1535-7163.MCT-15-0863. Epub May 18, 2016.
Berg et al., Biochemistry. 5th ed. New York. 2002. Accessible at https://www.ncbi.nlm.nih.gov/books/NBK22358/section5.5. Accessed Jun. 9, 2021. 4 pages.
Bernett et al., Abstract P122: Multiple bispecific checkpoint combinations enhance T cell activity. J Immunother Cancer. 2016;4(Suppl 1):P122. 2 pages.
Bernett et al., Multiple bispecific checkpoint combinations enhance T cell activity. Xencor Poster Presentation. 2016. 1 page.
Bodhankar et al., PD-L1 Monoclonal Antibody Treats Ischemic Stroke by Controlling Central Nervous System Inflammation. Stroke. Oct. 2015;46(10):2926-34. doi: 10.1161/STROKEAHA.115.010592. Epub Aug. 25, 2015.
Borlak et al., Immune-mediated liver injury of the cancer therapeutic antibody catumaxomab targeting EpCAM, CD3 and Fc? receptors. Oncotarget. May 10, 2016;7(19):28059-74. doi: 10.18632/oncotarget.8574.
Brewis, Development of an anti-PD-L1 Fcab. Presentation. Human Antibodies and Hybridomas Conference. Oct. 22, 2018. PDR 312.
Brewis, Identification of a PD-L1 binding Fcab: a potent inhibitor of immunosuppressive signals. Abstract. Huamn Antibodies and Hybridomas 2018. Jun. 11, 2018. 1 page. PDR282.
Brewis, The use of bispecific antibodies to modulate anti-tumour immune responses. Oral Presentation at ELRIG—Research and Innovation. Mar. 29, 2017. 33 pages. PDR177.
Brewis, The use of bispecific antibodies to modulate anti-tumour immune responses. Oral Presentation at PEPtalk. Jan. 12, 2017. 26 pages. PDR163.
Burova et al., Abstract 1484: Combined treatment with anti-LAG-3 and anti-PD-1 fully human monoclonal antibodies inhibits tumor growth in immunocompetent double-humanized LAG-3/PD-1 mice. Proceedings: AACR 107th Annual Meeting 2016. Apr. 16-20, 2016. New Orleans, LA. doi: 10.1158/1538-7445.AM2016-1484. Published Jul. 2016. 8 pages.
Burova et al., Abstract P195: A novel anti-human LAG-3 antibody in combination with anti-human PD-1 (REGN2810) shows enhanced anti-tumor activity in PD-1 × LAG-3 dual-humanized mice and favorable pharmacokinetic and safety profiles in cynomolgus monkey. J Immunother Cancer. 2016;4(Suppl 1):P195. 2 pages.
Callahan et al., Targeting T Cell Co-receptors for Cancer Therapy. Immunity. May 17, 2016;44(5):1069-78. doi: 10.1016/j.immuni.2016.04.023.
Camisaschi et al., LAG-3 expression defines a subset of CD4(+)CD25(high)Foxp3(+) regulatory T cells that are expanded at tumor sites. J Immunol. Jun. 1, 2010;184(11):6545-51. doi: 10.4049/jimmunol.0903879. Epub Apr. 26, 2010.
Cemerski et al., T cell activation and anti-tumor efficacy of anti-LAG-3 antibodies is independent of LAG-3-MHCII blocking capacity. Poster Presentation. 30th Annual Meeting and Associated Programs of the Society for Immunotherapy of Cancer (SITC 2015). National Harbor, MD. Nov. 4-8, 2015. 1 page.
Chatterjee et al., Noninvasive Imaging of Immune Checkpoint Ligand PD-L1 in Tumors and Metastases for Guiding Immunotherapy. Mol Imaging. Dec.-Jan. 2017;16:1536012117718459. doi: 10.1177/1536012117718459. 5 pages.

(56) References Cited

OTHER PUBLICATIONS

Chen et al., Enhancement and destruction of antibody function by somatic mutation: unequal occurrence is controlled by V gene combinatorial associations. EMBO J. Jun. 15, 1995;14(12):2784-94. doi: 10.1002/j.1460-2075.1995.tb07278.x.
Chen et al., Molecular mechanisms of T cell co-stimulation and co-inhibition. Nat Rev Immunol. Apr. 2013;13(4):227-42. doi: 10.1038/nri3405. Epub Mar. 8, 2013. Erratum in: Nat Rev Immunol. Jul. 2013;13(7):542.
Chiu et al., Antibody Structure and Function: The Basis for Engineering Therapeutics. Antibodies (Basel). Dec. 3, 2019;8(4):55. doi: 10.3390/antib8040055.
Chu et al., An Update on Anti-CD137 Antibodies in Immunotherapies for Cancer. Int J Mol Sci. Apr. 12, 2019;20(8):1822. doi: 10.3390/ijms20081822. 17 pages.
Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80. doi: 10.1073/pnas.0915174107. Epub Feb. 16, 2010.
Dahlén et al., Bispecific antibodies in cancer immunotherapy. Ther Adv Vaccines Immunother. Feb. 2018;6(1):3-17. doi: 10.1177/2515135518763280. Epub Mar. 28, 2018.
Davies, Analytical challenges for next generation biologics. Oral Presentation at Waters Biopharma Mini-Seminar. May 24, 2017. 20 pages. PDR191.
Davies, Bispecific Antibodies: New Opportunities for Novel Therapies. Oral Presentation at Bioprocess UK 2016. Nov. 26, 2016. 14 pages. PDR 135.
Davies, Overcoming the Manufacturing Challenges for Bisepcific mAbs. Oral Presentation at 5th Annual Cell Culture and Bioprocessing Congress. Nov. 6, 2016. 16 pages. PDR142.
Davies, Overcoming the Manufacturing Challenges for Bisepcific mAbs. Oral Presentation at Biopronet 3rd Annual Scientific Symposium. Oct. 20, 2016. 16 pages. PDR136.
Daxini et al., Vasculitis associated with immune checkpoint inhibitors—a systematic review. Clin Rheumatol. Sep. 2018;37(9):2579-2584. doi: 10.1007/s10067-018-4177-0. Epub Jun. 19, 2018.
Del Bano et al., A Bispecific Antibody-Based Approach for Targeting Mesothelin in Triple Negative Breast Cancer. Front Immunol. Jul. 10, 2019;10:1593. doi: 10.3389/fimmu.2019.01593.
Demeure et al., T Lymphocytes infiltrating various tumour types express the MHC class II ligand lymphocyte activation gene-3 (LAG-3): role of LAG-3/MHC class II interactions in cell-cell contacts. Eur J Cancer. Sep. 2001;37(13):1709-18. doi: 10.1016/s0959-8049(01)00184-8.
Deng et al., LAG-3 confers poor prognosis and its blockade reshapes antitumor response in head and neck squamous cell carcinoma. Oncoimmunology. Oct. 7, 2016;5(11):e1239005. doi: 10.1080/2162402X.2016.1239005.
Doody et al., Abstract B091: A LAG-3/PD-L1 bispecific antibody inhibits tumor growth in two syngeneic colon carcinoma models. Second CRI-CIMT-EATI-AACR International Cancer Immunotherapy Conference: Translating Science into Survival. Sep. 25-28, 2016. New York, NY. doi: 10.1158/23/26-6066.IMM2016-B091. Published Nov. 2016. 8 pages.
Doody, An anti-murine LAG-3/PD-L1 bispecific antibody which modulates T cell activity and inhibits tumour growth. Oral Presentation at 2nd Annual Advances in Immuno-Oncology Congress. May 16, 2017. 17 pages. PDR188.
Doody, In vivo Efficacy of bispecific antibodies targeting two immune-modulatory receptors. Oral Presentation at PEGS Europe. Nov. 4, 2016. 16 pages. PDR144.
Edwards et al., The remarkable flexibility of the human antibody repertoire; isolation of over one thousand different antibodies to a single protein, BLyS. J Mol Biol. Nov. 14, 2003;334(1):103-18. doi: 10.1016/j.jmb.2003.09.054.
El-Khoueiry et al., The relationship of pharmacodynamics (PD) and pharmacokinetics (PK) to clinical outcomes in a phase I study of OX40 agonistic monoclonal antibody (mAb) PF-04518600 (PF-8600). J Clin Oncol. May 20, 2017. 35(15_suppl):3027-3027. Meeting Abstract. 2017 ASCO Annual Meeting I. doi: 10.1200/JCO.2017.35.15_suppl.3027. 4 pages.
Everett et al., A LAG-3/PD-L1 bispecific antibody inhibits tumour growth in two syngeneic colon carcinoma models. Poster Presentation. AACR Tumor Immunology and Immunotherapy. Oct. 21, 2016. 1 page. PDR137.
Everett et al., Abstract PR06: A LAG-3/PD-L1 bispecific antibody inhibits tumour growth in two syngeneic colon carcinoma models. AACR Special Conference on Tumor Immunology and Immunotherapy. Oct. 20-23, 2016. Boston, MA. Doi: 10.1158/2326-6074.TUMIMM16-PR06. Published Mar. 2017. 8 pages.
Everett, A LAG-3/PD-L1 Bispecific Antibody Inhibits Tumour Growth in Two Syngeneic Colon Carcinoma Models. Oral Presentation at AACR Tumor Immunology and Immunotherapy. Boston, MA. Oct. 20-23, 2016. 5 pages. PDR141.
Faroudi et al., Abstract 2399: LAG-3/PD-L1 mAb2 can overcome PD-L1-mediated compensatory upregulation of LAG-3 induced by single-agent checkpoint blockade. Proceedings: AACR Annual Meeting 2019; Mar. 29-Apr. 3, 2019. Atlanta, GA. Doi: 10.1158/1538-7445.AM2019-2399. Published Jul. 2019.
Faroudi et al., Abstract B009: FS118, a LAG-3/PD-L1 bispecific antibody, capable of driving potent anti-tumour immune responses and overcome PD-(L)1-mediated compensatory. Sep. 25-28, 2019. Fifth CRI-CIMT-EATI-AACR International Cancer Immunotherapy Conference (2019): Translating Science into Survival. Paris. 1 page.
Faroudi et al., FS118, a LAG-3/PD-L1 bispecific antibody, capable of driving potent anti-tumour immune responses and overcome PD-(L)1-mediated compensatory. Sep. 25-28, 2019. Poster. Fifth CRI-CIMT-EATI-AACR International Cancer Immunotherapy Conference (2019): Translating Science into Survival. Paris. 1 page.
Fiehler, Development of an anti-PD-L1 Fcab. Presentation. European Antibody Congress. Oct. 29, 2018. 26 pages. PDR312.
Foy et al., Poxvirus-Based Active Immunotherapy with PD-1 and LAG-3 Dual Immune Checkpoint Inhibition Overcomes Compensatory Immune Regulation, Yielding Complete Tumor Regression in Mice. PLoS One. Feb. 24, 2016;11(2):e0150084. doi: 10.1371/journal.pone.0150084.
Frenzel et al., Phage display-derived human antibodies in clinical development and therapy. MAbs. Oct. 2016;8(7):1177-1194. doi: 10.1080/19420862.2016.1212149. Epub Jul. 14, 2016.
F-STAR, First-in-Class Bispecific Antibodies for Cancer Immunotherapy. Jul. 2016. Presentation. 14 pages. PDR119.
F-STAR, Next-Generation Bispecifics for Cancer Immunotherapy. Feb. 2020. Presented on Mar. 11, 2020 at Immuno-Oncology Summit Europe 2020. London. 46 pages.
F-STAR, Redirecting T Cells. Overcoming Cancer. Improving Lives. Oct. 2019 Presentation in Investor Meeting. 36 pages.
F-STAR, Redirecting T Cells. Overcoming Cancer. Improving Lives. Apr. 2020 Presentation in Investor Meeting. 43 pages.
F-STAR, Redirecting T Cells. Overcoming Cancer. Improving Lives. Jan. 2020 Presentation in Investor Meeting. 41 pages.
Gandhi et al., Expression of LAG-3 by tumor-infiltrating lymphocytes is coincident with the suppression of latent membrane antigen-specific CD8+ T-cell function in Hodgkin lymphoma patients. Blood. Oct. 1, 2006;108(7):2280-9. doi: 10.1182/blood-2006-04-015164. Epub Jun. 6, 2006.
Gaspar et al., FS120 mAb2, a dual agonist bispecific antibody targeting OX40 and CD137, activates T cells in vitro and induces FcyR-independent anti-tumour activity. SITC 2018. Nov. 7, 2018. Poster. 10 pages.
Gaspar, FS120 mAb2, a dual agonist bispecific antibody targeting OX40 and CD137. SITC 2018. Nov. 11, 2018. Presentation. 12 pages.
Geuijen et al., Abstract 541: An unbiased screen identifies a CD137xPD-L1 bispecific IgG1 antibody with unique T cell activation and binding properties. Cancer Res. 2019;79(13_Supplement):541. Poster Presentation AACR Conference 2019. Jul. 1, 2019. doi: 10.1158/1538-7445.AM2019-541. 4 pages.
Gliddon, Pushing all the buttons: innovating in immuno-oncology with mAb. Oral Presentation at Phacilitate Immunotherapy World 2017. Jan. 18, 2017. 11 pages. PDR165.

(56) References Cited

OTHER PUBLICATIONS

Glisson et al., Phase 1 study of MEDI0562, a humanized OX40 agonist monoclonal antibody (mAb), in adult patients (pts) with advanced solid tumors. Annals Onocol. Oct. 1, 2016;27(6):vi361. doi: 10.1093/annonc/mdw378.07.
Golfier et al., Anetumab ravtansine: a novel mesothelin-targeting antibody-drug conjugate cures tumors with heterogeneous target expression favored by bystander effect. Mol Cancer Ther. Jun. 2014;13(6):1537-48. doi: 10.1158/1535-7163.MCT-13-0926. Epub Apr. 8, 2014.
Grosso et al., Programmed death-ligand 1 (PD-L1) expression in various tumor types. J Immunother Cancer. 2013;1(Suppl 1):P53. http://www.immunotherapyofcancer.org/content/1/S1/P53. 1 page.
Gunde et al., Abstract 1532: A novel, monovalent tri-specific antibody-based molecule that simultaneously modulates PD-L1 and 4-1BB exhibits potent anti-tumoral activity in vivo. Cancer Res. 2019;79(13_Supplement):1532. AACR Conference 2019. Jul. 1, 2019. doi: 10.1158/1538-7445.AM2019-1532. 4 pages.
Haines et al., Abstract 4714: Blockade of LAG-3 amplifies immune activation signatures and augments curative antitumor responses to anti-PD-1 therapy in immune competent mouse models of cancer. Proceedings: AACR Annual Meeting 2017. Apr. 1-5, 2017. Washington, DC. doi: 10.1158/1538-7445.AM2017-4714. Published Jul. 2017. 8 pages.
Han et al., Bispecific anti-CD3 × anti-HER2 antibody mediates T cell cytolytic activity to HER2-positive colorectal cancer in vitro and in vivo. Int J Oncol. Dec. 2014;45(6):2446-54. doi: 10.3892/ijo.2014.2663. Epub Sep. 18, 2014.
Hassan et al., Mesothelin Immunotherapy for Cancer: Ready for Prime Time? J Clin Oncol. Dec. 2016;34(34):4171-4179. doi: 10.1200/JCO.2016.68.3672. Epub Oct. 31, 2016.
Hassan et al., Phase II clinical trial of amatuximab, a chimeric antimesothelin antibody with pemetrexed and cisplatin in advanced unresectable pleural mesothelioma. Clin Cancer Res. Dec. 1, 2014;20(23):5927-36. doi: 10.1158/1078-0432.CCR-14-0804. Epub Sep. 17, 2014.
Hebb et al., Administration of low-dose combination anti-CTLA4, anti-CD137, and anti-OX40 into murine tumor or proximal to the tumor draining lymph node induces systemic tumor regression. Cancer Immunol Immunother. Jan. 2018;67(1):47-60. doi: 10.1007/s00262-017-2059-y. Epub Sep. 13, 2017. Author Manuscript. 20 pages.
Herbst et al., Predictive correlates of response to the anti-PD-L1 antibody MPDL3280A in cancer patients. Nature. Nov. 27, 2014;515(7528):563-7. doi: 10.1038/nature14011. Author Manuscript.
Hid Cadena et al., Checks and Balances in Autoimmune Vasculitis. Front Immunol. Feb. 22, 2018;9:315. doi: 10.3389/fimmu.2018.00315.
Ho et al., A novel high-affinity human monoclonal antibody to mesothelin. Int J Cancer. May 1, 2011;128(9):2020-30. doi: 10.1002/ijc.25557.
Horn et al., CD3xPDL1 bi-specific T cell engager (BiTE) simultaneously activates T cells and NKT cells, kills PDL1$^+$tumor cells, and extends the survival of tumor-bearing humanized mice. Oncotarget. Aug. 3, 2017;8(35):57964-57980. doi: 10.18632/oncotarget.19865.
Huang et al., Abstract PR03: Combinatorial blockade of PD-1, CTLA-4, and LAG-3 pathways inhibits murine ovarian tumor growth. Abstracts: AACR Special Conference: Advances in Ovarian Cancer Research: Exploiting Vulnerabilities. Oct. 17-20, 2015. Orlando, FL. doi: 10.1158/1557-3265.OVCA15-PR03. Published Jan. 2016. 8 pages.
Iwai et al., Involvement of PD-L1 on tumor cells in the escape from host immune system and tumor immunotherapy by PD-L1 blockade. Proc Natl Acad Sci U S A. Sep. 17, 2002;99(19):12293-7. doi: 10.1073/pnas.192461099. Epub Sep. 6, 2002.
Jochems et al., Analyses of functions of an anti-PD-L1/TGFβR2 bispecific fusion protein (M7824). Oncotarget. Sep. 8, 2017;8(43):75217-75231. doi: 10.18632/oncotarget.20680.
Kehry et al., Abstract 271: Targeting PD-1, TIM-3 and LAG-3 in combination for improved immunotherapy combinations. AACR 106th Annual Meeting. Apr. 18-22, 2015. Philadelphia, PA. doi: 10.1158/1538-7445.AM2015-271. 8 pages.
Klooster et al., Abstract B088: Generation of immuno-modulatory receptor binding bispecific antibodies to modulate tumor immunity. Second CRI-CIMT-EATI-AACR International Cancer Immunotherapy Conference: Translating Science into Survival. Sep. 25-28, 2016. New York, NY. doi: 10.1158/2326-6066.IMM2016-B088. 4 pages.
Koenig et al., Mutational landscape of antibody variable domains reveals a switch modulating the interdomain conformational dynamics and antigen binding. Proc Natl Acad Sci U S A. Jan. 24, 2017;114(4):E486-E495. doi: 10.1073/pnas.1613231114. Epub Jan. 5, 2017.
Koopmans et al., A novel bispecific antibody for EGFR-directed blockade of the PD-1/PD-L1 immune checkpoint. Oncoimmunology. May 31, 2018;7(8):e1466016. doi: 10.1080/2162402X.2018.1466016.
Kraman et al., A LAG-3/PD-L1 bispecific antibody inhibits tumour growth in two syngeneic colon carcinoma models. Poster Presentation. BSI/NVVI Congress. Dec. 6, 2016. 1 page. PDR153.
Kraman et al., A LAG-3/PD-L1 bispecific antibody inhibits tumour growth in two syngeneic colon carcinoma models. Abstract B091. Poster Presentation. CRI-CIMT-EATI-AACR Cancer Immunotherapy Conference. Sep. 26, 2016. 1 page. PDR129.
Kraman et al., A LAG-3/PD-L1 bispecific antibody inhibits tumour growth in two syngeneic colon carcinoma models. Poster 003. Poster Presentation. 2nd Annual Advances in Immuno-Oncology Congress. May 15, 2017. 1 page. PDR185.
Kraman et al., A LAG-3/PD-L1 bispecific antibody inhibits tumour growth in two syngeneic colon carcinoma models. Poster 1103. Poster Presentation. Keystone Symposium—Cancer Immunology and Immunotherapy. Mar. 19, 2017. 1 page. PDR174.
Kraman et al., A LAG-3/PD-L1 bispecific antibody inhibits tumour growth in two syngeneic colon carcinoma models. Poster 128. Poster Presentation at SITC. Nov. 9, 2016. 1 page. PDR143.
Kraman et al., A LAG-3/PD-L1 bispecific antibody inhibits tumour growth in two syngeneic colon carcinoma models. Poster 5651. Poster Presentation. AACR Annual Meeting. Apr. 1, 2017. 1 page. PDR176.
Kraman et al., A Lag-3/PD-L1 bispecific antibody inhibits tumour growth in two syngeneic colon carcinoma models. Poster Presentation. International Conference on Human & Translational Immunology. Sep. 16, 2016. 1 page. PDR123.
Kraman et al., A LAG-3/PD-L1 bispecific antibody inhibits tumour growth in two syngeneic coon carcinoma models. Poster 3005. Poster Presentation. Keystome Symposium—Biobetters and Next-Generation Biologics. Jan. 22-26, 2017. 1 page. PDR164.
Kraman et al., Abstract 5651:A LAG-3/PD/L1 bispecific antibody inhibits tumor growth in two syngeneic colon carcinoma models. AACR Annual Meeting 2017. Apr. 1-5, 2017. Washington, DC. Doi: 10.1158/1538-7445.AM2017-5651. 8 pages.
Kraman et al., Dual blockade of PD-L1 and LAG-3 with FS118, a unique bispecific antibody, induces CD8+ T-cell activation and modulates the tumour microenvironment to promote anti-tumour immune responses. Apr. 14-18, 2018. Poster 2719. Proceedings of the American Association for Cancer Research Annual Meeting 2018. Chicago, IL. 2 pages.
Kraman et al., Dual blockade of PD-L1 and LAG-3 with FS118, a unique bispecific antibody, induces T-cell activation with the potential to drive potent anti-tumour immune responses. Nov. 7, 2017;5 Suppl 2 (87): Abstract P348. 32nd Annual Meeting and Pre-Conference Programs of the Society for Immunotherapy of Cancer (SITC). Part II. Nov. 8-12, 2017. National Harbor, MD. 2 pages.
Kraman et al., Dual blockade of PD-L1 and LAG-3 with FS118, a unique bispecific antibody, induces T-cell activation with the potential to drive potent anti-tumour immune responses. Apr. 14-18, 2018;78(13 Suppl);Abstract 2719. Proceedings of the American Association for Cancer Research Annual Meeting 2018. Chicago, IL. 5 pages.
Kraman et al., Dual blockade of PD-L1 and LAG-3 with FS118, a unique bispecific antibody, induces T-cell activation with the potential to drive potent anti-tumour immune responses. Poster P348.

(56) References Cited

OTHER PUBLICATIONS

32nd Annual Meeting and Pre-Conference Programs of the Society for Immunotherapy of Cancer (SITC). Part II. Nov. 8-12, 2017. National Harbor, MD. 1 page.
Kraman et al., FS118, a Bispecific Antibody Targeting LAG-3 and PD-L1, Enhances T-Cell Activation Resulting in Potent Antitumor Activity. Clin Cancer Res. Jul. 1, 2020;26(13):3333-3344. doi: 10.1158/1078-0432.CCR-19-3548. Epub Apr. 16, 2020.
Kunik et al., Structural consensus among antibodies defines the antigen binding site. PLoS Comput Biol. 2012;8(2):e1002388. doi: 10.1371/journal.pcbi.1002388. Epub Feb. 23, 2012. 12 pages.
Kussie et al., A single engineered amino acid substitution changes antibody fine specificity. J Immunol. Jan. 1, 1994;152(1):146-52.
Kvarnhammar et al., The CTLA-4 × OX40 bispecific antibody ATOR-1015 induces anti-tumor effects through tumor-directed immune activation. J Immunother Cancer. Apr. 11, 2019;7(1):103. doi: 10.1186/s40425-019-0570-8.
La Motte-Mohs et al., Abstract 3217: MGD013, a bispecific PD-1 × LAG-3 Dual-Affinity Re-Targeting (DART®) protein with T-cell immunomodulatory activity for cancer treatment. AACR 107th Annual Meeting. Apr. 16-20, 2016. New Orleans, LA. Doi: 10.1158/1538-7445.AM2016-3217. 8 pages.
La Motte-Mohs et al., MGD013, a bispecific PD-1 × LAG-3 Dual-Affinity Re-Targeting (DART®) protein with T-cell immunomodulatory activity for cancer treatment. Poster Presentation. 2016. http://ir.macrogenics.com/events.cfm. 1 page.
Lakins et al., FS222 mAb2, a bispecific conditional agonist antibody targeting CD137 and PD-L1, induces potent lymphocyte activation and has a favourable safety profile. F-star, Cambridge, UK. Poster Presentation. AACR Annual Meeting Mar. 29-Apr 3. 2019, Atlanta, GA. Poster No. 1540. 1 page.
Lakins et al., Optimising TNFRSF agonism and checkpoint blockade with a novel CD137/PD-L1 bispecific antibody. Abstracts Therapeutic Development. Dec. 1, 2018;29(Supplement 10):X30. doi: 10.1093/annonc/mdy487.014. 1 page.
Lamberts et al., ImmunoPET with Anti-Mesothelin Antibody in Patients with Pancreatic and Ovarian Cancer before Anti-Mesothelin Antibody-Drug Conjugate Treatment. Clin Cancer Res. Apr. 1, 2016;22(7):1642-52. doi: 10.1158/1078-0432.CCR-15-1272. Epub Nov. 20, 2015.
Larkin et al., Combined Nivolumab and Ipilimumab or Monotherapy in Untreated Melanoma. N Engl J Med. Jul. 2, 2015;373(1):23-34. doi: 10.1056/NEJMoa1504030. Epub May 31, 2015. Erratum in: N Engl J Med. Nov. 29, 2018;379(22):2185.
Levitan, Amgen Halts Rilotumumab Development Due to Increased Death Signal. Cancer Network. Nov. 26, 2014. Retrieved from www.cancernetwork.com/view/amgen-halts-rilotumumab-development-due-increased-death-signal. 3 pages.
Li et al., Discovery and preclinical characterization of the antagonist anti-PD-L1 monoclonal antibody LY3300054. J Immunother Cancer. Apr. 30, 2018;6(1):31. doi: 10.1186/s40425-018-0329-7. Erratum in: J Immunother Cancer. Jun. 4, 2018;6(1):45.
Link et al., Abstract 3752: Preclinical pharmacology of MP0310: A 4-1BB/FAP bispecific DARPin drug candidate promoting tumor-restricted T-cell costimulation. Cancer Res. Jul. 1, 2018;78(13_Supplement):3752.
Liu et al., Abstract 3642: Tumor-antigen expression-dependent activation of the CD137 costimulatory pathway by bispecific DART® proteins. Cancer Res. Jul. 1, 2017;77(13_Supplement):3642.
Liu et al., Dual Targeting of Innate and Adaptive Checkpoints on Tumor Cells Limits Immune Evasion. Cell Rep. Aug. 21, 2018;24(8):2101-2111. doi: 10.1016/j.celrep.2018.07.062.
Lo et al., Effector-attenuating Substitutions That Maintain Antibody Stability and Reduce Toxicity in Mice. J Biol Chem. Mar. 3, 2017;292(9):3900-3908. doi: 10.1074/jbc.M116.767749. Epub Jan. 11, 2017.
Ma et al., Recognition of mesothelin by the therapeutic antibody MORAb-009: structural and mechanistic insights. J Biol Chem. Sep. 28, 2012;287(40):33123-31. doi: 10.1074/jbc.M112.381756. Epub Jul. 11, 2012.
Mayes et al., Abstract 539: A bispecific Fc-silenced IgG1 antibody (MCLA-145) requires PD-L1 binding to activate CD137. Cancer Res. 2019;79(13_Supplement):539. AACR Presentation 2019. Jul. 1, 2019. doi: 10.1158/1538-7445.AM2019-539. 4 pages.
Mccourt et al., KY1055; a novel ICOS/PD-L1 bispecific antibody, enhance T cell activation and delivers potent monotherapy anti-tumour response in vivo. Abstract. CIMT 2018. Feb. 28, 2018. 1 page. PDR245.
Mccourt et al., KY1055; a novel ICOS/PD-L1 bispecific antibody, enhance T cell activation and delivers potent monotherapy anti-tumour response in vivo. Poster Presentation. CIMT Conference. May 9, 2018. 1 page. PDR 264.
Mccourt et al., KY1055; a novel ICOS/PD-L1 bispecific antibody, enhance T cell activation and delivers potent monotherapy anti-tumour response in vivo. Presentation. CIMT Conference. May 9, 2018. 13 pages. PDR265.
Mccourt, Development of an ICOS/PD-L1 Bispecific, Mar. 18-22, 2019. Abstract. Cambridge Healthtech Institute's 4th Annual Immuno-Oncology Summit Europe 2019 (London).
Melero et al., Clinical development of immunostimulatory monoclonal antibodies and opportunities for combination. Clin Cancer Res. Mar. 1, 2013;19(5):997-1008. doi: 10.1158/1078-0432.CCR-12-2214.
Michaelson et al., Anti-tumor activity of stability-engineered IgG-like bispecific antibodies targeting TRAIL-R2 and LTbetaR. MAbs. Mar.-Apr. 2009;1(2):128-41. doi: 10.4161/mabs.1.2.7631. Epub Mar. 11, 2009.
Munoz-Olaya, Development of an anti-PD-L1Fcab. Presentation. PEGS Lisbon. Nov. 16, 2018. 24 pages. PDR321.
Nalivaiko et al., A Recombinant Bispecific CD20×CD95 Antibody With Superior Activity Against Normal and Malignant B-cells. Mol Ther. Feb. 2016;24(2):298-305. doi: 10.1038/mt.2015.209. Epub Nov. 19, 2015.
Pavlidou et al., Simultaneous costimulatory T-cell engagement and checkpoint inhibition by PRS-344/ONC0055, a 4-1BB/PD-L1 bispecific compound for tumor localized activation of the immune system. SITC 2018. Poster Presentation. 2018. 1 page.
Perez-Ruiz et al., Anti-CD137 and PD-1/PD-L1 Antibodies En Route toward Clinical Synergy. Clin Cancer Res. Sep. 15, 2017;23(18):5326-5328. doi: 10.1158/1078-0432.CCR-17-1799. Epub Aug. 8, 2017.
Poon et al., Dual agonist bispecific antibody targeting OX40 and DC137 mediates anti-tumour immunity and synergises with PD-1/PD-L1 blockade to improve survival in a syngeneic mouse model. AACR 2019. Mar. 29, 2019. Poster. 9 pages.
Powles et al., MPDL3280A (anti-PD-L1) treatment leads to clinical activity in metastatic bladder cancer. Nature. Nov. 27, 2014;515(7528):558-62. doi: 10.1038/nature13904.
Reichen et al., Abstract 3029: FAP-mediated tumor accumulation of a T-cell agonistic FAP/4-1BB DARPin drug candidate analyzed by SPECT/CT and quantitative biodistribution. Cancer Res. Jul. 1, 2018;78(13_Supplement):3029.
Ryan et al., A novel biologic platform elicits profound T cell costimulatory activity and antitumor immunity in mice. Cancer Immunol Immunother. Apr. 2018;67(4):605-613. doi: 10.1007/s00262-018-2116-1. Epub Jan. 11, 2018.
Sainson et al., KY1055, a novel ICOS/PD-L1 bispecific antibody, efficiently enhances T cell activation and delivers a potent anti-tumour response in vivo. Abstract. AACR. Jan. 22, 2018. 1 page. PDR236.
Sainson et al., KY1055, a novel ICOS/PD-L1 bispecific antibody, efficiently enhances T cell activation and delivers a potent anti-tumour response in vivo. Poster Presentation. AACR 2018. Apr. 4, 2018. 1 page. PDR254.
Schroeder, Chapter 13: Immunoglobulins and Their Genes. From Arthritis and Allied Conditions: A Textbook of Rheumatology. 15th Ed. vol 1. Eds Koopman et al. Lippincot Williams & Wilkins. pp. 289-304. Supplied by the British Library Jul. 31, 2023.
Seckinger et al., Development and characterization of NILK-2301, a novel CEACAM5xCD3 κλ bispecific antibody for immunotherapy of CEACAM5-expressing cancers. J Hematol Oncol. Dec. 12, 2023;16(1):117. doi: 10.1186/s13045-023-01516-3.

(56) References Cited

OTHER PUBLICATIONS

Strauss et al., Phase I Trial of M7824 (MSB0011359C), a Bifunctional Fusion Protein Targeting PD-L1 and TGF?, in Advanced Solid Tumors. Clin Cancer Res. Mar. 15, 2018;24(6):1287-1295. doi: 10.1158/1078-0432.CCR-17-2653. Epub Jan. 3, 2018.

Tang et al., A human single-domain antibody elicits potent antitumor activity by targeting an epitope in mesothelin close to the cancer cell surface. Mol Cancer Ther. Apr. 2013;12(4):416-26. doi: 10.1158/1535-7163.MCT-12-0731. Epub Jan. 31, 2013.

Tuna, Delivering the next immuno-oncology breakthrough. PEGS Europe 2018. Nov. 11, 2018. Presentation. 24 pages.

Tuna, Identification of a PD-L1 binding FCAB: a potent inhibitor of immunosuppressive signals. Abstract. European Antibody Congress. May 3, 2018. 1 page. PDR270.

Tuna, The use of bispecific antibodies to modulate anti-tumour immune responses. Oral Presentation at 10th Annual Proteins and Antibodies Congress. Apr. 24, 2017. 26 pages. PDR183.

Vanamee et al., Structural principles of tumor necrosis factor superfamily signaling. Sci Signal. Jan. 2, 2018;11(511):eaao4910. doi: 10.1126/scisignal.aao4910. 12 pages.

Weismann, A LAG-3/PD-L1 Bispecific Antibody Inhibits Tumour Growth In Two Syngeneic Colon Carcinoma Models. International Conference on Human and Translational Immunology. Rhodes, Greece. Sep. 16-21, 2016. Presentation. 6 pages. PDR128.

Wherry, T cell exhaustion. Nat Immunol. Jun. 2011;12(6):492-9. doi: 10.1038/ni.2035.

Wilton, KY1055, a bispecific mAb2 targeting ICOS and PD-L1. Presentation. Feb. 21, 2018. 17 pages. PDR238.

Wolchok et al., Nivolumab plus ipilimumab in advanced melanoma. N Engl J Med. Jul. 11, 2013;369(2):122-33. doi: 10.1056/NEJMoa1302369. Epub Jun. 2, 2013. Erratum in: N Engl J Med. Nov. 29, 2018;379(22):2185. Author Manuscript.

Woo et al., Immune inhibitory molecules LAG-3 and PD-1 synergistically regulate T-cell function to promote tumoral immune escape. Cancer Res. Feb. 15, 2012;72(4):917-27. doi: 10.1158/0008-5472.CAN-11-1620. Epub Dec. 20, 2011.

Workman et al., Negative regulation of T cell homeostasis by lymphocyte activation gene-3 (CD223). J Immunol. Jan. 15, 2005;174(2):688-95. doi: 10.4049/jimmunol.174.2.688.

Workman et al., The CD4-related molecule, LAG-3 (CD223), regulates the expansion of activated T cells. Eur J Immunol. Apr. 2003;33(4):970-9. doi: 10.1002/eji.200323382.

Wydro, Bispecific antibodies: new opportunities for novel therapies. Oral Presentation at 7th Annual Biologics Symposium. Mar. 1, 2017. 24 pages. PDR172.

Wykes et al., Immune checkpoint blockade in infectious diseases. Nat Rev Immunol. Feb. 2018;18(2):91-104. doi: 10.1038/nri.2017.112. Epub Oct. 9, 2017.

Yap et al., A first-in-human phase I study of FS118, an anti-LAG-3/PD-L1 bispecific antibody in patients with solid tumors that have progressed on prior PD-1/PD-L1 therapy. Journal of Clinical Oncology. Jun. 1, 2019. Poster TPS2652. 2019 ASCO Annual Meeting Proceedings. 20 pages.

Yap et al., A first-in-human phase I study of FS118, an anti-LAG-3/PD-L1 bispecific antibody in patients with solid tumors that have progressed on prior PD-1/PD-L1 therapy. Journal of Clinical Oncology. May 26, 2019;37(15_suppl). 3 pages.

Yap et al., Abstract TPS2652: A first-in-human phase I study of FS118, an anti-LAG-3/PD-L1 bispecific antibody in patients with solid tumors that have progressed on prior PD-1/PD-L1 therapy. Journal of Clinical Oncology. May 15, 2019;37(15_suppl). 2019 ASCO Annual Meeting Proceedings. 4 pages.

Yonezawa et al., Boosting Cancer Immunotherapy with Anti-CD137 Antibody Therapy. Clin Cancer Res. Jul. 15, 2015;21(14):3113-20. doi: 10.1158/1078-0432.CCR-15-0263. Epub Apr. 23, 2015.

Zhang et al., Structural basis of a novel PD-L1 nanobody for immune checkpoint blockade. Cell Discov. Mar. 7, 2017;3:17004. doi: 10.1038/celldisc.2017.4.

Zhao et al., Novel Antibody Therapeutics Targeting Mesothelin In Solid Tumors. Clin Cancer Drugs. Oct. 2016;3(2):76-86. doi: 10.2174/2212697X03666160218215744.

* cited by examiner

| | | | | | | | | | | | | | | | AB | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|
| IMGT | 1.4 | 1.3 | 1.2 | 1.1 | 1 | 2 | 3 | 4 | 5 | 6 | 7 | 8 | 9 | 10 | 11 | 12 | 13 | 14 | 15 | 16 | 16.5 | 16.4 | 16.3 | 16.2 | 16.1 | 17 | 18 | 19 | 20 | 21 | 22 | 23 | 24 | 25 | 26 | 27 | 28 |
| IMGT exon numbering | 1 | 2 | 3 | 4 | 5 | 6 | 7 | 8 | 9 | 10 | 11 | 12 | 13 | 14 | 15 | 16 | 17 | 18 | 19 | 20 | | | | | | 21 | 22 | 23 | 24 | 25 | 26 | 27 | 28 | 29 | 30 | 31 | 32 |
| EU numbering | 341 | 342 | 343 | 344 | 345 | 346 | 347 | 348 | 349 | 350 | 351 | 352 | 353 | 354 | 355 | 356 | 357 | 358 | 359 | 360 | | | | | | 361 | 362 | 363 | 364 | 365 | 366 | 367 | 368 | 369 | 370 | 371 | 372 |
| Kabat numbering | 361 | 363 | 364 | 365 | 366 | 367 | 368 | 369 | 370 | 371 | 372 | 373 | 374 | 375 | 376 | 377 | 378 | 381 | 382 | 383 | | | | | | 384 | 385 | 386 | 387 | 388 | 389 | 390 | 391 | 392 | 393 | 394 | 395 |
| Wt Fcab | G | Q | P | R | E | P | Q | V | Y | T | L | P | P | S | R | D | E | L | T | K | | | | | | N | Q | V | S | L | T | C | L | V | K | G | F |
| FS22-053 | | | | | | | | | | | | | | | | | | | N | P | P | Y | L | F | S | | | | | | | | | | | | |
| FS22-053-008 | | | | | | | | | | | | | | | | | | | N | P | P | Y | L | F | S | | | | | | | | | | | | |
| FS22-053-009 | | | | | | | | | | | | | | | | | | | N | P | P | Y | L | F | S | | | | | | | | | | | | |
| FS22-053-010 | | | | | | | | | | | | | | | | | | | N | P | P | Y | L | F | S | | | | | | | | | | | | |
| FS22-053-011 | | | | | | | | | | | | | | | | | | | N | P | P | Y | L | F | S | | | | | | | | | | | | |
| FS22-053-012 | | | | | | | | | | | | | | | | | | | N | P | P | Y | L | F | S | | | | | | | | | | | | |
| FS22-053-013 | | | | | | | | | | | | | | | | | | | N | P | P | Y | L | F | S | | | | | | | | | | | | |
| FS22-053-014 | | | | | | | | | | | | | | | | | | | N | P | P | Y | L | F | S | | | | | | | | | | | | |
| FS22-053-015 | | | | | | | | | | | | | | | | | | | N | P | P | Y | L | F | S | | | | | | | | | | | | |
| FS22-053-016 | | | | | | | | | | | | | | | | | | | N | P | P | Y | L | F | S | | | | | | | | | | | | |
| FS22-053-017 | | | | | | | | | | | | | | | | | | | N | P | P | Y | L | F | S | | | | | | | | | | | | |
| FS22-172 | | | | | | | | | | | | | | | | | | | R | | Y | Y | P | P | Y | | | | | | | | | | | | |
| FS22-172-001 | | | | | | | | | | | | | | | | | | | P | F | V | M | P | P | Y | | | | | | | | | | | | |
| FS22-172-002 | | | | | | | | | | | | | | | | | | | P | F | Q | M | P | P | Y | | | | | | | | | | | | |
| FS22-172-003 | | | | | | | | | | | | | | | | | | | P | Y | I | I | P | P | Y | | | | | | | | | | | | |
| FS22-172-004 | | | | | | | | | | | | | | | | | | | N | Y | I | Y | P | P | Y | | | | | | | | | | | | |
| FS22-172-005 | | | | | | | | | | | | | | | | | | | Q | Q | V | Y | P | P | Y | | | | | | | | | | | | |
| FS22-172-006 | | | | | | | | | | | | | | | | | | | R | | Y | Y | P | P | Y | | | L | | | | | | | | | |

Figure 1A

| | | | | | | | | | | | CD | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|
| IMGT | 29 | 30 | 35 | 36 | 37 | 38 | 39 | 40 | 41 | 42 | 43 | 44 | 45 | 45.1 | 45.2 | 45.3 | 45.4 | 77 | 78 | 79 | 80 | 81 | 82 | 83 | 84 | 84.1 | 84.2 | 84.3 | 84.4 | 85.4 | 85.3 | 85.2 | 85.1 | 85 | 86 | 87 | 88 |
| IMGT exon numbering | 33 | 34 | 35 | 36 | 37 | 38 | 39 | 40 | 41 | 42 | 43 | 44 | 45 | 46 | 47 | 48 | 49 | 50 | 51 | 52 | 53 | 54 | 55 | 56 | 57 | 58 | 59 | 60 | 61 | 62 | 63 | 64 | 65 | 66 | 67 | 68 | 69 |
| EU numbering | 373 | 374 | 375 | 376 | 377 | 378 | 379 | 380 | 381 | 382 | 383 | 384 | 385 | 386 | 387 | 388 | 389 | 390 | 391 | 392 | 393 | 394 | 395 | 396 | 397 | 398 | 399 | 400 | 401 | 402 | 403 | 404 | 405 | 406 | 407 | 408 | 409 |
| Kabat numbering | 396 | 397 | 398 | 399 | 400 | 401 | 402 | 405 | 406 | 407 | 408 | 410 | 411 | 414 | 415 | 416 | 417 | 418 | 419 | 420 | 421 | 422 | 423 | 424 | 425 | 426 | 427 | 428 | 430 | 433 | 434 | 435 | 436 | 437 | 438 | 439 | 440 |
| **Wt Fcab** | Y | P | S | D | I | A | V | E | W | E | S | N | G | Q | P | E | N | N | Y | K | T | T | P | P | V | L | D | S | D | G | S | F | F | L | Y | S | K |
| FS22-053 | | | | | | | | | | | | | | | | | | | | | | | | | | | | | | | | | | | | | |
| FS22-053-008 | | | | | | | | | | | | | | | | | | | | | | | | | | | | | | | | | | | | | |
| FS22-053-009 | | | | | | | | | | | | | | | | | | | | | | | | | | | | | | | | | | | | | |
| FS22-053-010 | | | | | | | | | | | | | | | | | | | | | | | | | | | | | | | | | | | | | |
| FS22-053-011 | | | | | | | | | | | | | | | | | | | | | | | | | | | | | | | | | | | | | |
| FS22-053-012 | | | | | | | | | | | | | | | | | | | | | | | | | | | | | | | | | | | | | |
| FS22-053-013 | | | | | | | | | | | | | | | | | | | | | | | | | | | | | | | | | | | | | |
| FS22-053-014 | | | | | | | | | | | | | | | | | | | | | | | | | | | | | | | | | | | | | |
| FS22-053-015 | | | | | | | | | | | | | | | | | | | | | | | | | | | | | | | | | | | | | |
| FS22-053-016 | | | | | | | | | | | | | | | | | | | | | | | | | | | | | | | | | | | | | |
| FS22-053-017 | | | | | | | | | | | | | | | | | | | | | | | | | | | | | | | | | | | | | |
| FS22-172 | | | | | | | | | | | | | | | | | | | | | | | | | | | | | | | | | | | | | |
| FS22-172-001 | | | | | | | | | | | | | | | | | | | | | | | | | | | | | | | | | | | | | |
| FS22-172-002 | | | | | | | | | | | | | | | | | | | | | | | | | | | | | | | | | | | | | |
| FS22-172-003 | | | | | | | | | | | | | | | | | | | | | | | | | | | | | | | | | | | | | |
| FS22-172-004 | | | | | | | | | | | | | | | | | | | | | | | | | | | | | | | | | | | | | |
| FS22-172-005 | | | | | | | | | | | | | | | | | | | | | | | | | | | | | | | | | | | | | |
| FS22-172-006 | | | | | | | | | | | | | | | | | | | | | | | | | | | | | | | | | | | | | |

Figure 1B

| | | | | EF | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|
| IMGT | 89 | 90 | 91 | 92 | 93 | 94 | 95 | 96 | 97 | 98 | 99 | 100 | 101 | 102 | 103 | 104 | 105 | 106 | 107 | 108 | 109 | 110 | 112 | 113 | 114 | 115 | 116 | 117 | 118 | 119 | 120 | 121 | 122 | 123 | 124 | 125 | 129 |
| IMGT exon numbering | 70 | 71 | 72 | 73 | 74 | 75 | 76 | 77 | 78 | 79 | 80 | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | CHS 10 |
| EU numbering | 410 | 411 | 412 | 413 | 414 | 415 | 416 | 417 | 418 | 419 | 420 | 421 | 422 | 423 | 424 | 425 | 426 | 427 | 428 | 429 | 430 | 431 | 432 | 433 | 434 | 435 | 436 | 437 | 438 | 439 | 440 | 441 | 442 | 443 | 444 | 445 | 446 |
| Kabat numbering | 441 | 442 | 443 | 444 | 445 | 446 | 447 | 448 | 449 | 450 | 451 | 452 | 453 | 454 | 455 | 456 | 457 | 458 | 459 | 460 | 461 | 462 | 463 | 454 | 455 | 456 | 457 | 458 | 459 | 470 | 471 | 472 | 473 | 474 | 475 | 476 | 477 |
| **Wt Fcab** | L | T | V | D | K | S | R | W | Q | Q | G | N | V | F | S | C | S | V | M | H | E | A | L | H | N | H | Y | T | Q | K | S | L | S | L | S | P | G |
| FS22-053 | | | | Y | Y | N | | | | D | | | | | | | | | | | | | | | | | | | | | | | | | | | |
| FS22-053-008 | | | | | Y | W | | | L | E | | | | | | | | | | | | | | | | | | | | | | | | | | | |
| FS22-053-009 | | | | E | H | T | | | L | D | | | | | | | | | | | | | | | | | | | | | | | | | | | |
| FS22-053-010 | | | | | Y | M | | | L | D | | | | | | | | | | | | | | | | | | | | | | | | | | | |
| FS22-053-011 | | | | | Y | W | | | T | D | | | | | | | | | | | | | | | | | | | | | | | | | | | |
| FS22-053-012 | | | | | H | M | | | L | E | | | | | | | | | | | | | | | | | | | | | | | | | | | |
| FS22-053-013 | | | | G | Y | E | | | L | E | | | | | | | | | | | | | | | | | | | | | | | | | | | |
| FS22-053-014 | | | | Y | H | W | | | L | D | | | | | | | | | | | | | | | | | | | | | | | | | | | |
| FS22-053-015 | | | | | H | W | | | L | | | | | | | | | | | | | | | | | | | | | | | | | | | | |
| FS22-053-016 | | | | | Y | I | | | L | N | | | | | | | | | | | | | | | | | | | | | | | | | | | |
| FS22-053-017 | | | | Y | H | W | | | L | E | | | | | | | | | | | | | | | | | | | | | | | | | | | |
| FS22-172 | | | | G | A | D | | | L | E | | | | | | | | | | | | | | | | | | | | | | | | | | | |
| FS22-172-001 | | | | G | A | D | | | L | E | | | | | | | | | | | | | | | | | | | | | | | | | | | |
| FS22-172-002 | | | | G | A | D | | | L | E | | | | | | | | | | | | | | | | | | | | | | | | | | | |
| FS22-172-003 | | | | G | A | D | | | L | E | | | | | | | | | | | | | | | | | | | | | | | | | | | |
| FS22-172-004 | | | | G | A | D | | | L | E | | | | | | | | | | | | | | | | | | | | | | | | | | | |
| FS22-172-005 | | | | G | A | D | | | L | E | | | | | | | | | | | | | | | | | | | | | | | | | | | |
| FS22-172-006 | | | | G | A | D | | | L | E | | | | | | | | | | | | | | | | | | | | | | | | | | | |

Figure 1C

| Fcab clone | Percentage sequence identity in CH3 domain compared to CH3 domain of clone FS22-053 |
|---|---|
| FS22-053-008 | 96.4% |
| FS22-053-009 | 96.4% |
| FS22-053-010 | 97.3% |
| FS22-053-011 | 97.3% |
| FS22-053-012 | 95.5% |
| FS22-053-013 | 96.4% |
| FS22-053-014 | 97.3% |
| FS22-053-015 | 95.5% |
| FS22-053-016 | 96.4% |
| FS22-053-017 | 96.4% |

Figure 1D

| Fcab clone | Percentage sequence identity in CH3 domain compared to CH3 domain of clone FS22-172 |
|---|---|
| FS22-172-001 | 96.4% |
| FS22-172-002 | 96.4% |
| FS22-172-003 | 96.4% |
| FS22-172-004 | 97.3% |
| FS22-172-005 | 97.3% |
| FS22-172-006 | 99.1% |

SEQUENCE LISTING

```
<160> NUMBER OF SEQ ID NOS: 240

<210> SEQ ID NO 1
<211> LENGTH: 8
<212> TYPE: PRT
<213> ORGANISM: Artificial Sequence
<220> FEATURE:
<223> OTHER INFORMATION: WT Fcab AB loop

<400> SEQUENCE: 1

Arg Asp Glu Leu Thr Lys Asn Gln
1               5


<210> SEQ ID NO 2
```

```
<211> LENGTH: 9
<212> TYPE: PRT
<213> ORGANISM: Artificial Sequence
<220> FEATURE:
<223> OTHER INFORMATION: WT Fcab CD loop

<400> SEQUENCE: 2

Ser Asn Gly Gln Pro Glu Asn Asn Tyr
1               5


<210> SEQ ID NO 3
<211> LENGTH: 10
<212> TYPE: PRT
<213> ORGANISM: Artificial Sequence
<220> FEATURE:
<223> OTHER INFORMATION: WT Fcab EF loop

<400> SEQUENCE: 3

Asp Lys Ser Arg Trp Gln Gln Gly Asn Val
1               5                   10


<210> SEQ ID NO 4
<211> LENGTH: 106
<212> TYPE: PRT
<213> ORGANISM: Artificial Sequence
<220> FEATURE:
<223> OTHER INFORMATION: WT Fcab CH3 domain

<400> SEQUENCE: 4

Gly Gln Pro Arg Glu Pro Gln Val Tyr Thr Leu Pro Pro Ser Arg Asp
1               5                   10                  15

Glu Leu Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Lys Leu Thr Val Asp Lys Ser Arg Trp Gln Gln Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Pro Gly
            100                 105


<210> SEQ ID NO 5
<211> LENGTH: 110
<212> TYPE: PRT
<213> ORGANISM: Artificial Sequence
<220> FEATURE:
<223> OTHER INFORMATION: Fcab CH2 domain with LALA-PA mutation

<400> SEQUENCE: 5

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80
```

```
Gln Asp Trp Leu Asn Gly Lys Glu Tyr Lys Cys Lys Val Ser Asn Lys
                85                  90                  95

Ala Leu Ala Ala Pro Ile Glu Lys Thr Ile Ser Lys Ala Lys
            100                 105                 110


<210> SEQ ID NO 6
<211> LENGTH: 110
<212> TYPE: PRT
<213> ORGANISM: Artificial Sequence
<220> FEATURE:
<223> OTHER INFORMATION: Fcab CH2 domain with LALA mutation

<400> SEQUENCE: 6

Ala Pro Glu Ala Ala Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys
            100                 105                 110


<210> SEQ ID NO 7
<211> LENGTH: 6
<212> TYPE: PRT
<213> ORGANISM: Artificial Sequence
<220> FEATURE:
<223> OTHER INFORMATION: truncated Fcab hinge region

<400> SEQUENCE: 7

Thr Cys Pro Pro Cys Pro
1               5


<210> SEQ ID NO 8
<211> LENGTH: 223
<212> TYPE: PRT
<213> ORGANISM: Artificial Sequence
<220> FEATURE:
<223> OTHER INFORMATION: WT Fcab with LALA mutation

<400> SEQUENCE: 8

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95
```

```
Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly Lys
    210                 215                 220


<210> SEQ ID NO 9
<211> LENGTH: 222
<212> TYPE: PRT
<213> ORGANISM: Artificial Sequence
<220> FEATURE:
<223> OTHER INFORMATION: WT Fcab without LALA mutation

<400> SEQUENCE: 9

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Ala Leu
        195                 200                 205

His Asn His Tyr Thr Gln Lys Ser Leu Ser Leu Ser Pro Gly
    210                 215                 220


<210> SEQ ID NO 10
<211> LENGTH: 3
```

```
<212> TYPE: PRT
<213> ORGANISM: Artificial Sequence
<220> FEATURE:
<223> OTHER INFORMATION: PPY motif

<400> SEQUENCE: 10

Pro Pro Tyr
1


<210> SEQ ID NO 11
<211> LENGTH: 222
<212> TYPE: PRT
<213> ORGANISM: Artificial Sequence
<220> FEATURE:
<223> OTHER INFORMATION: Fcab FS22-033 with LALA mutation

<400> SEQUENCE: 11

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Tyr Phe Glu Gln Glu Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Ala Arg His Arg
            180                 185                 190

Trp Gln Leu Gly Asn Val Phe Ser Cys Ser Val Met His Glu Ala Leu
        195                 200                 205

His Asn His Tyr Thr Gln Lys Ser Leu Ser Leu Ser Pro Gly
    210                 215                 220


<210> SEQ ID NO 12
<211> LENGTH: 222
<212> TYPE: PRT
<213> ORGANISM: Artificial Sequence
<220> FEATURE:
<223> OTHER INFORMATION: Fcab FS22-033 without LALA mutation

<400> SEQUENCE: 12

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
```

```
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Tyr Phe Glu Gln Glu Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Ala Arg His Arg
            180                 185                 190

Trp Gln Leu Gly Asn Val Phe Ser Cys Ser Val Met His Glu Ala Leu
        195                 200                 205

His Asn His Tyr Thr Gln Lys Ser Leu Ser Leu Ser Pro Gly
    210                 215                 220


<210> SEQ ID NO 13
<211> LENGTH: 445
<212> TYPE: PRT
<213> ORGANISM: Artificial Sequence
<220> FEATURE:
<223> OTHER INFORMATION: heavy chain of FS22-033/HelD1.3 mock mAb2 with
      LALA mutation

<400> SEQUENCE: 13

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175
```

-continued

```
Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Tyr Phe Glu Gln Glu Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Ala Arg His Arg Trp
                405                 410                 415

Gln Leu Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445


<210> SEQ ID NO 14
<211> LENGTH: 445
<212> TYPE: PRT
<213> ORGANISM: Artificial Sequence
<220> FEATURE:
<223> OTHER INFORMATION: heavy chain of FS22-033/HelD1.3 mock mAb2
      without LALA mutation

<400> SEQUENCE: 14

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95
```

```
Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Tyr Phe Glu Gln Glu Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Ala Arg His Arg Trp
                405                 410                 415

Gln Leu Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445


<210> SEQ ID NO 15
<211> LENGTH: 227
<212> TYPE: PRT
<213> ORGANISM: Artificial Sequence
<220> FEATURE:
<223> OTHER INFORMATION: Fcab FS22-053 with LALA mutation

<400> SEQUENCE: 15

Thr Cys Pro Pro Cys Pro Ala Pro Glu Ala Ala Gly Gly Pro Ser Val
1               5                   10                  15
```

```
Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Asn Pro Pro Tyr Leu Phe Ser Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Tyr Tyr Asn Arg Trp Gln Asp Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225


<210> SEQ ID NO 16
<211> LENGTH: 227
<212> TYPE: PRT
<213> ORGANISM: Artificial Sequence
<220> FEATURE:
<223> OTHER INFORMATION: Fcab FS22-053 without LALA mutation

<400> SEQUENCE: 16

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Asn Pro Pro Tyr Leu Phe Ser Asn Gln Val
    130                 135                 140
```

Ser Leu Thr Cys Leu Val Lys Gly Phe Tyr Pro Ser Asp Ile Ala Val
145 150 155 160

Glu Trp Glu Ser Asn Gly Gln Pro Glu Asn Asn Tyr Lys Thr Thr Pro
165 170 175

Pro Val Leu Asp Ser Asp Gly Ser Phe Phe Leu Tyr Ser Lys Leu Thr
180 185 190

Val Tyr Tyr Asn Arg Trp Gln Asp Gly Asn Val Phe Ser Cys Ser Val
195 200 205

Met His Glu Ala Leu His Asn His Tyr Thr Gln Lys Ser Leu Ser Leu
210 215 220

Ser Pro Gly
225

<210> SEQ ID NO 17
<211> LENGTH: 450
<212> TYPE: PRT
<213> ORGANISM: Artificial Sequence
<220> FEATURE:
<223> OTHER INFORMATION: vy chain of FS22-053/HelD1.3 mock mAb2 with LALA mutation

<400> SEQUENCE: 17

Gln Val Gln Leu Gln Glu Ser Gly Pro Gly Leu Val Arg Pro Ser Gln
1 5 10 15

Thr Leu Ser Leu Thr Cys Thr Val Ser Gly Ser Thr Phe Ser Gly Tyr
20 25 30

Gly Val Asn Trp Val Arg Gln Pro Pro Gly Arg Gly Leu Glu Trp Ile
35 40 45

Gly Met Ile Trp Gly Asp Gly Asn Thr Asp Tyr Asn Ser Ala Leu Lys
50 55 60

Ser Arg Val Thr Met Leu Val Asp Thr Ser Lys Asn Gln Phe Ser Leu
65 70 75 80

Arg Leu Ser Ser Val Thr Ala Ala Asp Thr Ala Val Tyr Tyr Cys Ala
85 90 95

Arg Glu Arg Asp Tyr Arg Leu Asp Tyr Trp Gly Gln Gly Ser Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Ala Ala Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val

```
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Tyr Tyr Asn Arg Trp Gln Asp Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 18
<211> LENGTH: 450
<212> TYPE: PRT
<213> ORGANISM: Artificial Sequence
<220> FEATURE:
<223> OTHER INFORMATION: heavy chain of FS22-053/HelD1.3 mock mAb2
      without LALA mutation

<400> SEQUENCE: 18

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160
```

```
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Tyr Tyr Asn Arg Trp Gln Asp Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 19
<211> LENGTH: 7
<212> TYPE: PRT
<213> ORGANISM: Artificial Sequence
<220> FEATURE:
<223> OTHER INFORMATION: Fcab FS22-053-008 CH3 domain structural loop sequence

<400> SEQUENCE: 19

```
Asn Pro Pro Tyr Leu Phe Ser
1               5
```

<210> SEQ ID NO 20
<211> LENGTH: 7
<212> TYPE: PRT
<213> ORGANISM: Artificial Sequence
<220> FEATURE:
<223> OTHER INFORMATION: Fcab FS22-053-008 CH3 domain structural loop sequence

<400> SEQUENCE: 20

```
Asp Tyr Trp Arg Trp Leu Glu
1               5
```

<210> SEQ ID NO 21
<211> LENGTH: 111
<212> TYPE: PRT
<213> ORGANISM: Artificial Sequence
<220> FEATURE:
<223> OTHER INFORMATION: Fcab FS22-053-008 CH3 domain

<400> SEQUENCE: 21

```
Gly Gln Pro Arg Glu Pro Gln Val Tyr Thr Leu Pro Pro Ser Arg Asp
1               5                   10                  15

Glu Leu Asn Pro Pro Tyr Leu Phe Ser Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Asp Tyr Trp
65                  70                  75                  80

Arg Trp Leu Glu Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110
```

<210> SEQ ID NO 22
<211> LENGTH: 333
<212> TYPE: DNA
<213> ORGANISM: Artificial Sequence
<220> FEATURE:
<223> OTHER INFORMATION: Fcab FS22-053-008 CH3 domain

<400> SEQUENCE: 22

```
ggacagcctc gagaaccaca ggtgtacacc ctgcccccat cccgggatga gctgaacccg     60

ccgtacctgt tctctaacca ggtcagcctg acctgcctgg tcaaaggctt ctatcccagc    120

gacatcgccg tggagtggga gagcaatggg cagccggaga acaactacaa gaccacgcct    180

cccgtactgg actccgacgg ctccttcttc ctctacagca agctcaccgt ggattactgg    240

aggtggctgg aagggaacgt cttctcatgc tccgtgatgc atgaggcgct gcacaaccac    300

tacactcaga agagcttgtc cctgtcgccc ggt                                 333
```

<210> SEQ ID NO 23
<211> LENGTH: 227
<212> TYPE: PRT
<213> ORGANISM: Artificial Sequence
<220> FEATURE:
<223> OTHER INFORMATION: Fcab FS22-053-008 with LALA mutation

<400> SEQUENCE: 23

```
Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
```

50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
85 90 95

Cys Lys Val Ser Asn Lys Ala Leu Pro Ala Pro Ile Glu Lys Thr Ile
100 105 110

Ser Lys Ala Lys Gly Gln Pro Arg Glu Pro Gln Val Tyr Thr Leu Pro
115 120 125

Pro Ser Arg Asp Glu Leu Asn Pro Pro Tyr Leu Phe Ser Asn Gln Val
130 135 140

Ser Leu Thr Cys Leu Val Lys Gly Phe Tyr Pro Ser Asp Ile Ala Val
145 150 155 160

Glu Trp Glu Ser Asn Gly Gln Pro Glu Asn Asn Tyr Lys Thr Thr Pro
165 170 175

Pro Val Leu Asp Ser Asp Gly Ser Phe Phe Leu Tyr Ser Lys Leu Thr
180 185 190

Val Asp Tyr Trp Arg Trp Leu Glu Gly Asn Val Phe Ser Cys Ser Val
195 200 205

Met His Glu Ala Leu His Asn His Tyr Thr Gln Lys Ser Leu Ser Leu
210 215 220

Ser Pro Gly
225

<210> SEQ ID NO 24
<211> LENGTH: 681
<212> TYPE: DNA
<213> ORGANISM: Artificial Sequence
<220> FEATURE:
<223> OTHER INFORMATION: Fcab FS22-053-008 with LALA mutation

<400> SEQUENCE: 24
acttgcccgc cttgcccagc cccggaagct gccggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg ccagcctcga 360
gaaccacagg tgtacaccct gcccccatcc cgggatgagc tgaacccgcc gtacctgttc 420
tctaaccagg tcagcctgac ctgcctggtc aaaggcttct atcccagcga catcgccgtg 480
gagtgggaga gcaatgggca gccggagaac aactacaaga ccacgcctcc cgtgctggac 540
tccgacggct ccttcttcct ctacagcaag ctcaccgtgg attactggag gtggctggaa 600
gggaacgtct tctcatgctc cgtgatgcat gaggctctgc acaaccacta cacacagaag 660
agcctctccc tgtctccggg t 681

<210> SEQ ID NO 25
<211> LENGTH: 227
<212> TYPE: PRT
<213> ORGANISM: Artificial Sequence
<220> FEATURE:
<223> OTHER INFORMATION: Fcab FS22-053-008 without LALA mutation

<400> SEQUENCE: 25

-continued

Thr Cys Pro Pro Cys Pro Ala Pro Glu Leu Leu Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
85 90 95

Cys Lys Val Ser Asn Lys Ala Leu Pro Ala Pro Ile Glu Lys Thr Ile
100 105 110

Ser Lys Ala Lys Gly Gln Pro Arg Glu Pro Gln Val Tyr Thr Leu Pro
115 120 125

Pro Ser Arg Asp Glu Leu Asn Pro Pro Tyr Leu Phe Ser Asn Gln Val
130 135 140

Ser Leu Thr Cys Leu Val Lys Gly Phe Tyr Pro Ser Asp Ile Ala Val
145 150 155 160

Glu Trp Glu Ser Asn Gly Gln Pro Glu Asn Asn Tyr Lys Thr Thr Pro
165 170 175

Pro Val Leu Asp Ser Asp Gly Ser Phe Phe Leu Tyr Ser Lys Leu Thr
180 185 190

Val Asp Tyr Trp Arg Trp Leu Glu Gly Asn Val Phe Ser Cys Ser Val
195 200 205

Met His Glu Ala Leu His Asn His Tyr Thr Gln Lys Ser Leu Ser Leu
210 215 220

Ser Pro Gly
225

<210> SEQ ID NO 26
<211> LENGTH: 681
<212> TYPE: DNA
<213> ORGANISM: Artificial Sequence
<220> FEATURE:
<223> OTHER INFORMATION: Fcab FS22-053-008 without LALA mutation

<400> SEQUENCE: 26
acttgcccgc cttgcccagc cccggaactg ctgggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg ccagcctcga 360
gaaccacagg tgtacaccct gcccccatcc cgggatgagc tgaacccgcc gtacctgttc 420
tctaaccagg tcagcctgac ctgcctggtc aaaggcttct atcccagcga catcgccgtg 480
gagtgggaga gcaatgggca gccggagaac aactacaaga ccacgcctcc cgtgctggac 540
tccgacggct ccttcttcct ctacagcaag ctcaccgtgg attactggag gtggctggaa 600
gggaacgtct tctcatgctc cgtgatgcat gaggctctgc acaaccacta cacacagaag 660
agcctctccc tgtctccggg t 681

```
<210> SEQ ID NO 27
<211> LENGTH: 450
<212> TYPE: PRT
<213> ORGANISM: Artificial Sequence
<220> FEATURE:
<223> OTHER INFORMATION: heavy chain of FS22-053-008/HelD1.3 mock mAb2
      with LALA mutation

<400> SEQUENCE: 27

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365
```

```
Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Tyr Trp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 28
<211> LENGTH: 450
<212> TYPE: PRT
<213> ORGANISM: Artificial Sequence
<220> FEATURE:
<223> OTHER INFORMATION: heavy chain of FS22-053-008/HelD1.3 mock mAb2
      without LALA mutation

<400> SEQUENCE: 28

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
```

```
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Tyr Trp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 29
<211> LENGTH: 7
<212> TYPE: PRT
<213> ORGANISM: Artificial Sequence
<220> FEATURE:
<223> OTHER INFORMATION: Fcab FS22-053-009 CH3 domain structural loop
      sequence

<400> SEQUENCE: 29

Glu His Thr Arg Trp Leu Asp
1               5


<210> SEQ ID NO 30
<211> LENGTH: 111
<212> TYPE: PRT
<213> ORGANISM: Artificial Sequence
<220> FEATURE:
<223> OTHER INFORMATION: Fcab FS22-053-009 CH3 domain

<400> SEQUENCE: 30

Gly Gln Pro Arg Glu Pro Gln Val Tyr Thr Leu Pro Pro Ser Arg Asp
1               5                   10                  15

Glu Leu Asn Pro Pro Tyr Leu Phe Ser Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Glu His Thr
65                  70                  75                  80

Arg Trp Leu Asp Gly Asn Val Phe Ser Cys Ser Val Met His Glu Ala
                85                  90                  95
```

```
Leu His Asn His Tyr Thr Gln Lys Ser Leu Ser Leu Ser Pro Gly
            100                 105                 110


<210> SEQ ID NO 31
<211> LENGTH: 333
<212> TYPE: DNA
<213> ORGANISM: Artificial Sequence
<220> FEATURE:
<223> OTHER INFORMATION: Fcab FS22-053-009 CH3 domain

<400> SEQUENCE: 31

ggccagcctc gagaaccaca ggtgtacacc ctgcccccat cccgggatga gctgaacccg      60

ccgtacctgt tctctaacca ggtcagcctg acctgcctgg tcaaaggctt ctatcccagc     120

gacatcgccg tggagtggga gagcaatggg cagccggaga acaactacaa gaccacgcct     180

cccgtgctgg actccgacgg ctccttcttc ctctacagca agctcaccgt ggaacatact     240

aggtggctgg atgggaacgt cttctcatgc tccgtgatgc atgaggctct gcacaaccac     300

tacacacaga agagcctctc cctgtctccg ggt                                  333


<210> SEQ ID NO 32
<211> LENGTH: 227
<212> TYPE: PRT
<213> ORGANISM: Artificial Sequence
<220> FEATURE:
<223> OTHER INFORMATION: Fcab FS22-053-009 with LALA mutation

<400> SEQUENCE: 32

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Asn Pro Pro Tyr Leu Phe Ser Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Glu His Thr Arg Trp Leu Asp Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
```

225

<210> SEQ ID NO 33
<211> LENGTH: 681
<212> TYPE: DNA
<213> ORGANISM: Artificial Sequence
<220> FEATURE:
<223> OTHER INFORMATION: Fcab FS22-053-009 with LALA mutation

<400> SEQUENCE: 33
acttgcccgc cttgcccagc cccggaagct gccggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg ccagcctcga 360
gaaccacagg tgtacaccct gcccccatcc cgggatgagc tgaacccgcc gtacctgttc 420
tctaaccagg tcagcctgac ctgcctggtc aaaggcttct atcccagcga catcgccgtg 480
gagtgggaga gcaatgggca gccggagaac aactacaaga ccacgcctcc cgtgctggac 540
tccgacggct ccttcttcct ctacagcaag ctcaccgtgg aacatactag gtggctggat 600
gggaacgtct tctcatgctc cgtgatgcat gaggctctgc acaaccacta cacacagaag 660
agcctctccc tgtctccggg t 681

<210> SEQ ID NO 34
<211> LENGTH: 227
<212> TYPE: PRT
<213> ORGANISM: Artificial Sequence
<220> FEATURE:
<223> OTHER INFORMATION: Fcab FS22-053-009 without LALA mutation

<400> SEQUENCE: 34

Thr Cys Pro Pro Cys Pro Ala Pro Glu Leu Leu Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
85 90 95

Cys Lys Val Ser Asn Lys Ala Leu Pro Ala Pro Ile Glu Lys Thr Ile
100 105 110

Ser Lys Ala Lys Gly Gln Pro Arg Glu Pro Gln Val Tyr Thr Leu Pro
115 120 125

Pro Ser Arg Asp Glu Leu Asn Pro Pro Tyr Leu Phe Ser Asn Gln Val
130 135 140

Ser Leu Thr Cys Leu Val Lys Gly Phe Tyr Pro Ser Asp Ile Ala Val
145 150 155 160

Glu Trp Glu Ser Asn Gly Gln Pro Glu Asn Asn Tyr Lys Thr Thr Pro
165 170 175

```
Pro Val Leu Asp Ser Asp Gly Ser Phe Phe Leu Tyr Ser Lys Leu Thr
            180                 185                 190

Val Glu His Thr Arg Trp Leu Asp Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225


<210> SEQ ID NO 35
<211> LENGTH: 681
<212> TYPE: DNA
<213> ORGANISM: Artificial Sequence
<220> FEATURE:
<223> OTHER INFORMATION: Fcab FS22-053-009 without LALA mutation

<400> SEQUENCE: 35

acttgcccgc cttgcccagc cccggaactg ctgggtggtc cttcggtgtt cctcttcccg     60

cccaagccga aggataccct gatgatctca cggacccccg aagtgacctg tgtggtggtg    120

gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240

gtgctcactg tgctgcacca agactggctg aacgggaagg agtacaagtg caaagtgtcc    300

aacaaggcgc tgcctgcccc aattgagaaa actatctcga aagccaaggg ccagcctcga    360

gaaccacagg tgtacaccct gcccccatcc cgggatgagc tgaacccgcc gtacctgttc    420

tctaaccagg tcagcctgac ctgcctggtc aaaggcttct atcccagcga catcgccgtg    480

gagtgggaga gcaatgggca gccggagaac aactacaaga ccacgcctcc cgtgctggac    540

tccgacggct ccttcttcct ctacagcaag ctcaccgtgg aacatactag gtggctggat    600

gggaacgtct tctcatgctc cgtgatgcat gaggctctgc acaaccacta cacacagaag    660

agcctctccc tgtctccggg t                                               681


<210> SEQ ID NO 36
<211> LENGTH: 450
<212> TYPE: PRT
<213> ORGANISM: Artificial Sequence
<220> FEATURE:
<223> OTHER INFORMATION: eavy chain of FS22-053-009/HelD1.3 mock mAb2
      with LALA mutation

<400> SEQUENCE: 36

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
```

-continued

```
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Glu His Thr Arg Trp Leu Asp Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 37
<211> LENGTH: 450
<212> TYPE: PRT
<213> ORGANISM: Artificial Sequence
<220> FEATURE:
<223> OTHER INFORMATION: heavy chain of FS22-053-009/HelD1.3 mock mAb2
without LALA mutation

<400> SEQUENCE: 37

```
Gln Val Gln Leu Gln Glu Ser Gly Pro Gly Leu Val Arg Pro Ser Gln
1               5                   10                  15
```

```
Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Glu His Thr Arg Trp Leu Asp Gly Asn Val Phe Ser Cys Ser Val Met
            420                 425                 430

His Glu Ala Leu His Asn His Tyr Thr Gln Lys Ser Leu Ser Leu Ser
```

435 440 445

Pro Gly
450

<210> SEQ ID NO 38
<211> LENGTH: 7
<212> TYPE: PRT
<213> ORGANISM: Artificial Sequence
<220> FEATURE:
<223> OTHER INFORMATION: Fcab FS22-053-010 CH3 domain structural loop sequence

<400> SEQUENCE: 38

Asp Tyr Met Arg Trp Leu Asp
1 5

<210> SEQ ID NO 39
<211> LENGTH: 111
<212> TYPE: PRT
<213> ORGANISM: Artificial Sequence
<220> FEATURE:
<223> OTHER INFORMATION: Fcab FS22-053-010 CH3 domain

<400> SEQUENCE: 39

Gly Gln Pro Arg Glu Pro Gln Val Tyr Thr Leu Pro Pro Ser Arg Asp
1 5 10 15

Glu Leu Asn Pro Pro Tyr Leu Phe Ser Asn Gln Val Ser Leu Thr Cys
20 25 30

Leu Val Lys Gly Phe Tyr Pro Ser Asp Ile Ala Val Glu Trp Glu Ser
35 40 45

Asn Gly Gln Pro Glu Asn Asn Tyr Lys Thr Thr Pro Pro Val Leu Asp
50 55 60

Ser Asp Gly Ser Phe Phe Leu Tyr Ser Lys Leu Thr Val Asp Tyr Met
65 70 75 80

Arg Trp Leu Asp Gly Asn Val Phe Ser Cys Ser Val Met His Glu Ala
85 90 95

Leu His Asn His Tyr Thr Gln Lys Ser Leu Ser Leu Ser Pro Gly
100 105 110

<210> SEQ ID NO 40
<211> LENGTH: 333
<212> TYPE: DNA
<213> ORGANISM: Artificial Sequence
<220> FEATURE:
<223> OTHER INFORMATION: Fcab FS22-053-010 CH3 domain

<400> SEQUENCE: 40
ggccagcctc gagaaccaca ggtgtacacc ctgcccccat cccgggatga gctgaacccg 60
ccgtacctgt tctctaacca ggtcagcctg acctgcctgg tcaaaggctt ctatcccagc 120
gacatcgccg tggagtggga gagcaatggg cagccggaga acaactacaa gaccacgcct 180
cccgtgctgg actccgacgg ctccttcttc ctctacagca agctcaccgt ggattacatg 240
aggtggctgg atgggaacgt cttctcatgc tccgtgatgc atgaggctct gcacaaccac 300
tacacacaga agagcctctc cctgtctccg ggt 333

<210> SEQ ID NO 41
<211> LENGTH: 227
<212> TYPE: PRT
<213> ORGANISM: Artificial Sequence
<220> FEATURE:
<223> OTHER INFORMATION: Fcab FS22-053-010 with LALA mutation

<400> SEQUENCE: 41

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Asn Pro Pro Tyr Leu Phe Ser Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Tyr Met Arg Trp Leu Asp Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225

<210> SEQ ID NO 42
<211> LENGTH: 681
<212> TYPE: DNA
<213> ORGANISM: Artificial Sequence
<220> FEATURE:
<223> OTHER INFORMATION: Fcab FS22-053-010 with LALA mutation

<400> SEQUENCE: 42
acttgcccgc cttgcccagc cccggaagct gccggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg ccagcctcga 360
gaaccacagg tgtacaccct gcccccatcc cgggatgagc tgaacccgcc gtacctgttc 420
tctaaccagg tcagcctgac ctgcctggtc aaaggcttct atcccagcga catcgccgtg 480
gagtgggaga gcaatgggca gccggagaac aactacaaga ccacgcctcc cgtgctggac 540
tccgacggct ccttcttcct ctacagcaag ctcaccgtgg attacatgag gtggctggat 600
gggaacgtct tctcatgctc cgtgatgcat gaggctctgc acaaccacta cacacagaag 660
agcctctccc tgtctccggg t 681

<210> SEQ ID NO 43
<211> LENGTH: 227
<212> TYPE: PRT
<213> ORGANISM: Artificial Sequence
<220> FEATURE:
<223> OTHER INFORMATION: Fcab FS22-053-010 without LALA mutation

<400> SEQUENCE: 43

Thr Cys Pro Pro Cys Pro Ala Pro Glu Leu Leu Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
85 90 95

Cys Lys Val Ser Asn Lys Ala Leu Pro Ala Pro Ile Glu Lys Thr Ile
100 105 110

Ser Lys Ala Lys Gly Gln Pro Arg Glu Pro Gln Val Tyr Thr Leu Pro
115 120 125

Pro Ser Arg Asp Glu Leu Asn Pro Pro Tyr Leu Phe Ser Asn Gln Val
130 135 140

Ser Leu Thr Cys Leu Val Lys Gly Phe Tyr Pro Ser Asp Ile Ala Val
145 150 155 160

Glu Trp Glu Ser Asn Gly Gln Pro Glu Asn Asn Tyr Lys Thr Thr Pro
165 170 175

Pro Val Leu Asp Ser Asp Gly Ser Phe Phe Leu Tyr Ser Lys Leu Thr
180 185 190

Val Asp Tyr Met Arg Trp Leu Asp Gly Asn Val Phe Ser Cys Ser Val
195 200 205

Met His Glu Ala Leu His Asn His Tyr Thr Gln Lys Ser Leu Ser Leu
210 215 220

Ser Pro Gly
225

<210> SEQ ID NO 44
<211> LENGTH: 681
<212> TYPE: DNA
<213> ORGANISM: Artificial Sequence
<220> FEATURE:
<223> OTHER INFORMATION: Fcab FS22-053-010 without LALA mutation

<400> SEQUENCE: 44
acttgcccgc cttgcccagc cccggaactg ctgggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg ccagcctcga 360

```
gaaccacagg tgtacaccct gcccccatcc cgggatgagc tgaacccgcc gtacctgttc    420

tctaaccagg tcagcctgac ctgcctggtc aaaggcttct atcccagcga catcgccgtg    480

gagtgggaga gcaatgggca gccggagaac aactacaaga ccacgcctcc cgtgctggac    540

tccgacggct ccttcttcct ctacagcaag ctcaccgtgg attacatgag gtggctggat    600

gggaacgtct tctcatgctc cgtgatgcat gaggctctgc acaaccacta cacacagaag    660

agcctctccc tgtctccggg t                                              681
```

<210> SEQ ID NO 45
<211> LENGTH: 450
<212> TYPE: PRT
<213> ORGANISM: Artificial Sequence
<220> FEATURE:
<223> OTHER INFORMATION: heavy chain of FS22-053-010/HelD1.3 mock mAb2 with LALA mutation

<400> SEQUENCE: 45

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
```

```
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Tyr Met Arg Trp Leu Asp Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 46
<211> LENGTH: 450
<212> TYPE: PRT
<213> ORGANISM: Artificial Sequence
<220> FEATURE:
<223> OTHER INFORMATION: heavy chain of FS22-053-010/HelD1.3 mock mAb2 without LALA mutation

<400> SEQUENCE: 46

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190
```

```
Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Tyr Met Arg Trp Leu Asp Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 47
<211> LENGTH: 7
<212> TYPE: PRT
<213> ORGANISM: Artificial Sequence
<220> FEATURE:
<223> OTHER INFORMATION: Fcab FS22-053-011 CH3 domain structural loop sequence

<400> SEQUENCE: 47

```
Asp Tyr Trp Arg Trp Thr Asp
1               5
```

<210> SEQ ID NO 48
<211> LENGTH: 111
<212> TYPE: PRT
<213> ORGANISM: Artificial Sequence
<220> FEATURE:
<223> OTHER INFORMATION: Fcab FS22-053-011 CH3 domain

<400> SEQUENCE: 48

```
Gly Gln Pro Arg Glu Pro Gln Val Tyr Thr Leu Pro Pro Ser Arg Asp
1               5                   10                  15

Glu Leu Asn Pro Pro Tyr Leu Phe Ser Asn Gln Val Ser Leu Thr Cys
```

```
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Asp Tyr Trp
65                  70                  75                  80

Arg Trp Thr Asp Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110


<210> SEQ ID NO 49
<211> LENGTH: 333
<212> TYPE: DNA
<213> ORGANISM: Artificial Sequence
<220> FEATURE:
<223> OTHER INFORMATION: Fcab FS22-053-011 CH3 domain

<400> SEQUENCE: 49

ggacagcctc gagagcctca agtgtacacc ctgcccccat cccgggatga gctgaacccg      60

ccgtacctgt tctctaacca ggtcagcctg acctgcctgg tcaaaggctt ctatcccagc     120

gacatcgccg tggagtggga gagcaatggg cagccggaga acaactacaa gaccacgcct     180

cccgtgctgg actccgacgg ctccttcttc ctctacagca agctcaccgt ggattactgg     240

aggtggactg atgggaacgt cttctcatgc tccgtgatgc atgaggcgct gcacaaccac     300

tacactcaga agagcttgtc cctgtcgccc gga                                  333


<210> SEQ ID NO 50
<211> LENGTH: 227
<212> TYPE: PRT
<213> ORGANISM: Artificial Sequence
<220> FEATURE:
<223> OTHER INFORMATION: Fcab FS22-053-011 with LALA mutation

<400> SEQUENCE: 50

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Asn Pro Pro Tyr Leu Phe Ser Asn Gln Val
    130                 135                 140

Ser Leu Thr Cys Leu Val Lys Gly Phe Tyr Pro Ser Asp Ile Ala Val
145                 150                 155                 160
```

```
Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Tyr Trp Arg Trp Thr Asp Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225


<210> SEQ ID NO 51
<211> LENGTH: 681
<212> TYPE: DNA
<213> ORGANISM: Artificial Sequence
<220> FEATURE:
<223> OTHER INFORMATION: Fcab FS22-053-011 with LALA mutation

<400> SEQUENCE: 51

acttgcccgc cttgcccagc cccggaagct gccggtggtc cttcggtgtt cctcttcccg      60

cccaagccga aggataccct gatgatctca cggacccccg aagtgacctg tgtggtggtg     120

gacgtgtccc acgaggaccc ggaagtgaaa ttcaattggt acgtggatgg agtggaagtg     180

cacaacgcca agaccaagcc acgggaagaa cagtacaact ctacctaccg cgtggtgtcc     240

gtgctcactg tgctgcacca agactggctg aacgggaagg agtacaagtg caaagtgtcc     300

aacaaggcgc tgcctgcccc aattgagaaa actatctcga aagccaaggg ccagcctcga     360

gaaccacagg tgtacaccct gcccccatcc cgggatgagc tgaacccgcc gtacctgttc     420

tctaaccagg tcagcctgac ctgcctggtc aaaggcttct atcccagcga catcgccgtg     480

gagtgggaga gcaatgggca gccggagaac aactacaaga ccacgcctcc cgtgctggac     540

tccgacggct ccttcttcct ctacagcaag ctcaccgtgg attactggag gtggactgat     600

gggaacgtct tctcatgctc cgtgatgcat gaggctctgc acaaccacta cacacagaag     660

agcctctccc tgtctccggg t                                               681


<210> SEQ ID NO 52
<211> LENGTH: 227
<212> TYPE: PRT
<213> ORGANISM: Artificial Sequence
<220> FEATURE:
<223> OTHER INFORMATION: Fcab FS22-053-011 without LALA mutation

<400> SEQUENCE: 52

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110
```

```
Ser Lys Ala Lys Gly Gln Pro Arg Glu Pro Gln Val Tyr Thr Leu Pro
        115                 120                 125

Pro Ser Arg Asp Glu Leu Asn Pro Pro Tyr Leu Phe Ser Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Tyr Trp Arg Trp Thr Asp Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225


<210> SEQ ID NO 53
<211> LENGTH: 681
<212> TYPE: DNA
<213> ORGANISM: Artificial Sequence
<220> FEATURE:
<223> OTHER INFORMATION: Fcab FS22-053-011 without LALA mutation

<400> SEQUENCE: 53

acttgcccgc cttgcccagc cccggaactg ctgggtggtc cttcggtgtt cctcttcccg     60

cccaagccga aggataccct gatgatctca cggacccccg aagtgacctg tgtggtggtg    120

gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240

gtgctcactg tgctgcacca agactggctg aacgggaagg agtacaagtg caaagtgtcc    300

aacaaggcgc tgcctgcccc aattgagaaa actatctcga aagccaaggg ccagcctcga    360

gaaccacagg tgtacaccct gcccccatcc cgggatgagc tgaacccgcc gtacctgttc    420

tctaaccagg tcagcctgac ctgcctggtc aaaggcttct atcccagcga catcgccgtg    480

gagtgggaga gcaatgggca gccggagaac aactacaaga ccacgcctcc cgtgctggac    540

tccgacggct ccttcttcct ctacagcaag ctcaccgtgg attactggag gtggactgat    600

gggaacgtct tctcatgctc cgtgatgcat gaggctctgc acaaccacta cacacagaag    660

agcctctccc tgtctccggg t                                              681


<210> SEQ ID NO 54
<211> LENGTH: 450
<212> TYPE: PRT
<213> ORGANISM: Artificial Sequence
<220> FEATURE:
<223> OTHER INFORMATION: eavy chain of FS22-053-011/HelD1.3 mock mAb2
      with LALA mutation

<400> SEQUENCE: 54

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45
```

```
Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Tyr Trp Arg Trp Thr Asp Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

```
<210> SEQ ID NO 55
<211> LENGTH: 450
<212> TYPE: PRT
<213> ORGANISM: Artificial Sequence
<220> FEATURE:
<223> OTHER INFORMATION: heavy chain of FS22-053-011/HelD1.3 mock mAb2
      without LALA mutation

<400> SEQUENCE: 55

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365
```

```
Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Tyr Trp Arg Trp Thr Asp Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 56
<211> LENGTH: 7
<212> TYPE: PRT
<213> ORGANISM: Artificial Sequence
<220> FEATURE:
<223> OTHER INFORMATION: Fcab FS22-053-012 CH3 domain structural loop
      sequence

<400> SEQUENCE: 56

Asp His Met Arg Trp Leu Glu
1               5


<210> SEQ ID NO 57
<211> LENGTH: 111
<212> TYPE: PRT
<213> ORGANISM: Artificial Sequence
<220> FEATURE:
<223> OTHER INFORMATION: Fcab FS22-053-012 CH3 domain

<400> SEQUENCE: 57

Gly Gln Pro Arg Glu Pro Gln Val Tyr Thr Leu Pro Pro Ser Arg Asp
1               5                   10                  15

Glu Leu Asn Pro Pro Tyr Leu Phe Ser Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Asp His Met
65                  70                  75                  80

Arg Trp Leu Glu Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110


<210> SEQ ID NO 58
<211> LENGTH: 333
<212> TYPE: DNA
<213> ORGANISM: Artificial Sequence
<220> FEATURE:
<223> OTHER INFORMATION: Fcab FS22-053-012 CH3 domain

<400> SEQUENCE: 58

ggccagcctc gagaaccaca ggtgtacacc ctgcccccat cccgggatga gctgaacccg      60

ccgtacctgt tctctaacca ggtcagcctg acctgcctgg tcaaaggctt ctatcccagc     120

gacatcgccg tggagtggga gagcaatggg cagccggaga acaactacaa gaccacgcct     180
```

cccgtgctgg actccgacgg ctccttcttc ctctacagca agctcaccgt ggatcatatg 240
aggtggctgg aagggaacgt cttctcatgc tccgtgatgc atgaggctct gcacaaccac 300
tacacacaga agagcctctc cctgtctccg ggt 333

<210> SEQ ID NO 59
<211> LENGTH: 227
<212> TYPE: PRT
<213> ORGANISM: Artificial Sequence
<220> FEATURE:
<223> OTHER INFORMATION: Fcab FS22-053-012 with LALA mutation

<400> SEQUENCE: 59

Thr Cys Pro Pro Cys Pro Ala Pro Glu Ala Ala Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
85 90 95

Cys Lys Val Ser Asn Lys Ala Leu Pro Ala Pro Ile Glu Lys Thr Ile
100 105 110

Ser Lys Ala Lys Gly Gln Pro Arg Glu Pro Gln Val Tyr Thr Leu Pro
115 120 125

Pro Ser Arg Asp Glu Leu Asn Pro Pro Tyr Leu Phe Ser Asn Gln Val
130 135 140

Ser Leu Thr Cys Leu Val Lys Gly Phe Tyr Pro Ser Asp Ile Ala Val
145 150 155 160

Glu Trp Glu Ser Asn Gly Gln Pro Glu Asn Asn Tyr Lys Thr Thr Pro
165 170 175

Pro Val Leu Asp Ser Asp Gly Ser Phe Phe Leu Tyr Ser Lys Leu Thr
180 185 190

Val Asp His Met Arg Trp Leu Glu Gly Asn Val Phe Ser Cys Ser Val
195 200 205

Met His Glu Ala Leu His Asn His Tyr Thr Gln Lys Ser Leu Ser Leu
210 215 220

Ser Pro Gly
225

<210> SEQ ID NO 60
<211> LENGTH: 681
<212> TYPE: DNA
<213> ORGANISM: Artificial Sequence
<220> FEATURE:
<223> OTHER INFORMATION: Fcab FS22-053-012 with LALA mutation

<400> SEQUENCE: 60
acttgcccgc cttgcccagc cccggaagct gccggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240

-continued

```
gtgctcactg tgctgcacca agactggctg aacgggaagg agtacaagtg caaagtgtcc    300

aacaaggcgc tgcctgcccc aattgagaaa actatctcga aagccaaggg ccagcctcga    360

gaaccacagg tgtacaccct gcccccatcc cgggatgagc tgaacccgcc gtacctgttc    420

tctaaccagg tcagcctgac ctgcctggtc aaaggcttct atcccagcga catcgccgtg    480

gagtgggaga gcaatgggca gccggagaac aactacaaga ccacgcctcc cgtgctggac    540

tccgacggct ccttcttcct ctacagcaag ctcaccgtgg atcatatgag gtggctggaa    600

gggaacgtct tctcatgctc cgtgatgcat gaggctctgc acaaccacta cacacagaag    660

agcctctccc tgtctccggg t                                               681
```

```
<210> SEQ ID NO 61
<211> LENGTH: 227
<212> TYPE: PRT
<213> ORGANISM: Artificial Sequence
<220> FEATURE:
<223> OTHER INFORMATION: Fcab FS22-053-012 without LALA mutation

<400> SEQUENCE: 61

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Asn Pro Pro Tyr Leu Phe Ser Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp His Met Arg Trp Leu Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225


<210> SEQ ID NO 62
<211> LENGTH: 681
<212> TYPE: DNA
<213> ORGANISM: Artificial Sequence
<220> FEATURE:
<223> OTHER INFORMATION: Fcab FS22-053-012 without LALA mutation
```

<400> SEQUENCE: 62

```
acttgcccgc cttgcccagc cccggaactg ctgggtggtc cttcggtgtt cctcttcccg     60
cccaagccga aggataccct gatgatctca cggacccccg aagtgacctg tgtggtggtg    120
gacgtgtccc acgaggaccc ggaagtgaaa ttcaattggt acgtggatgg agtggaagtg    180
cacaacgcca agaccaagcc acgggaagaa cagtacaact ctacctaccg cgtggtgtcc    240
gtgctcactg tgctgcacca agactggctg aacgggaagg agtacaagtg caaagtgtcc    300
aacaaggcgc tgcctgcccc aattgagaaa actatctcga aagccaaggg ccagcctcga    360
gaaccacagg tgtacaccct gcccccatcc cgggatgagc tgaacccgcc gtacctgttc    420
tctaaccagg tcagcctgac ctgcctggtc aaaggcttct atcccagcga catcgccgtg    480
gagtgggaga gcaatgggca gccggagaac aactacaaga ccacgcctcc cgtgctggac    540
tccgacggct ccttcttcct ctacagcaag ctcaccgtgg atcatatgag gtggctggaa    600
gggaacgtct tctcatgctc cgtgatgcat gaggctctgc acaaccacta cacacagaag    660
agcctctccc tgtctccggg t                                              681
```

<210> SEQ ID NO 63
<211> LENGTH: 450
<212> TYPE: PRT
<213> ORGANISM: Artificial Sequence
<220> FEATURE:
<223> OTHER INFORMATION: heavy chain of FS22-053-012/HelD1.3 mock mAb2 with LALA mutation

<400> SEQUENCE: 63

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220
```

Cys Pro Pro Cys Pro Ala Pro Glu Ala Ala Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Asp Glu Leu Asn Pro Pro Tyr Leu Phe Ser Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Asp His Met Arg Trp Leu Glu Gly Asn Val Phe Ser Cys Ser Val Met
420 425 430

His Glu Ala Leu His Asn His Tyr Thr Gln Lys Ser Leu Ser Leu Ser
435 440 445

Pro Gly
450

<210> SEQ ID NO 64
<211> LENGTH: 450
<212> TYPE: PRT
<213> ORGANISM: Artificial Sequence
<220> FEATURE:
<223> OTHER INFORMATION: the heavy chain of FS22-053-012/HelD1.3 mock
mAb2 without LALA mutation

<400> SEQUENCE: 64

Gln Val Gln Leu Gln Glu Ser Gly Pro Gly Leu Val Arg Pro Ser Gln
1 5 10 15

Thr Leu Ser Leu Thr Cys Thr Val Ser Gly Ser Thr Phe Ser Gly Tyr
20 25 30

Gly Val Asn Trp Val Arg Gln Pro Pro Gly Arg Gly Leu Glu Trp Ile
35 40 45

Gly Met Ile Trp Gly Asp Gly Asn Thr Asp Tyr Asn Ser Ala Leu Lys
50 55 60

Ser Arg Val Thr Met Leu Val Asp Thr Ser Lys Asn Gln Phe Ser Leu
65 70 75 80

Arg Leu Ser Ser Val Thr Ala Ala Asp Thr Ala Val Tyr Tyr Cys Ala
85 90 95

Arg Glu Arg Asp Tyr Arg Leu Asp Tyr Trp Gly Gln Gly Ser Leu Val
100 105 110

Thr Val Ser Ser Ala Ser Thr Lys Gly Pro Ser Val Phe Pro Leu Ala
115 120 125

```
Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp His Met Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 65
<211> LENGTH: 7
<212> TYPE: PRT
<213> ORGANISM: Artificial Sequence
<220> FEATURE:
<223> OTHER INFORMATION: Fcab FS22-053-013 CH3 domain structural loop sequence

<400> SEQUENCE: 65

```
Gly Tyr Glu Arg Trp Leu Glu
1               5
```

<210> SEQ ID NO 66
<211> LENGTH: 111
<212> TYPE: PRT
<213> ORGANISM: Artificial Sequence
<220> FEATURE:
<223> OTHER INFORMATION: Fcab FS22-053-013 CH3 domain

<400> SEQUENCE: 66

```
Gly Gln Pro Arg Glu Pro Gln Val Tyr Thr Leu Pro Pro Ser Arg Asp
1               5                   10                  15

Glu Leu Asn Pro Pro Tyr Leu Phe Ser Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Gly Tyr Glu
65                  70                  75                  80

Arg Trp Leu Glu Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110
```

<210> SEQ ID NO 67
<211> LENGTH: 333
<212> TYPE: DNA
<213> ORGANISM: Artificial Sequence
<220> FEATURE:
<223> OTHER INFORMATION: Fcab FS22-053-013 CH3 domain

<400> SEQUENCE: 67

```
ggccagcctc gagaaccaca ggtgtacacc ctgcccccat cccgggatga gctgaacccg     60

ccgtacctgt tctctaacca ggtcagcctg acctgcctgg tcaaaggctt ctatcccagc    120

gacatcgccg tggagtggga gagcaatggg cagccggaga acaactacaa gaccacgcct    180

cccgtgctgg actccgacgg ctccttcttc ctctacagca agctcaccgt gggttacgaa    240

aggtggctgg aagggaacgt cttctcatgc tccgtgatgc atgaggctct gcacaaccac    300

tacacacaga agagcctctc cctgtctccg ggt                                 333
```

<210> SEQ ID NO 68
<211> LENGTH: 227
<212> TYPE: PRT
<213> ORGANISM: Artificial Sequence
<220> FEATURE:
<223> OTHER INFORMATION: Fcab FS22-053-013 with LALA mutation

<400> SEQUENCE: 68

```
Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95
```

```
Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Asn Pro Pro Tyr Leu Phe Ser Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Gly Tyr Glu Arg Trp Leu Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225


<210> SEQ ID NO 69
<211> LENGTH: 681
<212> TYPE: DNA
<213> ORGANISM: Artificial Sequence
<220> FEATURE:
<223> OTHER INFORMATION: Fcab FS22-053-013 with LALA mutation

<400> SEQUENCE: 69

acttgcccgc cttgcccagc cccggaagct gccggtggtc cttcggtgtt cctcttcccg      60

cccaagccga aggataccct gatgatctca cggacccccg aagtgacctg tgtggtggtg     120

gacgtgtccc acgaggaccc ggaagtgaaa ttcaattggt acgtggatgg agtggaagtg     180

cacaacgcca agaccaagcc acgggaagaa cagtacaact ctacctaccg cgtggtgtcc     240

gtgctcactg tgctgcacca agactggctg aacgggaagg agtacaagtg caaagtgtcc     300

aacaaggcgc tgcctgcccc aattgagaaa actatctcga aagccaaggg ccagcctcga     360

gaaccacagg tgtacaccct gcccccatcc cgggatgagc tgaacccgcc gtacctgttc     420

tctaaccagg tcagcctgac ctgcctggtc aaaggcttct atcccagcga catcgccgtg     480

gagtgggaga gcaatgggca gccggagaac aactacaaga ccacgcctcc cgtgctggac     540

tccgacggct ccttcttcct ctacagcaag ctcaccgtgg gttacgaaag gtggctggaa     600

gggaacgtct tctcatgctc cgtgatgcat gaggctctgc acaaccacta cacacagaag     660

agcctctccc tgtctccggg t                                               681


<210> SEQ ID NO 70
<211> LENGTH: 227
<212> TYPE: PRT
<213> ORGANISM: Artificial Sequence
<220> FEATURE:
<223> OTHER INFORMATION: Fcab FS22-053-013 without LALA mutation

<400> SEQUENCE: 70

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
```

```
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Asn Pro Pro Tyr Leu Phe Ser Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Gly Tyr Glu Arg Trp Leu Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225
```

<210> SEQ ID NO 71
<211> LENGTH: 681
<212> TYPE: DNA
<213> ORGANISM: Artificial Sequence
<220> FEATURE:
<223> OTHER INFORMATION: Fcab FS22-053-013 without LALA mutation

<400> SEQUENCE: 71

```
acttgcccgc cttgcccagc cccggaactg ctgggtggtc cttcggtgtt cctcttcccg     60

cccaagccga aggataccct gatgatctca cggacccccg aagtgacctg tgtggtggtg    120

gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240

gtgctcactg tgctgcacca agactggctg aacgggaagg agtacaagtg caaagtgtcc    300

aacaaggcgc tgcctgcccc aattgagaaa actatctcga aagccaaggg ccagcctcga    360

gaaccacagg tgtacaccct gcccccatcc cgggatgagc tgaacccgcc gtacctgttc    420

tctaaccagg tcagcctgac ctgcctggtc aaaggcttct atcccagcga catcgccgtg    480

gagtgggaga gcaatgggca gccggagaac aactacaaga ccacgcctcc cgtgctggac    540

tccgacggct ccttcttcct ctacagcaag ctcaccgtgg gttacgaaag gtggctggaa    600

gggaacgtct tctcatgctc cgtgatgcat gaggctctgc acaaccacta cacacagaag    660

agcctctccc tgtctccggg t                                              681
```

<210> SEQ ID NO 72
<211> LENGTH: 450
<212> TYPE: PRT
<213> ORGANISM: Artificial Sequence
<220> FEATURE:
<223> OTHER INFORMATION: heavy chain of FS22-053-013/HelD1.3 mock mAb2 with LALA mutation

<400> SEQUENCE: 72

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Val Leu Asp Ser Asp Gly Ser Phe Phe Leu Tyr Ser Lys Leu Thr Val
                405                 410                 415

Gly Tyr Glu Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 73
<211> LENGTH: 450
<212> TYPE: PRT
<213> ORGANISM: Artificial Sequence
<220> FEATURE:
<223> OTHER INFORMATION: heavy chain of FS22-053-013/HelD1.3 mock mAb2
      without LALA mutation

<400> SEQUENCE: 73

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Asp Glu Leu Asn Pro Pro Tyr Leu Phe Ser Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Gly Tyr Glu Arg Trp Leu Glu Gly Asn Val Phe Ser Cys Ser Val Met
420 425 430

His Glu Ala Leu His Asn His Tyr Thr Gln Lys Ser Leu Ser Leu Ser
435 440 445

Pro Gly
450

<210> SEQ ID NO 74
<211> LENGTH: 7
<212> TYPE: PRT
<213> ORGANISM: Artificial Sequence
<220> FEATURE:
<223> OTHER INFORMATION: Fcab FS22-053-014 CH3 domain structural loop sequence

<400> SEQUENCE: 74

Tyr His Trp Arg Trp Leu Asp
1 5

<210> SEQ ID NO 75
<211> LENGTH: 111
<212> TYPE: PRT
<213> ORGANISM: Artificial Sequence
<220> FEATURE:
<223> OTHER INFORMATION: Fcab FS22-053-014 CH3 domain

<400> SEQUENCE: 75

Gly Gln Pro Arg Glu Pro Gln Val Tyr Thr Leu Pro Pro Ser Arg Asp
1 5 10 15

Glu Leu Asn Pro Pro Tyr Leu Phe Ser Asn Gln Val Ser Leu Thr Cys
20 25 30

Leu Val Lys Gly Phe Tyr Pro Ser Asp Ile Ala Val Glu Trp Glu Ser
35 40 45

Asn Gly Gln Pro Glu Asn Asn Tyr Lys Thr Thr Pro Pro Val Leu Asp
50 55 60

Ser Asp Gly Ser Phe Phe Leu Tyr Ser Lys Leu Thr Val Tyr His Trp
65 70 75 80

Arg Trp Leu Asp Gly Asn Val Phe Ser Cys Ser Val Met His Glu Ala
85 90 95

Leu His Asn His Tyr Thr Gln Lys Ser Leu Ser Leu Ser Pro Gly
100 105 110

<210> SEQ ID NO 76
<211> LENGTH: 333

<212> TYPE: DNA
<213> ORGANISM: Artificial Sequence
<220> FEATURE:
<223> OTHER INFORMATION: Fcab FS22-053-014 CH3 domain

<400> SEQUENCE: 76
ggacagcctc gagagcctca agtgtacacc ctgcccccat cccgggatga gctgaacccg 60
ccgtacctgt tctctaacca ggtcagcctg acctgcctgg tcaaaggctt ctatcccagc 120
gacatcgccg tggagtggga gagcaatggg cagccggaga acaactacaa gaccacgcct 180
cccgtgctgg actccgacgg ctccttcttc ctctacagca agctcaccgt gtaccattgg 240
aggtggctgg atgggaacgt cttctcatgc tccgtgatgc atgaggcgct gcacaaccac 300
tacactcaga agagcttgtc cctgtcgccc gga 333

<210> SEQ ID NO 77
<211> LENGTH: 227
<212> TYPE: PRT
<213> ORGANISM: Artificial Sequence
<220> FEATURE:
<223> OTHER INFORMATION: Fcab FS22-053-014 with LALA mutation

<400> SEQUENCE: 77

Thr Cys Pro Pro Cys Pro Ala Pro Glu Ala Ala Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
85 90 95

Cys Lys Val Ser Asn Lys Ala Leu Pro Ala Pro Ile Glu Lys Thr Ile
100 105 110

Ser Lys Ala Lys Gly Gln Pro Arg Glu Pro Gln Val Tyr Thr Leu Pro
115 120 125

Pro Ser Arg Asp Glu Leu Asn Pro Pro Tyr Leu Phe Ser Asn Gln Val
130 135 140

Ser Leu Thr Cys Leu Val Lys Gly Phe Tyr Pro Ser Asp Ile Ala Val
145 150 155 160

Glu Trp Glu Ser Asn Gly Gln Pro Glu Asn Asn Tyr Lys Thr Thr Pro
165 170 175

Pro Val Leu Asp Ser Asp Gly Ser Phe Phe Leu Tyr Ser Lys Leu Thr
180 185 190

Val Tyr His Trp Arg Trp Leu Asp Gly Asn Val Phe Ser Cys Ser Val
195 200 205

Met His Glu Ala Leu His Asn His Tyr Thr Gln Lys Ser Leu Ser Leu
210 215 220

Ser Pro Gly
225

<210> SEQ ID NO 78
<211> LENGTH: 681
<212> TYPE: DNA
<213> ORGANISM: Artificial Sequence
<220> FEATURE:
<223> OTHER INFORMATION: Fcab FS22-053-014 with LALA mutation

<400> SEQUENCE: 78
acttgcccgc cttgcccagc cccggaagct gccggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg ccagcctcga 360
gaaccacagg tgtacaccct gcccccatcc cgggatgagc tgaacccgcc gtacctgttc 420
tctaaccagg tcagcctgac ctgcctggtc aaaggcttct atcccagcga catcgccgtg 480
gagtgggaga gcaatgggca gccggagaac aactacaaga ccacgcctcc cgtgctggac 540
tccgacggct ccttcttcct ctacagcaag ctcaccgtgt accattggag gtggctggat 600
gggaacgtct tctcatgctc cgtgatgcat gaggctctgc acaaccacta cacacagaag 660
agcctctccc tgtctccggg t 681

<210> SEQ ID NO 79
<211> LENGTH: 227
<212> TYPE: PRT
<213> ORGANISM: Artificial Sequence
<220> FEATURE:
<223> OTHER INFORMATION: Fcab FS22-053-014 without LALA mutation

<400> SEQUENCE: 79

Thr Cys Pro Pro Cys Pro Ala Pro Glu Leu Leu Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
85 90 95

Cys Lys Val Ser Asn Lys Ala Leu Pro Ala Pro Ile Glu Lys Thr Ile
100 105 110

Ser Lys Ala Lys Gly Gln Pro Arg Glu Pro Gln Val Tyr Thr Leu Pro
115 120 125

Pro Ser Arg Asp Glu Leu Asn Pro Pro Tyr Leu Phe Ser Asn Gln Val
130 135 140

Ser Leu Thr Cys Leu Val Lys Gly Phe Tyr Pro Ser Asp Ile Ala Val
145 150 155 160

Glu Trp Glu Ser Asn Gly Gln Pro Glu Asn Asn Tyr Lys Thr Thr Pro
165 170 175

Pro Val Leu Asp Ser Asp Gly Ser Phe Phe Leu Tyr Ser Lys Leu Thr
180 185 190

Val Tyr His Trp Arg Trp Leu Asp Gly Asn Val Phe Ser Cys Ser Val
195 200 205

Met His Glu Ala Leu His Asn His Tyr Thr Gln Lys Ser Leu Ser Leu 210 215 220

Ser Pro Gly
225

<210> SEQ ID NO 80
<211> LENGTH: 681
<212> TYPE: DNA
<213> ORGANISM: Artificial Sequence
<220> FEATURE:
<223> OTHER INFORMATION: Fcab FS22-053-014 without LALA mutation

<400> SEQUENCE: 80
acttgcccgc cttgcccagc cccggaactg ctgggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg ccagcctcga 360
gaaccacagg tgtacaccct gcccccatcc cgggatgagc tgaacccgcc gtacctgttc 420
tctaaccagg tcagcctgac ctgcctggtc aaaggcttct atcccagcga catcgccgtg 480
gagtgggaga gcaatgggca gccggagaac aactacaaga ccacgcctcc cgtgctggac 540
tccgacggct ccttcttcct ctacagcaag ctcaccgtgt accattggag gtggctggat 600
gggaacgtct tctcatgctc cgtgatgcat gaggctctgc acaaccacta cacacagaag 660
agcctctccc tgtctccggg t 681

<210> SEQ ID NO 81
<211> LENGTH: 450
<212> TYPE: PRT
<213> ORGANISM: Artificial Sequence
<220> FEATURE:
<223> OTHER INFORMATION: heavy chain of FS22-053-014/HelD1.3 mock mAb2
with LALA mutation

<400> SEQUENCE: 81

Gln Val Gln Leu Gln Glu Ser Gly Pro Gly Leu Val Arg Pro Ser Gln
1 5 10 15

Thr Leu Ser Leu Thr Cys Thr Val Ser Gly Ser Thr Phe Ser Gly Tyr
20 25 30

Gly Val Asn Trp Val Arg Gln Pro Pro Gly Arg Gly Leu Glu Trp Ile
35 40 45

Gly Met Ile Trp Gly Asp Gly Asn Thr Asp Tyr Asn Ser Ala Leu Lys
50 55 60

Ser Arg Val Thr Met Leu Val Asp Thr Ser Lys Asn Gln Phe Ser Leu
65 70 75 80

Arg Leu Ser Ser Val Thr Ala Ala Asp Thr Ala Val Tyr Tyr Cys Ala
85 90 95

Arg Glu Arg Asp Tyr Arg Leu Asp Tyr Trp Gly Gln Gly Ser Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

```
Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Tyr His Trp Arg Trp Leu Asp Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 82
<211> LENGTH: 450
<212> TYPE: PRT
<213> ORGANISM: Artificial Sequence
<220> FEATURE:
<223> OTHER INFORMATION: heavy chain of FS22-053-014/HelD1.3 mock mAb2
      without LALA mutation

<400> SEQUENCE: 82

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
```

```
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Tyr His Trp Arg Trp Leu Asp Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 83

<211> LENGTH: 7
<212> TYPE: PRT
<213> ORGANISM: Artificial Sequence
<220> FEATURE:
<223> OTHER INFORMATION: Fcab FS22-053-015 CH3 domain structural loop sequence

<400> SEQUENCE: 83

Asp His Trp Arg Trp Leu Gln
1               5

<210> SEQ ID NO 84
<211> LENGTH: 111
<212> TYPE: PRT
<213> ORGANISM: Artificial Sequence
<220> FEATURE:
<223> OTHER INFORMATION: Fcab FS22-053-015 CH3 domain

<400> SEQUENCE: 84

Gly Gln Pro Arg Glu Pro Gln Val Tyr Thr Leu Pro Pro Ser Arg Asp
1               5                   10                  15

Glu Leu Asn Pro Pro Tyr Leu Phe Ser Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Asp His Trp
65                  70                  75                  80

Arg Trp Leu Gln Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110

<210> SEQ ID NO 85

<400> SEQUENCE: 85

000

<210> SEQ ID NO 86
<211> LENGTH: 227
<212> TYPE: PRT
<213> ORGANISM: Artificial Sequence
<220> FEATURE:
<223> OTHER INFORMATION: Fcab FS22-053-015 with LALA mutation

<400> SEQUENCE: 86

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile

```
            100                 105                 110

Ser Lys Ala Lys Gly Gln Pro Arg Glu Pro Gln Val Tyr Thr Leu Pro
        115                 120                 125

Pro Ser Arg Asp Glu Leu Asn Pro Pro Tyr Leu Phe Ser Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp His Trp Arg Trp Leu Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225


<210> SEQ ID NO 87
<211> LENGTH: 681
<212> TYPE: DNA
<213> ORGANISM: Artificial Sequence
<220> FEATURE:
<223> OTHER INFORMATION: Fcab FS22-053-015 with LALA mutation

<400> SEQUENCE: 87

acttgcccgc cttgcccagc cccggaagct gccggtggtc cttcggtgtt cctcttcccg      60

cccaagccga aggataccct gatgatctca cggacccccg aagtgacctg tgtggtggtg     120

gacgtgtccc acgaggaccc ggaagtgaaa ttcaattggt acgtggatgg agtggaagtg     180

cacaacgcca agaccaagcc acgggaagaa cagtacaact ctacctaccg cgtggtgtcc     240

gtgctcactg tgctgcacca agactggctg aacgggaagg agtacaagtg caaagtgtcc     300

aacaaggcgc tgcctgcccc aattgagaaa actatctcga aagccaaggg ccagcctcga     360

gaaccacagg tgtacaccct gcccccatcc cgggatgagc tgaacccgcc gtacctgttc     420

tctaaccagg tcagcctgac ctgcctggtc aaaggcttct atcccagcga catcgccgtg     480

gagtgggaga gcaatgggca gccggagaac aactacaaga ccacgcctcc cgtgttggac     540

tccgacggct ccttcttcct ctacagcaag ctcaccgtgg atcattggag gtggctgcag     600

gggaacgtct tctcatgctc cgtgatgcat gaggctctgc acaaccacta cacacagaag     660

agcctctccc tgtctccggg t                                               681


<210> SEQ ID NO 88
<211> LENGTH: 227
<212> TYPE: PRT
<213> ORGANISM: Artificial Sequence
<220> FEATURE:
<223> OTHER INFORMATION: Fcab FS22-053-015 without LALA mutation

<400> SEQUENCE: 88

Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45
```

-continued

```
Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Asn Pro Pro Tyr Leu Phe Ser Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp His Trp Arg Trp Leu Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225
```

<210> SEQ ID NO 89
<211> LENGTH: 681
<212> TYPE: DNA
<213> ORGANISM: Artificial Sequence
<220> FEATURE:
<223> OTHER INFORMATION: Fcab FS22-053-015 without LALA mutation

<400> SEQUENCE: 89

```
acttgcccgc cttgcccagc cccggaactg ctgggtggtc cttcggtgtt cctcttcccg      60

cccaagccga aggataccct gatgatctca cggacccccg aagtgacctg tgtggtggtg     120

gacgtgtccc acgaggaccc ggaagtgaaa ttcaattggt acgtggatgg agtggaagtg     180

cacaacgcca agaccaagcc acgggaagaa cagtacaact ctacctaccg cgtggtgtcc     240

gtgctcactg tgctgcacca agactggctg aacgggaagg agtacaagtg caaagtgtcc     300

aacaaggcgc tgcctgcccc aattgagaaa actatctcga aagccaaggg ccagcctcga     360

gaaccacagg tgtacaccct gcccccatcc cgggatgagc tgaacccgcc gtacctgttc     420

tctaaccagg tcagcctgac ctgcctggtc aaaggcttct atcccagcga catcgccgtg     480

gagtgggaga gcaatgggca gccggagaac aactacaaga ccacgcctcc cgtgttggac     540

tccgacggct ccttcttcct ctacagcaag ctcaccgtgg atcattggag gtggctgcag     600

gggaacgtct tctcatgctc cgtgatgcat gaggctctgc acaaccacta cacacagaag     660

agcctctccc tgtctccggg t                                               681
```

<210> SEQ ID NO 90
<211> LENGTH: 450
<212> TYPE: PRT
<213> ORGANISM: Artificial Sequence
<220> FEATURE:
<223> OTHER INFORMATION: heavy chain of FS22-053-015/HelD1.3 mock mAb2
      with LALA mutation

<400> SEQUENCE: 90

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415
```

Asp His Trp Arg Trp Leu Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly
450

<210> SEQ ID NO 91
<211> LENGTH: 450
<212> TYPE: PRT
<213> ORGANISM: Artificial Sequence
<220> FEATURE:
<223> OTHER INFORMATION: heavy chain of FS22-053-015/HelD1.3 mock mAb2
without LALA mutation

<400> SEQUENCE: 91

Gln Val Gln Leu Gln Glu Ser Gly Pro Gly Leu Val Arg Pro Ser Gln
1 5 10 15

Thr Leu Ser Leu Thr Cys Thr Val Ser Gly Ser Thr Phe Ser Gly Tyr
20 25 30

Gly Val Asn Trp Val Arg Gln Pro Pro Gly Arg Gly Leu Glu Trp Ile
35 40 45

Gly Met Ile Trp Gly Asp Gly Asn Thr Asp Tyr Asn Ser Ala Leu Lys
50 55 60

Ser Arg Val Thr Met Leu Val Asp Thr Ser Lys Asn Gln Phe Ser Leu
65 70 75 80

Arg Leu Ser Ser Val Thr Ala Ala Asp Thr Ala Val Tyr Tyr Cys Ala
85 90 95

Arg Glu Arg Asp Tyr Arg Leu Asp Tyr Trp Gly Gln Gly Ser Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys 305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Asp Glu Leu Asn Pro Pro Tyr Leu Phe Ser Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Asp His Trp Arg Trp Leu Gln Gly Asn Val Phe Ser Cys Ser Val Met
420 425 430

His Glu Ala Leu His Asn His Tyr Thr Gln Lys Ser Leu Ser Leu Ser
435 440 445

Pro Gly
450

<210> SEQ ID NO 92
<211> LENGTH: 7
<212> TYPE: PRT
<213> ORGANISM: Artificial Sequence
<220> FEATURE:
<223> OTHER INFORMATION: Fcab FS22-053-016 CH3 domain structural loop sequence

<400> SEQUENCE: 92

Asp Tyr Ile Arg Trp Leu Asn
1 5

<210> SEQ ID NO 93
<211> LENGTH: 111
<212> TYPE: PRT
<213> ORGANISM: Artificial Sequence
<220> FEATURE:
<223> OTHER INFORMATION: Fcab FS22-053-016 CH3 domain

<400> SEQUENCE: 93

Gly Gln Pro Arg Glu Pro Gln Val Tyr Thr Leu Pro Pro Ser Arg Asp
1 5 10 15

Glu Leu Asn Pro Pro Tyr Leu Phe Ser Asn Gln Val Ser Leu Thr Cys
20 25 30

Leu Val Lys Gly Phe Tyr Pro Ser Asp Ile Ala Val Glu Trp Glu Ser
35 40 45

Asn Gly Gln Pro Glu Asn Asn Tyr Lys Thr Thr Pro Pro Val Leu Asp
50 55 60

Ser Asp Gly Ser Phe Phe Leu Tyr Ser Lys Leu Thr Val Asp Tyr Ile
65 70 75 80

Arg Trp Leu Asn Gly Asn Val Phe Ser Cys Ser Val Met His Glu Ala
85 90 95

Leu His Asn His Tyr Thr Gln Lys Ser Leu Ser Leu Ser Pro Gly
100 105 110

<210> SEQ ID NO 94
<211> LENGTH: 333
<212> TYPE: DNA
<213> ORGANISM: Artificial Sequence
<220> FEATURE:
<223> OTHER INFORMATION: Fcab FS22-053-016 CH3 domain

<400> SEQUENCE: 94
ggccagcctc gagaaccaca ggtgtacacc ctgcccccat cccgggatga gctgaacccg 60
ccgtacctgt tctctaacca ggtcagcctg acctgcctgg tcaaaggctt ctatcccagc 120
gacatcgccg tggagtggga gagcaatggg cagccggaga acaactacaa gaccacgcct 180
cccgtgctgg actccgacgg ctccttcttc ctctacagca agctcaccgt ggattacatc 240
aggtggctga acgggaacgt cttctcatgc tccgtgatgc atgaggctct gcacaaccac 300
tacacacaga agagcctctc cctgtctccg ggt 333

<210> SEQ ID NO 95
<211> LENGTH: 227
<212> TYPE: PRT
<213> ORGANISM: Artificial Sequence
<220> FEATURE:
<223> OTHER INFORMATION: Fcab FS22-053-016 with LALA mutation

<400> SEQUENCE: 95

Thr Cys Pro Pro Cys Pro Ala Pro Glu Ala Ala Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
85 90 95

Cys Lys Val Ser Asn Lys Ala Leu Pro Ala Pro Ile Glu Lys Thr Ile
100 105 110

Ser Lys Ala Lys Gly Gln Pro Arg Glu Pro Gln Val Tyr Thr Leu Pro
115 120 125

Pro Ser Arg Asp Glu Leu Asn Pro Pro Tyr Leu Phe Ser Asn Gln Val
130 135 140

Ser Leu Thr Cys Leu Val Lys Gly Phe Tyr Pro Ser Asp Ile Ala Val
145 150 155 160

Glu Trp Glu Ser Asn Gly Gln Pro Glu Asn Asn Tyr Lys Thr Thr Pro
165 170 175

Pro Val Leu Asp Ser Asp Gly Ser Phe Phe Leu Tyr Ser Lys Leu Thr
180 185 190

Val Asp Tyr Ile Arg Trp Leu Asn Gly Asn Val Phe Ser Cys Ser Val
195 200 205

Met His Glu Ala Leu His Asn His Tyr Thr Gln Lys Ser Leu Ser Leu
210 215 220

Ser Pro Gly
225

<210> SEQ ID NO 96
<211> LENGTH: 681
<212> TYPE: DNA
<213> ORGANISM: Artificial Sequence
<220> FEATURE:
<223> OTHER INFORMATION: Fcab FS22-053-016 with LALA mutation

<400> SEQUENCE: 96

```
acttgcccgc cttgcccagc cccggaagct gccggtggtc cttcggtgtt cctcttcccg      60
cccaagccga aggataccct gatgatctca cggacccccg aagtgacctg tgtggtggtg     120
gacgtgtccc acgaggaccc ggaagtgaaa ttcaattggt acgtggatgg agtggaagtg     180
cacaacgcca agaccaagcc acgggaagaa cagtacaact ctacctaccg cgtggtgtcc     240
gtgctcactg tgctgcacca agactggctg aacgggaagg agtacaagtg caaagtgtcc     300
aacaaggcgc tgcctgcccc aattgagaaa actatctcga aagccaaggg ccagcctcga     360
gaaccacagg tgtacaccct gcccccatcc cgggatgagc tgaacccgcc gtacctgttc     420
tctaaccagg tcagcctgac ctgcctggtc aaaggcttct atcccagcga catcgccgtg     480
gagtgggaga gcaatgggca gccggagaac aactacaaga ccacgcctcc cgtgctggac     540
tccgacggct ccttcttcct ctacagcaag ctcaccgtgg attacatcag gtggctgaac     600
gggaacgtct tctcatgctc cgtgatgcat gaggctctgc acaaccacta cacacagaag     660
agcctctccc tgtctccggg t                                               681
```

<210> SEQ ID NO 97
<211> LENGTH: 227
<212> TYPE: PRT
<213> ORGANISM: Artificial Sequence
<220> FEATURE:
<223> OTHER INFORMATION: Fcab FS22-053-016 without LALA mutation

<400> SEQUENCE: 97

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Asn Pro Pro Tyr Leu Phe Ser Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Tyr Ile Arg Trp Leu Asn Gly Asn Val Phe Ser Cys Ser Val
        195                 200                 205

Met His Glu Ala Leu His Asn His Tyr Thr Gln Lys Ser Leu Ser Leu
    210                 215                 220
```

Ser Pro Gly
225

<210> SEQ ID NO 98
<211> LENGTH: 681
<212> TYPE: DNA
<213> ORGANISM: Artificial Sequence
<220> FEATURE:
<223> OTHER INFORMATION: Fcab FS22-053-016 without LALA mutation

<400> SEQUENCE: 98
acttgcccgc cttgcccagc cccggaactg ctgggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg ccagcctcga 360
gaaccacagg tgtacaccct gcccccatcc cgggatgagc tgaacccgcc gtacctgttc 420
tctaaccagg tcagcctgac ctgcctggtc aaaggcttct atcccagcga catcgccgtg 480
gagtgggaga gcaatgggca gccggagaac aactacaaga ccacgcctcc cgtgctggac 540
tccgacggct ccttcttcct ctacagcaag ctcaccgtgg attacatcag gtggctgaac 600
gggaacgtct tctcatgctc cgtgatgcat gaggctctgc acaaccacta cacacagaag 660
agcctctccc tgtctccggg t 681

<210> SEQ ID NO 99
<211> LENGTH: 450
<212> TYPE: PRT
<213> ORGANISM: Artificial Sequence
<220> FEATURE:
<223> OTHER INFORMATION: heavy chain of FS22-053-016/HelD1.3 mock mAb2
with LALA mutation

<400> SEQUENCE: 99

Gln Val Gln Leu Gln Glu Ser Gly Pro Gly Leu Val Arg Pro Ser Gln
1 5 10 15

Thr Leu Ser Leu Thr Cys Thr Val Ser Gly Ser Thr Phe Ser Gly Tyr
20 25 30

Gly Val Asn Trp Val Arg Gln Pro Pro Gly Arg Gly Leu Glu Trp Ile
35 40 45

Gly Met Ile Trp Gly Asp Gly Asn Thr Asp Tyr Asn Ser Ala Leu Lys
50 55 60

Ser Arg Val Thr Met Leu Val Asp Thr Ser Lys Asn Gln Phe Ser Leu
65 70 75 80

Arg Leu Ser Ser Val Thr Ala Ala Asp Thr Ala Val Tyr Tyr Cys Ala
85 90 95

Arg Glu Arg Asp Tyr Arg Leu Asp Tyr Trp Gly Gln Gly Ser Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser

```
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Tyr Ile Arg Trp Leu Asn Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 100
<211> LENGTH: 450
<212> TYPE: PRT
<213> ORGANISM: Artificial Sequence
<220> FEATURE:
<223> OTHER INFORMATION: heavy chain of FS22-053-016/HelD1.3 mock mAb2
      without LALA mutation

<400> SEQUENCE: 100

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60
```

```
Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Tyr Ile Arg Trp Leu Asn Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 101
<211> LENGTH: 7
<212> TYPE: PRT

```
<213> ORGANISM: Artificial Sequence
<220> FEATURE:
<223> OTHER INFORMATION: Fcab FS22-053-017 CH3 domain structural loop
      sequence

<400> SEQUENCE: 101

Tyr His Trp Arg Trp Leu Glu
1               5


<210> SEQ ID NO 102
<211> LENGTH: 111
<212> TYPE: PRT
<213> ORGANISM: Artificial Sequence
<220> FEATURE:
<223> OTHER INFORMATION: Fcab FS22-053-017 CH3 domain

<400> SEQUENCE: 102

Gly Gln Pro Arg Glu Pro Gln Val Tyr Thr Leu Pro Pro Ser Arg Asp
1               5                   10                  15

Glu Leu Asn Pro Pro Tyr Leu Phe Ser Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Tyr His Trp
65                  70                  75                  80

Arg Trp Leu Glu Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110


<210> SEQ ID NO 103
<211> LENGTH: 333
<212> TYPE: DNA
<213> ORGANISM: Artificial Sequence
<220> FEATURE:
<223> OTHER INFORMATION: Fcab FS22-053-017 CH3 domain

<400> SEQUENCE: 103

ggacagcctc gagaaccaca ggtgtacact ctgcccccctt cacgcgacga actcaatccg      60

ccctacctgt tctccaacca agtctccctg acctgtcttg tgaagggttt ctacccatcc     120

gatatcgccg tggagtggga gagcaacgga cagccggaga acaactataa gactaccccg     180

cctgtgctgg actcggacgg cagcttcttc ttgtactcca aactgaccgt gtaccactgg     240

cggtggctgg aagggaacgt gtttagctgc tccgtcatgc atgaagccct gcacaaccac     300

tacacccaga agtccctctc gctctctccg ggt                                  333


<210> SEQ ID NO 104
<211> LENGTH: 227
<212> TYPE: PRT
<213> ORGANISM: Artificial Sequence
<220> FEATURE:
<223> OTHER INFORMATION: Fcab FS22-053-017 with LALA mutation

<400> SEQUENCE: 104

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30
```

-continued

```
Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Asn Pro Pro Tyr Leu Phe Ser Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Tyr His Trp Arg Trp Leu Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225
```

<210> SEQ ID NO 105
<211> LENGTH: 681
<212> TYPE: DNA
<213> ORGANISM: Artificial Sequence
<220> FEATURE:
<223> OTHER INFORMATION: Fcab FS22-053-017 with LALA mutation

<400> SEQUENCE: 105

```
acttgcccgc cttgcccagc cccggaagct gccggtggtc cttcggtgtt cctcttcccg      60

cccaagccga aggataccct gatgatctca cggacccccg aagtgacctg tgtggtggtg     120

gacgtgtccc acgaggaccc ggaagtgaaa ttcaattggt acgtggatgg agtggaagtg     180

cacaacgcca agaccaagcc acgggaagaa cagtacaact ctacctaccg cgtggtgtcc     240

gtgctcactg tgctgcacca agactggctg aacgggaagg agtacaagtg caaagtgtcc     300

aacaaggcgc tgcctgcccc aattgagaaa actatctcga aagccaaggg acagcctcga     360

gaaccacagg tgtacactct gccccccttca cgcgacgaac tcaatccgcc ctacctgttc     420

tccaaccaag tctccctgac ctgtcttgtg aagggtttct acccatccga tatcgccgtg     480

gagtgggaga gcaacggaca gccggagaac aactataaga ctaccccgcc tgtgctggac     540

tcggacggca gcttcttctt gtactccaaa ctgaccgtgt accactggcg gtggctggaa     600

gggaacgtgt ttagctgctc cgtcatgcat gaagccctgc acaaccacta cacccagaag     660

tccctctcgc tctctccggg t                                               681
```

<210> SEQ ID NO 106
<211> LENGTH: 227
<212> TYPE: PRT
<213> ORGANISM: Artificial Sequence
<220> FEATURE:

<223> OTHER INFORMATION: Fcab FS22-053-017 without LALA mutation

<400> SEQUENCE: 106

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Asn Pro Pro Tyr Leu Phe Ser Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Tyr His Trp Arg Trp Leu Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225
```

<210> SEQ ID NO 107
<211> LENGTH: 681
<212> TYPE: DNA
<213> ORGANISM: Artificial Sequence
<220> FEATURE:
<223> OTHER INFORMATION: Fcab FS22-053-017 without LALA mutation

<400> SEQUENCE: 107

```
acttgcccgc cttgcccagc cccggaactg ctgggtggtc cttcggtgtt cctcttcccg     60

cccaagccga aggataccct gatgatctca cggacccccg aagtgacctg tgtggtggtg    120

gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240

gtgctcactg tgctgcacca agactggctg aacgggaagg agtacaagtg caaagtgtcc    300

aacaaggcgc tgcctgcccc aattgagaaa actatctcga aagccaaggg acagcctcga    360

gaaccacagg tgtacactct gccccccttca cgcgacgaac tcaatccgcc ctacctgttc    420

tccaaccaag tctccctgac ctgtcttgtg aagggtttct acccatccga tatcgccgtg    480

gagtgggaga gcaacggaca gccggagaac aactataaga ctaccccgcc tgtgctggac    540

tcggacggca gcttcttctt gtactccaaa ctgaccgtgt accactggcg gtggctggaa    600
```

```
gggaacgtgt ttagctgctc cgtcatgcat gaagccctgc acaaccacta cacccagaag    660

tccctctcgc tctctccggg t                                               681


<210> SEQ ID NO 108
<211> LENGTH: 450
<212> TYPE: PRT
<213> ORGANISM: Artificial Sequence
<220> FEATURE:
<223> OTHER INFORMATION: heavy chain of FS22-053-017/HelD1.3 mock mAb2
      with LALA mutation

<400> SEQUENCE: 108

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
```

```
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Tyr His Trp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 109
<211> LENGTH: 450
<212> TYPE: PRT
<213> ORGANISM: Artificial Sequence
<220> FEATURE:
<223> OTHER INFORMATION: heavy chain of FS22-053-017/HelD1.3 mock mAb2
      without LALA mutation

<400> SEQUENCE: 109

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240
```

```
Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Pro Pro Tyr Leu Phe Ser Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Tyr His Trp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 110
<211> LENGTH: 7
<212> TYPE: PRT
<213> ORGANISM: Artificial Sequence
<220> FEATURE:
<223> OTHER INFORMATION: Fcab FS22-172 CH3 domain structural loop
      sequence

<400> SEQUENCE: 110

Arg Lys Tyr Tyr Pro Pro Tyr
1               5


<210> SEQ ID NO 111
<211> LENGTH: 7
<212> TYPE: PRT
<213> ORGANISM: Artificial Sequence
<220> FEATURE:
<223> OTHER INFORMATION: Fcab FS22-172 CH3 domain structural loop
      sequence

<400> SEQUENCE: 111

Gly Ala Asp Arg Trp Leu Glu
1               5


<210> SEQ ID NO 112
<211> LENGTH: 111
<212> TYPE: PRT
<213> ORGANISM: Artificial Sequence
<220> FEATURE:
<223> OTHER INFORMATION: Fcab FS22-172 CH3 domain

<400> SEQUENCE: 112
```

Gly Gln Pro Arg Glu Pro Gln Val Tyr Thr Leu Pro Pro Ser Arg Asp
1 5 10 15

Glu Leu Arg Lys Tyr Tyr Pro Pro Tyr Asn Gln Val Ser Leu Thr Cys
20 25 30

Leu Val Lys Gly Phe Tyr Pro Ser Asp Ile Ala Val Glu Trp Glu Ser
35 40 45

Asn Gly Gln Pro Glu Asn Asn Tyr Lys Thr Thr Pro Pro Val Leu Asp
50 55 60

Ser Asp Gly Ser Phe Phe Leu Tyr Ser Lys Leu Thr Val Gly Ala Asp
65 70 75 80

Arg Trp Leu Glu Gly Asn Val Phe Ser Cys Ser Val Met His Glu Ala
85 90 95

Leu His Asn His Tyr Thr Gln Lys Ser Leu Ser Leu Ser Pro Gly
100 105 110

<210> SEQ ID NO 113
<211> LENGTH: 333
<212> TYPE: DNA
<213> ORGANISM: Artificial Sequence
<220> FEATURE:
<223> OTHER INFORMATION: Fcab FS22-172 CH3 domain

<400> SEQUENCE: 113
ggccagcctc gagaaccaca ggtgtacacc ctgcccccat cccgggatga gctgcgtaaa 60
tactacccgc cgtacaacca ggtcagcctg acctgcctgg tcaaaggctt ctatcccagc 120
gacatcgccg tggagtggga gagcaatggg cagccggaga acaactacaa gaccacgcct 180
cccgtgctgg actccgacgg ctccttcttc ctctacagca agctcaccgt gggcgcagat 240
aggtggctgg aagggaacgt cttctcatgc tccgtgatgc atgaggctct gcacaaccac 300
tacacacaga agagcctctc cctgtctccg ggt 333

<210> SEQ ID NO 114
<211> LENGTH: 227
<212> TYPE: PRT
<213> ORGANISM: Artificial Sequence
<220> FEATURE:
<223> OTHER INFORMATION: Fcab FS22-172 with LALA mutation

<400> SEQUENCE: 114

Thr Cys Pro Pro Cys Pro Ala Pro Glu Ala Ala Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
85 90 95

Cys Lys Val Ser Asn Lys Ala Leu Pro Ala Pro Ile Glu Lys Thr Ile
100 105 110

Ser Lys Ala Lys Gly Gln Pro Arg Glu Pro Gln Val Tyr Thr Leu Pro
115 120 125

Pro Ser Arg Asp Glu Leu Arg Lys Tyr Tyr Pro Pro Tyr Asn Gln Val 130 135 140

Ser Leu Thr Cys Leu Val Lys Gly Phe Tyr Pro Ser Asp Ile Ala Val
145 150 155 160

Glu Trp Glu Ser Asn Gly Gln Pro Glu Asn Asn Tyr Lys Thr Thr Pro
165 170 175

Pro Val Leu Asp Ser Asp Gly Ser Phe Phe Leu Tyr Ser Lys Leu Thr
180 185 190

Val Gly Ala Asp Arg Trp Leu Glu Gly Asn Val Phe Ser Cys Ser Val
195 200 205

Met His Glu Ala Leu His Asn His Tyr Thr Gln Lys Ser Leu Ser Leu
210 215 220

Ser Pro Gly
225

<210> SEQ ID NO 115
<211> LENGTH: 681
<212> TYPE: DNA
<213> ORGANISM: Artificial Sequence
<220> FEATURE:
<223> OTHER INFORMATION: Fcab FS22-172 with LALA mutation

<400> SEQUENCE: 115
acttgcccgc cttgcccagc cccggaagct gccggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg ccagcctcga 360
gaaccacagg tgtacaccct gcccccatcc cgggatgagc tgcgtaaata ctacccgccg 420
tacaaccagg tcagcctgac ctgcctggtc aaaggcttct atcccagcga catcgccgtg 480
gagtgggaga gcaatgggca gccggagaac aactacaaga ccacgcctcc cgtgctggac 540
tccgacggct ccttcttcct ctacagcaag ctcaccgtgg gcgcagatag gtggctggaa 600
gggaacgtct tctcatgctc cgtgatgcat gaggctctgc acaaccacta cacacagaag 660
agcctctccc tgtctccggg t 681

<210> SEQ ID NO 116
<211> LENGTH: 227
<212> TYPE: PRT
<213> ORGANISM: Artificial Sequence
<220> FEATURE:
<223> OTHER INFORMATION: Fcab FS22-172 without LALA mutation

<400> SEQUENCE: 116

Thr Cys Pro Pro Cys Pro Ala Pro Glu Leu Leu Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Arg Lys Tyr Tyr Pro Pro Tyr Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Gly Ala Asp Arg Trp Leu Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225

<210> SEQ ID NO 117
<211> LENGTH: 681
<212> TYPE: DNA
<213> ORGANISM: Artificial Sequence
<220> FEATURE:
<223> OTHER INFORMATION: Fcab FS22-172 without LALA mutation

<400> SEQUENCE: 117
acttgcccgc cttgcccagc cccggaactg ctgggtggtc cttcggtgtt cctcttcccg     60
cccaagccga aggataccct gatgatctca cggacccccg aagtgacctg tgtggtggtg    120
gacgtgtccc acgaggaccc ggaagtgaaa ttcaattggt acgtggatgg agtggaagtg    180
cacaacgcca agaccaagcc acgggaagaa cagtacaact ctacctaccg cgtggtgtcc    240
gtgctcactg tgctgcacca agactggctg aacgggaagg agtacaagtg caaagtgtcc    300
aacaaggcgc tgcctgcccc aattgagaaa actatctcga aagccaaggg ccagcctcga    360
gaaccacagg tgtacaccct gcccccatcc cgggatgagc tgcgtaaata ctacccgccg    420
tacaaccagg tcagcctgac ctgcctggtc aaaggcttct atcccagcga catcgccgtg    480
gagtgggaga gcaatgggca gccggagaac aactacaaga ccacgcctcc cgtgctggac    540
tccgacggct ccttcttcct ctacagcaag ctcaccgtgg gcgcagatag gtggctggaa    600
gggaacgtct tctcatgctc cgtgatgcat gaggctctgc acaaccacta cacacagaag    660
agcctctccc tgtctccggg t                                              681

<210> SEQ ID NO 118
<211> LENGTH: 450
<212> TYPE: PRT
<213> ORGANISM: Artificial Sequence
<220> FEATURE:
<223> OTHER INFORMATION: heavy chain of FS22-172/HelD1.3 mock mAb2 with
      LALA mutation

<400> SEQUENCE: 118

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr

-continued

```
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Arg Lys Tyr Tyr Pro Pro Tyr Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445
```

Pro Gly
    450

<210> SEQ ID NO 119
<211> LENGTH: 450
<212> TYPE: PRT
<213> ORGANISM: Artificial Sequence
<220> FEATURE:
<223> OTHER INFORMATION: heavy chain of FS22-172/HelD1.3 mock mAb2
      without LALA mutation

<400> SEQUENCE: 119

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro

```
            340                 345                 350

Ser Arg Asp Glu Leu Arg Lys Tyr Tyr Pro Pro Tyr Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 120
<211> LENGTH: 7
<212> TYPE: PRT
<213> ORGANISM: Artificial Sequence
<220> FEATURE:
<223> OTHER INFORMATION: Fcab FS22-172-001 CH3 domain structural loop
      sequence

<400> SEQUENCE: 120

Pro Phe Val Met Pro Pro Tyr
1               5


<210> SEQ ID NO 121
<211> LENGTH: 111
<212> TYPE: PRT
<213> ORGANISM: Artificial Sequence
<220> FEATURE:
<223> OTHER INFORMATION: Fcab FS22-172-001 CH3 domain

<400> SEQUENCE: 121

Gly Gln Pro Arg Glu Pro Gln Val Tyr Thr Leu Pro Pro Ser Arg Asp
1               5                   10                  15

Glu Leu Pro Phe Val Met Pro Pro Tyr Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Gly Ala Asp
65                  70                  75                  80

Arg Trp Leu Glu Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110


<210> SEQ ID NO 122
<211> LENGTH: 333
<212> TYPE: DNA
<213> ORGANISM: Artificial Sequence
<220> FEATURE:
<223> OTHER INFORMATION: Fcab FS22-172-001 CH3 domain

<400> SEQUENCE: 122

ggccagcctc gagaaccaca ggtgtacacc ctgcccccat cccgggatga gctgccattc     60
```

```
gttatgccac catacaacca ggtcagcctg acctgcctgg tcaaaggctt ctatcccagc    120

gacatcgccg tggagtggga gagcaatggg cagccggaga acaactacaa gaccacgcct    180

cccgtgctgg actccgacgg ctccttcttc ctctacagca agctcaccgt gggcgcagat    240

aggtggctgg aagggaacgt cttctcatgc tccgtgatgc atgaggctct gcacaaccac    300

tacacacaga agagcctctc cctgtctccg ggt                                 333


<210> SEQ ID NO 123
<211> LENGTH: 227
<212> TYPE: PRT
<213> ORGANISM: Artificial Sequence
<220> FEATURE:
<223> OTHER INFORMATION: Fcab FS22-172-001 with LALA mutation

<400> SEQUENCE: 123

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Pro Phe Val Met Pro Pro Tyr Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Gly Ala Asp Arg Trp Leu Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225


<210> SEQ ID NO 124
<211> LENGTH: 681
<212> TYPE: DNA
<213> ORGANISM: Artificial Sequence
<220> FEATURE:
<223> OTHER INFORMATION: Fcab FS22-172-001 with LALA mutation

<400> SEQUENCE: 124

acttgcccgc cttgcccagc cccggaagct gccggtggtc cttcggtgtt cctcttcccg     60

cccaagccga aggataccct gatgatctca cggacccccg aagtgacctg tgtggtggtg    120
```

-continued

```
gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240

gtgctcactg tgctgcacca agactggctg aacgggaagg agtacaagtg caaagtgtcc    300

aacaaggcgc tgcctgcccc aattgagaaa actatctcga aagccaaggg ccagcctcga    360

gaaccacagg tgtacaccct gcccccatcc cgggatgagc tgccattcgt tatgccacca    420

tacaaccagg tcagcctgac ctgcctggtc aaaggcttct atcccagcga catcgccgtg    480

gagtgggaga gcaatgggca gccggagaac aactacaaga ccacgcctcc cgtgctggac    540

tccgacggct ccttcttcct ctacagcaag ctcaccgtgg gcgcagatag gtggctggaa    600

gggaacgtct tctcatgctc cgtgatgcat gaggctctgc acaaccacta cacacagaag    660

agcctctccc tgtctccggg t                                              681
```

<210> SEQ ID NO 125
<211> LENGTH: 227
<212> TYPE: PRT
<213> ORGANISM: Artificial Sequence
<220> FEATURE:
<223> OTHER INFORMATION: Fcab FS22-172-001 without LALA mutation

<400> SEQUENCE: 125

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Pro Phe Val Met Pro Pro Tyr Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Gly Ala Asp Arg Trp Leu Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225
```

<210> SEQ ID NO 126
<211> LENGTH: 681

-continued

<212> TYPE: DNA
<213> ORGANISM: Artificial Sequence
<220> FEATURE:
<223> OTHER INFORMATION: Fcab FS22-172-001 without LALA mutation

<400> SEQUENCE: 126

```
acttgcccgc cttgcccagc cccggaactg ctgggtggtc cttcggtgtt cctcttcccg      60

cccaagccga aggataccct gatgatctca cggacccccg aagtgacctg tgtggtggtg     120

gacgtgtccc acgaggaccc ggaagtgaaa ttcaattggt acgtggatgg agtggaagtg     180

cacaacgcca agaccaagcc acgggaagaa cagtacaact ctacctaccg cgtggtgtcc     240

gtgctcactg tgctgcacca agactggctg aacgggaagg agtacaagtg caaagtgtcc     300

aacaaggcgc tgcctgcccc aattgagaaa actatctcga aagccaaggg ccagcctcga     360

gaaccacagg tgtacaccct gcccccatcc cgggatgagc tgccattcgt tatgccacca     420

tacaaccagg tcagcctgac ctgcctggtc aaaggcttct atcccagcga catcgccgtg     480

gagtgggaga gcaatgggca gccggagaac aactacaaga ccacgcctcc cgtgctggac     540

tccgacggct ccttcttcct ctacagcaag ctcaccgtgg gcgcagatag gtggctggaa     600

gggaacgtct tctcatgctc cgtgatgcat gaggctctgc acaaccacta cacacagaag     660

agcctctccc tgtctccggg t                                               681
```

<210> SEQ ID NO 127
<211> LENGTH: 450
<212> TYPE: PRT
<213> ORGANISM: Artificial Sequence
<220> FEATURE:
<223> OTHER INFORMATION: heavy chain of FS22-172-001/HelD1.3 mock mAb2
      with LALA mutation

<400> SEQUENCE: 127

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
```

```
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Pro Phe Val Met Pro Pro Tyr Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 128
<211> LENGTH: 450
<212> TYPE: PRT
<213> ORGANISM: Artificial Sequence
<220> FEATURE:
<223> OTHER INFORMATION: heavy chain of FS22-172-001/HelD1.3 mock mAb2
      without LALA mutation

<400> SEQUENCE: 128

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95
```

-continued

```
Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Pro Phe Val Met Pro Pro Tyr Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 129
<211> LENGTH: 7
<212> TYPE: PRT
<213> ORGANISM: Artificial Sequence
<220> FEATURE:
<223> OTHER INFORMATION: Fcab FS22-172-002 CH3 domain structural loop sequence

<400> SEQUENCE: 129

```
Pro Phe Gln Met Pro Pro Tyr
1               5


<210> SEQ ID NO 130
<211> LENGTH: 111
<212> TYPE: PRT
<213> ORGANISM: Artificial Sequence
<220> FEATURE:
<223> OTHER INFORMATION: Fcab FS22-172-002 CH3 domain

<400> SEQUENCE: 130

Gly Gln Pro Arg Glu Pro Gln Val Tyr Thr Leu Pro Pro Ser Arg Asp
1               5                   10                  15

Glu Leu Pro Phe Gln Met Pro Pro Tyr Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Gly Ala Asp
65                  70                  75                  80

Arg Trp Leu Glu Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110


<210> SEQ ID NO 131
<211> LENGTH: 333
<212> TYPE: DNA
<213> ORGANISM: Artificial Sequence
<220> FEATURE:
<223> OTHER INFORMATION: Fcab FS22-172-002 CH3 domain

<400> SEQUENCE: 131

ggccagcctc gagaaccaca ggtgtacacc ctgcccccat cccgggatga gctgccattc      60

cagatgccac catacaacca ggtcagcctg acctgcctgg tcaaaggctt ctatcccagc     120

gacatcgccg tggagtggga gagcaatggg cagccggaga acaactacaa gaccacgcct     180

cccgtgctgg actccgacgg ctccttcttc ctctacagca agctcaccgt gggcgcagat     240

aggtggctgg aagggaacgt cttctcatgc tccgtgatgc atgaggctct gcacaaccac     300

tacacacaga agagcctctc cctgtctccg ggt                                  333


<210> SEQ ID NO 132
<211> LENGTH: 227
<212> TYPE: PRT
<213> ORGANISM: Artificial Sequence
<220> FEATURE:
<223> OTHER INFORMATION: Fcab FS22-172-002 with LALA mutation

<400> SEQUENCE: 132

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60
```

-continued

```
Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Pro Phe Gln Met Pro Pro Tyr Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Gly Ala Asp Arg Trp Leu Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225
```

<210> SEQ ID NO 133
<211> LENGTH: 681
<212> TYPE: DNA
<213> ORGANISM: Artificial Sequence
<220> FEATURE:
<223> OTHER INFORMATION: Fcab FS22-172-002 with LALA mutation

<400> SEQUENCE: 133

```
acttgcccgc cttgcccagc cccggaagct gccggtggtc cttcggtgtt cctcttcccg     60

cccaagccga aggataccct gatgatctca cggacccccg aagtgacctg tgtggtggtg    120

gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240

gtgctcactg tgctgcacca agactggctg aacgggaagg agtacaagtg caaagtgtcc    300

aacaaggcgc tgcctgcccc aattgagaaa actatctcga aagccaaggg ccagcctcga    360

gaaccacagg tgtacaccct gcccccatcc cgggatgagc tgccattcca gatgccacca    420

tacaaccagg tcagcctgac ctgcctggtc aaaggcttct atcccagcga catcgccgtg    480

gagtgggaga gcaatgggca gccggagaac aactacaaga ccacgcctcc cgtgctggac    540

tccgacggct ccttcttcct ctacagcaag ctcaccgtgg gcgcagatag gtggctggaa    600

gggaacgtct tctcatgctc cgtgatgcat gaggctctgc acaaccacta cacacagaag    660

agcctctccc tgtctccggg t                                              681
```

<210> SEQ ID NO 134
<211> LENGTH: 227
<212> TYPE: PRT
<213> ORGANISM: Artificial Sequence
<220> FEATURE:
<223> OTHER INFORMATION: Fcab FS22-172-002 without LALA mutation

<400> SEQUENCE: 134

```
Thr Cys Pro Pro Cys Pro Ala Pro Glu Leu Leu Gly Gly Pro Ser Val
1               5                   10                  15
```

```
Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Pro Phe Gln Met Pro Pro Tyr Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Gly Ala Asp Arg Trp Leu Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225
```

<210> SEQ ID NO 135
<211> LENGTH: 681
<212> TYPE: DNA
<213> ORGANISM: Artificial Sequence
<220> FEATURE:
<223> OTHER INFORMATION: Fcab FS22-172-002 without LALA mutation

<400> SEQUENCE: 135

```
acttgcccgc cttgcccagc cccggaactg ctgggtggtc cttcggtgtt cctcttcccg     60

cccaagccga aggataccct gatgatctca cggacccccg aagtgacctg tgtggtggtg    120

gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240

gtgctcactg tgctgcacca agactggctg aacgggaagg agtacaagtg caaagtgtcc    300

aacaaggcgc tgcctgcccc aattgagaaa actatctcga aagccaaggg ccagcctcga    360

gaaccacagg tgtacaccct gcccccatcc cgggatgagc tgccattcca gatgccacca    420

tacaaccagg tcagcctgac ctgcctggtc aaaggcttct atcccagcga catcgccgtg    480

gagtgggaga gcaatgggca gccggagaac aactacaaga ccacgcctcc cgtgctggac    540

tccgacggct ccttcttcct ctacagcaag ctcaccgtgg gcgcagatag gtggctggaa    600

gggaacgtct tctcatgctc cgtgatgcat gaggctctgc acaaccacta cacacagaag    660

agcctctccc tgtctccggg t                                              681
```

<210> SEQ ID NO 136

<211> LENGTH: 450
<212> TYPE: PRT
<213> ORGANISM: Artificial Sequence
<220> FEATURE:
<223> OTHER INFORMATION: heavy chain of FS22-172-002/HelD1.3 mock mAb2 with LALA mutation

<400> SEQUENCE: 136

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Pro Phe Gln Met Pro Pro Tyr Asn Gln Val Ser
        355                 360                 365

Leu Thr Cys Leu Val Lys Gly Phe Tyr Pro Ser Asp Ile Ala Val Glu

```
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 137
<211> LENGTH: 450
<212> TYPE: PRT
<213> ORGANISM: Artificial Sequence
<220> FEATURE:
<223> OTHER INFORMATION: heavy chain of FS22-172-002/HelD1.3 mock mAb2
      without LALA mutation

<400> SEQUENCE: 137

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270
```

```
Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Pro Phe Gln Met Pro Pro Tyr Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 138
<211> LENGTH: 7
<212> TYPE: PRT
<213> ORGANISM: Artificial Sequence
<220> FEATURE:
<223> OTHER INFORMATION: Fcab FS22-172-003 CH3 domain structural loop
      sequence

<400> SEQUENCE: 138

Pro Tyr Ile Ile Pro Pro Tyr
1               5


<210> SEQ ID NO 139
<211> LENGTH: 111
<212> TYPE: PRT
<213> ORGANISM: Artificial Sequence
<220> FEATURE:
<223> OTHER INFORMATION: Fcab FS22-172-003 CH3 domain

<400> SEQUENCE: 139

Gly Gln Pro Arg Glu Pro Gln Val Tyr Thr Leu Pro Pro Ser Arg Asp
1               5                   10                  15

Glu Leu Pro Tyr Ile Ile Pro Pro Tyr Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Gly Ala Asp
65                  70                  75                  80

Arg Trp Leu Glu Gly Asn Val Phe Ser Cys Ser Val Met His Glu Ala
                85                  90                  95

Leu His Asn His Tyr Thr Gln Lys Ser Leu Ser Leu Ser Pro Gly
```

100 105 110

<210> SEQ ID NO 140
<211> LENGTH: 333
<212> TYPE: DNA
<213> ORGANISM: Artificial Sequence
<220> FEATURE:
<223> OTHER INFORMATION: Fcab FS22-172-003 CH3 domain

<400> SEQUENCE: 140
ggacagcctc gagaaccaca ggtgtacacc ctgcccccat cccgggatga gctgccatac 60
atcatcccac catacaacca ggtcagcctg acctgcctgg tcaaaggctt ctatcccagc 120
gacatcgccg tggagtggga gagcaatggg cagccggaga acaactacaa gaccacgcct 180
cccgtgctgg actccgacgg ctccttcttc ctctacagca agctcaccgt gggcgcagat 240
aggtggctgg aagggaacgt cttctcatgc tccgtgatgc atgaggcgct gcacaaccac 300
tacactcaga agagcttgtc cctgtcgccc ggt 333

<210> SEQ ID NO 141
<211> LENGTH: 227
<212> TYPE: PRT
<213> ORGANISM: Artificial Sequence
<220> FEATURE:
<223> OTHER INFORMATION: Fcab FS22-172-003 with LALA mutation

<400> SEQUENCE: 141

Thr Cys Pro Pro Cys Pro Ala Pro Glu Ala Ala Gly Gly Pro Ser Val
1 5 10 15

Phe Leu Phe Pro Pro Lys Pro Lys Asp Thr Leu Met Ile Ser Arg Thr
20 25 30

Pro Glu Val Thr Cys Val Val Val Asp Val Ser His Glu Asp Pro Glu
35 40 45

Val Lys Phe Asn Trp Tyr Val Asp Gly Val Glu Val His Asn Ala Lys
50 55 60

Thr Lys Pro Arg Glu Glu Gln Tyr Asn Ser Thr Tyr Arg Val Val Ser
65 70 75 80

Val Leu Thr Val Leu His Gln Asp Trp Leu Asn Gly Lys Glu Tyr Lys
85 90 95

Cys Lys Val Ser Asn Lys Ala Leu Pro Ala Pro Ile Glu Lys Thr Ile
100 105 110

Ser Lys Ala Lys Gly Gln Pro Arg Glu Pro Gln Val Tyr Thr Leu Pro
115 120 125

Pro Ser Arg Asp Glu Leu Pro Tyr Ile Ile Pro Pro Tyr Asn Gln Val
130 135 140

Ser Leu Thr Cys Leu Val Lys Gly Phe Tyr Pro Ser Asp Ile Ala Val
145 150 155 160

Glu Trp Glu Ser Asn Gly Gln Pro Glu Asn Asn Tyr Lys Thr Thr Pro
165 170 175

Pro Val Leu Asp Ser Asp Gly Ser Phe Phe Leu Tyr Ser Lys Leu Thr
180 185 190

Val Gly Ala Asp Arg Trp Leu Glu Gly Asn Val Phe Ser Cys Ser Val
195 200 205

Met His Glu Ala Leu His Asn His Tyr Thr Gln Lys Ser Leu Ser Leu
210 215 220

Ser Pro Gly
225

<210> SEQ ID NO 142
<211> LENGTH: 681
<212> TYPE: DNA
<213> ORGANISM: Artificial Sequence
<220> FEATURE:
<223> OTHER INFORMATION: Fcab FS22-172-003 with LALA mutation

<400> SEQUENCE: 142

```
acttgcccgc cttgcccagc cccggaagct gccggtggtc cttcggtgtt cctcttcccg      60

cccaagccga aggataccct gatgatctca cggacccccg aagtgacctg tgtggtggtg     120

gacgtgtccc acgaggaccc ggaagtgaaa ttcaattggt acgtggatgg agtggaagtg     180

cacaacgcca agaccaagcc acgggaagaa cagtacaact ctacctaccg cgtggtgtcc     240

gtgctcactg tgctgcacca agactggctg aacgggaagg agtacaagtg caaagtgtcc     300

aacaaggcgc tgcctgcccc aattgagaaa actatctcga aagccaaggg acagcctcga     360

gaaccacagg tgtacaccct gcccccatcc cgggatgagc tgccatacat catcccacca     420

tacaaccagg tcagcctgac ctgcctggtc aaaggcttct atcccagcga catcgccgtg     480

gagtgggaga gcaatgggca gccggagaac aactacaaga ccacgcctcc cgtgctggac     540

tccgacggct ccttcttcct ctacagcaag ctcaccgtgg gcgcagatag gtggctggaa     600

gggaacgtct tctcatgctc cgtgatgcat gaggcgctgc acaaccacta cactcagaag     660

agcttgtccc tgtcgcccgg t                                               681
```

<210> SEQ ID NO 143
<211> LENGTH: 227
<212> TYPE: PRT
<213> ORGANISM: Artificial Sequence
<220> FEATURE:
<223> OTHER INFORMATION: Fcab FS22-172-003 without LALA mutation

<400> SEQUENCE: 143

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Pro Tyr Ile Ile Pro Pro Tyr Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190
```

```
Val Gly Ala Asp Arg Trp Leu Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225


<210> SEQ ID NO 144
<211> LENGTH: 681
<212> TYPE: DNA
<213> ORGANISM: Artificial Sequence
<220> FEATURE:
<223> OTHER INFORMATION: Fcab FS22-172-003 without LALA mutation

<400> SEQUENCE: 144

acttgcccgc cttgcccagc cccggaactg ctgggtggtc cttcggtgtt cctcttcccg      60

cccaagccga aggataccct gatgatctca cggacccccg aagtgacctg tgtggtggtg     120

gacgtgtccc acgaggaccc ggaagtgaaa ttcaattggt acgtggatgg agtggaagtg     180

cacaacgcca agaccaagcc acgggaagaa cagtacaact ctacctaccg cgtggtgtcc     240

gtgctcactg tgctgcacca agactggctg aacgggaagg agtacaagtg caaagtgtcc     300

aacaaggcgc tgcctgcccc aattgagaaa actatctcga aagccaaggg acagcctcga     360

gaaccacagg tgtacaccct gcccccatcc cgggatgagc tgccatacat catcccacca     420

tacaaccagg tcagcctgac ctgcctggtc aaaggcttct atcccagcga catcgccgtg     480

gagtgggaga gcaatgggca gccggagaac aactacaaga ccacgcctcc cgtgctggac     540

tccgacggct ccttcttcct ctacagcaag ctcaccgtgg gcgcagatag gtggctggaa     600

gggaacgtct tctcatgctc cgtgatgcat gaggcgctgc acaaccacta cactcagaag     660

agcttgtccc tgtcgcccgg t                                               681


<210> SEQ ID NO 145
<211> LENGTH: 450
<212> TYPE: PRT
<213> ORGANISM: Artificial Sequence
<220> FEATURE:
<223> OTHER INFORMATION: heavy chain of FS22-172-003/HelD1.3 mock mAb2
      with LALA mutation

<400> SEQUENCE: 145

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125
```

```
Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Pro Tyr Ile Ile Pro Pro Tyr Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 146
<211> LENGTH: 450
<212> TYPE: PRT
<213> ORGANISM: Artificial Sequence
<220> FEATURE:
<223> OTHER INFORMATION: heavy chain of FS22-172-003/HelD1.3 mock mAb2 without LALA mutation

<400> SEQUENCE: 146

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30
```

```
Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Pro Tyr Ile Ile Pro Pro Tyr Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445
```

Pro Gly
    450

<210> SEQ ID NO 147
<211> LENGTH: 7
<212> TYPE: PRT
<213> ORGANISM: Artificial Sequence
<220> FEATURE:
<223> OTHER INFORMATION: Fcab FS22-172-004 CH3 domain structural loop sequence

<400> SEQUENCE: 147

Asn Tyr Ile Tyr Pro Pro Tyr
1               5

<210> SEQ ID NO 148
<211> LENGTH: 111
<212> TYPE: PRT
<213> ORGANISM: Artificial Sequence
<220> FEATURE:
<223> OTHER INFORMATION: Fcab FS22-172-004 CH3 domain

<400> SEQUENCE: 148

Gly Gln Pro Arg Glu Pro Gln Val Tyr Thr Leu Pro Pro Ser Arg Asp
1               5                   10                  15

Glu Leu Asn Tyr Ile Tyr Pro Pro Tyr Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Gly Ala Asp
65                  70                  75                  80

Arg Trp Leu Glu Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110

<210> SEQ ID NO 149
<211> LENGTH: 333
<212> TYPE: DNA
<213> ORGANISM: Artificial Sequence
<220> FEATURE:
<223> OTHER INFORMATION: Fcab FS22-172-004 CH3 domain

<400> SEQUENCE: 149
ggacagcctc gagagcctca agtgtacacc ctgcccccat cccgggatga gctgaactac     60
atctacccac catacaacca ggtcagcctg acctgcctgg tcaaaggctt ctatcccagc    120
gacatcgccg tggagtggga gagcaatggg cagccggaga acaactacaa gaccacgcct    180
cccgtgctgg actccgacgg ctccttcttc ctctacagca agctcaccgt gggcgcagat    240
aggtggctgg aagggaacgt cttctcatgc tccgtgatgc atgaggcgct gcacaaccac    300
tacactcaga agagcttgtc cctgtcgccc gga                                 333

<210> SEQ ID NO 150
<211> LENGTH: 227
<212> TYPE: PRT
<213> ORGANISM: Artificial Sequence
<220> FEATURE:
<223> OTHER INFORMATION: Fcab FS22-172-004 with LALA mutation

<400> SEQUENCE: 150

```
Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Asn Tyr Ile Tyr Pro Pro Tyr Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Gly Ala Asp Arg Trp Leu Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225
```

<210> SEQ ID NO 151
<211> LENGTH: 681
<212> TYPE: DNA
<213> ORGANISM: Artificial Sequence
<220> FEATURE:
<223> OTHER INFORMATION: Fcab FS22-172-004 with LALA mutation

<400> SEQUENCE: 151

```
acttgcccgc cttgcccagc cccggaagct gccggtggtc cttcggtgtt cctcttcccg     60

cccaagccga aggataccct gatgatctca cggacccccg aagtgacctg tgtggtggtg    120

gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240

gtgctcactg tgctgcacca agactggctg aacgggaagg agtacaagtg caaagtgtcc    300

aacaaggcgc tgcctgcccc aattgagaaa actatctcga aagccaaggg ccagcctcga    360

gaaccacagg tgtacaccct gcccccatcc cgggatgagc tgaactacat ctacccacca    420

tacaaccagg tcagcctgac ctgcctggtc aaaggcttct atcccagcga catcgccgtg    480

gagtgggaga gcaatgggca gccggagaac aactacaaga ccacgcctcc cgtgctggac    540

tccgacggct ccttcttcct ctacagcaag ctcaccgtgg gcgcagatag gtggctggaa    600

gggaacgtct tctcatgctc cgtgatgcat gaggctctgc acaaccacta cacacagaag    660

agcctctccc tgtctccggg t                                              681
```

<210> SEQ ID NO 152
<211> LENGTH: 227
<212> TYPE: PRT
<213> ORGANISM: Artificial Sequence
<220> FEATURE:
<223> OTHER INFORMATION: Fcab FS22-172-004 without LALA mutation

<400> SEQUENCE: 152

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Asn Tyr Ile Tyr Pro Pro Tyr Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Gly Ala Asp Arg Trp Leu Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225
```

<210> SEQ ID NO 153
<211> LENGTH: 681
<212> TYPE: DNA
<213> ORGANISM: Artificial Sequence
<220> FEATURE:
<223> OTHER INFORMATION: Fcab FS22-172-004 without LALA mutation

<400> SEQUENCE: 153

```
acttgcccgc cttgcccagc cccggaactg ctgggtggtc cttcggtgtt cctcttcccg     60

cccaagccga aggataccct gatgatctca cggacccccg aagtgacctg tgtggtggtg    120

gacgtgtccc acgaggaccc ggaagtgaaa ttcaattggt acgtggatgg agtggaagtg    180

cacaacgcca agaccaagcc acgggaagaa cagtacaact ctacctaccg cgtggtgtcc    240

gtgctcactg tgctgcacca agactggctg aacgggaagg agtacaagtg caaagtgtcc    300

aacaaggcgc tgcctgcccc aattgagaaa actatctcga aagccaaggg ccagcctcga    360

gaaccacagg tgtacaccct gcccccatcc cgggatgagc tgaactacat ctacccacca    420
```

```
tacaaccagg tcagcctgac ctgcctggtc aaaggcttct atcccagcga catcgccgtg    480

gagtgggaga gcaatgggca gccggagaac aactacaaga ccacgcctcc cgtgctggac    540

tccgacggct ccttcttcct ctacagcaag ctcaccgtgg gcgcagatag gtggctggaa    600

gggaacgtct tctcatgctc cgtgatgcat gaggctctgc acaaccacta cacacagaag    660

agcctctccc tgtctccggg t                                              681
```

```
<210> SEQ ID NO 154
<211> LENGTH: 450
<212> TYPE: PRT
<213> ORGANISM: Artificial Sequence
<220> FEATURE:
<223> OTHER INFORMATION: heavy chain of FS22-172-004/HelD1.3 mock mAb2
      with LALA mutation

<400> SEQUENCE: 154

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300
```

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Asp Glu Leu Asn Tyr Ile Tyr Pro Pro Tyr Asn Gln Val Ser
355 360 365

Leu Thr Cys Leu Val Lys Gly Phe Tyr Pro Ser Asp Ile Ala Val Glu
370 375 380

Trp Glu Ser Asn Gly Gln Pro Glu Asn Asn Tyr Lys Thr Thr Pro Pro
385 390 395 400

Val Leu Asp Ser Asp Gly Ser Phe Phe Leu Tyr Ser Lys Leu Thr Val
405 410 415

Gly Ala Asp Arg Trp Leu Glu Gly Asn Val Phe Ser Cys Ser Val Met
420 425 430

His Glu Ala Leu His Asn His Tyr Thr Gln Lys Ser Leu Ser Leu Ser
435 440 445

Pro Gly
450

<210> SEQ ID NO 155
<211> LENGTH: 450
<212> TYPE: PRT
<213> ORGANISM: Artificial Sequence
<220> FEATURE:
<223> OTHER INFORMATION: heavy chain of FS22-172-004/HelD1.3 mock mAb2 without LALA mutation

<400> SEQUENCE: 155

Gln Val Gln Leu Gln Glu Ser Gly Pro Gly Leu Val Arg Pro Ser Gln
1 5 10 15

Thr Leu Ser Leu Thr Cys Thr Val Ser Gly Ser Thr Phe Ser Gly Tyr
20 25 30

Gly Val Asn Trp Val Arg Gln Pro Pro Gly Arg Gly Leu Glu Trp Ile
35 40 45

Gly Met Ile Trp Gly Asp Gly Asn Thr Asp Tyr Asn Ser Ala Leu Lys
50 55 60

Ser Arg Val Thr Met Leu Val Asp Thr Ser Lys Asn Gln Phe Ser Leu
65 70 75 80

Arg Leu Ser Ser Val Thr Ala Ala Asp Thr Ala Val Tyr Tyr Cys Ala
85 90 95

Arg Glu Arg Asp Tyr Arg Leu Asp Tyr Trp Gly Gln Gly Ser Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

```
Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Asn Tyr Ile Tyr Pro Pro Tyr Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 156
<211> LENGTH: 7
<212> TYPE: PRT
<213> ORGANISM: Artificial Sequence
<220> FEATURE:
<223> OTHER INFORMATION: Fcab FS22-172-005 CH3 domain structural loop
      sequence

<400> SEQUENCE: 156

Gln Gln Val Tyr Pro Pro Tyr
1               5


<210> SEQ ID NO 157
<211> LENGTH: 111
<212> TYPE: PRT
<213> ORGANISM: Artificial Sequence
<220> FEATURE:
<223> OTHER INFORMATION: Fcab FS22-172-005 CH3 domain

<400> SEQUENCE: 157

Gly Gln Pro Arg Glu Pro Gln Val Tyr Thr Leu Pro Pro Ser Arg Asp
1               5                   10                  15

Glu Leu Gln Gln Val Tyr Pro Pro Tyr Asn Gln Val Ser Leu Thr Cys
            20                  25                  30
```

```
Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Gly Ala Asp
65                  70                  75                  80

Arg Trp Leu Glu Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110
```

<210> SEQ ID NO 158
<211> LENGTH: 333
<212> TYPE: DNA
<213> ORGANISM: Artificial Sequence
<220> FEATURE:
<223> OTHER INFORMATION: Fcab FS22-172-005 CH3 domain

<400> SEQUENCE: 158

```
ggccagcctc gagaaccaca ggtgtacacc ctgcccccat cccgggatga gctgcagcag      60

gtttacccac catacaacca ggtcagcctg acctgcctgg tcaaaggctt ctatcccagc     120

gacatcgccg tggagtggga gagcaatggg cagccggaga acaactacaa gaccacgcct     180

cccgtgctgg actccgacgg ctccttcttc ctctacagca agctcaccgt gggcgcagat     240

aggtggctgg aagggaacgt cttctcatgc tccgtgatgc atgaggctct gcacaaccac     300

tacacacaga agagcctctc cctgtctccg ggt                                  333
```

<210> SEQ ID NO 159
<211> LENGTH: 227
<212> TYPE: PRT
<213> ORGANISM: Artificial Sequence
<220> FEATURE:
<223> OTHER INFORMATION: Fcab FS22-172-005 with LALA mutation

<400> SEQUENCE: 159

```
Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Gln Gln Val Tyr Pro Pro Tyr Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175
```

```
Pro Val Leu Asp Ser Asp Gly Ser Phe Phe Leu Tyr Ser Lys Leu Thr
            180                 185                 190

Val Gly Ala Asp Arg Trp Leu Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225
```

<210> SEQ ID NO 160
<211> LENGTH: 681
<212> TYPE: DNA
<213> ORGANISM: Artificial Sequence
<220> FEATURE:
<223> OTHER INFORMATION: Fcab FS22-172-005 with LALA mutation

<400> SEQUENCE: 160

```
acttgcccgc cttgcccagc cccggaagct gccggtggtc cttcggtgtt cctcttcccg      60

cccaagccga aggataccct gatgatctca cggacccccg aagtgacctg tgtggtggtg     120

gacgtgtccc acgaggaccc ggaagtgaaa ttcaattggt acgtggatgg agtggaagtg     180

cacaacgcca agaccaagcc acgggaagaa cagtacaact ctacctaccg cgtggtgtcc     240

gtgctcactg tgctgcacca agactggctg aacgggaagg agtacaagtg caaagtgtcc     300

aacaaggcgc tgcctgcccc aattgagaaa actatctcga aagccaaggg ccagcctcga     360

gaaccacagg tgtacaccct gcccccatcc cgggatgagc tgcagcaggt ttacccacca     420

tacaaccagg tcagcctgac ctgcctggtc aaaggcttct atcccagcga catcgccgtg     480

gagtgggaga gcaatgggca gccggagaac aactacaaga ccacgcctcc cgtgctggac     540

tccgacggct ccttcttcct ctacagcaag ctcaccgtgg gcgcagatag gtggctggaa     600

gggaacgtct tctcatgctc cgtgatgcat gaggctctgc acaaccacta cacacagaag     660

agcctctccc tgtctccggg t                                               681
```

<210> SEQ ID NO 161
<211> LENGTH: 227
<212> TYPE: PRT
<213> ORGANISM: Artificial Sequence
<220> FEATURE:
<223> OTHER INFORMATION: Fcab FS22-172-005 without LALA mutation

<400> SEQUENCE: 161

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
```

```
        115                 120                 125

Pro Ser Arg Asp Glu Leu Gln Gln Val Tyr Pro Pro Tyr Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Gly Ala Asp Arg Trp Leu Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225


<210> SEQ ID NO 162
<211> LENGTH: 681
<212> TYPE: DNA
<213> ORGANISM: Artificial Sequence
<220> FEATURE:
<223> OTHER INFORMATION: Fcab FS22-172-005 without LALA mutation

<400> SEQUENCE: 162

acttgcccgc cttgcccagc cccggaactg ctgggtggtc cttcggtgtt cctcttcccg      60

cccaagccga aggataccct gatgatctca cggacccccg aagtgacctg tgtggtggtg     120

gacgtgtccc acgaggaccc ggaagtgaaa ttcaattggt acgtggatgg agtggaagtg     180

cacaacgcca agaccaagcc acgggaagaa cagtacaact ctacctaccg cgtggtgtcc     240

gtgctcactg tgctgcacca agactggctg aacgggaagg agtacaagtg caaagtgtcc     300

aacaaggcgc tgcctgcccc aattgagaaa actatctcga aagccaaggg ccagcctcga     360

gaaccacagg tgtacaccct gcccccatcc cgggatgagc tgcagcaggt ttacccacca     420

tacaaccagg tcagcctgac ctgcctggtc aaaggcttct atcccagcga catcgccgtg     480

gagtgggaga gcaatgggca gccggagaac aactacaaga ccacgcctcc cgtgctggac     540

tccgacggct ccttcttcct ctacagcaag ctcaccgtgg gcgcagatag gtggctggaa     600

gggaacgtct tctcatgctc cgtgatgcat gaggctctgc acaaccacta cacacagaag     660

agcctctccc tgtctccggg t                                               681


<210> SEQ ID NO 163
<211> LENGTH: 450
<212> TYPE: PRT
<213> ORGANISM: Artificial Sequence
<220> FEATURE:
<223> OTHER INFORMATION: heavy chain of FS22-172-005/HelD1.3 mock mAb2
      with LALA mutation

<400> SEQUENCE: 163

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60
```

```
Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Gln Gln Val Tyr Pro Pro Tyr Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 164
<211> LENGTH: 450

<212> TYPE: PRT
<213> ORGANISM: Artificial Sequence
<220> FEATURE:
<223> OTHER INFORMATION: heavy chain of FS22-172-005/HelD1.3 mock mAb2 without LALA mutation

<400> SEQUENCE: 164

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Gln Gln Val Tyr Pro Pro Tyr Asn Gln Val Ser
        355                 360                 365

Leu Thr Cys Leu Val Lys Gly Phe Tyr Pro Ser Asp Ile Ala Val Glu
    370                 375                 380
```

-continued

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 165
<211> LENGTH: 111
<212> TYPE: PRT
<213> ORGANISM: Artificial Sequence
<220> FEATURE:
<223> OTHER INFORMATION: Fcab FS22-172-006 CH3 domain

<400> SEQUENCE: 165

Gly Gln Pro Arg Glu Pro Gln Val Tyr Thr Leu Pro Pro Ser Arg Asp
1               5                   10                  15

Glu Leu Arg Lys Tyr Tyr Pro Pro Tyr Asn Gln Leu Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Gly Ala Asp
65                  70                  75                  80

Arg Trp Leu Glu Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110


<210> SEQ ID NO 166
<211> LENGTH: 333
<212> TYPE: DNA
<213> ORGANISM: Artificial Sequence
<220> FEATURE:
<223> OTHER INFORMATION: Fcab FS22-172-006 CH3 domain

<400> SEQUENCE: 166

ggccagcctc gagaaccaca ggtgtacacc ctgcccccat cccgggatga gctgcgtaaa      60

tactacccgc cgtacaacca gctcagcctg acctgcctgg tcaaaggctt ctatcccagc     120

gacatcgccg tggagtggga gagcaatggg cagccggaga acaactacaa gaccacgcct     180

cccgtgctgg actccgacgg ctccttcttc ctctacagca agctcaccgt gggcgcagat     240

aggtggctgg aagggaacgt cttctcatgc tccgtgatgc atgaggctct gcacaaccac     300

tacacacaga agagcctctc cctgtctccg ggt                                  333


<210> SEQ ID NO 167
<211> LENGTH: 227
<212> TYPE: PRT
<213> ORGANISM: Artificial Sequence
<220> FEATURE:
<223> OTHER INFORMATION: Fcab FS22-172-006 with LALA mutation

<400> SEQUENCE: 167
```

-continued

Thr Cys Pro Pro Cys Pro Ala Pro Glu Ala Ala Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Arg Lys Tyr Tyr Pro Pro Tyr Asn Gln Leu
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Gly Ala Asp Arg Trp Leu Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225

<210> SEQ ID NO 168
<211> LENGTH: 681
<212> TYPE: DNA
<213> ORGANISM: Artificial Sequence
<220> FEATURE:
<223> OTHER INFORMATION: Fcab FS22-172-006 with LALA mutation

<400> SEQUENCE: 168
acttgcccgc cttgcccagc cccggaagct gccggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg ccagcctcga 360
gaaccacagg tgtacaccct gcccccatcc cgggatgagc tgcgtaaata ctacccgccg 420
tacaaccagc tcagcctgac ctgcctggtc aaaggcttct atcccagcga catcgccgtg 480
gagtgggaga gcaatgggca gccggagaac aactacaaga ccacgcctcc cgtgctggac 540
tccgacggct ccttcttcct ctacagcaag ctcaccgtgg gcgcagatag gtggctggaa 600
gggaacgtct tctcatgctc cgtgatgcat gaggctctgc acaaccacta cacacagaag 660
agcctctccc tgtctccggg t 681

<210> SEQ ID NO 169
<211> LENGTH: 227
<212> TYPE: PRT
<213> ORGANISM: Artificial Sequence
<220> FEATURE:
<223> OTHER INFORMATION: Fcab FS22-172-006 without LALA mutation

<400> SEQUENCE: 169

```
Thr Cys Pro Pro Cys Pro Ala Pro Glu Leu Leu Gly Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Ala Leu Pro Ala Pro Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Asp Glu Leu Arg Lys Tyr Tyr Pro Pro Tyr Asn Gln Leu
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Gly Ala Asp Arg Trp Leu Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225
```

<210> SEQ ID NO 170
<211> LENGTH: 681
<212> TYPE: DNA
<213> ORGANISM: Artificial Sequence
<220> FEATURE:
<223> OTHER INFORMATION: Fcab FS22-172-006 without LALA mutation

<400> SEQUENCE: 170

```
acttgcccgc cttgcccagc cccggaactg ctgggtggtc cttcggtgtt cctcttcccg      60

cccaagccga aggataccct gatgatctca cggacccccg aagtgacctg tgtggtggtg     120

gacgtgtccc acgaggaccc ggaagtgaaa ttcaattggt acgtggatgg agtggaagtg     180

cacaacgcca agaccaagcc acgggaagaa cagtacaact ctacctaccg cgtggtgtcc     240

gtgctcactg tgctgcacca agactggctg aacgggaagg agtacaagtg caaagtgtcc     300

aacaaggcgc tgcctgcccc aattgagaaa actatctcga aagccaaggg ccagcctcga     360

gaaccacagg tgtacaccct gcccccatcc cgggatgagc tgcgtaaata ctacccgccg     420
```

```
tacaaccagc tcagcctgac ctgcctggtc aaaggcttct atcccagcga catcgccgtg    480

gagtgggaga gcaatgggca gccggagaac aactacaaga ccacgcctcc cgtgctggac    540

tccgacggct ccttcttcct ctacagcaag ctcaccgtgg gcgcagatag gtggctggaa    600

gggaacgtct tctcatgctc cgtgatgcat gaggctctgc acaaccacta cacacagaag    660

agcctctccc tgtctccggg t                                              681


<210> SEQ ID NO 171
<211> LENGTH: 450
<212> TYPE: PRT
<213> ORGANISM: Artificial Sequence
<220> FEATURE:
<223> OTHER INFORMATION: heavy chain of FS22-172-006/HelD1.3 mock mAb2
      with LALA mutation

<400> SEQUENCE: 171

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
```

```
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Arg Lys Tyr Tyr Pro Pro Tyr Asn Gln Leu Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 172
<211> LENGTH: 450
<212> TYPE: PRT
<213> ORGANISM: Artificial Sequence
<220> FEATURE:
<223> OTHER INFORMATION: heavy chain of FS22-172-006/HelD1.3 mock mAb2
      without LALA mutation

<400> SEQUENCE: 172

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205
```

-continued

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Arg Lys Tyr Tyr Pro Pro Tyr Asn Gln Leu Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Gly Ala Asp Arg Trp Leu Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450

<210> SEQ ID NO 173
<211> LENGTH: 214
<212> TYPE: PRT
<213> ORGANISM: Artificial Sequence
<220> FEATURE:
<223> OTHER INFORMATION: light chain of HelD1.3 mock mAb2

<400> SEQUENCE: 173

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Tyr
            20                  25                  30

Leu Ala Trp Tyr Gln Gln Lys Gln Gly Lys Ser Pro Gln Leu Leu Val
        35                  40                  45

Tyr Asn Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Thr Pro Arg
                85                  90                  95

Thr Phe Gly Gly Gly Thr Lys Leu Glu Ile Lys Arg Thr Val Ala Ala
            100                 105                 110

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 174
<211> LENGTH: 7
<212> TYPE: PRT
<213> ORGANISM: Artificial Sequence
<220> FEATURE:
<223> OTHER INFORMATION: Fcab FS22-053 CH3 domain structural loop
      sequence

<400> SEQUENCE: 174

Tyr Tyr Asn Arg Trp Gln Asp
1               5


<210> SEQ ID NO 175
<211> LENGTH: 111
<212> TYPE: PRT
<213> ORGANISM: Artificial Sequence
<220> FEATURE:
<223> OTHER INFORMATION: Fcab FS22-053 CH3 domain

<400> SEQUENCE: 175

Gly Gln Pro Arg Glu Pro Gln Val Tyr Thr Leu Pro Pro Ser Arg Asp
1               5                   10                  15

Glu Leu Asn Pro Pro Tyr Leu Phe Ser Asn Gln Val Ser Leu Thr Cys
            20                  25                  30

Leu Val Lys Gly Phe Tyr Pro Ser Asp Ile Ala Val Glu Trp Glu Ser
        35                  40                  45

Asn Gly Gln Pro Glu Asn Asn Tyr Lys Thr Thr Pro Pro Val Leu Asp
    50                  55                  60

Ser Asp Gly Ser Phe Phe Leu Tyr Ser Lys Leu Thr Val Tyr Tyr Asn
65                  70                  75                  80

Arg Trp Gln Asp Gly Asn Val Phe Ser Cys Ser Val Met His Glu Ala
                85                  90                  95

Leu His Asn His Tyr Thr Gln Lys Ser Leu Ser Leu Ser Pro Gly
            100                 105                 110


<210> SEQ ID NO 176
<211> LENGTH: 333
<212> TYPE: DNA
<213> ORGANISM: Artificial Sequence
<220> FEATURE:
<223> OTHER INFORMATION: Fcab FS22-053 CH3 domain

<400> SEQUENCE: 176

ggccagcctc gagaaccaca ggtgtacacc ctgcccccat cccgggatga gctgaacccg      60

ccgtacctgt tctctaacca ggtcagcctg acctgcctgg tcaaaggctt ctatcccagc     120
```

gacatcgccg tggagtggga gagcaatggg cagccggaga acaactacaa gaccacgcct 180
cccgtgctgg actccgacgg ctccttcttc ctctacagca agctcaccgt gtattataac 240
aggtggcagg atgggaacgt cttctcatgc tccgtgatgc atgaggctct gcacaaccac 300
tacacacaga agagcctctc cctgtctccg ggt 333

<210> SEQ ID NO 177
<211> LENGTH: 681
<212> TYPE: DNA
<213> ORGANISM: Artificial Sequence
<220> FEATURE:
<223> OTHER INFORMATION: Fcab FS22-053 Fcab with LALA

<400> SEQUENCE: 177
acttgcccgc cttgcccagc cccggaagct gccggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg ccagcctcga 360
gaaccacagg tgtacaccct gcccccatcc cgggatgagc tgaacccgcc gtacctgttc 420
tctaaccagg tcagcctgac ctgcctggtc aaaggcttct atcccagcga catcgccgtg 480
gagtgggaga gcaatgggca gccggagaac aactacaaga ccacgcctcc cgtgctggac 540
tccgacggct ccttcttcct ctacagcaag ctcaccgtgt attataacag gtggcaggat 600
gggaacgtct tctcatgctc cgtgatgcat gaggctctgc acaaccacta cacacagaag 660
agcctctccc tgtctccggg t 681

<210> SEQ ID NO 178
<211> LENGTH: 681
<212> TYPE: DNA
<213> ORGANISM: Artificial Sequence
<220> FEATURE:
<223> OTHER INFORMATION: Fcab FS22-053 Fcab without LALA

<400> SEQUENCE: 178
acttgcccgc cttgcccagc cccggaactg ctgggtggtc cttcggtgtt cctcttcccg 60
cccaagccga aggataccct gatgatctca cggacccccg aagtgacctg tgtggtggtg 120
gacgtgtccc acgaggaccc ggaagtgaaa ttcaattggt acgtggatgg agtggaagtg 180
cacaacgcca agaccaagcc acgggaagaa cagtacaact ctacctaccg cgtggtgtcc 240
gtgctcactg tgctgcacca agactggctg aacgggaagg agtacaagtg caaagtgtcc 300
aacaaggcgc tgcctgcccc aattgagaaa actatctcga aagccaaggg ccagcctcga 360
gaaccacagg tgtacaccct gcccccatcc cgggatgagc tgaacccgcc gtacctgttc 420
tctaaccagg tcagcctgac ctgcctggtc aaaggcttct atcccagcga catcgccgtg 480
gagtgggaga gcaatgggca gccggagaac aactacaaga ccacgcctcc cgtgctggac 540
tccgacggct ccttcttcct ctacagcaag ctcaccgtgt attataacag gtggcaggat 600
gggaacgtct tctcatgctc cgtgatgcat gaggctctgc acaaccacta cacacagaag 660
agcctctccc tgtctccggg t 681

<210> SEQ ID NO 179

<211> LENGTH: 15
<212> TYPE: PRT
<213> ORGANISM: Artificial Sequence
<220> FEATURE:
<223> OTHER INFORMATION: full-length immunoglobulin hinge region

<400> SEQUENCE: 179

```
Glu Pro Lys Ser Cys Asp Lys Thr His Thr Cys Pro Pro Cys Pro
1               5                   10                  15
```

<210> SEQ ID NO 180
<211> LENGTH: 232
<212> TYPE: PRT
<213> ORGANISM: Homo sapiens

<400> SEQUENCE: 180

```
Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln Ile Ile Ser Phe Phe Leu Ala Leu Thr Ser Thr Ala Leu
                165                 170                 175

Leu Phe Leu Leu Phe Phe Leu Thr Leu Arg Phe Ser Val Val Lys Arg
            180                 185                 190

Gly Arg Lys Lys Leu Leu Tyr Ile Phe Lys Gln Pro Phe Met Arg Pro
        195                 200                 205

Val Gln Thr Thr Gln Glu Glu Asp Gly Cys Ser Cys Arg Phe Pro Glu
    210                 215                 220

Glu Glu Glu Gly Gly Cys Glu Leu
225                 230
```

<210> SEQ ID NO 181
<211> LENGTH: 163
<212> TYPE: PRT
<213> ORGANISM: Homo sapiens

<400> SEQUENCE: 181

```
Leu Gln Asp Pro Cys Ser Asn Cys Pro Ala Gly Thr Phe Cys Asp Asn
1               5                   10                  15

Asn Arg Asn Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
```

```
        35                  40                  45

Phe Arg Thr Arg Lys Glu Cys Ser Ser Thr Ser Asn Ala Glu Cys Asp
    50                  55                  60

Cys Thr Pro Gly Phe His Cys Leu Gly Ala Gly Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Val Thr Pro Pro Ala Pro Ala Arg Glu Pro Gly His
145                 150                 155                 160

Ser Pro Gln


<210> SEQ ID NO 182
<211> LENGTH: 231
<212> TYPE: PRT
<213> ORGANISM: Macaca fascicularis

<400> SEQUENCE: 182

Leu Gln Asp Leu Cys Ser Asn Cys Pro Ala Gly Thr Phe Cys Asp Asn
1               5                   10                  15

Asn Arg Ser Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Lys Thr Arg Lys Glu Cys Ser Ser Thr Ser Asn Ala Glu Cys Asp
    50                  55                  60

Cys Ile Ser Gly Tyr His Cys Leu Gly Ala Glu Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Ala Thr Pro Pro Ala Pro Ala Arg Glu Pro Gly His
145                 150                 155                 160

Ser Pro Gln Ile Ile Phe Phe Leu Ala Leu Thr Ser Thr Val Val Leu
                165                 170                 175

Phe Leu Leu Phe Phe Leu Val Leu Arg Phe Ser Val Val Lys Arg Ser
            180                 185                 190

Arg Lys Lys Leu Leu Tyr Ile Phe Lys Gln Pro Phe Met Arg Pro Val
        195                 200                 205

Gln Thr Thr Gln Glu Glu Asp Gly Cys Ser Cys Arg Phe Pro Glu Glu
    210                 215                 220

Glu Glu Gly Gly Cys Glu Leu
225                 230
```

<210> SEQ ID NO 183
<211> LENGTH: 163
<212> TYPE: PRT
<213> ORGANISM: Macaca fascicularis

<400> SEQUENCE: 183

Leu Gln Asp Leu Cys Ser Asn Cys Pro Ala Gly Thr Phe Cys Asp Asn
1               5                   10                  15

Asn Arg Ser Gln Ile Cys Ser Pro Cys Pro Pro Asn Ser Phe Ser Ser
            20                  25                  30

Ala Gly Gly Gln Arg Thr Cys Asp Ile Cys Arg Gln Cys Lys Gly Val
        35                  40                  45

Phe Lys Thr Arg Lys Glu Cys Ser Ser Thr Ser Asn Ala Glu Cys Asp
    50                  55                  60

Cys Ile Ser Gly Tyr His Cys Leu Gly Ala Glu Cys Ser Met Cys Glu
65                  70                  75                  80

Gln Asp Cys Lys Gln Gly Gln Glu Leu Thr Lys Lys Gly Cys Lys Asp
                85                  90                  95

Cys Cys Phe Gly Thr Phe Asn Asp Gln Lys Arg Gly Ile Cys Arg Pro
            100                 105                 110

Trp Thr Asn Cys Ser Leu Asp Gly Lys Ser Val Leu Val Asn Gly Thr
        115                 120                 125

Lys Glu Arg Asp Val Val Cys Gly Pro Ser Pro Ala Asp Leu Ser Pro
    130                 135                 140

Gly Ala Ser Ser Ala Thr Pro Pro Ala Pro Ala Arg Glu Pro Gly His
145                 150                 155                 160

Ser Pro Gln

<210> SEQ ID NO 184
<211> LENGTH: 233
<212> TYPE: PRT
<213> ORGANISM: Mus musculus

<400> SEQUENCE: 184

Val Gln Asn Ser Cys Asp Asn Cys Gln Pro Gly Thr Phe Cys Arg Lys
1               5                   10                  15

Tyr Asn Pro Val Cys Lys Ser Cys Pro Pro Ser Thr Phe Ser Ser Ile
            20                  25                  30

Gly Gly Gln Pro Asn Cys Asn Ile Cys Arg Val Cys Ala Gly Tyr Phe
        35                  40                  45

Arg Phe Lys Lys Phe Cys Ser Ser Thr His Asn Ala Glu Cys Glu Cys
    50                  55                  60

Ile Glu Gly Phe His Cys Leu Gly Pro Gln Cys Thr Arg Cys Glu Lys
65                  70                  75                  80

Asp Cys Arg Pro Gly Gln Glu Leu Thr Lys Gln Gly Cys Lys Thr Cys
                85                  90                  95

Ser Leu Gly Thr Phe Asn Asp Gln Asn Gly Thr Gly Val Cys Arg Pro
            100                 105                 110

Trp Thr Asn Cys Ser Leu Asp Gly Arg Ser Val Leu Lys Thr Gly Thr
        115                 120                 125

Thr Glu Lys Asp Val Val Cys Gly Pro Pro Val Val Ser Phe Ser Pro
    130                 135                 140

Ser Thr Thr Ile Ser Val Thr Pro Glu Gly Gly Pro Gly Gly His Ser
145                 150                 155                 160

Leu Gln Val Leu Thr Leu Phe Leu Ala Leu Thr Ser Ala Leu Leu Leu
                165                 170                 175

```
Ala Leu Ile Phe Ile Thr Leu Leu Phe Ser Val Leu Lys Trp Ile Arg
            180                 185                 190

Lys Lys Phe Pro His Ile Phe Lys Gln Pro Phe Lys Lys Thr Thr Gly
        195                 200                 205

Ala Ala Gln Glu Glu Asp Ala Cys Ser Cys Arg Cys Pro Gln Glu Glu
    210                 215                 220

Glu Gly Gly Gly Gly Gly Tyr Glu Leu
225                 230


<210> SEQ ID NO 185
<211> LENGTH: 164
<212> TYPE: PRT
<213> ORGANISM: Mus musculus

<400> SEQUENCE: 185

Val Gln Asn Ser Cys Asp Asn Cys Gln Pro Gly Thr Phe Cys Arg Lys
1               5                   10                  15

Tyr Asn Pro Val Cys Lys Ser Cys Pro Pro Ser Thr Phe Ser Ser Ile
            20                  25                  30

Gly Gly Gln Pro Asn Cys Asn Ile Cys Arg Val Cys Ala Gly Tyr Phe
        35                  40                  45

Arg Phe Lys Lys Phe Cys Ser Ser Thr His Asn Ala Glu Cys Glu Cys
    50                  55                  60

Ile Glu Gly Phe His Cys Leu Gly Pro Gln Cys Thr Arg Cys Glu Lys
65                  70                  75                  80

Asp Cys Arg Pro Gly Gln Glu Leu Thr Lys Gln Gly Cys Lys Thr Cys
                85                  90                  95

Ser Leu Gly Thr Phe Asn Asp Gln Asn Gly Thr Gly Val Cys Arg Pro
            100                 105                 110

Trp Thr Asn Cys Ser Leu Asp Gly Arg Ser Val Leu Lys Thr Gly Thr
        115                 120                 125

Thr Glu Lys Asp Val Val Cys Gly Pro Pro Val Val Ser Phe Ser Pro
    130                 135                 140

Ser Thr Thr Ile Ser Val Thr Pro Glu Gly Gly Pro Gly Gly His Ser
145                 150                 155                 160

Leu Gln Val Leu


<210> SEQ ID NO 186
<211> LENGTH: 445
<212> TYPE: PRT
<213> ORGANISM: Artificial Sequence
<220> FEATURE:
<223> OTHER INFORMATION: heavy chain of G1/HelD1.3 mAb

<400> SEQUENCE: 186

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
```

-continued

```
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445


<210> SEQ ID NO 187
<211> LENGTH: 290
<212> TYPE: PRT
<213> ORGANISM: Homo sapiens

<400> SEQUENCE: 187

Met Arg Ile Phe Ala Val Phe Ile Phe Met Thr Tyr Trp His Leu Leu
1               5                   10                  15
```

-continued

```
Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290


<210> SEQ ID NO 188
<211> LENGTH: 290
<212> TYPE: PRT
<213> ORGANISM: Mus musculus

<400> SEQUENCE: 188

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val
    50                  55                  60

Ile Gln Phe Val Ala Gly Glu Glu Asp Leu Lys Pro Gln His Ser Asn
65                  70                  75                  80

Phe Arg Gly Arg Ala Ser Leu Pro Lys Asp Gln Leu Leu Lys Gly Asn
                85                  90                  95
```

Ala Ala Leu Gln Ile Thr Asp Val Lys Leu Gln Asp Ala Gly Val Tyr
100 105 110

Cys Cys Ile Ile Ser Tyr Gly Gly Ala Asp Tyr Lys Arg Ile Thr Leu
115 120 125

Lys Val Asn Ala Pro Tyr Arg Lys Ile Asn Gln Arg Ile Ser Val Asp
130 135 140

Pro Ala Thr Ser Glu His Glu Leu Ile Cys Gln Ala Glu Gly Tyr Pro
145 150 155 160

Glu Ala Glu Val Ile Trp Thr Asn Ser Asp His Gln Pro Val Ser Gly
165 170 175

Lys Arg Ser Val Thr Thr Ser Arg Thr Glu Gly Met Leu Leu Asn Val
180 185 190

Thr Ser Ser Leu Arg Val Asn Ala Thr Ala Asn Asp Val Phe Tyr Cys
195 200 205

Thr Phe Trp Arg Ser Gln Pro Gly Gln Asn His Thr Ala Glu Leu Ile
210 215 220

Ile Pro Glu Leu Pro Ala Thr His Pro Pro Gln Asn Arg Thr His Trp
225 230 235 240

Val Leu Leu Gly Ser Ile Leu Leu Phe Leu Ile Val Val Ser Thr Val
245 250 255

Leu Leu Phe Leu Arg Lys Gln Val Arg Met Leu Asp Val Glu Lys Cys
260 265 270

Gly Val Glu Asp Thr Ser Ser Lys Asn Arg Asn Asp Thr Gln Phe Glu
275 280 285

Glu Thr
290

<210> SEQ ID NO 189
<211> LENGTH: 303
<212> TYPE: PRT
<213> ORGANISM: Mus musculus

<400> SEQUENCE: 189

Asp Ala Glu Gln Lys Ala Cys Pro Pro Gly Lys Glu Pro Tyr Lys Val
1 5 10 15

Asp Glu Asp Leu Ile Phe Tyr Gln Asn Trp Glu Leu Glu Ala Cys Val
20 25 30

Asp Gly Thr Met Leu Ala Arg Gln Met Asp Leu Val Asn Glu Ile Pro
35 40 45

Phe Thr Tyr Glu Gln Leu Ser Ile Phe Lys His Lys Leu Asp Lys Thr
50 55 60

Tyr Pro Gln Gly Tyr Pro Glu Ser Leu Ile Gln Gln Leu Gly His Phe
65 70 75 80

Phe Arg Tyr Val Ser Pro Glu Asp Ile His Gln Trp Asn Val Thr Ser
85 90 95

Pro Asp Thr Val Lys Thr Leu Leu Lys Val Ser Lys Gly Gln Lys Met
100 105 110

Asn Ala Gln Ala Ile Ala Leu Val Ala Cys Tyr Leu Arg Gly Gly Gly
115 120 125

Gln Leu Asp Glu Asp Met Val Lys Ala Leu Gly Asp Ile Pro Leu Ser
130 135 140

Tyr Leu Cys Asp Phe Ser Pro Gln Asp Leu His Ser Val Pro Ser Ser
145 150 155 160

Val Met Trp Leu Val Gly Pro Gln Asp Leu Asp Lys Cys Ser Gln Arg

```
                165                 170                 175

His Leu Gly Leu Leu Tyr Gln Lys Ala Cys Ser Ala Phe Gln Asn Val
            180                 185                 190

Ser Gly Leu Glu Tyr Phe Glu Lys Ile Lys Thr Phe Leu Gly Gly Ala
        195                 200                 205

Ser Val Lys Asp Leu Arg Ala Leu Ser Gln His Asn Val Ser Met Asp
    210                 215                 220

Ile Ala Thr Phe Lys Arg Leu Gln Val Asp Ser Leu Val Gly Leu Ser
225                 230                 235                 240

Val Ala Glu Val Gln Lys Leu Leu Gly Pro Asn Ile Val Asp Leu Lys
                245                 250                 255

Thr Glu Glu Asp Lys Ser Pro Val Arg Asp Trp Leu Phe Arg Gln His
            260                 265                 270

Gln Lys Asp Leu Asp Arg Leu Gly Leu Gly Leu Gln Gly Gly Ile Pro
        275                 280                 285

Asn Gly Tyr Leu Val Leu Asp Phe Asn Val Arg Glu Ala Phe Ser
    290                 295                 300


<210> SEQ ID NO 190
<211> LENGTH: 447
<212> TYPE: PRT
<213> ORGANISM: Artificial Sequence
<220> FEATURE:
<223> OTHER INFORMATION: heavy chain of FS22m-063-AA/FS28m-228 mAb2

<400> SEQUENCE: 190

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Phe Met Val Trp Val Arg Gln Ala Pro Gly Lys Gly Leu Glu Trp Val
        35                  40                  45

Ser Met Ile Ser Pro Lys Ser Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Phe Thr Pro Ala Arg Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
```

-continued 225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Pro Tyr Trp Ser Tyr Val Ser Leu Thr Cys
355 360 365

Leu Val Lys Gly Phe Tyr Pro Ser Asp Ile Ala Val Glu Trp Glu Ser
370 375 380

Asn Gly Gln Pro Glu Asn Asn Tyr Lys Thr Thr Pro Pro Val Leu Asp
385 390 395 400

Ser Asp Gly Ser Phe Phe Leu Tyr Ser Lys Leu Thr Val Met Asn Tyr
405 410 415

Arg Trp Glu Leu Gly Asn Val Phe Ser Cys Ser Val Met His Glu Ala
420 425 430

Leu His Asn His Tyr Thr Gln Lys Ser Leu Ser Leu Ser Pro Gly
435 440 445

<210> SEQ ID NO 191
<211> LENGTH: 215
<212> TYPE: PRT
<213> ORGANISM: Artificial Sequence
<220> FEATURE:
<223> OTHER INFORMATION: light chain of FS22m-063-AA/FS28m-228 mAb2

<400> SEQUENCE: 191

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Pro Phe Pro Phe Ser
85 90 95

Phe Thr Phe Gly Gln Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser

-continued

```
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 192
<211> LENGTH: 445
<212> TYPE: PRT
<213> ORGANISM: Artificial Sequence
<220> FEATURE:
<223> OTHER INFORMATION: heavy chain of G1AA/HelD1.3 mAb (with LALA)

<400> SEQUENCE: 192

Gln Val Gln Leu Gln Glu Ser Gly Pro Gly Leu Val Arg Pro Ser Gln
1               5                   10                  15

Thr Leu Ser Leu Thr Cys Thr Val Ser Gly Ser Thr Phe Ser Gly Tyr
            20                  25                  30

Gly Val Asn Trp Val Arg Gln Pro Pro Gly Arg Gly Leu Glu Trp Ile
        35                  40                  45

Gly Met Ile Trp Gly Asp Gly Asn Thr Asp Tyr Asn Ser Ala Leu Lys
    50                  55                  60

Ser Arg Val Thr Met Leu Val Asp Thr Ser Lys Asn Gln Phe Ser Leu
65                  70                  75                  80

Arg Leu Ser Ser Val Thr Ala Ala Asp Thr Ala Val Tyr Tyr Cys Ala
                85                  90                  95

Arg Glu Arg Asp Tyr Arg Leu Asp Tyr Trp Gly Gln Gly Ser Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
```

```
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445


<210> SEQ ID NO 193
<211> LENGTH: 452
<212> TYPE: PRT
<213> ORGANISM: Artificial Sequence
<220> FEATURE:
<223> OTHER INFORMATION: heavy chain of FS22-172-004-AA/S70 (with LALA)

<400> SEQUENCE: 193

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
```

```
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Asn Tyr Ile Tyr Pro Pro Tyr Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Gly Ala Asp Arg Trp Leu Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450


<210> SEQ ID NO 194
<211> LENGTH: 452
<212> TYPE: PRT
<213> ORGANISM: Artificial Sequence
<220> FEATURE:
<223> OTHER INFORMATION: heavy chain of FS22-172-004-AA/S70 (without
      LALA)

<400> SEQUENCE: 194

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110
```

-continued

```
Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Asn Tyr Ile Tyr Pro Pro Tyr Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Gly Ala Asp Arg Trp Leu Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450
```

<210> SEQ ID NO 195
<211> LENGTH: 452
<212> TYPE: PRT
<213> ORGANISM: Artificial Sequence
<220> FEATURE:
<223> OTHER INFORMATION: heavy chain of FS22-172-003-AA/S70 (with LALA)

<400> SEQUENCE: 195

```
Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Pro Tyr Ile Ile Pro Pro Tyr Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Gly Ala Asp Arg Trp Leu Glu Gly Asn Val Phe Ser Cys Ser
            420                 425                 430

Val Met His Glu Ala Leu His Asn His Tyr Thr Gln Lys Ser Leu Ser
```

```
        435                 440                 445

Leu Ser Pro Gly
    450


<210> SEQ ID NO 196
<211> LENGTH: 452
<212> TYPE: PRT
<213> ORGANISM: Artificial Sequence
<220> FEATURE:
<223> OTHER INFORMATION: heavy chain of FS22-172-003-AA/S70 (without
      LALA)

<400> SEQUENCE: 196

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335
```

-continued

```
Ile Ser Lys Ala Lys Gly Gln Pro Arg Glu Pro Gln Val Tyr Thr Leu
            340                 345                 350

Pro Pro Ser Arg Asp Glu Leu Pro Tyr Ile Ile Pro Pro Tyr Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Gly Ala Asp Arg Trp Leu Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450


<210> SEQ ID NO 197
<211> LENGTH: 452
<212> TYPE: PRT
<213> ORGANISM: Artificial Sequence
<220> FEATURE:
<223> OTHER INFORMATION: heavy chain of FS22-172-002-AA/S70 (with LALA)

<400> SEQUENCE: 197

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240
```

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val
290 295 300

Ser Val Leu Thr Val Leu His Gln Asp Trp Leu Asn Gly Lys Glu Tyr
305 310 315 320

Lys Cys Lys Val Ser Asn Lys Ala Leu Pro Ala Pro Ile Glu Lys Thr
325 330 335

Ile Ser Lys Ala Lys Gly Gln Pro Arg Glu Pro Gln Val Tyr Thr Leu
340 345 350

Pro Pro Ser Arg Asp Glu Leu Pro Phe Gln Met Pro Pro Tyr Asn Gln
355 360 365

Val Ser Leu Thr Cys Leu Val Lys Gly Phe Tyr Pro Ser Asp Ile Ala
370 375 380

Val Glu Trp Glu Ser Asn Gly Gln Pro Glu Asn Asn Tyr Lys Thr Thr
385 390 395 400

Pro Pro Val Leu Asp Ser Asp Gly Ser Phe Phe Leu Tyr Ser Lys Leu
405 410 415

Thr Val Gly Ala Asp Arg Trp Leu Glu Gly Asn Val Phe Ser Cys Ser
420 425 430

Val Met His Glu Ala Leu His Asn His Tyr Thr Gln Lys Ser Leu Ser
435 440 445

Leu Ser Pro Gly
450

<210> SEQ ID NO 198
<211> LENGTH: 452
<212> TYPE: PRT
<213> ORGANISM: Artificial Sequence
<220> FEATURE:
<223> OTHER INFORMATION: heavy chain of FS22-172-002-AA/S70 (without LALA)

<400> SEQUENCE: 198

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp Ser
20 25 30

Trp Ile His Trp Val Arg Gln Ala Pro Gly Lys Gly Leu Glu Trp Val
35 40 45

Ala Trp Ile Ser Pro Tyr Gly Gly Ser Thr Tyr Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ala Arg Arg His Trp Pro Gly Gly Phe Asp Tyr Trp Gly Gln Gly Thr
100 105 110

Leu Val Thr Val Ser Ala Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Pro Phe Gln Met Pro Pro Tyr Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Gly Ala Asp Arg Trp Leu Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450


<210> SEQ ID NO 199
<211> LENGTH: 452
<212> TYPE: PRT
<213> ORGANISM: Artificial Sequence
<220> FEATURE:
<223> OTHER INFORMATION: FS22-172-002-AA/S70 Heavy chain

<400> SEQUENCE: 199

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45
```

```
Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Pro Phe Gln Met Pro Pro Tyr Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Gly Ala Asp Arg Trp Leu Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450
```

<210> SEQ ID NO 200
<211> LENGTH: 452
<212> TYPE: PRT
<213> ORGANISM: Artificial Sequence
<220> FEATURE:
<223> OTHER INFORMATION: FS22-172-002-AA/S70 Heavy chain (with LALA)

<400> SEQUENCE: 200

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Pro Phe Gln Met Pro Pro Tyr Asn Gln
        355                 360                 365
```

```
Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Gly Ala Asp Arg Trp Leu Glu Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450


<210> SEQ ID NO 201
<211> LENGTH: 452
<212> TYPE: PRT
<213> ORGANISM: Artificial Sequence
<220> FEATURE:
<223> OTHER INFORMATION: FS22-053-011-AA/S70 Heavy chain (without LALA)

<400> SEQUENCE: 201

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270
```

-continued

```
Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Asn Pro Pro Tyr Leu Phe Ser Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Tyr Trp Arg Trp Thr Asp Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450


<210> SEQ ID NO 202
<211> LENGTH: 452
<212> TYPE: PRT
<213> ORGANISM: Artificial Sequence
<220> FEATURE:
<223> OTHER INFORMATION: FS22-053-011-AA/S70 Heavy chain (with LALA)

<400> SEQUENCE: 202

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175
```

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Asn Pro Pro Tyr Leu Phe Ser Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Tyr Trp Arg Trp Thr Asp Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450


<210> SEQ ID NO 203
<211> LENGTH: 452
<212> TYPE: PRT
<213> ORGANISM: Artificial Sequence
<220> FEATURE:
<223> OTHER INFORMATION: FS22-053-008-AA/S70 Heavy chain (with LALA)

<400> SEQUENCE: 203

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80
```

-continued

```
Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Asn Pro Pro Tyr Leu Phe Ser Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Glu His Thr Arg Trp Leu Asp Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450
```

<210> SEQ ID NO 204
<211> LENGTH: 452
<212> TYPE: PRT
<213> ORGANISM: Artificial Sequence
<220> FEATURE:
<223> OTHER INFORMATION: FS22-053-008-AA/S70 Heavy chain (without LALA)

<400> SEQUENCE: 204

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Asn Pro Pro Tyr Leu Phe Ser Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu

```
                405                 410                 415

Thr Val Glu His Thr Arg Trp Leu Asp Gly Asn Val Phe Ser Cys Ser
            420                 425                 430

Val Met His Glu Ala Leu His Asn His Tyr Thr Gln Lys Ser Leu Ser
        435                 440                 445

Leu Ser Pro Gly
    450


<210> SEQ ID NO 205
<211> LENGTH: 447
<212> TYPE: PRT
<213> ORGANISM: Artificial Sequence
<220> FEATURE:
<223> OTHER INFORMATION: FS22m-063-AA/F2 Heavy chain (without LALA)

<400> SEQUENCE: 205

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Asn Trp Gly Ser Tyr Phe Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
```

```
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Pro Tyr Trp Ser Tyr Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Met Asn Tyr
                405                 410                 415

Arg Trp Glu Leu Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 206
<211> LENGTH: 447
<212> TYPE: PRT
<213> ORGANISM: Artificial Sequence
<220> FEATURE:
<223> OTHER INFORMATION: FS22m-063-AA/F2 Heavy chain (without LALA)

<400> SEQUENCE: 206

Glu Val Gln Leu Val Gln Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Glu Asn Trp Gly Ser Tyr Phe Asp Leu Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
```

```
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Pro Tyr Trp Ser Tyr Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Met Asn Tyr
                405                 410                 415

Arg Trp Glu Leu Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 207
<211> LENGTH: 214
<212> TYPE: PRT
<213> ORGANISM: Artificial Sequence
<220> FEATURE:
<223> OTHER INFORMATION: FS22m-063-AA/F2 Light chain

<400> SEQUENCE: 207

Asp Ile Val Met Thr Gln Ser Pro Ser Thr Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Arg Ala Pro Lys Val Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Trp
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
```

145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 208
<211> LENGTH: 447
<212> TYPE: PRT
<213> ORGANISM: Artificial Sequence
<220> FEATURE:
<223> OTHER INFORMATION: FS22m-063/FS28m-228 Heavy chain (without LALA)

<400> SEQUENCE: 208

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Phe Met Val Trp Val Arg Gln Ala Pro Gly Lys Gly Leu Glu Trp Val
35 40 45

Ser Met Ile Ser Pro Lys Ser Ser Asn Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Trp Phe Thr Pro Ala Arg Phe Asp Tyr Trp Gly Gln Gly Thr
100 105 110

Leu Val Thr Val Ser Ser Ala Ser Thr Lys Gly Pro Ser Val Phe Pro
115 120 125

Leu Ala Pro Ser Ser Lys Ser Thr Ser Gly Gly Thr Ala Ala Leu Gly
130 135 140

Cys Leu Val Lys Asp Tyr Phe Pro Glu Pro Val Thr Val Ser Trp Asn
145 150 155 160

Ser Gly Ala Leu Thr Ser Gly Val His Thr Phe Pro Ala Val Leu Gln
165 170 175

Ser Ser Gly Leu Tyr Ser Leu Ser Ser Val Val Thr Val Pro Ser Ser
180 185 190

Ser Leu Gly Thr Gln Thr Tyr Ile Cys Asn Val Asn His Lys Pro Ser
195 200 205

Asn Thr Lys Val Asp Lys Lys Val Glu Pro Lys Ser Cys Asp Lys Thr
210 215 220

His Thr Cys Pro Pro Cys Pro Ala Pro Glu Leu Leu Gly Gly Pro Ser
225 230 235 240

Val Phe Leu Phe Pro Pro Lys Pro Lys Asp Thr Leu Met Ile Ser Arg
245 250 255

Thr Pro Glu Val Thr Cys Val Val Val Asp Val Ser His Glu Asp Pro
260 265 270

Glu Val Lys Phe Asn Trp Tyr Val Asp Gly Val Glu Val His Asn Ala
275 280 285

Lys Thr Lys Pro Arg Glu Glu Gln Tyr Asn Ser Thr Tyr Arg Val Val

-continued

```
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Pro Tyr Trp Ser Tyr Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Met Asn Tyr
                405                 410                 415

Arg Trp Glu Leu Gly Asn Val Phe Ser Cys Ser Val Met His Glu Ala
            420                 425                 430

Leu His Asn His Tyr Thr Gln Lys Ser Leu Ser Leu Ser Pro Gly
        435                 440                 445


<210> SEQ ID NO 209
<211> LENGTH: 214
<212> TYPE: PRT
<213> ORGANISM: Artificial Sequence
<220> FEATURE:
<223> OTHER INFORMATION: light chain of FS22-172-004-AA/S70

<400> SEQUENCE: 209

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

-continued

210

<210> SEQ ID NO 210
<211> LENGTH: 8
<212> TYPE: PRT
<213> ORGANISM: Artificial Sequence
<220> FEATURE:
<223> OTHER INFORMATION: FS22-172-003-AA/E12v2 and FS22-053-008-AA/E12v2
VH domain HCDR1 (IMGT)

<400> SEQUENCE: 210

```
Gly Tyr Pro Phe Thr Ser Tyr Gly
1               5
```

<210> SEQ ID NO 211
<211> LENGTH: 5
<212> TYPE: PRT
<213> ORGANISM: Artificial Sequence
<220> FEATURE:
<223> OTHER INFORMATION: FS22-172-003-AA/E12v2 and FS22-053-008-AA/E12v2
VH domain HCDR1 (Kabat)

<400> SEQUENCE: 211

```
Ser Tyr Gly Ile Ser
1               5
```

<210> SEQ ID NO 212
<211> LENGTH: 8
<212> TYPE: PRT
<213> ORGANISM: Artificial Sequence
<220> FEATURE:
<223> OTHER INFORMATION: FS22-172-003-AA/E12v2 and FS22-053-008-AA/E12v2
VH domain HCDR2 (IMGT)

<400> SEQUENCE: 212

```
Ile Ser Ala Tyr Ser Gly Gly Thr
1               5
```

<210> SEQ ID NO 213
<211> LENGTH: 17
<212> TYPE: PRT
<213> ORGANISM: Artificial Sequence
<220> FEATURE:
<223> OTHER INFORMATION: FS22-172-003-AA/E12v2 and FS22-053-008-AA/E12v2
VH domain HCDR2 (Kabat)

<400> SEQUENCE: 213

```
Trp Ile Ser Ala Tyr Ser Gly Gly Thr Asn Tyr Ala Gln Lys Leu Gln
1               5                   10                  15

Gly
```

<210> SEQ ID NO 214
<211> LENGTH: 16
<212> TYPE: PRT
<213> ORGANISM: Artificial Sequence
<220> FEATURE:
<223> OTHER INFORMATION: FS22-172-003-AA/E12v2 and FS22-053-008-AA/E12v2
VH domain HCDR3 (IMGT)

<400> SEQUENCE: 214

```
Ala Arg Asp Leu Phe Pro Thr Ile Phe Gly Val Ser Tyr Tyr Tyr Tyr
1               5                   10                  15
```

<210> SEQ ID NO 215
<211> LENGTH: 14
<212> TYPE: PRT
<213> ORGANISM: Artificial Sequence
<220> FEATURE:
<223> OTHER INFORMATION: FS22-172-003-AA/E12v2 and FS22-053-008-AA/E12v2
VH domain HCDR3 (Kabat)

<400> SEQUENCE: 215

Asp Leu Phe Pro Thr Ile Phe Gly Val Ser Tyr Tyr Tyr Tyr
1 5 10

<210> SEQ ID NO 216
<211> LENGTH: 123
<212> TYPE: PRT
<213> ORGANISM: Artificial Sequence
<220> FEATURE:
<223> OTHER INFORMATION: FS22-172-003-AA/E12v2 and FS22-053-008-AA/E12v2
VH domain

<400> SEQUENCE: 216

Glu Val Gln Leu Val Gln Ser Gly Ala Glu Val Lys Arg Pro Gly Ala
1 5 10 15

Ser Val Lys Val Ser Cys Lys Ala Ser Gly Tyr Pro Phe Thr Ser Tyr
20 25 30

Gly Ile Ser Trp Val Arg Gln Ala Pro Gly Gln Gly Leu Glu Trp Met
35 40 45

Gly Trp Ile Ser Ala Tyr Ser Gly Gly Thr Asn Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Asp Leu Phe Pro Thr Ile Phe Gly Val Ser Tyr Tyr Tyr Tyr
100 105 110

Trp Gly Gln Gly Thr Leu Val Thr Val Ser Ser
115 120

<210> SEQ ID NO 217
<211> LENGTH: 6
<212> TYPE: PRT
<213> ORGANISM: Artificial Sequence
<220> FEATURE:
<223> OTHER INFORMATION: FS22-172-003-AA/E12v2 and FS22-053-008-AA/E12v2
VL domain LCDRR1 (IMGT)

<400> SEQUENCE: 217

Gln Ser Ile Gly Asn Arg
1 5

<210> SEQ ID NO 218
<211> LENGTH: 11
<212> TYPE: PRT
<213> ORGANISM: Artificial Sequence
<220> FEATURE:
<223> OTHER INFORMATION: FS22-172-003-AA/E12v2 and FS22-053-008-AA/E12v2
VL domain LCDR1 (Kabat)

<400> SEQUENCE: 218

Arg Ala Ser Gln Ser Ile Gly Asn Arg Leu Ala
1 5 10

<210> SEQ ID NO 219
<211> LENGTH: 3
<212> TYPE: PRT
<213> ORGANISM: Artificial Sequence
<220> FEATURE:
<223> OTHER INFORMATION: FS22-172-003-AA/E12v2 and FS22-053-008-AA/E12v2

VL domain LCDR2 (IMGT)

<400> SEQUENCE: 219

Glu Ala Ser
1

<210> SEQ ID NO 220
<211> LENGTH: 7
<212> TYPE: PRT
<213> ORGANISM: Artificial Sequence
<220> FEATURE:
<223> OTHER INFORMATION: FS22-172-003-AA/E12v2 and FS22-053-008-AA/E12v2 VL domain LCDR2 (Kabat)

<400> SEQUENCE: 220

Glu Ala Ser Thr Ser Glu Thr
1 5

<210> SEQ ID NO 221
<211> LENGTH: 9
<212> TYPE: PRT
<213> ORGANISM: Artificial Sequence
<220> FEATURE:
<223> OTHER INFORMATION: FS22-172-003-AA/E12v2 and FS22-053-008-AA/E12v2 VL domain LCDR3 (IMGT)

<400> SEQUENCE: 221

Gln Gln Ser Tyr Ser Thr Pro Tyr Thr
1 5

<210> SEQ ID NO 222
<211> LENGTH: 9
<212> TYPE: PRT
<213> ORGANISM: Artificial Sequence
<220> FEATURE:
<223> OTHER INFORMATION: FS22-172-003-AA/E12v2 and FS22-053-008-AA/E12v2 VL domain LCDR3 (Kabat)

<400> SEQUENCE: 222

Gln Gln Ser Tyr Ser Thr Pro Tyr Thr
1 5

<210> SEQ ID NO 223
<211> LENGTH: 107
<212> TYPE: PRT
<213> ORGANISM: Artificial Sequence
<220> FEATURE:
<223> OTHER INFORMATION: FS22-172-003-AA/E12v2 and FS22-053-008-AA/E12v2 VL domain

<400> SEQUENCE: 223

Asp Ile Gln Met Thr Gln Ser Pro Ser Thr Leu Ser Ala Ser Val Arg
1 5 10 15

Asp Arg Val Ile Ile Thr Cys Arg Ala Ser Gln Ser Ile Gly Asn Arg
20 25 30

Leu Ala Trp Tyr Gln His Lys Pro Gly Lys Ala Pro Lys Leu Leu Ile
35 40 45

Tyr Glu Ala Ser Thr Ser Glu Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Tyr
85 90 95

Thr Phe Gly Gln Gly Thr Lys Leu Glu Ile Lys 100 105

<210> SEQ ID NO 224
<211> LENGTH: 457
<212> TYPE: PRT
<213> ORGANISM: Artificial Sequence
<220> FEATURE:
<223> OTHER INFORMATION: Heavy chain FS22-172-003-AA/E12v2

<400> SEQUENCE: 224

Glu Val Gln Leu Val Gln Ser Gly Ala Glu Val Lys Arg Pro Gly Ala
1 5 10 15

Ser Val Lys Val Ser Cys Lys Ala Ser Gly Tyr Pro Phe Thr Ser Tyr
20 25 30

Gly Ile Ser Trp Val Arg Gln Ala Pro Gly Gln Gly Leu Glu Trp Met
35 40 45

Gly Trp Ile Ser Ala Tyr Ser Gly Gly Thr Asn Tyr Ala Gln Lys Leu
50 55 60

Gln Gly Arg Val Thr Met Thr Thr Asp Thr Ser Thr Ser Thr Ala Tyr
65 70 75 80

Met Glu Leu Arg Ser Leu Arg Ser Asp Asp Thr Ala Val Tyr Tyr Cys
85 90 95

Ala Arg Asp Leu Phe Pro Thr Ile Phe Gly Val Ser Tyr Tyr Tyr Tyr
100 105 110

Trp Gly Gln Gly Thr Leu Val Thr Val Ser Ser Ala Ser Thr Lys Gly
115 120 125

Pro Ser Val Phe Pro Leu Ala Pro Ser Ser Lys Ser Thr Ser Gly Gly
130 135 140

Thr Ala Ala Leu Gly Cys Leu Val Lys Asp Tyr Phe Pro Glu Pro Val
145 150 155 160

Thr Val Ser Trp Asn Ser Gly Ala Leu Thr Ser Gly Val His Thr Phe
165 170 175

Pro Ala Val Leu Gln Ser Ser Gly Leu Tyr Ser Leu Ser Ser Val Val
180 185 190

Thr Val Pro Ser Ser Ser Leu Gly Thr Gln Thr Tyr Ile Cys Asn Val
195 200 205

Asn His Lys Pro Ser Asn Thr Lys Val Asp Lys Lys Val Glu Pro Lys
210 215 220

Ser Cys Asp Lys Thr His Thr Cys Pro Pro Cys Pro Ala Pro Glu Ala
225 230 235 240

Ala Gly Gly Pro Ser Val Phe Leu Phe Pro Pro Lys Pro Lys Asp Thr
245 250 255

Leu Met Ile Ser Arg Thr Pro Glu Val Thr Cys Val Val Val Asp Val
260 265 270

Ser His Glu Asp Pro Glu Val Lys Phe Asn Trp Tyr Val Asp Gly Val
275 280 285

Glu Val His Asn Ala Lys Thr Lys Pro Arg Glu Glu Gln Tyr Asn Ser
290 295 300

Thr Tyr Arg Val Val Ser Val Leu Thr Val Leu His Gln Asp Trp Leu
305 310 315 320

Asn Gly Lys Glu Tyr Lys Cys Lys Val Ser Asn Lys Ala Leu Pro Ala
325 330 335

Pro Ile Glu Lys Thr Ile Ser Lys Ala Lys Gly Gln Pro Arg Glu Pro
340 345 350

Gln Val Tyr Thr Leu Pro Pro Ser Arg Asp Glu Leu Pro Tyr Ile Ile

```
        355                 360                 365

Pro Pro Tyr Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Gly Ala Asp Arg Trp Leu Glu Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly
    450                 455


<210> SEQ ID NO 225
<211> LENGTH: 214
<212> TYPE: PRT
<213> ORGANISM: Artificial Sequence
<220> FEATURE:
<223> OTHER INFORMATION: Light chain FS22-172-003-AA/E12v2 and Light
      chain FS22-053-008-AA/E12v2

<400> SEQUENCE: 225

Asp Ile Gln Met Thr Gln Ser Pro Ser Thr Leu Ser Ala Ser Val Arg
1               5                   10                  15

Asp Arg Val Ile Ile Thr Cys Arg Ala Ser Gln Ser Ile Gly Asn Arg
            20                  25                  30

Leu Ala Trp Tyr Gln His Lys Pro Gly Lys Ala Pro Lys Leu Leu Ile
        35                  40                  45

Tyr Glu Ala Ser Thr Ser Glu Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 226
<211> LENGTH: 457
<212> TYPE: PRT
<213> ORGANISM: Artificial Sequence
<220> FEATURE:
```

<223> OTHER INFORMATION: Heavy chain FS22-053-008-AA/E12v2

<400> SEQUENCE: 226

```
Glu Val Gln Leu Val Gln Ser Gly Ala Glu Val Lys Arg Pro Gly Ala
1               5                   10                  15

Ser Val Lys Val Ser Cys Lys Ala Ser Gly Tyr Pro Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Ser Gly Gly Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Leu Phe Pro Thr Ile Phe Gly Val Ser Tyr Tyr Tyr Tyr
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Ala
225                 230                 235                 240

Ala Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Asp Glu Leu Asn Pro Pro Tyr
        355                 360                 365

Leu Phe Ser Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400
```

-continued

```
Asn Tyr Lys Thr Thr Pro Pro Val Leu Asp Ser Asp Gly Ser Phe Phe
                405                 410                 415

Leu Tyr Ser Lys Leu Thr Val Asp Tyr Trp Arg Trp Leu Glu Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly
    450                 455


<210> SEQ ID NO 227
<211> LENGTH: 8
<212> TYPE: PRT
<213> ORGANISM: Artificial Sequence
<220> FEATURE:
<223> OTHER INFORMATION: FS28-256-271 VH domain CDR1 (IMGT)

<400> SEQUENCE: 227

Gly Phe Thr Phe Thr His Thr Tyr
1               5


<210> SEQ ID NO 228
<211> LENGTH: 5
<212> TYPE: PRT
<213> ORGANISM: Artificial Sequence
<220> FEATURE:
<223> OTHER INFORMATION: FS28-256-271 VH domain CDR1 (Kabat)

<400> SEQUENCE: 228

His Thr Tyr Met Ser
1               5


<210> SEQ ID NO 229
<211> LENGTH: 8
<212> TYPE: PRT
<213> ORGANISM: Artificial Sequence
<220> FEATURE:
<223> OTHER INFORMATION: FS28-256-271 VH domain CDR2 (IMGT)

<400> SEQUENCE: 229

Ile Ser Pro Thr Tyr Ser Thr Thr
1               5


<210> SEQ ID NO 230
<211> LENGTH: 17
<212> TYPE: PRT
<213> ORGANISM: Artificial Sequence
<220> FEATURE:
<223> OTHER INFORMATION: FS28-256-271 VH domain CDR2 (Kabat)

<400> SEQUENCE: 230

Ala Ile Ser Pro Thr Tyr Ser Thr Thr Asn Tyr Ala Asp Ser Val Lys
1               5                   10                  15

Gly


<210> SEQ ID NO 231
<211> LENGTH: 12
<212> TYPE: PRT
<213> ORGANISM: Artificial Sequence
<220> FEATURE:
<223> OTHER INFORMATION: FS28-256-271 VH domain CDR3 (IMGT)

<400> SEQUENCE: 231

Ala Arg Tyr Asn Ala Tyr His Ala Ala Leu Asp Tyr
1               5                   10
```

<210> SEQ ID NO 232
<211> LENGTH: 10
<212> TYPE: PRT
<213> ORGANISM: Artificial Sequence
<220> FEATURE:
<223> OTHER INFORMATION: FS28-256-271 VH domain CDR3 (Kabat)

<400> SEQUENCE: 232

Tyr Asn Ala Tyr His Ala Ala Leu Asp Tyr
1               5                   10

<210> SEQ ID NO 233
<211> LENGTH: 119
<212> TYPE: PRT
<213> ORGANISM: Artificial Sequence
<220> FEATURE:
<223> OTHER INFORMATION: FS28-256-271 VH domain

<400> SEQUENCE: 233

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Thr His Thr
            20                  25                  30

Tyr Met Ser Trp Val Arg Gln Ala Pro Gly Lys Gly Leu Glu Trp Val
        35                  40                  45

Ser Asn Ile Ser Pro Thr Tyr Ser Thr Thr Asn Tyr Ala Asp Ser Val
    50                  55                  60

Lys Gly Arg Phe Thr Ile Ser Arg Asp Asn Asn Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Asn Ala Tyr His Ala Ala Leu Asp Tyr Trp Gly Gln Gly
            100                 105                 110

Thr Leu Val Thr Val Ser Ser
        115

<210> SEQ ID NO 234
<211> LENGTH: 7
<212> TYPE: PRT
<213> ORGANISM: Artificial Sequence
<220> FEATURE:
<223> OTHER INFORMATION: FS28-256-271 VL domain LCDR1 (IMGT)

<400> SEQUENCE: 234

Gln Ser Val Ser Ser Ser Tyr
1               5

<210> SEQ ID NO 235
<211> LENGTH: 12
<212> TYPE: PRT
<213> ORGANISM: Artificial Sequence
<220> FEATURE:
<223> OTHER INFORMATION: FS28-256-271 VL domain LCDR1 (Kabat)

<400> SEQUENCE: 235

Arg Ala Ser Gln Ser Val Ser Ser Ser Tyr Leu Ala
1               5                   10

<210> SEQ ID NO 236
<211> LENGTH: 3
<212> TYPE: PRT
<213> ORGANISM: Artificial Sequence
<220> FEATURE:

-continued

<223> OTHER INFORMATION: FS28-256-271 VL domain LCDR2 (IMGT)

<400> SEQUENCE: 236

Gly Ala Ser
1

<210> SEQ ID NO 237
<211> LENGTH: 7
<212> TYPE: PRT
<213> ORGANISM: Artificial Sequence
<220> FEATURE:
<223> OTHER INFORMATION: FS28-256-271 VL domain LCDR2 (Kabat)

<400> SEQUENCE: 237

Gly Ala Ser Ser Arg Ala Thr
1 5

<210> SEQ ID NO 238
<211> LENGTH: 9
<212> TYPE: PRT
<213> ORGANISM: Artificial Sequence
<220> FEATURE:
<223> OTHER INFORMATION: FS28-256-271 VL domain LCDR3 (IMGT)

<400> SEQUENCE: 238

Gln Gln Thr Val Pro Tyr Pro Tyr Thr
1 5

<210> SEQ ID NO 239
<211> LENGTH: 9
<212> TYPE: PRT
<213> ORGANISM: Artificial Sequence
<220> FEATURE:
<223> OTHER INFORMATION: FS28-256-271 VL domain LCDR3 (Kabat)

<400> SEQUENCE: 239

Gln Gln Thr Val Pro Tyr Pro Tyr Thr
1 5

<210> SEQ ID NO 240
<211> LENGTH: 108
<212> TYPE: PRT
<213> ORGANISM: Artificial Sequence
<220> FEATURE:
<223> OTHER INFORMATION: FS28-256-271 VL domain

<400> SEQUENCE: 240

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Thr Val Pro Tyr Pro
85 90 95

Tyr Thr Phe Gly Gln Gly Thr Lys Val Glu Ile Lys
100 105

FC BINDING FRAGMENTS COMPRISING A CD137 ANTIGEN-BINDING SITE

RELATED APPLICATION

This application is a national stage filing under 35 U.S.C. 371 of International Patent Application Serial No. PCT/EP2019/068803, filed Jul. 12, 2019, the entire contents of which is incorporated herein by reference in its entirety.

FIELD OF THE INVENTION

The invention relates to specific binding members that bind CD137. The specific binding members comprise a CD137 antigen-binding site located in a constant domain of the specific binding member and find application in the treatment of cancer and infectious diseases, for example.

BACKGROUND TO THE INVENTION

Cell signalling is an essential part of the life of all organisms and normally involves cell surface receptors that interact with soluble or surface expressed ligands. This interaction results in changes to the receptor, the ligand or both. For example, ligand binding can induce conformational changes in the receptors causing them to cluster together into dimers or oligomers. This clustering effect then results in activation of intracellular signalling pathways. There are numerous receptors that are activated in this way, including members of the tumour necrosis factor receptor superfamily (TNFRSF), such as CD137.

CD137 (4-1 BB; TNFRSF9) is a co-stimulatory molecule of the tumour necrosis factor receptor superfamily (TNFRSF). CD137 is widely known to be upregulated on $CD8^+$ T cells following activation, and can also be expressed on activated $CD4^+$ helper T cells, B cells, regulatory T cells, natural killer (NK) cells, natural killer T (NKT) cells and dendritic cells (DCs) (Bartkowiak & Curran, 2015). The primary functional role of CD137 in enhancing T cell cytotoxicity was first described in 1997 (Shuford et al., 1997), and soon thereafter anti-CD137 mAbs were proposed as anti-cancer therapeutics.

CD137 is a transmembrane protein with four extracellular cysteine-rich domains, referred to as CRD1-4, and a cytoplasmic region responsible for CD137 signalling. The ligand for CD137 is CD137L. Although no crystal structure exists for the CD137/CD137L complex, it is predicted that CD137 forms a trimer/trimer complex with CD137L (Won et al., 2010). Engagement of CD137L results in receptor trimer formation and subsequent clustering of multiple receptor trimers, and leads to the activation of the CD137 signalling cascade. This signalling cascade provides a survival signal to T cells against activation-induced cell death (Hurtado et al., 1997) thereby playing a critical role in sustaining effective T cell immune responses and generating immunological memory (Bartkowiak & Curran, 2015).

The role of CD137 in leukocyte biology is generally well understood with a clear biological rationale behind its role in tumour immunology. CD137 is expressed by activated T cells and has been used as a marker to identify antigen-specific $CD4^+$ and $CD8^+$ T cells. Typically, expression of CD137 is higher on $CD8^+$ T cells than $CD4^+$ T cells (Wen et al., 2002). In the case of $CD8^+$ T cells, proliferation, survival and cytotoxic effector function via the production of interferon gamma and interleukin 2 have been attributed to CD137 clustering. CD137 clustering also contributes to the differentiation and maintenance of memory $CD8^+$ T cells. In some subsets of $CD4^+$ T cells, CD137 clustering similarly leads to proliferation and activation and results in the release of cytokines such as interleukin 2 (Makkouk et al., 2016).

Natural killer (NK)-mediated antibody-dependent cellular cytotoxicity (ADCC) via tumour-targeting mAbs has been demonstrated to be enhanced as a consequence of CD137 stimulation via agonistic anti-CD137 monoclonal antibodies in vitro and in vivo (Bartkowiak & Curran, 2015). NK cells bind antibodies via their Fc receptor and, depending on the antibody isotype, this can lead to NK cell activation, eliciting cytotoxic granule release and the lysis of target cells (Kohrt et al., 2012). Kohrt and colleagues demonstrated that an anti-CD137 agonistic antibody enhanced the antitumor activity of therapeutic antibodies rituximab, trastuzumab, and cetuximab by enhancing ADCC when dosed in combination therewith (Kohrt et al., 2014; Kohrt et al., 2011). In addition, human NK cells upregulate expression of CD137 after encountering cell-bound antibodies via their FcγR. Subsequent stimulation of these NK cells with an anti-CD137 antibody has been shown to enhance their ADCC against tumour cells (Chester et al., 2015; Chester et al., 2016).

B lymphocytes also express CD137 upon activation. Binding of CD137 ligand to CD137 enhances B cell proliferation, survival and cytokine production. CD137 expression is also induced on normal and malignant human B cells following binding of CD40 to its ligand CD154 (CD40 ligand), resulting in enhanced B cell survival if CD137 is subsequently activated. (Vinay and Kwon, 2011).

CD137 has also been demonstrated to be expressed on tumour-reactive subsets of tumour-infiltrating lymphocytes (TILs). CD137 monotherapy has been shown to be efficacious in several preclinical immunogenic tumour models such as MC38, CT26 and B cell lymphomas. Combination of CD137 engagement with other anti-cancer agents such as chemotherapy, cytokines and other checkpoint regulators has been demonstrated to result in enhanced growth reduction of established tumours. Specifically, combination of anti-CD137 antibodies with anti-CD20, anti-EGFR, and anti-HER-2 antibodies has been shown to result in a synergistic effect on tumour growth reduction in various preclinical xenograft models (Kohrt et al., 2014; Kohrt et al., 2012; Kohrt et al., 2011).

Coupling a tumour-targeted monoclonal antibody therapy with treatment with an anti-CD137 agonist antibody has shown promising results in preclinical models for lymphoma (Kohrt et al., 2011), head and neck cancer, colorectal cancer (Kohrt et al., 2014) and breast cancer (Kohrt et al., 2012). A number of tumour-targeting monoclonal antibodies have also been tested in combination with CD137 agonist antibodies in the clinic, including the anti-CD20 mAb rituximab (NCT01307267, NCT02951156), anti-EGFR mAb cetuximab (NCT02110082) and anti-CS1 mAb elotuzumab (NCT02252263). However, clinical development has been slowed due to dose-limiting high-grade liver inflammation associated with CD137 agonist antibody treatment. Urelumab (BMS-663513), a non-ligand blocking human IgG4 isotype antibody (Chester et al, 2018), was the first anti-CD137 antibody to enter clinical trials but these were halted after significant, on target, dose-dependent liver toxicity was observed (Chester et al., 2018). More recently, clinical trials of urelumab in the treatment of solid cancers was recommenced in which urelumab treatment was combined with radiotherapy (NCT03431948) or with other therapeutic antibodies, such as rituximab (NCT01775631), cetuximab (NCT02110082), anti-PD-1 antibody nivolumab (NCT02253992, NCT02534506, NCT02845323), and a combination of nivolumab and the anti-LAG-3 antibody BMS986016 (NCT02658981). However, to reduce liver toxicity associated with urelumab treatment, dosing of urelumab in these trials had to be limited and efficacy results were disappointing (Chester et al., 2018).

No dose-limiting toxicity has been observed with Pfizer's anti-CD137 antibody utomilumab (PF-05082566), a human IgG2 isotype antibody, in the dose range 0.03 mg/kg up to 10 mg/kg in Phase I clinical trials of advanced cancer (Chester et al. 2016; Segal et al., 2018). However, the overall objective response rate with this antibody was only 3.8% in patients with solid tumours, potentially indicating that utomilumab has a weaker potency and clinical efficacy than urelumab, whilst having a more favourable safety profile (Chester et al., 2018; Segal et al., 2018). Utomilumab has been tested in combination with radiotherapy (NCT03217747) or chemotherapy, as well as in combination with other antibody therapies, including anti-PD-L1 antibody avelumab (NCT02554812), and anti-PD-1 antibody pembrolizumab (NCT02179918), to assess the safety, tolerability, dose-limiting toxicities (DLTs), maximum tolerated dose (MTD) and efficacy of the different treatment combinations. These trials are ongoing with early results showing no DLTs for doses up to 5 mg/kg and a 26% patient response rate for the combination of utomilumab and pembrolizumab. Triple combinations of utomilumab with avelumab and other immunooncology therapies are also being tested (NCT02554812, NCT03217747).

A number of bispecific molecules targeting CD137 are also in early stage development, many of which are derived from non-antibody-based scaffold or fusion protein technology. Development of a bispecific molecule targeting CD137 and FAPalpha using DARPin scaffold protein based technology has been reported (Link et al., 2018; Reichen et al., 2018). T cell activation via tumour targeting of CD137 agonism using HER2- and EphA2-targeted DART molecules has also been shown (Liu et al., 2017). CD137L fusion proteins which target tumours via FAPalpha or CD19 in solid tumours and lymphomas are also being developed. The most clinically advanced CD137 bispecific (and the only one containing a full-length antibody) is PRS-343, a CD137/HER2 bispecific molecule. In this molecule, CD137 is bound via an artificial binding protein (anticalin) attached to the Fc portion of the HER2-targeting antibody trastuzumab in IgG4 format. PRS-343 has been reported to provide tumour target-dependent activation of CD137 on lymphocytes at sites where HER2 is overexpressed in a humanised mouse model, but no improvement in tumour growth inhibition over trastuzumab treatment alone was observed (Hinner et al., 2016 and WO 2016/177802 A1). PRS-343 has recently entered Phase I clinical trials for treatment of a range of solid tumours to assess its safety, tolerability and efficacy (NCT03330561).

STATEMENTS OF INVENTION

As explained in the background section above, clinical development of CD137 agonist molecules has been held back due to treatment being either associated with dose-limiting high-grade liver inflammation (urelumab) or low clinical efficacy (utomilumab).

The present inventors recognised that there is a need in the art for CD137 agonist molecules which exhibit high activity but are not associated with dose-limiting liver inflammation. Such molecules could be administered to individuals at doses which optimize the potency and therefore efficacy of the molecule, and could be employed in the treatment of cancer as immunotherapeutic agents, for example, or in the treatment of infectious diseases.

Without wishing to be bound by theory, it is thought that T cells present in the liver may have the potential to be activated by anti-CD137 agonist molecules, leading to liver inflammation. CD8+ T cells have been shown to promote liver inflammation and apoptosis after sepsis/viral infection (Wesche-Soldato et al., 2007). Anti-CD137 agonist antibody therapy in mice has been shown to result in CD137-dependent T cell infiltration into the liver (Dubrot J et al., 2010). The results from these studies, when taken together, indicate that anti-CD137 agonist antibodies with high activity, such as urelumab, may cause infiltration of activated CD8+ T cells into the liver, thereby leading to liver inflammation. Alternatively, the dose-limiting liver toxicity observed with urelumab treatment may be due to the particular epitope bound by this antibody.

The present inventors performed an extensive selection and affinity maturation program to isolate a panel of antigen-binding Fc fragments (also referred to as "Fcabs" herein) which comprise a CD137 binding site in their CH3 domain and bind to dimeric CD137 with a higher affinity than to monomeric CD137.

'Affinity' as referred to herein may refer to the strength of the binding interaction between an antibody molecule and its cognate antigen as measured by $K_D$. As would be readily apparent to the skilled person, where the antibody molecule is capable of forming multiple binding interactions with an antigen (e.g. where the antibody molecule is capable of binding the antigen bivalently and, optionally, the antigen is dimeric) the affinity, as measured by $K_D$, may also be influenced by avidity, whereby avidity refers to the overall strength of an antibody-antigen complex.

Expression of CD137 by T cells is upregulated on activation. Without wishing to be bound by theory, it is thought that due to the high expression of CD137 on activated T cells, CD137 will be in the form of dimers, trimers and higher-order multimers on the surface of such cells. In contrast, naïve immune cells, such as naïve T cells, express low or negligible levels of CD137 on their cell surface and any CD137 present is therefore likely to be in monomeric form. It is therefore expected that Fcabs which bind to dimeric CD137 with higher affinity than to monomeric CD137, will preferentially bind to activated immune cells, such as activated T cells, as opposed to naïve immune cells, for example.

The Fcabs of the invention were also capable of binding dimeric cynomolgus CD137. This is beneficial as it permits toxicology and efficacy testing to be performed in cynomolgus monkeys during preclinical development. This is of particular advantage in the context of antibody molecules binding to CD137, given the liver inflammation seen with some anti-CD137 antibodies. Two of the Fcabs isolated, FS22-053-014 and FS22-053-017 also bound to mouse CD137. This is advantageous as it allows the same Fcab to be tested in mice before administration to cynomolgus monkeys or humans. Under normal circumstances an Fcab which binds to mouse CD137 is needed for this purpose.

The present inventors surprisingly found that the anti-CD137 Fcab molecules isolated which preferentially bound to dimeric rather than monomeric CD137 and were capable of being affinity matured all comprised the motif PPY, as well as a 5 amino acid insertion, in the AB loop of their CH3 domain. Another lineage of anti-CD137 Fcabs isolated following the initial library screen did not have these features and were not capable of being affinity matured and thus not pursued further. Without wishing to be bound by theory, it is thought that the presence of the PPY motif may promote the formation of an extended antigen-binding region by forming a more rigid or exposed loop structure as a result of the limited flexibility of proline residues. Alternatively, the PPY sequence may represent a specific conserved motif involved in binding to CD137, as proline rich sequences have been demonstrated to bind to aromatic sequences in SH3 domain proteins, for example. Further, since the PPY conserved sequence has been selected for independently in two separate lineages of Fcabs, it may be important for epitope binding on CD137. Additionally, a conserved LE or LD sequence was present in the EF loops of the CH3 domain of most of the Fcabs isolated, suggesting that this amino acid sequence may also be important for CD137 binding.

As described in the background section above, initial ligation of a CD137 ligand to its receptor, CD137, initiates a chain of events that leads to CD137 trimerisation, followed by receptor clustering, activation the NFkB intracellular signalling pathway and subsequent immune cell activation. For a therapeutic agent to efficiently activate CD137, several CD137 monomers need to be bridged together in a way that mimics a trimeric ligand.

Utomilumab is an IgG2 molecule and is dependent on crosslinking by Fcγ receptors for its agonist activity. Urelumab is an IgG4 molecule with constitutive activity and so does not require crosslinking by Fcγ receptors for activity, although its agonist activity is enhanced on crosslinking by some Fcγ receptors. Fcγ receptors are found throughout the human body. The immune cell activation activity of utomilumab and urelumab is therefore not limited to particular sites in the body and thus may occur in the liver or elsewhere in the body.

The present inventors have shown that the Fcabs of the invention require crosslinking in order to cluster and activate CD137. However, it should be noted that this is not an intrinsic feature of Fcabs which bind CD137. Rather, many of the Fcabs isolated during the screening program bound to CD137 but did not require crosslinking for CD137 clustering and activation or induced limited CD137 clustering and activation in the absence of crosslinking.

As mentioned above, Fcγ receptor-mediated crosslinking has the disadvantage that Fcγ receptors are found throughout the human body and thus CD137 activation is not limited to a particular site. The present inventors therefore introduced mutations into the CH2 domain of the Fcabs to reduce or abrogate Fcγ receptor binding. Thus, in the absence of crosslinking through an agent other than Fcγ receptors, the Fcabs of the invention do not exhibit CD137 agonist activity and thus are not expected to induce liver inflammation.

The present inventors have recognised that the anti-CD137 Fcabs of the invention can be used to prepare multispecific, e.g. bispecific, molecules which bind a second antigen in addition to CD137, such as a tumour antigen. Preferably the multispecific molecule binds the second antigen bivalently, although it is expected that where the second antigen is a cell-bound tumour antigen, monovalent binding of the antigen will be sufficient to crosslink the specific binding member/antibody molecule and induce CD137 clustering and activation. Specifically, the present inventors have prepared antibody molecules comprising the anti-CD137 Fcabs of the invention which bind a second antigen bivalently via their Fab region. The present inventors have shown that such bispecific antibody molecules are capable of activating CD137 conditionally in the presence of said second antigen without the need for e.g. Fcγ receptor-mediated crosslinking as require by conventional antibody molecules. It is thought that binding of the antibody molecules to the second antigen causes crosslinking of the antibody molecules at the site of said antigen, which in turn leads to clustering and activation of CD137 on the T cell surface. The agonistic activity of the antibody molecules is therefore dependent on both the second antigen and CD137 being present. In other words, the agonistic activity is conditional on both antigens being present. In addition, crosslinking of the antibodies in the presence of the second antigen is thought to assist with clustering of CD137 bound via constant domain antigen-binding site of the antibody molecule. Where the second antigen is a disease antigen, such as a tumour antigen, the antibody molecules are therefore expected to be capable of activating immune cells in a disease-dependent manner, for example in a tumour microenvironment. This targeted activation of immune cells is expected to be beneficial in avoiding the liver inflammation seen with urelumab treatment, for example.

The present inventors have also shown that bispecific antibody molecules comprising an anti-CD137 Fcab of the invention are capable of suppressing tumour growth in vivo where the second antigen bound by the antibody molecule was an immune cell antigen, a tumour antigen, or an antigen expressed both on tumour cells and immune cells. Furthermore, more effective tumour growth suppression was observed with the bispecific antibody molecules as compared to a combination of two monospecific antibody molecules where one of the antibody molecules comprised the same constant domain and the other antibody molecule the same variable domain binding site as the bispecific molecule, demonstrating that enhanced clustering and signalling of CD137, and thus T cell activation and corresponding anti-tumour effects, are seen when the two binding sites are present in the same molecule.

Antibody molecules comprising an anti-CD137 Fcab of the invention and a Fab region specific for a second antigen, preferably bind both CD137 and the second antigen bivalently. This is advantageous, as the bivalent binding of both targets is expected to make the bridging between the T cell expressing CD137 and the second antigen more stable and thereby extend the time during which the T cell is localised at a particular site, such as a tumour microenvironment, and can act on the disease, e.g. the tumour. This is different to the vast majority of conventional bispecific antibody formats which are heterodimeric and bind each target antigen monovalently via one Fab arm. Such a monovalent interaction is expected to be not only less stable but in many cases is insufficient to induce clustering of TNF receptors such as CD137 in the first place.

In an alternative preferred embodiment, the antibody molecule comprises an anti-CD137 Fcabs of the invention capable of binding CD137 bivalently and a monovalent binding site specific for a second antigen, such as a single Fab domain. The monovalent binding site may bind a tumour-associated antigen, for example. In the context of such molecules, monovalent binding of the second antigen is expected to allow tighter packing of the antibody molecules on the cell surface, resulting in enhanced clustering of CD137 and thus T cell activation.

A further feature of the antibody molecules comprising an anti-CD137 Fcab of the invention is that the two antigen binding sites for CD137 and the second antigen are both contained within the antibody structure itself. In particular, the antibody molecules do not require other proteins to be fused to the antibody molecule via linkers or other means to result in molecule that binds bivalently to both of its targets. This has a number of advantages. Specifically, the antibody molecules can be produced using methods similar to those employed for the production of standard antibodies, as they do not comprise any additional fused portions. The structure is also expected to result in improved antibody stability, as linkers may degrade over time, resulting in a heterogeneous population of antibody molecules. Those antibodies in the population having only one protein fused may not be able to induce conditional agonism of TNF receptors such as CD137 as efficiently as those having two fused proteins. Cleavage/degradation of the linker could take place prior to administration or after administration of the therapeutic to the patient (e.g. through enzymatic cleavage or the in vivo pH of the patient), thereby resulting in a reduction of its effectiveness whilst circulating in the patient. As there are no linkers in the antibody molecules, the antibody molecules are expected to retain the same number of binding sites both before and after administration. Furthermore, the structure of the antibody molecules is also preferred from the perspective of immunogenicity of the molecules, as the introduction of fused proteins or linkers or both may induce immunogenicity when the molecules are administered to a patient, resulting in reduced effectiveness of the therapeutic.

The present inventors have further shown that the rigid positioning and/or close proximity of the CD137 antigen-binding sites, which results from the rigid structure of the Fcab molecules of the invention, is advantageous for inducing CD137 clustering as compared with molecules where the CD137 binding site is not integral to the antibody structure but provided e.g. by binding moieties attached to e.g. an antibody molecule, or part thereof, via flexible linkers.

Thus, the present invention provides:

[1] A specific binding member that binds CD137 and comprises a CD137 antigen-binding site located in a CH3 domain of the specific binding member, the CD137 antigen-binding site comprising a first sequence located in the AB structural loop of the CH3 domain, wherein said sequence comprises the sequence PPY (SEQ ID NO: 10).

[2] The specific binding member according to [1], wherein the specific binding member comprises an insertion in the AB structural loop.

[3] The specific binding member according to [2], wherein said insertion is between 1 and 10 amino acids in length.

[4] The specific binding member according to [3], wherein said insertion is between 4 and 6 amino acids in length.

[5] The specific binding member according to [4], wherein said insertion is 5 amino acids in length.

[6] The specific binding member according to any one of [2] to [5], wherein the insertion is located between positions 10 and 19 of the CH3 domain of the specific binding member, wherein the amino acid residue numbering is according to the ImMunoGeneTics (IMGT) numbering scheme.

[7] The specific binding member according to [6], wherein the insertion is located between positions 14 and 17 of the CH3 domain of the specific binding member.

[8] The specific binding member according to [7], wherein the insertion is located between positions 16 and 17 of the CH3 domain of the specific binding member.

[9] The specific binding member according to any one of [2] to [8], wherein the insertion is located at positions 16.5 to 16.1 of the CH3 domain of the specific binding member, wherein the amino acid residue numbering is according to the ImMunoGeneTics (IMGT) numbering scheme

[10] The specific binding member according to any one of [1] to [9], wherein PPY sequence is located between positions 15 and 17 of the CH3 domain, and wherein the amino acid residue numbering is according to the IMGT numbering scheme.

[11] The specific binding member according to any one of [1] to [10], wherein PPY sequence is located between positions 16 and 17 of the CH3 domain, and wherein the amino acid residue numbering is according to the IMGT numbering scheme.

[12] The specific binding member according to [11], wherein the PPY sequence is located at positions 16.3, 16.2 and 16.1 of the CH3 domain.

[13] The specific binding member according to any one of [1] to [12], wherein the first sequence is the first sequence of specific binding member:

(i) FS22-172-003 set forth in SEQ ID NO: 138;
(ii) FS22-172-002 set forth in SEQ ID NO: 129;
(iii) FS22-172-004 set forth in SEQ ID NO: 147;
(iv) FS22-172-001 set forth in SEQ ID NO: 120;
(v) FS22-172-005 set forth in SEQ ID NO: 156;
(vi) FS22-172-006 set forth in SEQ ID NO: 110; or
(vii) FS22-172 set forth in SEQ ID NO: 110.

[14] The specific binding member according to [13], wherein the first sequence is the first sequence of specific binding member:

(i) FS22-172-003 set forth in SEQ ID NO: 138;
(ii) FS22-172-002 set forth in SEQ ID NO: 129;
(iii) FS22-172-004 set forth in SEQ ID NO: 147;
(iv) FS22-172-001 set forth in SEQ ID NO: 120;
(v) FS22-172-005 set forth in SEQ ID NO: 156; or
(vi) FS22-172-006 set forth in SEQ ID NO: 110.

[15] The specific binding member according to [14], wherein the first sequence is the first sequence of specific binding member:

(i) FS22-172-003 set forth in SEQ ID NO: 138;
(ii) FS22-172-002 set forth in SEQ ID NO: 129; or
(iii) FS22-172-004 set forth in SEQ ID NO: 147.

[16] The specific binding member according to [15], wherein the first sequence is the first sequence of specific binding member FS22-172-003 set forth in SEQ ID NO: 138.

[17] The specific binding member according to [10], wherein the PPY sequence is located at positions 16, 16.5 and 16.4 of the CH3 domain.

[18] The specific binding member according to any one of [1] to [10] or [17], wherein the first sequence is the first sequence of specific binding member FS22-053-008, FS22-053-009, FS22-053-011, FS22-053-017, FS22-053-014, FS22-053-010, FS22-053-012, FS22-053-013, FS22-053-015, FS22-053-016, or FS22-053, preferably specific binding member FS22-053-008, set forth in SEQ ID NO: 19.

[19] The specific binding member according to any one of [13] to [16] or [18], wherein the first sequence is located between positions 14 and 17 of the CH3 domain of the specific binding member, wherein the amino acid residue numbering is according to the IMGT numbering scheme.

[20] The specific binding member according to [19], wherein the first sequence is located at positions 15, 16, 16.5, 16.4, 16.3, 16.2, and 16.1 of the CH3 domain of the specific binding member.

[21] The specific binding member according to any of one of [1] to [20], wherein the specific binding member further comprises a second sequence located in the EF structural loop of the CH3 domain.

[22] The specific binding member according to [21], wherein the second sequence is the second sequence of specific binding member FS22-172-003, FS22-172-002, FS22-172-004, FS22-172-001, FS22-172-005, FS22-172-006, or FS22-172, preferably specific binding member FS22-172-003, set forth in SEQ ID NO: 111.

[23] The specific binding member according to [21], wherein the second sequence is the second sequence of specific binding member:

(i) FS22-053-008 set forth in SEQ ID NO: 20;
(ii) FS22-053-009 set forth in SEQ ID NO: 29;
(iii) FS22-053-011 set forth in SEQ ID NO: 47;
(iv) FS22-053-017 set forth in SEQ ID NO: 101;
(v) FS22-053-014 set forth in SEQ ID NO: 74;
(vi) FS22-053-010 set forth in SEQ ID NO: 38;
(vii) FS22-053-012 set forth in SEQ ID NO: 56;
(viii) FS22-053-013 set forth in SEQ ID NO: 65;
(ix) FS22-053-015 set forth in SEQ ID NO: 83;
(x) FS22-053-016 set forth in SEQ ID NO: 92; or
(xi) FS22-053 set forth in SEQ ID NO: 174.

[24] The specific binding member according to [23], wherein the second sequence is the second sequence of specific binding member:

(i) FS22-053-008 set forth in SEQ ID NO: 20;
(ii) FS22-053-009 set forth in SEQ ID NO: 29;
(iii) FS22-053-011 set forth in SEQ ID NO: 47;
(iv) FS22-053-017 set forth in SEQ ID NO: 101; or
(v) FS22-053-014 set forth in SEQ ID NO: 74.

[25] The specific binding member according to [24], wherein the second sequence is the second sequence of specific binding member:

(i) FS22-053-008 set forth in SEQ ID NO: 20;
(ii) FS22-053-009 set forth in SEQ ID NO: 29;
(iii) FS22-053-011 set forth in SEQ ID NO: 47; or
(iv) FS22-053-017 set forth in SEQ ID NO: 101.

[26] The specific binding member according to [25], wherein the second sequence is the second sequence of specific binding member FS22-053-008 set forth in SEQ ID NO: 20.

[27] The specific binding member according to any one of [21] to [26], wherein the second sequence is located at positions 92 to 98 of the CH3 domain of the specific binding member, wherein the amino acid residue numbering is according to the IMGT numbering scheme.

[28] The specific binding member according to any one of [1] to [27], wherein the specific binding member further comprises a third sequence located in the CD structural loop of the CH3 domain.

[29] The specific binding member according to [28], wherein the third sequence is located at positions 43 to 78 of the specific binding member, wherein the amino acid residue numbering is according to the IMGT numbering scheme.

[30] The specific binding member according to any one of [28] to [29], wherein the third sequence has the sequence set forth in SEQ ID NO: 2.

[31] The specific binding member according to any one of [1] to [30], wherein the CH3 domain is a human IgG1 CH3 domain.

[32] The specific binding member according to any one of [1] to [16], [19] to [22] and [27] to [31], wherein the specific binding member comprises the CH3 domain sequence of specific binding member:

(i) FS22-172-003 set forth in SEQ ID NO: 139;
(ii) FS22-172-002 set forth in SEQ ID NO: 130;
(iii) FS22-172-004 set forth in SEQ ID NO: 148;
(iv) FS22-172-001 set forth in SEQ ID NO: 121;
(v) FS22-172-005 set forth in SEQ ID NO: 157;
(vi) FS22-172-006 set forth in SEQ ID NO: 165; or
(vii) FS22-172 set forth in SEQ ID NO: 112.

[33] The specific binding member according to [32], wherein the specific binding member comprises the CH3 domain sequence of specific binding member:

(i) FS22-172-003 set forth in SEQ ID NO: 139;
(ii) FS22-172-002 set forth in SEQ ID NO: 130;
(iii) FS22-172-004 set forth in SEQ ID NO: 148;
(iv) FS22-172-001 set forth in SEQ ID NO: 121;
(v) FS22-172-005 set forth in SEQ ID NO: 157; or
(vi) FS22-172-006 set forth in SEQ ID NO: 165.

[34] The specific binding member according to [33], wherein the specific binding member comprises the CH3 domain sequence of specific binding member:

(i) FS22-172-003 set forth in SEQ ID NO: 139;
(ii) FS22-172-002 set forth in SEQ ID NO: 130; or
(iii) FS22-172-004 set forth in SEQ ID NO: 148.

[35] The specific binding member according to [34], wherein the specific binding member comprises the CH3 domain sequence of specific binding member FS22-172-003 set forth in SEQ ID NO: 139.

[36] The specific binding member according to any one of [1] to [10], [17] to [18], [19] to [21] and [23] to [31] wherein the specific binding member comprises the CH3 domain sequence of specific binding member:

(i) FS22-053-008 set forth in SEQ ID NO: 21;
(ii) FS22-053-009 set forth in SEQ ID NO: 30;
(iii) FS22-053-011 set forth in SEQ ID NO: 48;
(iv) FS22-053-017 set forth in SEQ ID NO: 102;
(v) FS22-053-014 set forth in SEQ ID NO: 75;
(vi) FS22-053-010 set forth in SEQ ID NO: 39;
(vii) FS22-053-012 set forth in SEQ ID NO: 57;
(viii) FS22-053-013 set forth in SEQ ID NO: 66;
(ix) FS22-053-015 set forth in SEQ ID NO: 84;
(x) FS22-053-016 set forth in SEQ ID NO: 93; or
(xi) FS22-053 set forth in SEQ ID NO: 175.

[37] The specific binding member according to [36], wherein the specific binding member comprises the CH3 domain sequence of specific binding member:

(i) FS22-053-008 set forth in SEQ ID NO: 21;
(ii) FS22-053-009 set forth in SEQ ID NO: 30;
(iii) FS22-053-011 set forth in SEQ ID NO: 48;
(iv) FS22-053-017 set forth in SEQ ID NO: 102; or
(v) FS22-053-014 set forth in SEQ ID NO: 75.

[38] The specific binding member according to [37], wherein the specific binding member comprises the CH3 domain sequence of specific binding member:

(i) FS22-053-008 set forth in SEQ ID NO: 21;
(ii) FS22-053-009 set forth in SEQ ID NO: 30;
(iii) FS22-053-011 set forth in SEQ ID NO: 48; or
(iv) FS22-053-017 set forth in SEQ ID NO: 102.

[39] The specific binding member according to [38], wherein the specific binding member comprises the CH3 domain sequence of specific binding member FS22-053-008 set forth in SEQ ID NO: 21.

[40] The specific binding member according to [37], wherein the specific binding member comprises the CH3 domain sequence of specific binding member FS22-053-017 set forth in SEQ ID NO: 102.

[41] The specific binding member according to [37], wherein the specific binding member comprises the CH3 domain sequence of specific binding member FS22-053-014 set forth in SEQ ID NO: 75.

[42] The specific binding member according to any one of [1] to [41], wherein the specific binding member further comprises a CH2 domain, preferably the CH2 domain of human IgG1.

[43] The specific binding member according to any one of [1] to [42], wherein the specific binding member is a dimer of two identical polypeptide chains, each comprising a CH2 and a CH3 domain.

[44] The specific binding member according to [42] or [43], wherein the CH2 domain has the sequence set forth in SEQ ID NO: 6 or 5.

[45] The specific binding member according to any one of [42] to [44] further comprising an immunoglobulin hinge region, or part thereof, at the N-terminus of the CH2 domain, preferably a human IgG1 hinge region, or part thereof.

[46] The specific binding member according to [45], wherein the hinge region has the sequence set forth in SEQ ID NO: 179 or a fragment thereof

[47] The specific binding member according to [46], wherein the hinge region has the sequence set forth in SEQ ID NO: 7.

[48] The specific binding member according to any one of [1] to [16], [19] to [22], [27] to [35], and [42] to [47], wherein the specific binding member comprises the sequence of specific binding member FS22-172-003, FS22-172-002, FS22-172-004, FS22-172-001, FS22-172-005, FS22-172-006, or FS22-172 set forth in SEQ ID NO: 141, 132, 150, 123, 159, 167, and 114, respectively.

[49] The specific binding member according to [48], wherein the specific binding member comprises the sequence of specific binding member FS22-172-003, FS22-172-002, FS22-172-004, FS22-172-001, FS22-172-005, or FS22-172-006 set forth in SEQ ID NO: 141, 132, 150, 123, 159 and 167, respectively.

[50] The specific binding member according to [49], wherein the specific binding member comprises the sequence of specific binding member FS22-172-003, FS22-172-002, or FS22-172-004 set forth in SEQ ID NO: 141, 132 and 150, respectively.

[51] The specific binding member according to [50], wherein the specific binding member comprises the sequence of specific binding member FS22-172-003 set forth in SEQ ID NO: 141.

[52] The specific binding member according to any one of [1] to [10], [17] to [18], [19] to [21], [23] to [31], and [36] to [47], wherein the specific binding member comprises the sequence of specific binding member FS22-053-008, FS22-053-009, FS22-053-011, FS22-053-017, FS22-053-014, FS22-053-010, FS22-053-012, FS22-053-013, FS22-053-015, FS22-053-016, or FS22-053 set forth in SEQ ID NO: 23, 32, 50, 104, 77, 41, 59, 68, 86, 95 and 175, respectively.

[53] The specific binding member according [52], wherein the specific binding member comprises the sequence of specific binding member FS22-053-008, FS22-053-009, FS22-053-011, FS22-053-017, or FS22-053-014 set forth in SEQ ID NO: 23, 32, 50, 104, and 77, respectively.

[54] The specific binding member according to [53], wherein the specific binding member comprises the sequence of specific binding member FS22-053-008, FS22-053-009, FS22-053-011, or FS22-053-017 set forth in SEQ ID NO: 23, 32, 50, and 103, respectively.

[55] The specific binding member according to [54], wherein the specific binding member comprises the sequence of specific binding member FS22-053-008 set forth in SEQ ID NO: 23.

[56] The specific binding member according to any one of [1] to [55], wherein the specific binding member binds human CD137.

[57] The specific binding member according to [56], wherein the human CD137 has, comprises or consists of the sequence set forth SEQ ID NO: 181.

[58] The specific binding member according to any one of [1] to [55], wherein the specific binding member binds to dimeric CD137 with higher affinity than to monomeric CD137.

[59] The specific binding member according to any one of [1] to [58], wherein the specific binding member binds cynomolgus CD137.

[60] The specific binding member or antibody molecule according to [59], wherein the cynomolgus CD137 has, comprises or consists of the sequence set forth in SEQ ID NO: 183.

[61] The specific binding member according to any one of [1] to [60], wherein the specific binding member further comprises a second antigen-binding site.

[62] The specific binding member according to [61], wherein specific binding member is a multispecific molecule.

[63] The specific binding member according to [62], wherein specific binding member is a bispecific, trispecific, or tetraspecific molecule.

[64] The specific binding member according to [63], wherein specific binding member is a bispecific molecule.

[65] The specific binding member according to any one of [61] to [64], wherein the second antigen-binding site is a CDR-based antigen-binding site.

[66] The specific binding member according to [65], wherein the second antigen-binding site comprises a heavy chain variable domain CDR1, CDR2, and CDR3, and a light chain variable domain CDR1, CDR2, and CDR3.

[67] The specific binding member according to any one of [61] to [66], wherein the second antigen-binding site comprises a heavy chain variable and a light chain variable domain.

[68] The specific binding member according to any one of [61] to [67], wherein the specific binding member is an antibody molecule.

[69] An antibody molecule according to [68], wherein the antibody molecule is a human IgG1 molecule.

[70] The antibody molecule according to any one of [65] to [69], wherein the CDR-based antigen-binding site of the antibody molecule binds a second antigen selected from the group consisting of: an immune cell antigen, and a disease antigen.

[71] The antibody molecule according to [70], wherein the disease antigen is a tumour antigen or a pathogenic antigen.

[72] The antibody molecule according to [70], wherein the immune cell antigen is an immune regulatory molecule, such as PD-L1.

[73] The antibody molecule according to [70], wherein the immune cell antigen is a member of the tumour necrosis factor receptor superfamily (TNFRSF).

[74] The antibody molecule according to [71], wherein the tumour antigen is a tumour-associated antigen (TAA).

[75] The antibody molecule according to [71] or [74], wherein the tumour antigen is a cell surface antigen on a cancer cell.

[76] The antibody molecule according to [71], wherein the tumour antigen is a soluble multimer.

[77] The antibody molecule according to [76], wherein soluble multimer is at least a dimer.

[78] The antibody molecule according to [77], wherein soluble multimer is at least a trimer.

[79] The antibody molecule according to [71], wherein the pathogenic antigen is a bacterial or viral antigen.

[80] The antibody molecule according to any one of [70] to [79], wherein the antibody molecule is capable of activating CD137 present on an immune cell in the presence of the second antigen.

[81] The antibody molecule according to any one of [70] to [80], wherein binding of the antibody molecule to CD137 and the second antigen causes clustering of CD137 on the immune cell.
[82] The antibody molecule according to [80] or [81], wherein the immune cell is a T cell.
[83] The specific binding member or antibody molecule according to any one of [1] to [82], wherein the specific binding member or antibody molecule has been modified to reduce or abrogate binding of the CH2 domain of the specific binding member or antibody molecule to one or more Fcγ receptors.
[84] The specific binding member or antibody molecule according to any one of [1] to [83] wherein the specific binding member or antibody molecule does not activate Fcγ receptors.
[85] The specific binding member or antibody molecule according to [83] or [84], wherein the Fcγ receptor is selected from the group consisting of: FcγRI, FcγRIIa, FcγRIIb and FcγRIII.
[86] The specific binding member or antibody molecule according to any one of [1] to [85], wherein the specific binding member or antibody molecule is conjugated to a bioactive molecule.
[87] The specific binding member or antibody molecule according to any one of [1] to [85], wherein the specific binding member or antibody molecule is conjugated to a detectable label.
[88] A nucleic acid molecule encoding the specific binding member or antibody molecule according to any one of [1] to [85].
[89] The nucleic acid molecule according to [88], wherein the nucleic acid molecule(s) comprise(s):

(i) the CH3 domain nucleic acid sequence of specific binding member FS22-053-008, FS22-053-009, FS22-053-011, FS22-053-017, FS22-053-014, FS22-053-010, FS22-053-012, FS22-053-013, FS22-053-015, FS22-053-016, or FS22-053 set forth in SEQ ID NO: 22, 31, 49, 103, 76, 40, 58, 67, 85, 94, and 176, respectively; or (ii) the CH3 domain nucleic acid sequence of specific binding member FS22-172-003, FS22-172-002, FS22-172-004, FS22-172-001, FS22-172-005, FS22-172-006, or FS22-172 set forth in SEQ ID NO: 140, 131, 149, 122, 158, 166, and 113, respectively.

[90] The nucleic acid molecule according to [88] or [89], wherein the nucleic acid molecule comprises the nucleic acid sequence of: specific binding member:

(i) FS22-053-008, FS22-053-009, FS22-053-011, FS22-053-017, FS22-053-014, FS22-053-010, FS22-053-012, FS22-053-013, FS22-053-015, FS22-053-016, or FS22-053 set forth in SEQ ID NO: 24, 33, 51, 105, 78, 42, 60, 69, 87, 96, and 177, respectively; or (ii) FS22-172-003, FS22-172-002, FS22-172-004, FS22-172-001, FS22-172-005, FS22-172-006, or FS22-172 set forth in SEQ ID NO: 142, 133, 151, 124, 160, 168, and 115, respectively.

[91] The nucleic acid molecule according to [89] or [90], wherein the nucleic acid molecule comprises the CH3 domain nucleic acid sequence, or the nucleic acid sequence, of specific binding member:

(i) FS22-172-003; or (ii) FS22-053-008.

[92] A vector comprising the nucleic acid according to any one of [88] to [91].
[93] A recombinant host cell comprising the nucleic acid according to any one of [88] to [91], or the vector of [92].
[94] A method of producing a specific binding member or antibody molecule according to any one of [1] to [85], comprising culturing the recombinant host cell of [93] under conditions for production of the specific binding member or antibody molecule.
[95] The method of [94] further comprising isolating and/or purifying the specific binding member or antibody molecule.
[96] A pharmaceutical composition comprising a specific binding member or antibody molecule according to any one of [1] to [87] and a pharmaceutically acceptable excipient.
[97] The specific binding member or antibody molecule according to any one of [1] to [87] for use in a method for treatment of the human or animal body by therapy.
[98] A method of treating a disease or disorder in an individual comprising administering to the individual a therapeutically effective amount of the specific binding member or antibody molecule according to any one of [1] to [87].
[99] The specific binding member or antibody molecule for use according to [97], or the method according to [98] wherein the treatment is the treatment of cancer or an infectious disease in an individual.
[100] The specific binding member or antibody molecule for use according to [97] or [99], or the method according to [98] or [99], wherein the method of treatment comprises administering the specific binding member or antibody molecule to the individual in combination with a second therapeutic.

BRIEF DESCRIPTION OF THE FIGURES

FIG. 1: FIGS. 1A, B and C show an alignment of the sequences of the CH3 domains of Fcabs FS22-053, FS22-053-008, FS22-053-009, FS22-053-010, FS22-053-011, FS22-053-012, FS22-053-013, FS22-053-014, FS22-053-015, FS22-053-016, FS22-053-017, FS22-172, FS22-172-001, FS22-172-002, FS22-172-003, FS22-172-004, FS22-172-005 and FS22-172-006 as well as the wild-type (WT) Fcab. The numbers of the residues according to the IMGT, IMGT exon (consecutive numbering), EU and Kabat numbering systems is indicated. FIG. 1D shows the percentage sequence identity of the CH3 domain of clones FS22-053-008 to FS22-053-016 and FS22-053-017 (see Example 10.1) compared to the parent FS22-053 CH3 domain. FIG. 1E shows the percentage sequence identity of the CH3 domain of clones FS22-172-001 to FS22-172-006 compared to the parent FS22-053 CH3 domain.

DETAILED DESCRIPTION

Figure 2:
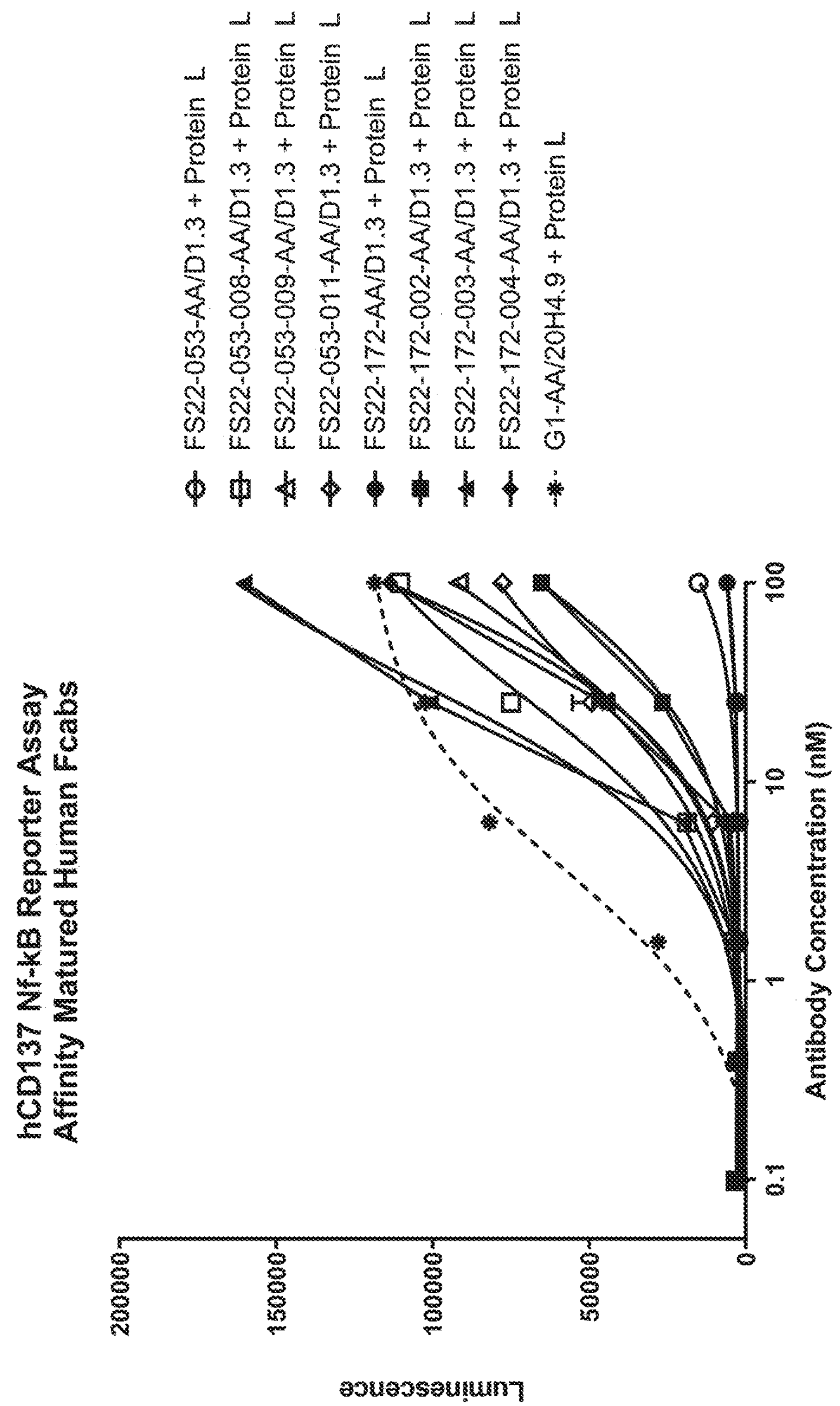
FIG. 2 shows NF-kB signalling determined by luminescence values as a measure of luciferase production caused by CD137 clustering and activation. The anti-human CD137 parental Fcabs FS22-053 and FS22-172 in HelD1.3 mock $mAb^2$ format drive limited CD137 clustering and NF-kB signalling when crosslinked with Protein L in a HEK hCD137 NF-kB reporter assay (open and filled circles). The affinity-matured anti-human CD137 Fcabs FS22-053-008, -009, -011 (open squares, triangles, and diamonds) and FS22-172-002, -003, -004 (filled squares, triangles, and diamonds) in HelD1.3 mock $mAb^2$ format drive stronger CD137 clustering and NF-kB signalling when crosslinked with Protein L in a HEK hCD137 NF-kB reporter assay compared with the parental clones. The positive control anti-human CD137 mAb, 20H4.9, showed an increase in luminescence when crosslinked with Protein L (dotted line), with a smaller EC50 value compared with the affinity matured anti-human CD137 Fcabs.

The present invention relates to specific binding members that bind CD137. CD137 is also known as tumour necrosis factor receptor superfamily member 9 (TNFRSF9) or 4-1BB. The specific binding member preferably binds human CD137, more preferably human and cynomolgus CD137, yet more preferably dimeric human and cynomolgus CD137. The portion of CD137 bound by the specific binding member is preferably the CD137 extracellular domain. The extracellular domain of human and cynomolgus CD137 may comprise or consist of the sequence set forth in SEQ ID NOs 181 and 183, respectively. The specific binding member is preferably capable of binding to CD137 expressed on the surface of a cell. The cell is preferably an immune cell, such as a $CD8^+$ or $CD4^+$ T cell or regulatory T (Treg) cell, preferably a $CD8^+$ T cell, or a B cell, natural killer (NK) cell, natural killer T (NKT) cell, dendritic cell (DC), or a tumour-infiltrating lymphocyte (TIL).

The specific binding member preferably binds CD137 specifically. The term "specific" may refer to the situation in which the specific binding member will not show any significant binding to molecules other than its specific binding partner(s), here CD137. The term "specific" is also applicable where the specific binding member is specific for particular epitopes, such as epitopes on CD137, that are carried by a number of antigens, in which case the specific binding member will be able to bind to the various antigens carrying the epitope. The specific binding member preferably does not bind, or does not show any significant binding, to CD40, OX40 and/or GITR.

As explained in the background section above, treatment of patients with the anti-CD137 antibody urelumab was associated with dose-limiting high-grade liver inflammation. Without wishing to be bound by theory, it is thought that the liver inflammation seen with urelumab treatment may have been due to activation of T cells present in the liver, or infiltration and accumulation of activated T cells in the liver of the patients. In order to select for molecules with reduced or no liver inflammation, the present inventors selected for Fcabs with high avidity for CD137. Specifically, the present inventors selected Fcabs which bound to dimeric CD137 with higher affinity than monomeric CD137. Expression of CD137 by T cells is upregulated on priming and activation. It is thought that due to the higher expression of CD137 on activated T cells, CD137 will be in the form of dimers, trimers and higher-order multimers on the surface of such cells. In contrast, CD137 expression by inactive T cells express low or even undetectable. It is therefore thought that CD137, in so far as this is expressed at all on the surface of such T cells, is likely to be in monomeric form. Fcabs which bind to CD137 with high avidity are therefore thought to preferentially bind to activated T cells, as opposed to inactive T cells, such as inactive T cells present in the liver, and therefore exhibit reduced or no liver inflammation.

The specific binding member preferably binds to dimeric human CD137 with an affinity ($K_D$) of 60 nM, 50 nM, 40 nM, 30 nM, 20 nM, 10 nM, 5 nM, 4 nM, 3 nM, or 2 nM, or with a higher affinity.

In a preferred embodiment, the specific binding member binds to dimeric CD137 with a higher affinity than monomeric CD137. In a preferred embodiment, the specific binding member binds to dimeric CD137 with an affinity which is at least 50-fold, 60-fold, 70-fold, 80-fold, 90-fold, 100-fold, 110-fold, 120-fold, 130-fold, 140-fold, 150-fold, 160-fold, 170-fold or 200-fold higher than the affinity of the specific binding member for monomeric CD137.

The human CD137 may, for example, have the sequence set forth in SEQ ID NO: 183. The sequence is identical regardless of whether the antigen is in monomeric or dimeric form.

Specific binding members from the FS22-53 and FS22-172 lineages have also been shown to bind dimeric cynomolgus CD137. Binding to cynomolgus CD137 as well as human CD137 is beneficial as it permits testing of the specific binding member in cynomolgus monkeys for efficacy and toxicity prior to administration to humans.

In a preferred embodiment, the specific binding member may bind to dimeric cynomolgus CD137 with an affinity ($K_D$) of 250 nM, 200 nM, 150 nM, 140 nM, 120 nM, 100 nM, 90 nM, 80 nM, 70 nM, 60 nM, 50 nM, 40 nM, 30 nM, 20 nM, 10 nM, 5 nM, 4 nM, 3 nM, or 2 nM or with a higher affinity. Preferably, the specific binding member binds to cynomolgus CD137, with an affinity ($K_D$) of 2 nM, or with a higher affinity.

The specific binding member may bind to dimeric human CD137 and dimeric cynomolgus CD137 with similar affinity. This is thought to be beneficial for carrying out efficacy and toxicity studies with the specific binding member in cynomolgus monkeys which may be predictive of the efficacy and toxicity of the specific binding member in humans.

Thus, in a preferred embodiment, the specific binding member binds to dimeric cynomolgus CD137 with an affinity which is no more than 10-fold, preferably no more than 5-fold lower or higher than the affinity with which the specific binding member binds dimeric human CD137.

The specific binding member may bind to dimeric mouse CD137, dimeric cynomolgus CD137 and dimeric human CD137. This is thought to be beneficial as the same specific binding member could be used to perform initial efficiacy studies in mice, toxicity studies in cynomolgus monkeys and clinical trials in human, thus potentially simplifying the path to the clinic. Specifically, specific binding members FS22-053-014 and FS22-053-017 were surprisingly found to bind to dimeric mouse, human and cynomolgus CD137.

The binding affinity of a specific binding member to a cognate antigen, such as human or cynomolgus CD137 can be determined by surface plasmon resonance (SPR), such as Biacore, for example.

The term “specific binding member” describes an immunoglobulin, or fragment thereof, comprising a constant domain comprising a CD137 antigen-binding site. The term “specific binding member”, as used herein, thus includes antigen-binding fragments, provided said antigen-binding fragments comprise a CD137 antigen-binding site located in a constant domain of the specific binding member. The constant domain may be a CL, CH1, CH2, CH3, or CH4 domain, preferably the constant domain is a CH1, CH2, or CH3 domain, more preferably a CH2 or CH3 domain, most preferably a CH3 domain. The specific binding member may be partly, or wholly, synthetically produced.

Preferably, the specific binding member comprises a CH2 and CH3 domain, wherein the CH2 or CH3 domain, preferably the CH3 domain, comprises a CD137 antigen-binding site. The specific binding member is preferably a dimer of two (identical) polypeptide chains, each comprising a CH2 and a CH3 domain. In a preferred embodiment, the specific binding member further comprises an immunoglobulin hinge region, or part thereof, at the N-terminus of the CH2 domain. Such a molecule is also referred to herein as an antigen-binding Fc fragment, or Fcab™. The hinge region may consist of or comprise the sequence set forth in SEQ ID NO: 179 or a fragment thereof. Preferably, the fragment is a C-terminal fragment of the sequence set forth in SEQ ID NO: 179. The fragment may be up to 20, up to 10, up to 8 or up to 6 amino acids in length. The fragment may be at least 3, at least 4, at least 5, or at least 6 amino acids in length. In a preferred embodiment, the hinge region has the sequence set forth in SEQ ID NO: 7.

In a preferred embodiment, the specific binding member is an antibody molecule, preferably a monoclonal antibody, or a fragment thereof. The antibody molecule is preferably human or humanised. The antibody molecule may be an immunoglobulin G molecule, such as an IgG1, IgG2, IgG3 or IgG4 molecule, preferably an IgG1, IgG2 or IgG4 molecule, more preferably an IgG1 molecule, or a fragment thereof.

As antibodies can be modified in a number of ways, the term “antibody molecule” should be construed as covering antibody fragments, derivatives, functional equivalents and homologues of antibodies, whether natural or wholly or partially synthetic. An example of an antibody fragment comprising a CH3 domain is an Fc domain of an antibody. An example of an antibody fragment comprising both CDR sequences and a CH3 domain is a minibody, which comprises an scFv joined to a CH3 domain (Hu et al. (1996), Cancer Res., 56(13):3055-61).

The specific binding member comprises a CD137 antigen-binding site. The CD137 antigen-binding site is located in a constant domain of the specific binding member, preferably a CH3 domain. The CD137 antigen-binding site comprises one or more modified structural loops in a constant domain of the specific binding member. Engineering antibody constant domain structural loops to create antigen-binding sites for target antigens is known in the art and is described, for example, Wozniak-Knopp G et al. (2010); WO2006/072620 and WO2009/132876.

Following an extensive selection and affinity maturation program, the inventors isolated two panels of Fcabs which preferentially bound to dimeric rather than monomeric human CD137. Surprisingly, the isolated Fcabs all comprised the sequence PPY, as well as a five amino acid insertion, in their AB structural loop. The two panels of Fcabs were selected independently from different selection campaigns, each using a library comprising a five amino acid insertion in the structural AB loop. The PPY sequence was therefore selected for independently twice, indicating the importance of this sequence for CD137 binding. Anti-CD137 Fcabs isolated from Fcab libraries not comprising a five amino acid insertion in the AB structural loop were not pursued further, for example because the selected Fcabs could not be affinity matured. This indicates that the amino acid insertion present in the AB structural loop may also be important for CD137 binding. Thus, the presence of the sequence PPY and the 5 amino acid insertion in the AB structural loop, wherein the PPY sequence may optionally be wholly or partially present within the 5 amino acid insertion, may be important for CD137 binding.

Thus, the CD137 antigen-binding site of the specific binding member may comprise a first and/or second sequence, preferably a first and second sequence, wherein the first and second sequence are located in the AB and EF structural loops of the constant domain, preferably the CH3 domain, of the specific binding member, respectively.

In a preferred embodiment, the residues at positions 95 and 96 of the CH3 domain of the specific binding member are wild-type, i.e. are preferably arginine (R) and tryptophan (W), respectively. Both of these residues are located in the EF structural loop. Amino acid residue positions are numbered herein according to the ImMunoGeneTics (IMGT) numbering scheme, unless otherwise indicated. The IMGT numbering scheme is described in Lefranc et al., 2005.

The first sequence preferably comprises the sequence PPY (SEQ ID NO: 10).

The PPY sequence may be located between positions 10 and 19, preferably positions 15 and 17 of the CH3 domain of the specific binding member. In a preferred embodiment, the PPY sequence is located at positions 16, 16.5 and 16.4 of the CH3 domain. Alternatively, the PPY sequence may be located between positions 16 and 17 of the CH3 domain. In an alternative preferred embodiment, the PPY sequence is located at positions 16.3, 16.2 and 16.1 of the CH3 domain. In the IMGT numbering scheme, inserted residues are numbered according to the direction of the loop in which they are located. If the loop goes “up” the inserted residues take the number of the residue immediately preceding the insertion with the number of the inserted residue in the sequence being indicated by an ascending decimal number, e.g. 16, 16.1, 16.2, 16.3, where there are three mutations following residue 16. If the loop goes “down”, the inserted residues take the number of the residue immediately preceding the insertion with the number of the inserted residue in the sequence being indicated by descending decimal number, e.g. 16, 16.3, 16.2, 16.1, where again there are three mutations following residue 16 (LeFranc et al., 2005, and LeFranc et al. 2015).

In a preferred embodiment, the AB structural loop comprises an amino acid insertion. The insertion may be 1 to 10, 2 to 9, 3 to 7, 4 to 6 or 5 amino acids in length. Preferably, the insertion is 5 amino acids in length.

The insertion may be located between positions 10 and 19, preferably between positions 14 and 17, more preferably between positions 16 and 17 of the CH3 domain of the specific binding member. In a preferred embodiment, the insertion is located at positions 16.5 to 16.1 of the CH3 domain of the specific binding member as shown in FIG. 1.

The majority of the specific binding members identified following affinity maturation comprised a leucine (L) residue at position 97 of the CH3 domain. Many of the specific binding members also comprised an aspartic acid (D) residue or glutamic acid (E) residue at positions 98 of the CH3 domain of the specific binding member. Both of these amino acid changes are located in the EF structural loop. These results suggests that one or both of these residues may be important for CD137 binding. Thus, the second sequence preferably comprises the sequence LD or LE, wherein the LD or LE sequence is preferably located at positions 97 and 98 of the CH3 domain of the specific binding member.

The first sequence and second sequence may be a first and second sequence of the CH3 domain of: specific binding member FS22-172-003, FS22-172-002, FS22-172-004, FS22-172-001, FS22-172-005, FS22-172-006, or FS22-172, preferably specific binding member FS22-172-003, FS22-172-002, FS22-172-004, FS22-172-001, FS22-172-005, or FS22-172-006, more preferably specific binding member FS22-172-003, FS22-172-002, or FS22-172-004, yet more preferably specific binding member FS22-172-003.

Alternatively, the first sequence and second sequence may be a first and second sequence of the CH3 domain of: specific binding member FS22-053-008, FS22-053-009, FS22-053-011, FS22-053-017, FS22-053-014, FS22-053-010, FS22-053-012, FS22-053-013, FS22-053-015, or FS22-053-016, or FS22-053, preferably specific binding member FS22-053-008, FS22-053-009, FS22-053-011, FS22-053-017, or FS22-053-014, more preferably specific binding member FS22-053-008, FS22-053-009, FS22-053-011, or FS22-053-017, yet more preferably specific binding member FS22-053-008. In an alternative preferred embodiment, the first sequence and second sequence are the first and second sequence of the CH3 domain of specific binding member FS22-053-017 or FS22-053-014, more preferably specific binding member FS22-053-017.

The CH3 domain sequence of specific binding member FS22-053, FS22-053-008, FS22-053-009, FS22-053-010, FS22-053-011, FS22-053-012, FS22-053-013, FS22-053-014, FS22-053-015, FS22-053-016, FS22-053-017, FS22-172, FS22-172-001, FS22-172-002, FS22-172-003, FS22-172-004, FS22-172-005, and FS22-172-006 is set forth in SEQ ID NOs: 175, 21, 30, 39, 49, 58, 66, 75, 84, 93, 102, 112, 121, 130, 139, 148, 157 and 166, respectively.

The first and second sequence of specific binding member FS22-053, FS22-053-008, FS22-053-009, FS22-053-010, FS22-053-011, FS22-053-012, FS22-053-013, FS22-053-014, FS22-053-015, FS22-053-016, FS22-053-017, FS22-172, FS22-172-001, FS22-172-002, FS22-172-003, FS22-172-004, FS22-172-005, and FS22-172-006 may be the sequence between positions 14 and 17, and positions 91 and 99, of the CH3 domain of specific binding member FS22-053, FS22-053-008, FS22-053-009, FS22-053-010, FS22-053-011, FS22-053-012, FS22-053-013, FS22-053-014, FS22-053-015, FS22-053-016, FS22-053-017, FS22-172, FS22-172-001, FS22-172-002, FS22-172-003, FS22-172-004, FS22-172-005, and FS22-172-006, respectively.

Alternatively, the first and second sequence of specific binding member FS22-053-008, FS22-053-010, FS22-053-011, FS22-053-012, and FS22-053-016 may be the sequence between positions 14 and 17, and positions 92 and 99, of the CH3 domain of specific binding member FS22-053-008, FS22-053-010, FS22-053-011, FS22-053-012, and FS22-053-016, respectively.

The first and second sequence of specific binding member FS22-053-015 may alternatively be the sequence between positions 14 and 17, and positions 92 and 98, of the CH3 domain of specific binding member FS22-053-015, respectively.

The CD loop sequence of the specific binding member is preferably unmodified, i.e. wild-type. The CD loop sequence therefore preferably has the sequence set forth in SEQ ID NO: 2. The CD loop sequence is preferably located at positions 43 to 78 of the CH3 domain of the specific binding member.

The first and second sequences may be the complete AB and EF structural loop sequences, of specific binding member FS22-172-003, FS22-172-002, FS22-172-004, FS22-172-001, FS22-172-005, FS22-172-006, FS22-172, FS22-053-008, FS22-053-009, FS22-053-011, FS22-053-017, FS22-053-014, FS22-053-010, FS22-053-012, FS22-053-013, FS22-053-015, FS22-053-016, or FS22-053, respectively. Determination of the location of the AB, CD, and EF structural loops in a CH3 domain sequence, for example in accordance with the IMGT, IMGT exon, EU, or Kabat numbering systems, is within the capabilities of the skilled person and described in Hasenhindl et al. (2013). In a preferred embodiment, the AB, CD and EF structural loops according to the IMGT numbering system are located between positions 10 and 19, 42 and 79, and 91 and 102 of the CH3 domain of the specific binding member, respectively. In a preferred embodiment, the first, second and third sequence are therefore the sequence between positions 10 and 19, 42 and 79, and 91 and 102 of the CH3 domain of specific binding member FS22-053-008, FS22-053-009, FS22-053-011, FS22-053-017, FS22-053-014, FS22-053-010, FS22-053-012, FS22-053-013, FS22-053-015, FS22-053-016, FS22-053, FS22-172-003, FS22-172-002, FS22-172-004, FS22-172-001, FS22-172-005, FS22-172-006, or FS22-172, respectively.

In a preferred embodiment, the specific binding member comprises the first and/or second, preferably the first and second sequence of specific binding member:

(i) FS22-172-003 set forth in SEQ ID NO: 141;
(ii) FS22-172-002 set forth in SEQ ID NO: 132;
(iii) FS22-172-004 set forth in SEQ ID NO: 150;
(iv) FS22-172-001 set forth in SEQ ID NO: 123;
(v) FS22-172-005 set forth in SEQ ID NO: 159;
(vi) FS22-172-006 set forth in SEQ ID NO: 167; or
(vii) FS22-172 set forth in SEQ ID NO: 114; wherein the first and second sequence are preferably located between positions 14 and 17, and 91 and 99 of the CH3 domain of the specific binding member, respectively.

In a more preferred embodiment, the specific binding member comprises the first and/or second, preferably the first and second sequence of specific binding member:

(i) FS22-172-003 set forth in SEQ ID NO: 141;
(ii) FS22-172-002 set forth in SEQ ID NO: 132;
(iii) FS22-172-004 set forth in SEQ ID NO: 150;
(iv) FS22-172-001 set forth in SEQ ID NO: 123;

(v) FS22-172-005 set forth in SEQ ID NO: 159; or
(vi) FS22-172-006 set forth in SEQ ID NO: 167.

In a yet preferred embodiment, the specific binding member comprises the first and/or second, preferably the first and second sequence of specific binding member:
(i) FS22-172-003 set forth in SEQ ID NO: 141;
(ii) FS22-172-002 set forth in SEQ ID NO: 132; or
(iii) FS22-172-004 set forth in SEQ ID NO: 150.

In an even more preferred embodiment, the specific binding member comprises the first and/or second, preferably the first and second sequence of specific binding member FS22-172-003 set forth in SEQ ID NO: 141.

In a preferred embodiment, the specific binding member, in particular a specific binding member comprising the first and/or second, preferably the first and second, sequence of specific binding member FS22-172-006, may comprise a leucine (L) at position 19 of the CH3 domain of the specific binding member.

In an alternative preferred embodiment, the specific binding member comprises the first and/or second, preferably the first and second sequence of specific binding member:
(i) FS22-053-008 set forth in SEQ ID NO: 23;
(ii) FS22-053-009 set forth in SEQ ID NO: 32;
(iii) FS22-053-011 set forth in SEQ ID NO: 50;
(iv) FS22-053-017 set forth in SEQ ID NO: 104;
(v) FS22-053-014 set forth in SEQ ID NO: 77;
(vi) FS22-053-010 set forth in SEQ ID NO: 41;
(vii) FS22-053-012 set forth in SEQ ID NO: 59;
(viii) FS22-053-013 set forth in SEQ ID NO: 68;
(ix) FS22-053-015 set forth in SEQ ID NO: 86;
(x) FS22-053-016 set forth in SEQ ID NO: 95; or
(xi) FS22-053 set forth in SEQ ID NO: 15; wherein the first and second sequence are preferably located between positions 14 and 17, and 91 and 99 of the CH3 domain of the specific binding member, respectively.

In a more preferred embodiment, the specific binding member comprises the first and/or second, preferably the first and second sequence of specific binding member:
(i) FS22-053-008 set forth in SEQ ID NO: 23;
(ii) FS22-053-009 set forth in SEQ ID NO: 32;
(iii) FS22-053-011 set forth in SEQ ID NO: 50;
(iv) FS22-053-017 set forth in SEQ ID NO: 104; or
(v) FS22-053-014 set forth in SEQ ID NO: 77.

In a yet more preferred embodiment, the specific binding member comprises the first and/or second, preferably the first and second sequence of the CH3 domain of specific binding member:
(i) FS22-053-008 set forth in SEQ ID NO: 23;
(ii) FS22-053-009 set forth in SEQ ID NO: 32;
(iii) FS22-053-011 set forth in SEQ ID NO: 50; or
(iv) FS22-053-017 set forth in SEQ ID NO: 104.

In an even more preferred embodiment, the specific binding member comprises the first and/or second, preferably the first and second sequence of specific binding member FS22-053-008 set forth in SEQ ID NO: 23.

As an alternative to IMGT numbering, amino acid residue positions, including the position of amino acid sequences, substitutions, deletions and insertions as described herein, may be numbered according to IMGT exon numbering (also referred to as consecutive numbering), EU numbering, or Kabat numbering. The concordance between IMGT numbering, IMGT exon numbering, EU numbering, and Kabat numbering of the residue positions of the CH3 domain are shown in FIG. 1. Thus, for example, where the present application refers to the first sequence being located between positions 14 and 17 of the CH3 domain of the specific binding member, respectively, where the residue positions are numbered in accordance with the IMGT numbering scheme, the first sequence is located between positions 18 and 21 of the CH3 domain, where the residue positions are numbered in accordance with the IMGT exon numbering scheme, as shown in FIG. 1. Alternatively, the position of amino acid residues in the CH3 domain, including the position of amino acid sequences, substitutions, deletions and insertions in the CH3 domain, as described herein, may be defined by reference to their position in the wild-type CH3 domain sequence set forth in SEQ ID NO: 4. The concordance between IMGT numbering and the wild-type CH3 domain sequence is also shown in FIG. 1.

In a preferred embodiment, the specific binding member comprises a CH3 domain which comprises, has, or consists of the CH3 domain sequence of specific binding member FS22-172-003, FS22-172-002, FS22-172-004, FS22-172-001, FS22-172-005, FS22-172-006, or FS22-172, preferably the CH3 domain sequence of specific binding member FS22-172-003, FS22-172-002, FS22-172-004, FS22-172-001, FS22-172-005, or FS22-172-006, more preferably the CH3 domain sequence of specific binding member FS22-172-003, FS22-172-002, or FS22-172-004, yet more preferably the CH3 domain sequence of specific binding member FS22-172-003.

In an alternative preferred embodiment, the specific binding member comprises a CH3 domain which comprises, has, or consists of the CH3 domain sequence of specific binding member FS22-053-008, FS22-053-009, FS22-053-011, FS22-053-017, FS22-053-014, FS22-053-010, FS22-053-012, FS22-053-013, FS22-053-015, FS22-053-016, or FS22-053, preferably the CH3 domain sequence of specific binding member FS22-053-008, FS22-053-009, FS22-053-011, FS22-053-017, or FS22-053-014, more preferably the CH3 domain sequence of specific binding member FS22-053-008, FS22-053-009, FS22-053-011, or FS22-053-017, yet more preferably the CH3 domain sequence of specific binding member FS22-053-008.

The CH3 domain of the specific binding member may optionally comprise an additional lysine residue (K) at the immediate C-terminus of the CH3 domain sequence.

It is possible to take monoclonal and other antibodies and use techniques of recombinant DNA technology to produce other antibodies or chimeric molecules which retain the specificity of the original antibody. Such techniques may involve introducing the CDRs, or variable regions, into a different immunoglobulin. Introduction of the CDRs of one immunoglobulin into another immunoglobulin is described, for example, in EP-A-184187, GB 2188638A and EP-A-239400. Similar techniques could be employed to introduce the constant domain sequences making up the CD137 antigen-binding site of a specific binding member according to the invention into a constant domain, e.g. a CH3 domain, of another specific binding member, thereby resulting in a specific binding member comprising a CD137 antigen-binding site in its constant domain. Alternatively, an entire constant domain sequence of a specific binding member could be replaced with the constant domain sequence of a specific binding member according to the invention to prepare a specific binding member comprising an CD137 antigen-binding site in its constant domain. Similarly a fragment of the constant domain sequence of a specific binding member could be replaced with a corresponding fragment of a constant domain sequence of a specific binding member according to the invention comprising the CD137 antigen-binding site.

The CH2 domain of the specific binding member may comprise one or more mutations that reduce or abrogate binding of the CH2 domain to one or more Fcγ receptors, such as FcγRI, FcγRIIa, FcγRIIb, FcγRIII, and/or to complement. The inventors postulate that reducing or abrogating binding to Fcγ receptors will decrease or eliminate ADCC mediated by the specific binding member. Similarly, reducing or abrogating binding to complement is expected to reduce or eliminate CDC mediated by the specific binding member. Mutations to decrease or abrogate binding of the CH2 domain to one or more Fcγ receptors and/or complement are known in the art (Wang et al., 2018). These mutations include the "LALA mutation" described in Bruhns et al., 2009 and Hezareh et al., 2001, which involves substitution of the leucine residues at IMGT positions 1.3 and 1.2 of the CH2 domain with alanine (L1.3A and L1.2A). Alternatively, the generation of a-glycosyl antibodies through mutation of the conserved N-linked glycosylation site by mutating the aparagine (N) at IMGT position 84.4 of the CH2 domain to alanine, glycine or glutamine (N84.4A, N84.4G or N84.4Q) is also known to decrease IgG1 effector function (Wang et al., 2018). As a further alternative, complement activation (C1q binding) and ADCC are known to be reduced through mutation of the proline at IMGT position 114 of the CH2 domain to alanine or glycine (P114A or P114G) (Idusogie et al., 2000; Klein et al., 2016). These mutations may also be combined in order to generate specific binding members with further reduced or no ADCC or CDC activity.

Thus, the specific binding member may comprise a CH2 domain, wherein the CH2 domain preferably comprises:

(i) alanine residues at positions 1.3 and 1.2; and/or
(ii) an alanine or glycine at position 114; and/or
(iii) an alanine, glutamine or glycine at position 84.4;
wherein the amino acid residue numbering is according to the IMGT numbering scheme.

In a preferred embodiment, the specific binding member comprises a CH2 domain, wherein the CH2 domain preferably comprises:

(i) alanine residues at positions 1.3 and 1.2; and/or
(ii) an alanine or glycine at position 114;

wherein the amino acid residue numbering is according to the IMGT numbering scheme.

In another preferred embodiment, the specific binding member comprises a CH2 domain, wherein the CH2 domain comprises:

(i) an alanine residue at position 1.3; and
(ii) an alanine residue at position 1.2;
wherein the amino acid residue numbering is according to the IMGT numbering scheme.

For example, the CH2 domain may have the sequence set forth in SEQ ID NO: 6. [LALA]

In an alternative preferred embodiment, the specific binding member comprises a CH2 domain, wherein the CH2 domain comprises:

(i) an alanine residue at position 1.3;
(ii) an alanine residue at position 1.2; and
(iii) an alanine at position 114;
wherein the amino acid residue numbering is according to the IMGT numbering scheme.

For example, the CH2 domain may have the sequence set forth in SEQ ID NO: 5. [LALA-PA]

In a preferred embodiment, the specific binding member comprises, has, or consists of: the CH2 and CH3 domain sequence of specific binding member FS22-172-003, FS22-172-002, FS22-172-004, FS22-172-001, FS22-172-005, FS22-172-006, or FS22-172, preferably the CH2 and CH3 domain sequence of specific binding member FS22-172-003, FS22-172-002, FS22-172-004, FS22-172-001, FS22-172-005, or FS22-172-006, more preferably the CH2 and CH3 domain sequence of specific binding member FS22-172-003, FS22-172-002, or FS22-172-004, yet more preferably the CH2 and CH3 domain sequence of specific binding member FS22-172-003, wherein the CH2 and CH3 domain sequence of specific binding member FS22-172-003, FS22-172-002, FS22-172-004, FS22-172-001, FS22-172-005, FS22-172-006, and FS22-172 is shown in SEQ ID NOs 141, 132, 150, 123, 159, 167, and 114, respectively, starting at amino acid 7 onwards.

In an alternative preferred embodiment, the specific binding member comprises, has, or consists of: the CH2 and CH3 domain sequence of specific binding member FS22-053-008, FS22-053-009, FS22-053-011, FS22-053-017, FS22-053-014, FS22-053-010, FS22-053-012, FS22-053-013, FS22-053-015, FS22-053-016, or FS22-053, preferably the CH2 and CH3 domain sequence of specific binding member FS22-053-008, FS22-053-009, FS22-053-011, FS22-053-017, or FS22-053-014, more preferably the CH2 and CH3 domain sequence of specific binding member FS22-053-008, FS22-053-009, FS22-053-011, or FS22-053-017, yet more preferably the CH2 and CH3 domain sequence of specific binding member FS22-053-008, wherein the CH2 and CH3 domain sequence of specific binding member FS22-053-008, FS22-053-009, FS22-053-011, FS22-053-017, FS22-053-014, FS22-053-010, FS22-053-012, FS22-053-013, FS22-053-015, FS22-053-016, and FS22-053 is shown in SEQ ID NOs 23, 32, 50, 104, 77, 41, 59, 68, 86, 95, and 15 respectively, starting at amino acid 7 onwards.

In an alternative preferred embodiment, the specific binding member comprises, has, or consists of the sequence of specific binding member FS22-053-008, FS22-053-009, FS22-053-011, FS22-053-017, FS22-053-014, FS22-053-010, FS22-053-012, FS22-053-013, FS22-053-015, FS22-053-016, or FS22-053, preferably the sequence of specific binding member FS22-053-008, FS22-053-009, FS22-053-011, FS22-053-017, or FS22-053-014, more preferably the sequence of specific binding member FS22-053-008, FS22-053-009, FS22-053-011, or FS22-053-017, yet more preferably the sequence of specific binding member FS22-053-008, wherein the sequence of specific binding member FS22-053-008, FS22-053-009, FS22-053-011, FS22-053-017, FS22-053-014, FS22-053-010, FS22-053-012, FS22-053-013, FS22-053-015, FS22-053-016, and FS22-053 is set forth in SEQ ID NOs 23, 32, 50, 104, 77, 41, 59, 68, 86, 95, and 15, respectively.

In a preferred embodiment, he specific binding member may comprise one or more further antigen-binding sites that bind one or more further antigens, in addition to the CD137 antigen-binding site located in the constant domain of the specific binding member. The one or more further antigen-binding sites preferably bind their cognate antigens specifically.

The one or more further antigen-binding sites may bind CD137 or another antigen. The specific binding member may thus be a multispecific, for example a bispecific, trispecific, or tetraspecific molecule, preferably a bispecific molecule. In a preferred embodiment, the specific binding member is capable of simultaneously binding to CD137 and the one or more further antigens.

Antibody molecules are known to have a modular architecture comprising discrete domains, which can be combined in a multitude of different ways to create multispecific, e.g. bispecific, trispecific, or tetraspecific antibody formats. Exemplary multispecific antibody formats are described in Spiess et al. (2015) and Kontermann (2012), for example. The specific binding members of the present invention may be employed in such multispecific antibody formats. This has the additional advantage of introducing a further antigen-binding site into such multispecific antibody format through the presence of the antigen-binding site the constant domain, e.g. the CH3 domain, of the specific binding member.

For example, the specific binding member of the invention may be a heterodimeric antibody molecule, such as a heterodimeric complete immunoglobulin molecule, or a fragment thereof. In this case, one part of the antibody molecule will have a sequence or sequences as described herein. For example, where the specific binding member of the invention is a bispecific heterodimeric antibody molecule, the specific binding member may comprise a heavy chain comprising a CH3 domain as described herein paired with a heavy chain which binds an antigen other than CD137. Techniques for preparing heterodimeric antibodies are known in the art and include knobs-into-holes (KIHs) technology, which involves engineering the CH3 domains of an antibody molecule to create either a "knob" or a "hole" to promote chain heterodimerization. Alternatively, heterodimeric antibodies can be prepared through the introduction of charge pairs into the antibody molecule to avoid homodimerization of CH3 domains by electrostatic repulsion and to direct heterodimerization by electrostatic attraction. Examples of heterodimeric antibody formats include CrossMab, mAb-Fv, SEED-body, and KIH IgG.

Alternatively, a multispecific specific binding member of the invention may comprise a complete immunoglobulin molecule or a fragment thereof and an additional antigen-binding moiety or moieties. The antigen-binding moiety may for example be an Fv, scFv or single domain antibody, and may be fused to the complete immunoglobulin molecule or a fragment thereof. Examples of multispecific antibody molecules comprising additional antigen-binding moieties fused to a complete immunoglobulin molecule include DVD-IgG, DVI-IgG, scFv4-IgG, IgG-scFv, and scFv-IgG molecules (Spiess et al., 2015; FIG. 1). Examples of multispecific antibody molecules comprising additional antigen-binding moieties fused to an immunoglobulin fragment comprising a CH3 domain include scDiabody-CH3, Diabody-CH3, and scFv-CH3 KIH, for example (Spiess et al., 2015; FIG. 1).

Other suitable multispecific formats would be readily apparent to the skilled person.

In a preferred embodiment, the specific binding member comprises a second antigen-binding site that binds a second antigen, wherein the second antigen-binding site preferably is a CDR-based antigen-binding site. A CDR-based antigen-binding site is an antigen-binding site in an antibody variable region. A CDR-based antigen-binding site is formed by six CDRs; three light chain variable domain (VL) CDRs and three heavy chain variable domain (VH) CDRs.

The preparation of antibody molecules against a given antigen and determination of the CDR sequences of such antibody molecules, is well established and many suitable techniques are known in the art. The CDR sequences may, for example, be determined according to Kabat et al., 1991 or the international ImMunoGeneTics information system (IMGT) (Lefranc et al., 2015).

For example, the specific binding member may be a $mAb^2$ (TM) bispecific antibody. A $mAb^2$ bispecific antibody, as referred to herein, is an IgG immunoglobulin which includes a CDR-based antigen-binding site in each of its variable regions and at least one antigen binding site in a constant domain. Where the specific binding member of the invention is in a $mAb^2$ format, the specific binding member thus comprises a CDR-based antigen-binding site in each of its variable regions, in addition to an CD137 antigen-binding site in a constant domain of the specific binding member.

The three VH domain CDRs of the antigen-binding site may be located within an immunoglobulin VH domain and the three VL domain CDRs may be located within an immunoglobulin VL domain. For example, the CDR-based antigen-binding site may be located in an antibody variable region.

The specific binding member may have one or preferably more than one, for example two, CDR-based antigen binding sites for the second antigen. The specific binding member thus may comprise one VH and one VL domain but preferably comprises two VH and two VL domains, i.e. two VH/VL domain pairs, as is the case in naturally-occurring IgG molecules.

In some preferred embodiments, the specific binding member may be an immunoglobulin comprising two variable regions, each variable region comprising a CDR-based antigen binding site for the second antigen.

In a preferred embodiment, the antibody is thus an antibody molecule that binds CD137 and a second antigen, the antibody molecule comprising:

(i) two antigen-binding sites for CD137 located in the two CH3 domains of the antibody molecule; and (ii) two CDR-based antigen-binding sites for the second antigen, each formed by an immunoglobulin VH domain and an immunoglobulin VL domain.

In a more preferred embodiment, the antibody is a complete immunoglobulin molecule, e.g. a complete IgG1 molecule, that binds CD137 and a second antigen, the antibody molecule comprising:

(i) two antigen-binding sites for CD137 located in the two CH3 domains of the antibody molecule; and (ii) two CDR-based antigen-binding sites for the second antigen, each formed by an immunoglobulin VH domain and an immunoglobulin VL domain; and wherein the immunoglobulin molecule further comprises CH1, CH2 and CL domains. Activation of CD137 requires clustering of CD137 on the immune cell surface, e.g. the T cell surface, which in turn stimulates intracellular signalling pathways and immune cell activation. Binding of specific binding members to CD137 on the immune cell surface in the absence of crosslinking of the specific binding members may not cause CD137 to form clusters, and consequently may not result in immune cell activation.

The present inventors have shown that the specific binding members of the FS22-53 and FS22-172 lineages do not cause T cell activation in the absence of crosslinking of the specific binding member (see Example 5).

As explained above, crosslinking of antibody molecules through binding to Fcγ receptors is both inefficient and cannot be targeted to a particular location e.g. the site of a disease, as Fcγ receptor expressing cells are present throughout the human body. The second antigen bound by the second antigen-binding site is therefore preferably not an Fcγ receptor.

In a preferred embodiment, the specific binding members of the invention therefore comprise a second antigen binding site that binds a second antigen, wherein the second antigen is capable of binding to and crosslinking multiple specific binding members.

For example, the present inventors have shown that where the second antigen is a multimeric molecule, binding of the specific binding member to the second antigen results in, or enhances, T cell activation. The second antigen is therefore preferably a multimeric antigen, such as a dimer, trimer or higher-order multimer, and thus able to crosslink several specific binding members.

The present inventors have also shown using CD137/second antigen $mAb^2$ molecules that where the second antigen is a surface antigen, such as a cell-surface antigen, which can be monomeric or multimeric and is present in high concentrations and/or clustered at a surface, e.g. a cell surface, binding of the antibody molecule to the second antigen results in, or enhances, T cell activation. Without wishing to be bound by theory, it is thought that binding of the antibody molecule to an abundant cell-surface antigen, for example, results in a high concentration of antibody molecules bound to the cell surface which places the antibody molecules in sufficiently close proximity to be able to drive clustering of CD137 and immune cell activation. In a preferred embodiment, the second antigen is therefore a surface antigen which is expressed at a high concentration on a surface, e.g. a cell surface.

A specific binding member comprising a second antigen-binding site that binds a second antigen, as described herein, and which activates immune cells, such as T cells, only on binding to the second antigen, or whose immune cell activation activity is enhanced on binding to the second antigen, is also referred to as a conditional agonist. This immune cell activation activity on binding to the second antigen is independent of binding of the specific binding member to Fcγ receptors and/or external crosslinking agents, such as protein A or G or secondary antibodies, and therefore allows the conditional agonist activity of the specific binding member to be targeted to sites where the second antigen is present. For example, where the second antigen is a disease antigen, the specific binding member may activate the immune cell selectively at the site of disease and not elsewhere in an individual.

In addition, a specific binding member which activates immune cells, such as T cells, only on binding to a second antigen, preferably has increased immune cell activation activity compared with specific binding members that rely on crosslinking by other mechanisms, such as external crosslinking agents, or crosslinking via Fcγ receptor interaction. Because the activation of CD137 is more efficient, immune cell activation may be achieved at lower concentrations of specific binding members described herein relative to other specific binding members.

Thus, the specific binding member of the invention preferably induces increased activation of immune cells, such as T cells, when the specific binding member is crosslinked, e.g. through binding to a second antigen, than when the specific binding member is not crosslinked.

The ability of an antibody molecule or specific binding member to activate T cells may be measured using a T cell activation assay. T cells release IL-2 on activation. A T cell activation assay may therefore measure IL-2 release to determine the level of T cell activation induced by the antibody molecule or specific binding member.

For example, the ability of the antibody molecule or specific binding member to activate T cells may be determined by measuring the concentration of the antibody molecule or specific binding member required to achieve half-maximal release of IL-2 by the T cells in a T cells activation assay when the specific binding member or antibody molecule is crosslinked. This is referred to as the EC50 of the antibody molecule or specific binding member below. A lower EC50 indicates that a lower concentration of the antibody molecule or specific binding member is needed to achieve half-maximal release of IL-2 by the T cells in the T cells activation assay, and thus that the antibody molecule or specific binding member has a higher T cell activation activity. The specific binding member or antibody molecule may be crosslinked using an anti-CH2 antibody, for example.

In a preferred embodiment, the antibody molecule or specific binding member has an $EC_{50}$ in a T cell activation assay which is within 10-fold, 5-fold, 4-fold, 3-fold, or 2-fold of the $EC_{50}$ of FS22-172-003/HeID1.3 (comprising the LALA mutation) in the same assay, wherein FS22-172-003/HeID1.3 (LALA) consists of or comprises the heavy chain set forth in SEQ ID NO: 145 and the light chain set forth in SEQ ID NO: 173.

In an alternative preferred embodiment, the antibody molecule or specific binding member has an $EC_{50}$ in a T cell activation assay which is within 10-fold, 5-fold, 4-fold, 3-fold, or 2-fold of the $EC_{50}$ of FS22-053-008/HeID1.3 (comprising the LALA mutation) in the same assay, wherein FS22-053-008/HeID1.3 (LALA) consists of or comprises the heavy chain set forth in SEQ ID NO: 27 and the light chain set forth in SEQ ID NO: 173.

For example, the antibody molecule or specific binding member may have an $EC_{50}$ in a T cell activation assay of 5 nM or less, 4 nM or less, 3 nM or less, 2 nM or less, 1 nM or less, or 0.5 nM or less.

In addition, or alternatively, the ability of an antibody molecule or specific binding member to activate T cells may be determined by measuring the maximum concentration of IL-2 released by the T cells in a T cell activation assay in the presence of the antibody molecule or specific binding member, wherein the antibody molecule or specific binding member is crosslinked.

In a preferred embodiment, the maximum concentration of IL-2 released by the T cells in a T cell activation assay in the presence of the antibody molecule or specific binding member in the presence of crosslinking is within 3-fold, 2-fold, or 1.5-fold of the maximum concentration of IL-2 released by the T cells in the presence of FS22-053-008/HeID1.3 (comprising the LALA mutation) or FS22-172-003/HeID1.3 (comprising the LALA mutation).

The T cell activation assay may be a T cell assay as described herein, such as a CD8+ T cell assay, as described in the present Examples, see e.g. Example 5.4.

For example, a T cell activation assay may be an IL-2 release assay based on CD8+ T cells isolated from human Peripheral Blood Mononuclear Cells (PBMCs). For example, the T cell activation assay may comprise isolating human PBMCs from leucocyte depletion cones. Methods for isolating PBMCs are known in the art and described in the present examples. The CD8+ T cells may then be isolated from the PBMCs. Methods for isolating CD8+ T cells from PBMCs are known in the art and described in the present examples.

The CD8+ T cells may then be added to multiwall plates coated with an anti-human CD3 antibody. A suitable dilution of each test antibody molecule or specific binding member may be prepared and added to the wells. The T cells may then be incubated at 37° C., 5% $CO_2$ for 24 hours with the test antibody. Supernatants may be collected and assayed to determine the concentration of IL-2 in the supernatant. Methods for determining the concentration of IL-2 in a solution are known in the art and described in the present examples. The concentration of human IL-2 may be plotted versus the log concentration of the antibody molecule or specific binding member. The resulting curves may be fitted using the log (agonist) versus response equation.

The second antigen bound by the second antigen-binding site of the specific binding member may be an immune cell antigen, or a disease antigen. Disease antigens include pathogenic antigens and tumour antigens.

The immune cell antigen bound by the specific binding member may be present on the same immune cell or on a different immune cell to CD137.

The immune cell antigen may be a member of the tumour necrosis factor receptor superfamily (TNFRSF) other than CD137. TNFRSF receptors are membrane-bound cytokine receptors that comprise an extracellular cysteine rich domain that binds one or more ligands of the tumour necrosis factor superfamily (TNFSF).

The TNFRSF receptor may be located on the surface of an immune cell. Upon binding of a TNFRSF ligand, TNFRSF receptors form clusters on the immune cell surface which activates the immune cell. For example, ligand bound TNFRSF receptors may form multimers, such as trimers, or clusters of multimers. The presence of clusters of ligand-bound TNFRSF receptors stimulates intracellular signalling pathways which activate the immune cell.

Without wishing to be bound by theory it is thought that by engaging both CD137 and a second TNFRSF receptor on an immune cell surface, the specific binding members will cause both CD137 and the second TNFRSF receptor to cluster and activate the immune cell(s). In other words, the specific binding member will act as a TNFRSF receptor agonist when both targets are bound.

TNFRSF receptors include CD27, CD40, EDA2R, EDAR, FAS, LTBR, RELT, TNFRSF1A, TNFRSF1B, TNFRSF4, TNFRSF6B, TNFRSF8, TNFRSF10A-10D, TNFRSF11A, TNFRSF11B, TNFRSF12A, TNFRSF13B, TNFRSF13C, TNFRSF14, TNFRSF17, TNFRSF18, TNFRSF19, TNFRSF21 and TNFRSF25.

CD27 (TNFRSF7: Gene ID 939) has the reference amino acid sequence of NP_001233.1 and may be encoded by the reference nucleotide sequence of NM_001242.4. CD40 (TNFRSF5: Gene ID 958) has the reference amino acid sequence of NP_001241.1 and may be encoded by the reference nucleotide sequence of NM_001250.5. EDA2R (TNFRSF27: Gene ID 60401) has the reference amino acid sequence of NP_001186616.1 and may be encoded by the reference nucleotide sequence of NM_001199687.2. EDAR (Gene ID 10913) has the reference amino acid sequence of NP_071731.1 and may be encoded by the reference nucleotide sequence of NM_022336, 3. FAS (TNFRSF6: Gene ID 355) has the reference amino acid sequence of NP_000034.1 and may be encoded by the reference nucleotide sequence of NM_000043.5. LTBR (TNFRSF3: Gene ID 4055) has the reference amino acid sequence of NP_001257916.1 and may be encoded by the reference nucleotide sequence of NM_001270987.1. RELT (TNFRSF19L: Gene ID 84957) has the reference amino acid sequence of NP_116260.2 and may be encoded by the reference nucleotide sequence of NM_032871.3. TNFRSF1A (Gene ID 7132) has the reference amino acid sequence of NP_001056.1 and may be encoded by the reference nucleotide sequence of NM_001065.3. TNFRSF1B (Gene ID 7133) has the reference amino acid sequence of NP_001057.1 and may be encoded by the reference nucleotide sequence of NM_001066.2. TNFRSF4 (Gene ID 7293) has the reference amino acid sequence of NP_003318 and may be encoded by the reference nucleotide sequence of NM_003327). TNFRSF6B (Gene ID 8771) has the reference amino acid sequence of NP_003814.1 and may be encoded by the reference nucleotide sequence of NM_003823.3. TNFRSF8 (Gene ID 943) has the reference amino acid sequence of NP_001234.3 and may be encoded by the reference nucleotide sequence of NM_001243.4. TNFRSF10A (Gene ID 8797) has the reference amino acid sequence of NP_003835.3 and may be encoded by the reference nucleotide sequence of NM_003844.3. TNFRSF10B (Gene ID 8795) has the reference amino acid sequence of NP_003833.4 and may be encoded by the reference nucleotide sequence of NM_003842.4. TNFRSF10C (Gene ID 8794) has the reference amino acid sequence of NP_003832.2 and may be encoded by the reference nucleotide sequence of NM_003841.4. TNFRSF10D (Gene ID 8793) has the reference amino acid sequence of NP_003831.2 and may be encoded by the reference nucleotide sequence of NM_003840.4. TNFRSF11A (Gene ID 8792) has the reference amino acid sequence of XP_011524547.1 and may be encoded by the reference nucleotide sequence of XM_11526245.2. TNFRSF11B (Gene ID 4982) has the reference amino acid sequence of NP_002537.3 and may be encoded by the reference nucleotide sequence of NM_002546.3. TNFRSF12A (Gene ID 51330) has the reference amino acid sequence of NP_057723.1 and may be encoded by the reference nucleotide sequence of NM_016639.2. TNFRSF13B (Gene ID 23495) has the reference amino acid sequence of NP_0036584.1 and may be encoded by the reference nucleotide sequence of NM_012452.2. TNFRSF13C (Gene ID 115650) has the reference amino acid sequence of NP_443177.1 and may be encoded by the reference nucleotide sequence of NM_052945.3. TNFRSF14 (Gene ID 8764) has the reference amino acid sequence of NP_001284534.1 and may be encoded by the reference nucleotide sequence of NM_001297605.1. TNFRSF17 (Gene ID 608) has the reference amino acid sequence of NP_001183.2 and may be encoded by the reference nucleotide sequence of NM_001192.2. TNFRSF18 (Gene ID 8784) has the reference amino acid sequence of NP_004195.2 and may be encoded by the reference nucleotide sequence of NM_004186.1. TNFRSF19 (Gene ID 55504) has the reference amino acid sequence of NP_001191387.1 and may be encoded by the reference nucleotide sequence of NM_001204458.1. NFRSF21 (Gene ID 27242) has the reference amino acid sequence of NP_055267.1 and may be encoded by the reference nucleotide sequence of NM_014452.4. TNFRSF25 (DR3: Gene ID 8718) binds to ligand TNFSF15 (TL1A) has the reference amino acid sequence of NP_001034753.1 and may be encoded by the reference nucleotide sequence of NM_001039664.1.

Alternatively, the immune cell antigen bound by the second antigen-binding site may be a molecule which has a regulatory function in the immune system other than a TNFRSF member, e.g. an immune costimulatory molecule or an inhibitory checkpoint molecule. Examples of such immune regulatory molecules include ICOS (CD278), LAG3, PD1, PD-L1, PD-L2, B7H3, B7H4, CTLA4, TIGIT, BTLA, HVEM, T cell immunoglobulin, mucin-domain containing-3 (TIM-3), CD47, CD73, A2aR, CD200, CD200R, Colony stimulating factor 1 receptor (CSF-1R), VISTA CD28, CD80, LLT1, galectin-9, NKG2A, NKG2D, and KIR.

The immune cell on which the immune cell antigen is present may belong to any immune cell subset and can be a T cell, a tumour-infiltrating leukocyte (TIL), a myeloid lineage cell such as an antigen presenting cell (APC), an NK cell and/or a B cell. When the immune cell antigen is a TNFRSF receptor, the immune cell on which the TNFRSF receptor is present is preferably a T cell.

Alternatively, the second antigen-binding site may bind to a disease antigen as mentioned above. Without wishing to be bound by theory, it is thought that binding of the specific binding member to CD137 and a disease antigen will result in the activation of T cells in the vicinity of the disease. The activated T cells may then then initiate, promote or take part in an immune response, for example an immune response against a pathogen or a cancer cell. An overview of the role the immune system plays in recognizing and eradicating cancer cells is provided by Chen and Mellman (2013).

In a preferred embodiment, the disease antigen is a tumour antigen. A tumour antigen is an antigen that is predominantly present in the environment of a tumour, and is not ubiquitously present elsewhere in an individual. For example, the tumour antigen may be present on the surface of tumour cells or may be present on other stromal cells of the tumour microenvironment or in biological fluids in the vicinity of a tumour. The tumour antigen is therefore a marker of the location of tumour cells in an individual.

In some embodiments, the tumour antigen may be an antigen that is located on the surface of a cancer cell. Preferably, the tumour antigen is upregulated or overexpressed on tumour cells, whereas it is not abundantly expressed by the corresponding normal somatic cells from the same tissue in the absence of a tumour.

In some embodiments, the tumour antigen is upregulated or overexpressed on stromal cells of the tumour microenvironment, compared with stromal cells of the corresponding normal tissue in the absence of a tumour.

Preferred tumour antigens exist on the cell surface and are not rapidly internalised.

Tumour antigens that are suitable for targeting by the specific binding members may be identified using methods that are known in the art. For example, a specific binding member targeting CD137 receptor and a tumour antigen can be used in an assay where a CD137 expressing cell is co-cultured with a tumour antigen expressing cell and activation of the CD137 expressing cell is measured, for example by a T cell activation assay, a proliferation assay or cytotoxicity assay.

A cell surface tumour antigen may be a Tumour-Associated Antigen (TAA) or a Tumour-specific antigen (TSA).

Tumour antigens expressed by cancer cells may include, for example, cancer-testis (CT) antigens encoded by cancer-germ line genes, such as MAGE-A1, MAGE-A2, MAGE-A3, MAGE-A4, MAGE-A5, MAGE-A6, MAGE-A7, MAGE-A8, MAGE-A9, MAGE-A10, MAGE-A11, MAGE-A12, GAGE-I, GAGE-2, GAGE-3, GAGE-4, GAGE-5, GAGE-6, GAGE-7, GAGE-8, BAGE-I, RAGE-1, LB33/MUM-1, PRAME, NAG, MAGE-Xp2 (MAGE-B2), MAGE-Xp3 (MAGE-B3), MAGE-Xp4 (MAGE-B4), MAGE-C1/CT7, MAGE-C2, NY-ESO-I, LAGE-I, SSX-I, SSX-2 (HOM-MEL-40), SSX-3, SSX-4, SSX-5, SCP-I and XAGE and immunogenic fragments or variants thereof (Simpson et al., 2005; Gure et al., 2005; Velazquez et al., 2007; Andrade et al., 2008; Tinguely et al., 2008; Napoletano et al., 2008).

Other cell surface tumour antigens include, for example, AFP, $\alpha_v\beta_3$ (vitronectin receptor), $\alpha_v\beta_6$, B-cell maturation agent (BCMA), CA125 (MUC16), CD4, CD20, CD22, CD33, CD52, CD56, CD66e, CD80, CD140b, CD227 (MUC1), EGFR (HER1), EpCAM, GD3 ganglioside, HER2, prostate-specific membrane antigen (PSMA), prostate specific antigen (PSA), CD5, CD19, CD21, CD25, CD37, CD30, CD33, CD45, HLA-DR, anti-idiotype, carcinoembyronic antigen (CEA), e.g. carcinoembryonic antigen-related cell adhesion molecule 5 (CEACAM5), TAG-72, Folate-binding protein, A33, G250, ferritin, glycolipids such as gangliosides, carbohydrates such as CA-125, IL-2 receptor, fibroblast activation protein (FAP), IGF1R, B7H3, B7H4, PD-L1, CD200, EphA2, and mesothelin or variants thereof. These and other cell surface tumour antigens are described in Carter et al., 2004; Scott and Renner, 2001; and Cheever et al., 2009; Tai and Anderson, 2015; and Podojil and Miller, 2017.

Other tumour antigens include out-of-frame peptide-MHC complexes generated by the non-AUG translation initiation mechanisms employed by "stressed" cancer cells (Malarkannan et al., 1999).

Other tumour antigens include peptide-MHC complexes on the surface of tumour cells or of cells of the tumour microenvironment, where the peptide-MHC complexes comprise a tumour-specific neoantigen peptide fragment of a mutated intracellular tumour antigen, and where the peptide neoantigen harbours one or more tumour-specific mutations (Gubin et al., 2015). Other tumour antigens are well-known in the art (see for example WO00/20581;

Cancer Vaccines and Immunotherapy (2000) Eds Stern, Beverley and Carroll, Cambridge University Press, Cambridge). The sequences of these tumour antigens are readily available from public databases but are also found in WO1992/020356 A1, WO1994/005304 A1, WO1994/023031 A1, WO1995/020974 A1, WO1995/023874 A1 and WO1996/026214 A1.

Preferred tumour antigens include HER2, FAP, EpCAM, CEACAM5, CD20, CD73, PSMA, mesothelin, EphA2, IGF1R, CD200, $\alpha_v\beta_6$, BCMA, PD-L1, B7H3, B7H4 and EGFR.

In a more preferred embodiment, the tumour antigen is mesothelin (MSLN).

In an alternative more preferred embodiment, the tumour antigen is PD-L1.

HER2 (ERBB2; Gene ID 2064) may have the reference amino acid sequence of NP_001005862.1 and may be encoded by the reference nucleotide sequence of NM_001005862.2. FAP (Gene ID 2191) may have the reference amino acid sequence of NP_001278736.1 and may be encoded by the reference nucleotide sequence of NM_001291807.1. EpCAM (Gene ID 4072) may have the reference amino acid sequence of NP_002345.2 and may be encoded by the reference nucleotide sequence of NM_002354.2. CEACAM5 (Gene ID 1048) may have the reference amino acid sequence of NP_001278413.1 and may be encoded by the reference nucleotide sequence of NM_001291484.2. CD20 (MS4A1; Gene ID 931) may have the reference amino acid sequence of NP_068769.2 and may be encoded by the reference nucleotide sequence of NM_021950.3. CD73 (NTSE; Gene ID 4907) may have the reference amino acid sequence of NP_001191742.1 and may be encoded by the reference nucleotide sequence of NM_001204813.1. PSMA (FOLH1; Gene ID 2346) may have the reference amino acid sequence of NP_001014986.1 and may be encoded by the reference nucleotide sequence of NM_001014986.1. Mesothelin (MSLN; Gene ID 10232) may have the reference amino acid sequence of NP_001170826.1 and may be encoded by the reference nucleotide sequence of NM_001177355.2. EphA2 (Gene ID 1969) may have the reference amino acid sequence of NP_001316019.1 and may be encoded by the reference nucleotide sequence of NM_001329090.1. IGF1R (Gene ID 3480) may have the reference amino acid sequence of NP_000866.1 and may be encoded by the reference nucleotide sequence of NM_000875.4. CD200 (Gene ID 4345) may have the reference amino acid sequence of NP_001004196.2 and may be encoded by the reference nucleotide sequence of NM_001004196.3. $\alpha_v\beta_6$ is a heterodimer composed of the integrin subunit alpha V and integrin subunit beta 6. Integrin subunit alpha V (ITGAV; Gene ID 3685) may have the reference amino acid sequence of NP_001138471.1 and may be encoded by the reference nucleotide sequence of NM_001144999.2. Integrin subunit beta 6 (ITGB6; Gene ID 3694) may have the reference amino acid sequence of NP_000879.2 and may be encoded by the reference nucleotide sequence of NM_000888.4. BCMA (TNFRSF17; Gene ID 608) may have the reference amino acid sequence of NP_001183.2 and may be encoded by the reference nucleotide sequence of NM_001192.2. PD-L1 (CD274; Gene ID 29126) may have the reference amino acid sequence of NP_001254635.1 and may be encoded by the reference nucleotide sequence of NM_001267706.1. B7H3 (CD276; Gene ID 80381) may have the reference amino acid sequence of NP_001019907.1 and may be encoded by the reference nucleotide sequence of NM_001024736.1. B7H4 (VTCN1; Gene ID 79679) may have the reference amino acid sequence of NP_001240778.1 and may be encoded by the reference nucleotide sequence of NM_001253849.1. EGFR (Gene ID 1956) may have the reference amino acid sequence of NP_001333826.1 and may be encoded by the reference nucleotide sequence of NM_001346897.1.

In other embodiments, the tumour antigen may be a soluble tumour antigen, for example a growth factor that is produced by or in response to cancer cells. A soluble factor may be upregulated or overexpressed in biological fluids in the vicinity of a tumour. A soluble tumour antigen may be multimeric, for example a dimer or a trimer. A soluble tumour antigen may be present in higher concentrations at the tumour site or in the tumour microenvironment than elsewhere in the body of an individual. The tumour microenvironment and associated soluble tumour antigens are described in more detail in Bhome et al. (2015).

Suitable soluble tumour antigens include VEGF, HGF, SDF1 and TGF-beta, e.g. TGF-beta-1, TGF-beta-2, TGF-beta-3 and TGF-beta-4.

VEGF (VEGFA; gene ID 7422) has the reference amino acid sequence of NP_001020537.2 and may be encoded by the reference nucleotide sequence of NM_001025366.2. HGF (gene ID 3082) has the reference amino acid sequence of NP_000592.3 and may be encoded by the reference nucleotide sequence of NM_000601.5. SDF1 (CXCL12; gene ID 6387) has the reference amino acid sequence of NP_000600.1 and may be encoded by the reference nucleotide sequence of NM_000609.6. TGF-beta-1 (TGFB1; gene ID 7040) may have the reference amino acid sequence of NP_000651.3 and may be encoded by the reference nucleotide sequence of NM_000660.6. TGF-beta-2 (TGFB2; gene ID 7042) may have the reference amino acid sequence of NP_001129071.1 and may be encoded by the reference nucleotide sequence of NM_001135599.3. TGF-beta-3 (TGFB3; gene ID 7043) may have the reference amino acid sequence of NP_001316867.1 and may be encoded by the reference nucleotide sequence of NM_001329938.1. TGF-beta-4 (LEFTY2; gene ID 7044) may have the reference amino acid sequence of NP_001165896.1 and may be encoded by the reference nucleotide sequence of NM_001172425.2.

In an alternative preferred embodiment, the disease antigen is a pathogenic antigen.

Activation of immune cells, such as T cells, NK cells and/or macrophages by the specific binding member in the vicinity of a site of an infectious disease is expected to be useful in the treatment of the infectious disease. The infectious disease may be an acute or persistent infectious diseases but preferably is a persistent infectious diseases.

The pathogenic antigen is preferably an antigen expressed by a human pathogen, such as a viral, bacterial, fungal or parasitic antigen (e.g. a protozoal antigen), preferably a viral or bacterial antigen. A pathogenic antigen is an antigen that is predominantly present on a pathogen, or in the vicinity of a site of an infectious disease, and is not ubiquitously present elsewhere in an individual.

For example, the pathogenic antigen may be an antigen present on the surface of a virus, bacterium, fungus or parasite, or a soluble antigen expressed by a virus, bacterium, fungus or parasite. The virus, bacterium, fungus, or parasite may be a virus, bacterium, fungus, or parasite as referred to elsewhere herein.

Where the pathogenic antigen is a soluble antigen, the antigen may be upregulated or overexpressed in biological fluids in the vicinity of the site of the infectious disease. For example, a soluble pathogenic antigen may be present in higher concentrations at, or in the vicinity of, the site of the infectious disease than elsewhere in the body of an individual. The soluble pathogenic antigen may be multimeric, for example a dimer or a trimer.

Pathogenic antigens that are suitable for targeting by the specific binding member may be identified using methods that are known in the art. For example, a specific binding member targeting CD137 and a pathogenic antigen can be used in an assay where a CD137 expressing cell is co-cultured with a pathogen or pathogenic antigen and activation of the OX40 expressing cell is measured, for example by T cell activation assay, a proliferation assay or cytotoxicity assay.

Many pathogenic antigens suitable for targeting by the specific binding member are further more known in the art and can be selected by the skilled person according to the infectious disease to be treated. Examples of viral antigens include proteins p24, gp120, and gp41 expressed by human immunodeficiency virus (HIV), hepatitis B surface antigen (HBsAg) expressed by hepatitis B virus (HBV), and haemagglutinin and neuraminidase expressed by influenza virus. Examples of bacterial antigens include Rv1733, Rv2389 and Rv2435n expressed by *Mycobacterium tuberculosis*.

The specific binding member may also comprise a variant of a first or second sequence, AB CD or EF structural loop sequence, CH3 domain, CH2 domain, Fcab, CDR, VH domain, VL domain, light chain and/or heavy chain sequence as disclosed herein. Suitable variants can be obtained by means of methods of sequence alteration, or mutation, and screening. In a preferred embodiment, a specific binding member comprising one or more variant sequences retains one or more of the functional characteristics of the parent specific binding member, such as binding specificity and/or binding affinity for CD137. For example, a specific binding member comprising one or more variant sequences preferably binds to CD137 with the same affinity as, or a higher affinity than, the (parent) specific binding member. The parent specific binding member is a specific binding member which does not comprise the amino acid substitution(s), deletion(s), and/or insertion(s) which has (have) been incorporated into the variant specific binding member.

For example, a specific binding member may comprise a first, second or third sequence, AB, CD or EF structural loop sequence, CH3 domain, CH2 domain, Fcab, CDR, VH domain, VL domain, light chain and/or heavy chain sequence which has at least 70%, at least 75%, at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to a first, second or third sequence, AB, CD or EF structural loop sequence, CH3 domain, CH2 domain, Fcab, CDR, VH domain, VL domain, light chain or heavy chain sequence disclosed herein.

In a preferred embodiment, the specific binding member has or comprises a CH3 domain sequence which has at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity, preferably at least 99%, at least 99.1%, at least 99.2%, at least 99.3%, at least 99.4%, at least 99.5%, at least 99.6%, at least 99.7%, at least 99.8%, or at least 99.9% sequence identity, to the CH3 domain sequence set forth in SEQ ID NO: 21, 30, 48, 102, 75, 39, 57, 66, 84, 93, 175, 139, 130, 148, 121, 157, 165 or 112.

In a further preferred embodiment, the specific binding member has or comprises a CH2 domain sequence, which has at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to the CH2 domain sequence set forth in SEQ ID NO: 5 or 6.

In another preferred embodiment, the specific binding member has, comprises, or consists of, a sequence, which has at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to the Fcab sequence set forth in SEQ ID NO: 23, 32, 50, 104, 77, 41, 59, 68, 86, 95, 15, 141, 132, 150, 123, 159, 167, 114, 25, 34, 52, 106, 79, 43, 61, 70, 88, 97, 16, 143, 134, 152, 125, 161, 169, or 116.

Sequence identity is commonly defined with reference to the algorithm GAP (Wisconsin GCG package, Accelerys Inc, San Diego USA). GAP uses the Needleman and Wunsch algorithm to align two complete sequences, maximising the number of matches and minimising the number of gaps. Generally, default parameters are used, with a gap creation penalty equalling 12 and a gap extension penalty equalling 4. Use of GAP may be preferred but other algorithms may be used, e.g. BLAST (which uses the method of Altschul et al. (1990)), FASTA (which uses the method of Pearson and Lipman (1988)), or the Smith-Waterman algorithm (Smith and Waterman (1981)), or the TBLASTN program, of Altschul et al. (1990) supra, generally employing default parameters. In particular, the psi-Blast algorithm may be used.

A specific binding member may comprise a first, second or third sequence, AB, CD or EF structural loop sequence, CH3 domain, CH2 domain, Fcab, CDR, VH domain, VL domain, light chain or heavy chain sequence which has one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with a first, second or third sequence, AB, CD or EF structural loop sequence, CH3 domain, CH2 domain, Fcab, CDR, VH domain, VL domain, light chain or heavy chain sequence disclosed herein.

In a preferred embodiment, the specific binding member may comprise a CH3 domain sequence with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the CH3 domain sequence set forth in SEQ ID NO: 21, 30, 48, 102, 75, 39, 57, 66, 84, 93, 175, 139, 130, 148, 121, 157, 165 or 112.

In a further preferred embodiment, the specific binding member comprises a CH2 domain sequence, with one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the CH2 domain sequence set forth in SEQ ID NO: 5 or 6.

In a further preferred embodiment, the specific binding member comprises or consists of a sequence, with one or more amino acid sequence alterations (addition, deletion, substitution and/or insertion of an amino acid residue), preferably 40 alterations or fewer, 30 alterations or fewer, 20 alterations or fewer, 15 alterations or fewer, 10 alterations or fewer, 5 alterations or fewer, 4 alterations or fewer, 3 alterations or fewer, 2 alterations or fewer, or 1 alteration compared with the Fcab sequence set forth in SEQ ID NO: 23, 32, 50, 104, 77, 41, 59, 68, 86, 95, 15, 141, 132, 150, 123, 159, 167, 114, 25, 34, 52, 106, 79, 43, 61, 70, 88, 97, 16, 143, 134, 152, 125, 161, 169, or 116.

Where the specific binding member comprises a variant of a first sequence, AB structural loop sequence, CH3 domain, Fcab, or heavy chain sequence as disclosed herein, the specific binding member preferably retains the sequence PPY between positions 11 and 19, preferably positions 15 and 17, of the CH3 domain of the specific binding member. In addition, the specific binding member preferably retains an insertion, preferably a 5 amino acid insertion between positions 16 and 17 of the CH3 domain of the specific binding member. In a further preferred embodiment, the specific binding member preferably retains the sequence at positions 97 and 98 of the CH3 domain of the specific binding member.

In particular, the specific binding member may be (or antibody molecule may comprise) a variant of specific binding member FS22-053, wherein the variant:

(i) comprises one or more amino acid sequence alterations (addition, deletion, substitution and/or insertion of an amino acid residue), preferably 20 alterations or fewer, 15 alterations or fewer, 10 alterations or fewer, 5 alterations or fewer, 4 alterations or fewer, 3 alterations or fewer, 2 alterations or fewer, or 1 alteration compared with the sequence of specific binding member FS22-053 disclosed herein; or (ii) has at least 70%, at least 75%, at least 80%, at least 85%, at least 90%, at least 95%, at least 96%, at least 97%, at least 98%, at least 99%, at least 99.1%, at least 99.2%, at least 99.3%, at least 99.4%, at least 99.5%, at least 99.6%, at least 99.7%, at least 99.8%, or at least 99.9% sequence identity to the sequence of specific binding member FS22-053 disclosed herein; and wherein the specific binding member or antibody molecule comprises the sequence PPY between positions 15 and 17, and optionally comprises a 5 amino acid insertion between positions 16 and 17, of the CH3 domain of the specific binding member or antibody molecule; and wherein the residue numbering is according to the IMGT residue numbering scheme.

In addition, or alternatively, where the specific binding member comprises a variant of CH3 domain, CH2 and CH3 domain, Fcab, light chain or heavy chain sequence disclosed herein, the variant preferably does not comprise any amino acid alterations in the first, second and third sequence located in the AB, CD and EF structural loops of the CH3 domain of the specific binding member. For example, the variant may not comprise any amino acid alterations in the AB, CD and EF structural loops of the CH3 domain of the specific binding member.

In preferred embodiments in which one or more amino acids are substituted with another amino acid, the substitutions may conservative substitutions, for example according to the following Table. In some embodiments, amino acids in the same category in the middle column are substituted for one another, i.e. a non-polar amino acid is substituted with another non-polar amino acid, for example. In some embodiments, amino acids in the same line in the rightmost column are substituted for one another.

| | | |
|---|---|---|
| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

In some embodiments, substitution(s) may be functionally conservative. That is, in some embodiments the substitution may not affect (or may not substantially affect) one or more functional properties (e.g. binding affinity) of the specific binding member comprising the substitution as compared to the equivalent unsubstituted specific binding member.

Also contemplated is a specific binding member which comprises a CD137 antigen-binding site located in a constant domain, preferably a CH3 domain, of the specific binding member and which competes with a specific binding member of the invention for binding to CD137, or that binds to the same epitope on CD137 as a specific binding member of the invention. Methods for determining competition for an antigen by two specific binding members are known in the art. For example, competition of binding to an antigen by two specific binding members can be determined using surface plasmon resonance, such as Biacore. Methods for mapping the epitope bound by a specific binding member are similarly known in the art.

In some embodiments, the specific binding member may not comprise a CDR-based antigen-binding site.

In particular, the specific binding member may not comprise a CDR-based antigen-binding site that binds PD-L1.

In addition, or alternatively, the specific binding member may not comprise a CDR-based antigen-binding site that binds mesothelin (MSLN).

For example, the specific binding member may not comprise a CDR-based antigen-binding site that binds PD-L1 or MSLN, wherein the specific binding member comprises the first, second and third sequence located in the AB, CD and EF structural loops of the CH3 domain of specific binding member FS22-53-008, or FS22-172-003, the complete AB and EF structural loop sequences of the CH3 domain of specific binding member FS22-53-008, or FS22-172-003, and/or the CH3 domain sequence of specific binding member FS22-53-008, or FS22-172-003.

In particular, the specific binding member may not comprise the CDRs, VH and/or VL domains, and/or heavy and/or light chain sequences of FS22-172-003-AA/E12v2 and FS22-053-008-AA/E12v2 set forth below.

FS22-172-003-AA/E12v2 and FS22-053-008-AA/E12v2
VH domain CDRs
HCDR1 (IMGT)
GYPFTSYG HCDR1 (Kabat)
SYGIS

HCDR2 (IMGT)
ISAYSGGT

HCDR2 (Kabat)
WISAYSGGTNYAQKLQG

HCDR3 (IMGT)
ARDLFPTIFGVSYYYY

HCDR3 (Kabat)
DLFPTIFGVSYYYY

FS22-172-003-AA/E12v2 and FS22-053-008-AA/E12v2
VH domain
EVQLVQSGAEVKRPGASVKVSCKASGYPFTSYGISWVRQAPGQG

LEWMGWISAYSGGTNYAQKLQGRVTMTTDTSTSTAYMELRSLRS

DDTAVYYCARDLFPTIFGVSYYYYWGQGTLVTVSS

FS22-172-003-AA/E12v2 and FS22-053-008-AA/E12v2
VL domain CDRs
LCDR1 (IMGT)
QSIGNR LCDR1 (Kabat)
RASQSIGNRLA

LCDR2 (IMGT)
EAS

LCDR2 (Kabat)
EASTSET

LCDR3 (IMGT)
QQSYSTPYT

LCDR3 (Kabat)
QQSYSTPYT

FS22-172-003-AA/E12v2 and FS22-053-008-AA/E12v2
VL domain
DIQMTQSPSTLSASVRDRVIITCRASQSIGNRLAWYQHKPGKAP

KLLIYEASTSETGVPSRFSGSGSGTDFTLTISSLQPEDFATYYC

QQSYSTPYTFGQGTKLEIK

Heavy chain FS22-172-003-AA/E12v2
*EVQLVQSGAEVKRPGASVKVSCKASGYPFTSYGISWVRQAPGQGLEW*

*MGWISAYSGGTNYAQKLQGRVTMTTDTSTSTAYMELRSLRSDDTAVY*

*YCARDLFPTIFGVSYYYYWGQGTLVTVSS*ASTKGPSVFPLAPSSKST

SGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPC

PAPEAAGGPSVFLFPPKPKDTLMISRTPEVTCVVVDVSHEDPEVKFN

WYVDGVEVHNAKTKPREEQYNSTYRVVSVLTVLHQDWLNGKEYKCKV

SNKALPAPIEKTISKAKGQPREPQVYTLPPSRDELPYIIPPYNQVSL

-continued

TCLVKGFYPSDIAVEWESNGQPENNYKTTPPVLDSDGSFFLYSKLTV

GADRWLEGNVFSCSVMHEALHNHYTQKSLSLSPG

Light chain FS22-172-003-AA/E12v2
*DIQMTQSPSTLSASVRDRVIITCRASQSIGNRLAWYQHKPGKAPKLL*

*IYEASTSETGVPSRFSGSGSGTDFTLTISSLQPEDFATYYC*

*QQSYSTPYTFGQGTKLEIK*RTVAAPSVFIFPPSDEQLKSGTASVVCL

LNNFYPREAKVQWKVDNALQSGNSQESVTEQDSKDSTYSLSSTLTLS

KADYEKHKVYACEVTHQGLSSPVTKSFNRGEC

Heavy chain FS22-053-008-AA/E12v2
*EVQLVQSGAEVKRPGASVKVSCKASGYPFTSYGISWVRQAPGQGLEW*

*MGWISAYSGGTNYAQKLQGRVTMTTDTSTSTAYMELRSLRSDDTAVY*

*YCARDLFPTIFGVSYYYYWGQGTLVTVSS*ASTKGPSVFPLAPSSKST

SGGTAALGCLVKDYFPEPVTVSWNSGALTSGVHTFPAVLQSSGLYSL

SSVVTVPSSSLGTQTYICNVNHKPSNTKVDKKVEPKSCDKTHTCPPC

PAPEAAGGPSVFLFPPKPKDTLMISRTPEVTCVVVDVSHEDPEVKFN

WYVDGVEVHNAKTKPREEQYNSTYRVVSVLTVLHQDWLNGKEYKCKV

SNKALPAPIEKTISKAKGQPREPQVYTLPPSRDELNPPYLFSNQVSL

TCLVKGFYPSDIAVEWESNGQPENNYKTTPPVLDSDGSFFLYSKLTV

DYWRWLEGNVFSCSVMHEALHNHYTQKSLSLSPG

Light chain FS22-053-008-AA/E12v2
*DIQMTQSPSTLSASVRDRVIITCRASQSIGNRLAWYQHKPGKAPKLL*

*IYEASTSETGVPSRFSGSGSGTDFTLTISSLQPEDFATYYC*

*QQSYSTPYTFGQGTKLEIK*RTVAAPSVFIFPPSDEQLKSGTASVVCL

LNNFYPREAKVQWKVDNALQSGNSQESVTEQDSKDSTYSLSSTLTLS

KADYEKHKVYACEVTHQGLSSPVTKSFNRGEC

In addition, or alternatively, the specific binding member may not comprise the CDRs and/or VH and/or VL domains of anti-MSLN antibody FS28-256-271 set forth below.

FS28-256-271 VH domain CDRs
HCDR1 (AA) (IMGT)
GFTFTHTY

HCDR1 (AA) (Kabat)
HTYMS

HCDR2 (AA) (IMGT)
ISPTYSTT

HCDR2 (AA) Kabat)
AISPTYSTTNYADSVKG

HCDR3 (AA) (IMGT)
ARYNAYHAALDY

HCDR3 (AA) (Kabat)
YNAYHAALDY

FS28-256-271 VH domain
EVQLLESGGGLVQPGGSLRLSCAASGFTFTHTYMSWVRQAPGKGLEW

VSNISPTYSTTNYADSVKGRFTISRDNNKNTLYLQMNSLRAEDTAVY

YCARYNAYHAALDYWGQGTLVTVSS

FS28-256-271 VL domain CDRs

-continued

LCDR1 (AA) (IMGT)
QSVSSSY

LCDR1 (AA) (Kabat)
RASQSVSSSYLA

LCDR2 (AA) (IMGT)
GAS

LCDR2 (AA) (Kabat)
GASSRAT

LCDR3 (AA) (IMGT)
QQTVPYPYT

LCDR3 (AA) (Kabat)
QQTVPYPYT

FS28-256-271 VL domain
EIVLTQSPGTLSLSPGERATLSCRASQSVSSSYLAWYQQKPGQAPRL

LIYGASSRATGIPDRFSGSGSGTDFTLTISRLEPEDFAVYYCQQTVP

YPYTFGQGTKVEIK

The specific binding member may be conjugated to a bioactive molecule or a detectable label. In this case, the specific binding member may be referred to as a conjugate. Such conjugates find application in the treatment of diseases as described herein.

For example, the bioactive molecule may be an immune system modulator, such as a cytokine, preferably a human cytokine. For example, the cytokine may be a cytokine which stimulates T cell activation and/or proliferation. Examples of cytokines for conjugation to the specific binding member include IL-2, IL-10, IL-12, IL-15, IL-21, GM-CSF and IFN-gamma.

Alternatively, the bioactive molecule may be a ligand trap, such as a ligand trap of a cytokine, e.g. of TGF-beta or IL-6.

Suitable detectable labels which may be conjugated to specific binding members are known in the art and include radioisotopes such as iodine-125, iodine-131, yttrium-90, indium-111 and technetium-99; fluorochromes, such as fluorescein, rhodamine, phycoerythrin, Texas Red and cyanine dye derivatives for example, Cy7 and Alexa750; chromogenic dyes, such as diaminobenzidine; latex beads; enzyme labels such as horseradish peroxidase; phosphor or laser dyes with spectrally isolated absorption or emission characteristics; and chemical moieties, such as biotin, which may be detected via binding to a specific cognate detectable moiety, e.g. labelled avidin.

The specific binding member may be conjugated to the bioactive molecule or detectable label by means of any suitable covalent or non-covalent linkage, such as a disulphide or peptide bond. Where the bioactive molecule is a cytokine, the cytokine may be joined to the specific binding member by means of a peptide linker. Suitable peptide linkers are known in the art and may be 5 to 25, 5 to 20, 5 to 15, 10 to 25, 10 to 20, or 10 to 15 amino acids in length.

In some embodiments, the bioactive molecule may be conjugated to the specific binding member by a cleavable linker. The linker may allow release of the bioactive molecule from the specific binding member at a site of therapy. Linkers may include amide bonds (e.g. peptidic linkers), disulphide bonds or hydrazones. Peptide linkers for example may be cleaved by site specific proteases, disulphide bonds may be cleaved by the reducing environment of the cytosol and hydrazones may be cleaved by acid-mediated hydrolysis.

The conjugate may be a fusion protein comprising the specific binding member and the bioactive molecule. In this case the bioactive molecule may be conjugated to the specific binding member by means of a peptide linker or peptide bond. Where the specific binding member is a multichain molecule, such as where the specific binding member is or comprises an Fcab or is a $mAb^2$, the bioactive molecule may be conjugated to one or more chains of the specific binding member. For example, the bioactive molecule may be conjugated to one or both of the heavy chains of the $mAb^2$ molecule. Fusion proteins have the advantage of being easier to produce and purify, facilitating the production of clinical-grade material.

The invention also provides an isolated nucleic acid molecule or molecules encoding a specific binding member of the invention. The skilled person would have no difficulty in preparing such nucleic acid molecules using methods well-known in the art.

In a preferred embodiment, the nucleic acid molecule encodes the CH3 domain of specific binding member: FS22-172-003, FS22-172-002, FS22-172-004, FS22-172-001, FS22-172-005, FS22-172-006, or FS22-172, preferably FS22-172-003, FS22-172-002, FS22-172-004, FS22-172-001, FS22-172-005, or FS22-172-006, more preferably FS22-172-003, FS22-172-002, or FS22-172-004, yet more preferably FS22-172-003.

In an alternative preferred embodiment, the nucleic acid molecule encodes the CH3 domain of specific binding member: FS22-053-008, FS22-053-009, FS22-053-011, FS22-053-017, FS22-053-014, FS22-053-010, FS22-053-012, FS22-053-013, FS22-053-015, FS22-053-016, or FS22-053, preferably FS22-053-008, FS22-053-009, FS22-053-011, FS22-053-017, or FS22-053-014, more preferably FS22-053-008, FS22-053-009, FS22-053-011, or FS22-053-017, yet more preferably FS22-053-008.

The CH3 domain sequences of these specific binding members are described herein.

For example, a nucleic acid molecule which encodes the CH3 domain of specific binding member:

(i) FS22-053-008, FS22-053-009, FS22-053-011, FS22-053-017, FS22-053-014, FS22-053-010, FS22-053-012, FS22-053-013, FS22-053-015, FS22-053-016, or FS22-053 set forth in SEQ ID NO: 22, 31, 49, 103, 76, 40, 58, 67, 85, 94, and 176, respectively; or (ii) FS22-172-003, FS22-172-002, FS22-172-004, FS22-172-001, FS22-172-005, FS22-172-006, or FS22-172 set forth in SEQ ID NO: 140, 131, 149, 122, 158, 166, and 113, respectively.

In a preferred embodiment, the nucleic acid molecule encodes specific binding member: FS22-172-003, FS22-172-002, FS22-172-004, FS22-172-001, FS22-172-005, FS22-172-006, or FS22-172, preferably FS22-172-003, FS22-172-002, FS22-172-004, FS22-172-001, FS22-172-005, or FS22-172-006, more preferably FS22-172-003, FS22-172-002, or FS22-172-004, yet more preferably FS22-172-003.

In an alternative preferred embodiment, the nucleic acid molecule encodes specific binding member: FS22-053-008, FS22-053-009, FS22-053-011, FS22-053-017, FS22-053-014, FS22-053-010, FS22-053-012, FS22-053-013, FS22-053-015, FS22-053-016, or FS22-053, preferably FS22-053-008, FS22-053-009, FS22-053-011, FS22-053-017, or FS22-053-014, more preferably FS22-053-008, FS22-053-009, FS22-053-011, or FS22-053-017, yet more preferably FS22-053-008.

For example, a nucleic acid molecule which encodes the specific binding member:

(i) FS22-053-008, FS22-053-009, FS22-053-011, FS22-053-017, FS22-053-014, FS22-053-010, FS22-053-012, FS22-053-013, FS22-053-015, FS22-053-016, or FS22-053 set forth in SEQ ID NO: 24, 33, 51, 105, 78, 42, 60, 69, 87, 96, and 177, respectively; or (ii) FS22-172-003, FS22-172-002, FS22-172-004, FS22-172-001, FS22-172-005, FS22-172-006, or FS22-172 set forth in SEQ ID NO: 142, 133, 151, 124, 160, 168, and 115, respectively.

An isolated nucleic acid molecule may be used to express a specific binding member of the invention. The nucleic acid will generally be provided in the form of a recombinant vector for expression. Another aspect of the invention thus provides a vector comprising a nucleic acid as described above. Suitable vectors can be chosen or constructed, containing appropriate regulatory sequences, including promoter sequences, terminator fragments, polyadenylation sequences, enhancer sequences, marker genes and other sequences as appropriate. Preferably, the vector contains appropriate regulatory sequences to drive the expression of the nucleic acid in a host cell. Vectors may be plasmids, viral e.g. phage, or phagemid, as appropriate.

A nucleic acid molecule or vector as described herein may be introduced into a host cell. Techniques for the introduction of nucleic acid or vectors into host cells are well established in the art and any suitable technique may be employed. A range of host cells suitable for the production of recombinant specific binding members are known in the art, and include bacterial, yeast, insect or mammalian host cells. A preferred host cell is a mammalian cell, such as a CHO, NS0, or HEK cell, for example a HEK293 cell. A most preferred host cell is a CHO cell.

Another aspect of the invention provides a method of producing a specific binding member of the invention comprising expressing a nucleic acid encoding the specific binding member in a host cell and optionally isolating and/or purifying the specific binding member thus produced. Methods for culturing host cells are well-known in the art. The method may further comprise isolating and/or purifying the specific binding member. Techniques for the purification of recombinant specific binding members are well-known in the art and include, for example HPLC, FPLC or affinity chromatography, e.g. using Protein A or Protein L. In some embodiments, purification may be performed using an affinity tag on specific binding member. The method may also comprise formulating the specific binding member into a pharmaceutical composition, optionally with a pharmaceutically acceptable excipient or other substance as described below.

As explained above, CD137 is expressed on cells of the immune system, including $CD8^+$ T cells, $CD4^+$ T cells, Treg cells, B cells, NK cells, NKT cells, dendritic cells, and tumour-infiltrating lymphocytes (TILs). In particular, CD137 activation has been shown to play a role in enhancing proliferation, survival and the cytotoxic effector function of $CD8^+$ T cells, as well as $CD8^+$ T cell differentiation and maintenance of memory $CD8^+$ T cells. CD137 is expressed at a lower level on $CD4^+$ T cells than $CD8^+$ T cells but has also been shown to be involved in inducing proliferation and activation of some subsets of $CD4^+$ T cells. Activation of CD137 has also been demonstrated to enhance NK cell-mediated ADCC, as well as B cell proliferation, survival and cytokine production.

In light of the immune response enhancing activity of CD137, CD137 agonist molecules have been investigated in the context of cancer treatment, as well as the treatment of chronic infections.

The specific binding members as described herein may thus be useful for therapeutic applications, in particular in the treatment of cancer. In addition, the specific binding members are expected to be useful in the treatment of infectious diseases, such as persistent infectious diseases.

A specific binding member as described herein may be used in a method of treatment of the human or animal body. Related aspects of the invention provide;

(i) a specific binding member described herein for use as a medicament, (ii) a specific binding member described herein for use in a method of treatment of a disease or disorder, (iii) the use of a specific binding member described herein in the manufacture of a medicament for use in the treatment of a disease or disorder; and, (iv) a method of treating a disease or disorder in an individual, wherein the method comprises administering to the individual a therapeutically effective amount of a specific binding member as described herein.

The individual may be a patient, preferably a human patient.

Treatment may be any treatment or therapy in which some desired therapeutic effect is achieved, for example, the inhibition or delay of the progress of the condition, and includes a reduction in the rate of progress, a halt in the rate of progress, amelioration of the condition, cure or remission (whether partial or total) of the condition, preventing, ameliorating, delaying, abating or arresting one or more symptoms and/or signs of the condition or prolonging survival of an individual or patient beyond that expected in the absence of treatment.

Treatment as a prophylactic measure (i.e. prophylaxis) is also included. For example, an individual susceptible to or at risk of the occurrence or re-occurrence of a disease such as cancer may be treated as described herein. Such treatment may prevent or delay the occurrence or re-occurrence of the disease in the individual.

A method of treatment as described may be comprise administering at least one further treatment to the individual in addition to the specific binding member. The specific binding member described herein may thus be administered to an individual alone or in combination with one or more other treatments. Where the specific binding member is administered to the individual in combination with another treatment, the additional treatment may be administered to the individual concurrently with, sequentially to, or separately from the administration of the specific binding member. Where the additional treatment is administered concurrently with the specific binding member, the specific binding member and additional treatment may be administered to the individual as a combined preparation. For example, the additional therapy may be a known therapy or therapeutic agent for the disease to be treated.

Whilst a specific binding member may be administered alone, specific binding members will usually be administered in the form of a pharmaceutical composition, which may comprise at least one component in addition to the specific binding member. Another aspect of the invention therefore provides a pharmaceutical composition comprising a specific binding member as described herein. A method comprising formulating a specific binding member into a pharmaceutical composition is also provided.

Pharmaceutical compositions may comprise, in addition to the specific binding member, a pharmaceutically acceptable excipient, carrier, buffer, stabilizer or other materials well known to those skilled in the art. The term “pharmaceutically acceptable” as used herein pertains to compounds, materials, compositions, and/or dosage forms which are, within the scope of sound medical judgement, suitable for use in contact with the tissues of a subject (e.g., human) without excessive toxicity, irritation, allergic response, or other problem or complication, commensurate with a reasonable benefit/risk ratio. Each carrier, excipient, etc. must also be “acceptable” in the sense of being compatible with the other ingredients of the formulation. The precise nature of the carrier or other material will depend on the route of administration, which may be by infusion, injection or any other suitable route, as discussed below.

For parenteral, for example subcutaneous or intravenous administration, e.g. by injection, the pharmaceutical composition comprising the specific binding member may be in the form of a parenterally acceptable aqueous solution which is pyrogen-free and has suitable pH, isotonicity and stability. Those of relevant skill in the art are well able to prepare suitable solutions using, for example, isotonic vehicles, such as Sodium Chloride Injection, Ringer’s Injection, Lactated Ringer’s Injection. Preservatives, stabilizers, buffers, antioxidants and/or other additives may be employed as required including buffers such as phosphate, citrate and other organic acids; antioxidants, such as ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3'-pentanol; and m-cresol); low molecular weight polypeptides; proteins, such as serum albumin, gelatin or immunoglobulins; hydrophilic polymers, such as polyvinylpyrrolidone; amino acids, such as glycine, glutamine, asparagines, histidine, arginine, or lysine; monosaccharides, disaccharides and other carbohydrates including glucose, mannose or dextrins; chelating agents, such as EDTA; sugars, such as sucrose, mannitol, trehalose or sorbitol; salt-forming counter-ions, such as sodium; metal complexes (e.g. Zn-protein complexes); and/or non-ionic surfactants, such as TWEEN™, PLURONICS™ or polyethylene glycol (PEG).

In some embodiments, specific binding members may be provided in a lyophilised form for reconstitution prior to administration. For example, lyophilised specific binding members may be re-constituted in sterile water and mixed with saline prior to administration to an individual.

Administration may be in a “therapeutically effective amount”, this being sufficient to show benefit to an individual. The actual amount administered, and rate and time-course of administration, will depend on the nature and severity of what is being treated, the particular individual being treated, the clinical condition of the individual, the cause of the disorder, the site of delivery of the composition, the type of specific binding member, the method of administration, the scheduling of administration and other factors known to medical practitioners. Prescription of treatment, e.g. decisions on dosage etc., is within the responsibility of general practitioners and other medical doctors, and may depend on the severity of the symptoms and/or progression of a disease being treated. Appropriate doses of immunoglobulins are well known in the art (Ledermann et al. (1991) Int. J. Cancer 47: 659-664; and Bagshawe et al. (1991) Antibody, Immunoconjugates and Radiopharmaceuticals 4: 915-922). Specific dosages indicated herein, or in the Physician's Desk Reference (2003) as appropriate for an antibody molecule being administered, may be used. As for antibody molecules, a therapeutically effective amount or suitable dose of a specific binding member can be determined by comparing in vitro activity and in vivo activity in an animal model. Methods for extrapolation of effective dosages in mice and other test animals to humans are known. The precise dose will depend upon a number of factors, including whether the size and location of the area to be treated, and the precise nature of the specific binding member.

A typical immunoglobulin dose is in the range 100 μg to 1 g for systemic applications, and 1 μg to 1 mg for topical applications. An initial higher loading dose, followed by one or more lower doses, may be administered. This is a dose for a single treatment of an adult individual, which may be proportionally adjusted for children and infants, and also adjusted for other specific binding member formats in proportion to molecular weight.

Treatments may be repeated at daily, twice-weekly, weekly or monthly intervals, at the discretion of the physician. The treatment schedule for an individual may be dependent on the pharmocokinetic and pharmacodynamic properties of the specific binding member composition, the route of administration and the nature of the condition being treated.

Treatment may be periodic, and the period between administrations may be about two weeks or more, e.g. about three weeks or more, about four weeks or more, about once a month or more, about five weeks or more, or about six weeks or more. For example, treatment may be every two to four weeks or every four to eight weeks. Suitable formulations and routes of administration are described above.

In a preferred embodiment, a specific binding member as described herein may be for use in a method of treating cancer.

Cancer may be characterised by the abnormal proliferation of malignant cancer cells. Where a particular type of cancer, such as breast cancer, is referred to, this refers to an abnormal proliferation of malignant cells of the relevant tissue, such as breast tissue. A secondary cancer which is located in the breast but is the result of abnormal proliferation of malignant cells of another tissue, such as ovarian tissue, is not a breast cancer as referred to herein but an ovarian cancer.

The cancer may be a primary or a secondary cancer. Thus, a specific binding member as described herein may be for use in a method of treating cancer in an individual, wherein the cancer is a primary tumour and/or a tumour metastasis.

A tumour of a cancer to be treated using a specific binding member as described herein may comprise TILs that express CD137, e.g. on their cell surface. In one embodiment, the tumour may have been determined to comprise TILs that express CD137. Methods for determining the expression of an antigen on a cell surface are known in the art and include, for example, flow cytometry.

For example, the cancer to be treated using a specific binding member as described herein may be selected from the group consisting of leukaemias, such as acute myeloid leukaemia (AML), chronic myeloid leukaemia (CML), acute lymphoblastic leukaemia (ALL) and chronic lymphocytic leukaemia (CLL); lymphomas, such as Hodgkin's lymphoma, non-Hodgkin's lymphoma and multiple myeloma; and solid cancers, such as sarcomas (e.g. soft tissue sarcomas), skin cancer (e.g. Merkel cell carcinoma), melanoma, bladder cancer (e.g. urothelial carcinoma), brain cancer (e.g. glioblastoma multiforme), breast cancer, uterus/endometrial cancer, ovarian cancer (e.g. ovarian serous cystadenoma), prostate cancer, lung cancer (e.g. non-small cell lung carcinoma (NSCLC) and small cell lung cancer (SCLC)), colorectal cancer (e.g. colorectal adenocarcinoma), cervical cancer (e.g. cervical squamous cell cancer and cervical adenocarcinoma), liver cancer (e.g. hepatocellular carcinoma), head and neck cancer (e.g. head and neck squamous-cell carcinoma), oesophageal cancer, pancreatic cancer, renal cancer (e.g. renal cell cancer), adrenal cancer, stomach cancer, testicular cancer, cancer of the gall bladder and biliary tracts (e.g. cholangiocarcinoma), thyroid cancer, thymus cancer, bone cancer, and cerebral cancer.

In a preferred embodiment, the cancer to be treated using a specific binding member as described herein is a solid cancer. More preferably, the cancer to be treated using a specific binding member as described herein is a solid cancer selected from the group consisting of: sarcoma, melanoma, bladder cancer, brain cancer, breast cancer, uterine/endometrial cancer, ovarian cancer, prostate cancer, lung cancer, colorectal cancer, cervical cancer, liver cancer, head and neck cancer, pancreatic cancer, renal cancer and stomach cancer.

In the context of cancer, treatment may include inhibiting cancer growth, including complete cancer remission, and/or inhibiting cancer metastasis, as well as inhibiting cancer recurrence. Cancer growth generally refers to any one of a number of indices that indicate change within the cancer to a more developed form. Thus, indices for measuring an inhibition of cancer growth include a decrease in cancer cell survival, a decrease in tumour volume or morphology (for example, as determined using computed tomographic (CT), sonography, or other imaging method), a delayed tumour growth, a destruction of tumour vasculature, improved performance in delayed hypersensitivity skin test, an increase in the activity of anti-cancer immune cells or other anti-cancer immune responses, and a decrease in levels of tumour-specific antigens. Activating or enhancing immune responses to cancerous tumours in an individual may improve the capacity of the individual to resist cancer growth, in particular growth of a cancer already present in the subject and/or decrease the propensity for cancer growth in the individual.

In the context of cancer treatment, a specific binding member as described herein may be administered to an individual in combination with another anti-cancer therapy or therapeutic agent, such as an anti-cancer therapy or therapeutic agent which has been shown to be suitable, or is expected to be suitable, for the treatment of the cancer in question. For example, the specific binding member may be administered to the individual in combination with a chemotherapeutic agent, radiotherapy, an immunotherapeutic agent, an anti-tumour vaccine, an oncolytic virus, an adoptive cell transfer (ACT) therapy (such as adoptive NK cell therapy or therapy with chimeric antigen receptor (CAR) T-cells, autologous tumour infiltrating lymphocytes (TILs), or gamma/delta T cells, or an agent for hormone therapy.

Without wishing to be bound by theory, it is thought that the specific binding member described herein may act as an adjuvant in anti-cancer therapy. Specifically, it is thought that administration of the specific binding member to an in individual in combination with chemotherapy and/or radiotherapy, or in combination with an anti-tumour vaccine, for example, will trigger a greater immune response against the cancer than is achieved with chemotherapy and/or radiotherapy, or with an anti-tumour vaccine, alone.

One or more chemotherapeutic agents for administration in combination with a specific binding member as described herein may be selected from the group consisting of: taxanes, cytotoxic antibiotics, tyrosine kinase inhibitors, PARP inhibitors, B-Raf enzyme inhibitors, MEK inhibitors, c-MET inhibitors, VEGFR inhibitors, PDGFR inhibitors, alkylating agents, platinum analogues, nucleoside analogues, antifolates, thalidomide derivatives, antineoplastic chemotherapeutic agents and others. Taxanes include docetaxel, paclitaxel and nab-paclitaxel; cytotoxic antibiotics include actinomycin, bleomycin, and anthracyclines such as doxorubicin, mitoxantrone and valrubicin; tyrosine kinase inhibitors include erlotinib, gefitinib, axitinib, PLX3397, imatinib, cobemitinib and trametinib; PARP inhibitors include piraparib; B-Raf enzyme inhibitors include vemurafenib and dabrafenib; alkylating agents include dacarbazine, cyclophosphamide and temozolomide; platinum analogues include carboplatin, cisplatin and oxaliplatin; nucleoside analogues include azacitidine, capecitabine, fludarabine, fluorouracil and gemcitabine; antifolates include methotrexate and pemetrexed. Other chemotherapeutic agents suitable for use in the present invention include defactinib, entinostat, eribulin, irinotecan and vinblastine.

Preferred therapeutic agents for administration with an antibody molecule as described herein are doxorubicin, mitoxantrone, cyclophosphamide, cisplatin, and oxaliplatin.

A radiotherapy for administration in combination with a specific binding member as described herein may be external beam radiotherapy or brachytherapy.

An immunotherapeutic agent for administration in combination with a specific binding member as described herein may be a therapeutic antibody molecule, nucleic acid cytokine, or cytokine-based therapy. For example, the therapeutic antibody molecule may bind to an immune regulatory molecule, e.g. an inhibitory checkpoint molecule or an immune costimulatory molecule, or a tumour antigen, e.g. a cell surface tumour antigen or a soluble tumour antigen. Examples of immune regulatory molecules to which the therapeutic antibody molecule may bind include CTLA-4, LAG-3, TIGIT, TIM-3, VISTA, PD-L1, PD-1, CD47, CD73, CSF-1R, KIR, CD40, HVEM, IL-10 and CSF-1. Examples of receptors of the innate immune system to which the therapeutic antibody molecule may bind include TLR1, TLR2, TLR4, TLR5, TLR7, TLR9, RIG-I-like receptors (e.g. RIG-I and MDA-5), and STING. Examples of tumour antigens to which the therapeutic antibody molecule may bind include HER2, EGFR, CD20 and TGF-beta.

The nucleic acid for administration in combination with a specific binding member as described herein may be an siRNA.

The cytokines or cytokine-based therapy may be selected from the group consisting of: IL-2, prodrug of conjugated IL-2, GM-CSF, IL-7, IL-12, IL-9, IL-15, IL-18, IL-21, and type I interferon.

Anti-tumour vaccines for the treatment of cancer have both been implemented in the clinic and discussed in detail within scientific literature (such as Rosenberg, S. 2000). This mainly involves strategies to prompt the immune system to respond to various cellular markers expressed by autologous or allogenic cancer cells by using those cells as a vaccination method, both with or without granulocyte-macrophage colony-stimulating factor (GM-CSF). GM-CSF provokes a strong response in antigen presentation and works particularly well when employed with said strategies.

The chemotherapeutic agent, radiotherapy, immunotherapeutic agent, anti-tumour vaccine, oncolytic virus, ACT therapy, or agent for hormone therapy is preferably a chemotherapeutic agent, radiotherapy, immunotherapeutic agent, anti-tumour vaccine, oncolytic virus, ACT therapy, or agent for hormone therapy for the cancer in question, i.e. a chemotherapeutic agent, radiotherapy, immunotherapeutic agent, anti-tumour vaccine, oncolytic virus, ACT therapy, or agent for hormone therapy which has been shown to be effective in the treatment of the cancer in question. The selection of a suitable chemotherapeutic agent, radiotherapy, immunotherapeutic agent, anti-tumour vaccine, oncolytic virus, ACT therapy, or agent for hormone therapy which has been shown to be effective for the cancer in question is well within the capabilities of the skilled practitioner.

In light of the immune response enhancing activity of CD137, CD137 agonist molecules are expected to find application in the treatment of infectious diseases. Thus, in another preferred embodiment, the antibody molecule as described herein may be for use in a method of treating an infectious disease, such as an acute or a persistent infectious disease.

Without wishing to be bound by theory, it is thought that CD137 agonist molecules may be able to enhance the immune response against an acute infectious disease caused by a pathogen by inducing rapid infiltration and activation of innate immune cells, such as neutrophils and monocytes, thereby facilitating the clearance of the pathogen responsible for the acute infectious disease. Therefore, in a further embodiment, the antibody molecule as described herein may be for use in a method of treating an acute infectious disease, such as an acute bacterial disease. In a preferred embodiment, the acute infectious disease is an acute bacterial disease caused by an infection by a gram-positive bacterium, such as a bacterium of the genus *Listeria, Streptococcus pneumoniae* or *Staphylococcus aureus.*

Infectious diseases are normally cleared by the immune system but some infections persist for long periods of time, such as months or years, and are ineffectively combatted by the immune system. Such infections are also referred to as persistent or chronic infections.

Preferably, the antibody molecule as described herein is used to treat a persistent infectious disease, such as a persistent viral, bacterial, fungal or parasitic infection, preferably a persistent viral or bacterial infection.

In a preferred embodiment, the persistent viral infection to be treated using an antibody molecule as described herein is a persistent infection by: human immunodeficiency virus (HIV), Epstein-Barr virus, Cytomegalovirus, Hepatitis B virus, Hepatitis C virus, or Varicella Zoster virus.

In a preferred embodiment, the persistent bacterial infection to be treated using an antibody molecule as described herein is a persistent infection of: *Staphylococcus aureus, Hemophilus influenza, Mycobacterium tuberculosis, Mycobacterium leprae, Salmonella typhi, Helicobacter pylori, Treponema pallidum*, or *Streptococcus pneumoniae.*

CD137 agonism has been described to be beneficial in the context of treatment of infections by gram positive bacteria. Thus, in a preferred embodiment, the persistent bacterial infection to be treated using an antibody molecule as described herein is a persistent infection by a gram-positive bacterium. In a more preferred embodiment, the persistent bacterial infection is a persistent infection by a gram-positive bacterium selected from the group consisting of: *Staphylococcus aureus, Mycobacterium leprae*, and *Streptococcus pneumoniae.*

In a preferred embodiment, the persistent fungal infection to be treated using a specific binding member as described herein is a persistent infection of: *Candida* (e.g. *Candida albicans*), *Cryptococcus* (e.g. *Cryptococcus gattii* or *Cryptococcus neoformans*), *Talaromyces* (*Penicillium*) (e.g. *Tala-*

*romyces marneffe*), *Microsporum* (e.g. *Microsporum audouinii*), or *Trichophyton tonsurans.*

In a preferred embodiment, the persistent parasitic infection to be treated using a specific binding member as described herein is a persistent infection of: *Plasmodium*, such as *Plasmodium falciparum*, or *Leishmania*, such as *Leishmania donovani.*

In the context of the treatment of a persistent infectious disease, treatment may include eliminating the infection, reducing the pathogenic load of the individual, preventing recurrence of the infection. For example, the treatment may comprise preventing, ameliorating, delaying, abating or arresting one or more symptoms and/or signs of the persistent infection. Alternatively, the treatment may include preventing an infectious disease.

In the context of the treatment of infectious diseases, the specific binding member as described herein may be administered to an individual in combination with another therapeutic agent for the treatment of the infectious disease, such as a therapeutic agent which has been shown to be suitable, or is expected to be suitable, for the treatment of the infectious disease in question. For example, the specific binding member may be administered to the individual in combination with an immunotherapeutic agent. An immunotherapeutic agent for administration in combination with an antibody molecule as described herein may be a therapeutic antibody molecule. For example, the therapeutic antibody molecule may bind to a receptor of the innate immune system. Examples of receptors of the innate immune system to which the therapeutic antibody molecule may bind include TLR1, TLR2, TLR4, TLR5, TLR7, TLR9, RIG-I-like receptors (e.g. RIG-I and MDA-5), and STING.

Where the specific binding member is used to prevent an infectious disease, the specific binding member may be administered in combination with a vaccine for the pathogen in question. Without wishing to be bound by theory, it is thought that the specific binding member described herein may act as an adjuvant in vaccination. Specifically, it is thought that administration of the specific binding member to an in individual in combination with vaccine, will trigger a greater immune response against the pathogen than is achieved with the vaccine alone.

Further aspects and embodiments of the invention will be apparent to those skilled in the art given the present disclosure including the following experimental exemplification.

All documents mentioned in this specification are incorporated herein by reference in their entirety.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Other aspects and embodiments of the invention provide the aspects and embodiments described above with the term "comprising" replaced by the term "consisting of" or "consisting essentially of", unless the context dictates otherwise.

Certain aspects and embodiments of the invention will now be illustrated by way of example and with reference to the figures described above.

EXAMPLES

Example 1: Production, Characterisation and Selection of Human, Mouse and Cyno Antigens

1.1 Recombinant Antigens

Tumour necrosis factor receptor superfamily (TNFRSF) members are known for their tendency to form multimers which cluster together when bound to their cognate ligands (Croft, M. 2003). This propensity to aggregate for their functionality makes it challenging to produce soluble recombinant proteins that do not aggregate in solution for use in in vitro selections such as phage and yeast display and for characterisation of selected proteins.

Several commercially available recombinant antigens were tested and the majority found to be unsuitable for use in these selections due to the levels of aggregates present. Of those tested only the biotinylated, human secreted CD137, hFc-fusion protein (BPS Biosciences, catalogue no. 71171), designated 'hCD137-hFc-Avi-BPS' hereinafter, had sufficiently low aggregation to be suitable and was used in selections, though with limited success (see Example 2).

As the majority of commercially available antigens were deemed unsuitable, the following recombinant dimeric and monomeric CD137 antigens (see Table 1), were produced in-house for use in selections:

TABLE 1

| Type | Designation | Species | Soluble or cell | Biotinylated | Antigen Format |
|---|---|---|---|---|---|
| Recombinant | mCD137-mFc-Avi | Mouse | Soluble | Yes | Dimer |
| Recombinant | mCD137-Avi-His | Mouse | Soluble | Yes | Monomer |
| Recombinant | hCD137-mFc-Avi | Human | Soluble | Yes | Dimer |
| Recombinant | hCD137-Avi-His | Human | Soluble | Yes | Monomer |
| Recombinant | cCD137-mFc-Avi | Cyno | Soluble | Yes | Dimer |

Monomeric antigens were produced by cloning DNA encoding the extracellular domain of the human (SEQ ID NO: 181) or mouse CD137 (SEQ ID NO: 185) along with an Avi sequence and six C-terminal histidine residues into modified pFUSE vectors (Invivogen cat no pfuse-mg2afc2) using EcoRI-HF and BamHI-HF restriction enzymes. The vectors were transfected into HEK293-6E cells (National Research Council of Canada), and expressed CD137 was purified using HisTrap™ excel nickel column (GE Life-Sciences 29048586) and size-exclusion chromatography (SEC) to ensure antigen was a single species and did not contain aggregates.

To produce the dimeric antigens, DNA constructs encoding the extracellular domain of the human, mouse or cynomolgus CD137 fused with the mIgG2a Fc domain along with an Avi sequence were cloned into modified pFUSE vectors and transfected into HEK293-6E cells. Recombinant CD137 was purified using MabSelect SuRe™ protein A column (GE Healthcare, 11003494) and size-exclusion chromatography (SEC) to ensure antigen was a single species and did not contain aggregates.

Each of the dimeric and monomeric antigens were biotinylated using a BirA biotin-biotin protein ligase reaction kit (Avidity LLC, BirA500) to produce monomeric CD137 antigens labelled with a single biotin molecule and dimeric CD137 antigens labelled with two biotin molecules, one on each of the two monomers. 3 mg of antigen was mixed with 7.8 μl BirA enzyme mix to a molar ratio of enzyme to substrate of 1:50. Additives were then added in accordance with the manufacturer's recommendations (142 μl Biomix A, 142 μl Biomix B, 142μ Biotin) and the reaction mix was incubated for two hours at room temperature. The reaction mix was immediately buffer exchanged to DPBS (Life Technologies 14190-169) using Amicon 30 μm filters (Merck Millipore UFC503096).

Proteins were further purified by SEC to ensure removal of the BirA enzyme and production of a final high quality monodispersed protein preparation with no high molecular weight aggregates. In more detail, materials from the same production lot were mixed together and analysed for stability and purity by size-exclusion high-performance liquid chromatography (SE-HPLC), SDS polyacrylamide gel electrophoresis (SDS-PAGE), and size-exclusion chromatography with multi-angle light scattering (SEC-MALS). Complete biotinylation of the proteins was confirmed in a streptavidin-shifting SDS-PAGE gel. The recombinant human and mouse antigens were confirmed to bind anti-CD137 positive-control antibodies (20H4.9 (U.S. Pat. No. 7,288,638)) and Lob12.3 (University of Southampton), respectively) in vitro by surface-plasmon resonance (SPR) and to DO11.10 cells expressing human and mouse CD137 ligand by flow cytometry. Cells were incubated with the CD137 antigens for 1 hour, and then a fluorescently-labelled anti mouse Fc fragment antibody was used to detect cell binding. The recombinant cyno antigen was confirmed to bind to DO11.10 cells (National Jewish Health) expressing cyno CD137 ligand by flow cytometry as described above. To ensure as high a purity as possible for the materials used in selection protocols, thorough protein characterisation of the antigens was performed to ensure the presence of protein aggregates did not exceed 2%.

1.2 Cell-Expressed Antigens

DO11.10 cells (National Jewish Health) expressing full-length mouse CD137 (SEQ ID NO: 184) or human CD137 (SEQ ID NO: 180), designated DO11.10.mCD137' and DO11.10.hCD137' respectively, were produced in order to present the antigen in a membrane-bound conformation, most similar to its natural form, for selections and further characterisation of selected Fcabs, as listed in Table 2.

Lentiviral transduction was used to generate these DO11.10 cells over-expressing human or mouse CD137 receptors using the Lenti-X HTX Packaging System (Takara, catalogue no. 631249). Lenti-X expression vector (pLVX) (Takara, catalogue no. 631253) containing cDNA encoding human CD137 (SEQ ID NO: 180) or mouse CD137 (SEQ ID NO: 184) was co-transfected with a Lenti-X HTX Packaging Mix into the Lenti-X 293T Cell Line (Takara, catalogue no. 632180) to generate virus. The DO11.10 cell line was then transduced with these lentiviral vectors.

Expression of human CD137 or mouse CD137 on these cells was confirmed by binding of 20H4.9 and Lob12.3 anti-CD137 positive control antibodies, respectively, to the cells by flow cytometry. Cells were incubated with the human or mouse positive control antibodies for 1 hour and then a fluorescently-labelled anti-human Fc detection antibody (Stratech Scientific Ltd, catalogue no. 109-546-098-JIR) was used to detect cell binding.

DO11.10 cells expressing cynomolgus CD137, designated DO11.10.cCD137', were also generated using the same lentiviral transduction methodology and used to test crossreactivity of anti-human CD137 Fcabs with cynomolgus CD137. Expression of cynomolgus CD137 was confirmed by binding of an anti-CD137 positive control antibody (MOR_7480.1, US 2012/0237498 A1) to the cells by flow cytometry as described earlier.

TABLE 2

| Type | Designation | Species | Presentation |
|---|---|---|---|
| Cell | DO11.10.hCD137 | Human | Cell- Expressed |
| Cell | DO11.10.mCD137 | Mouse | Cell- Expressed |
| Cell | DO11.10.cCD137 | Cyno | Cell- Expressed |

Example 2: Naïve Selection of Anti-Human CD137 Fcabs

In order to find Fcabs that bind to human CD137, and to maximise the diversity of identified binders, both yeast and phage display selection campaigns were employed. Since CD137 is expressed at low levels in a number of non-immune cell types, it was decided to select for anti-human CD137 Fcabs that selectively target cells that expressed CD137 abundantly, such as activated T cells. Without wishing to be bound by theory, it was hypothesised that cells with very low or negligible levels of CD137 expression would be more likely to have CD137 in monomeric state on their cell surface, unlike activated T cells with highly upregulated CD137 expression, where most of the protein is expected to be present in dimeric, trimeric, or higher multimeric states on the cell surface.

Cells overexpressing CD137, or recombinant dimeric human CD137 proteins, were used in Fcab selections in order to expose those representative epitopes that facilitated binding interactions with cells with highly upregulated multimeric CD137. In addition, using dimeric antigens was deemed beneficial to select for bivalent Fcabs that bound avidly to CD137, and stayed engaged to the target for longer, which in turn was hypothesised to facilitate preferential binding to cells with upregulated expression levels of CD137. In this context, monomeric recombinant CD137 was not used in order to prevent the selection of very high affinity monovalent Fcab binders that could bind CD137 too strongly.

The aim of this selection strategy was to obtain Fcabs that would preferentially bind activated T cells and not bind well to naïve T cells displaying only monomeric CD137, or to other cells that express very low levels of CD137. By selecting CD137 Fcabs which bind bivalently and preferentially to dimeric and multimeric antigen versus monomeric antigen, it was thought that potential off-targeted T cell activation would be reduced, with associated reduced toxicity.

Phage Display

Six naïve phage libraries displaying the CH3 domain of human IgG1 were used for selections by phage display. All six libraries comprised randomised AB loops (comprising residues at positions 14-18 according to IMGT numbering) and randomised EF loops (comprising residues at positions 92-101 according to IMGT numbering). One of the libraries comprised clones with an insertion of either two or four amino acids (encoded by two or four NNK codons) at position 101 in the EF loop (inserted residues are at positions 101.4-101.1 according to IMGT numbering).

A total of 12 selection campaigns were performed to identify anti-human CD137 binders. In-house hCD137-mFc-Avi antigen or commercially sourced hCD137-hFc-Avi-BPS antigen and/or DO11.10.hCD137 antigen-expressing cells were used in selections using the six phage libraries. Since only one functional Fcab sequence was identified from early selections using the hCD137-hFc-Avi-BPS recombinant antigen, in house hCD137-mFc-Avi was used in the remaining rounds of selections on recombinant CD137. Initial rounds were performed using 100 nM biotinylated antigen, with a deselection step using 500 nM unlabelled recombinant human Fc fragment produced in-house. Phage binders were captured by magnetic beads coated with either streptavidin or neutravidin. For selection outputs where non-specific binding to the Fc fragment was detected by phage ELISA (A450-630 nm higher than 0.4), a further deselection step was introduced whereby biotinylated Fc fragment (produced in house) was incubated with the phage outputs. Non-Fc binders were separated from Fc binders by magnetic capture of biotinylated Fc-binding phage.

In order to find binders to the membrane-bound natural conformation of CD137, cell selections were performed as follows: phage outputs from recombinant antigen selections were incubated with DO11.10 cells lacking human CD137 to discard undesired binders, such as those binding non-specifically to cells. Next, phage were incubated with $1\times10^7$ DO11.10.hCD137 cells, binders were eluted by trypsin digestion and then propagated for the next round. Round 3 followed a similar process, increasing selection pressure by decreasing the number of DO11.10.hCD137 cells to $5\times10^6$.

Phage ELISAs were performed after each round of selection to determine the enrichment of antigen-specific phage. 96-well streptavidin plates were coated overnight with 1 μg/ml biotinylated antigen. After blocking the plates with 4% marvel PBS, 50 μl phage-containing bacterial supernatant were added to each well and incubated for 1 hour at room temperature with shaking at 450 rpm. Phage solution was discarded by inverting the plate and washing 4 times with PBS 0.1% Tween and 4 times with PBS. Anti-M13 phage-HRP conjugated antibody was then added to detect phage bound to immobilised antigen. Phage solution was discarded by inverting the plate and washing 4 times with PBS 0.1% Tween and 4 times with PBS. TMB microwell peroxidase solution was added to each well and allowed to develop colour for up to 30 minutes. The reaction was stopped with 1M sulphuric acid, and the plate read at $OD_{450-630}$ in a microtitre plate reader. Specific hits were defined as those presenting signal strengths to recombinant CD137 at least 4-fold higher than background as defined by a negative control, i.e. PBS or a negative non-binder phage such as wild-type CH3, and at least 10-fold higher than the binding strength to biotinylated recombinant Fc fragment.

Phage fluorescence-activated cell sorting (phage FACS) assays were performed on cell selection outputs from rounds 2 and 3. Briefly, $2\times10^5$ cells were transferred to a round bottom microtitre plate. Phage supernatant was added to the cells and incubated for 1 hour at 4° C. Cells were then washed twice in ice-cold PBS 2% BSA buffer, resuspended in a solution of 100 μl anti-M13 antibody and a goat anti-mouse IgG F(ab') fragment conjugated with FITC and incubated with cells for 1 hour on ice. Cells were analysed in a flow cytometer after 3 washes in PBS. In phage FACS, specific hits were defined as those presenting geometric mean fluorescence intensity (MFI) to CD137 positive cells of at least 10-fold higher binding signal to recombinant CD137 and at least 4-fold higher than background as defined by a negative control (PBS)

3230 phage clones were screened by phage ELISA for binding to dimeric recombinant hCD137 antigen and recombinant Fc was used as a negative control. 1140 phage clones were screened by phage FACS for specific binding to DO11.10.hCD137 cells. Individual hits were then sequenced and the resulting 76 unique sequences were assigned an Fcab clone identifier and subcloned into a pTT5 expression vector (National Research Council of Canada) containing a HelD1.3 IgG1 heavy chain expression cassette for the purpose of expressing the Fcab clones in $mAb^2$ format (see Example 3.1).

Yeast Display

Four naïve yeast libraries displaying CH1 to CH3 domains of human IgG1 were used for selection by yeast display. All four libraries comprised randomised AB loops (comprising residues at positions 14 to 18 according to IMGT numbering) and randomised EF loops (comprising residues at positions 92 to 101 according to IMGT numbering) in the CH3 domain. Two of the libraries further comprised an insertion of five amino acid residues at position 16 in the AB loop of the CH3 domain (residues at positions 16.5 to 16.1 according to IMGT numbering).

In-house hCD137-mFc-Avi antigen or commercially sourced hCD137-hFc-Avi-BPS antigen were used in selections using the four yeast libraries, though similarly to the phage selections, the commercially sourced antigen was not used after early rounds of selection and the in-house antigen was used instead. For each library, a first round of selection was performed using magnetic cell separation (MACS). The libraries were grown, induced and $1\times10^{10}$ cells were incubated with 250 or 300 nM biotinylated recombinant antigen after a deselection step with 1.25 μM unlabelled human or mouse Fc. Yeast binders were separated by adding streptavidin magnetic beads and using MACS LS columns (Miltenyi Biotech 130-042-401). Subsequent rounds of selections were performed by fluorescence-activated cell sorting (FACS) on FACS-Aria II instruments (BD Bioscience) by using fluorescently-labelled antibodies to detect bound antigen (anti-Biotin-APC (Miltenyi Biotech 130-090-856), streptavidin-APC (BD Biosciences 349024), or neutravidin-DyLight-488 (Thermo Fisher 22832), correctly folded IgG scaffolds (anti-human IgG CH2 domain-FITC (Biorad AbD Serotec (MCA647F)), or expression of the aga2-IgG construct (anti-Xpress (Life Technologies R91025) and anti-mouse IgG-FITC (Sigma F2653-.5ML)). Whenever possible, antigen marker was used in conjunction with one of the structural markers to normalise binding intensity signal by Fcab expression on yeast surface. Unstained and control yeast populations were used to set up the sorting gates as follows: yeast cells in a FSC-A and SSC-A plot, FSC-W and FSC-H plots to discriminate singlets from multiplets or budding yeast cells, and FITC-A and APC-A plots to detect binding Fcab double positives.

The antigen concentration used in each round was determined empirically by performing output quality control using the antigen concentration used in the previous round. If binding enrichment increased over the previous round (>5-fold), the antigen concentration was dropped 1:2 or 1:3, otherwise it was maintained constant. This process was also followed to determine how many rounds of selections were needed and whether the selection branch was deemed to be exhausted (if diversity drops to only a few dominant sequences or antigen binding does not increase after 2 rounds).

2784 yeast single clones identified from library selections were individually screened as follows: after each selection round, single yeast cells were spotted on SDCAA agar plates using a FACS-Aria II (BD Biosciences) instrument and screened in the following flow cytometry antigen binding assay: single-clone colonies were grown until colonies reached a diameter of 2 mm and then transferred onto a deep-well plate containing 600 μl of SDCAA liquid media. Cultures were grown at 30° C. with 1000 rpm shaking overnight. Expression of the aga2-IgG protein scaffold was induced by replacing the growth media with induction media SGRCAA at an optical density of 1 (OD600=1). Cells were incubated with either biotinylated recombinant dimeric human antigen or mouse Fc fragment to discriminate against yeast clones binding to the Fc portion of the recombinant hCD137 antigen. Yeast cells that bound either protein were labelled using streptavidin-APC. An anti-CH2-FITC antibody was also used as a structural IgG marker. To analyse the outcome of the screening, binding to Fc fragment was plotted and any clone that bound to biotinylated Fc was discarded. Binding was defined as higher than 0.2% of cells that were positive for APC fluorescence with the gate placed using unstained and negative control samples.

Selections were repeated with varying antigen concentrations and conditions, such as increasing induction temperature, decreasing the selection stringency or reducing the number of rounds in order to increase the number of hits. Hit sequencing revealed considerably low output diversity, with only 9 Fcab clones having unique sequences identified: FS22-053, FS22-172, FS22-173, FS22-174, FS22-175, FS22-176, FS22-177, FS22-178 and FS22-179.

Example 3: Characterisation of Anti-Human CD137 Fcabs from Naïve Selections 3.1 Preparation of Anti-Human CD137 Fcabs in "Mock" $mAb^2$ Format "Mock" $mAb^2$ antibodies consisting of IgG1 molecules comprising the 76 anti-human CD137 Fcab clones isolated from phage and 9 clones isolated from yeast selections were produced to allow characterisation of the Fcabs in a $mAb^2$ format. The mock $mAb^2$ were prepared by substituting part of the CH3 domain Fcabs comprising the AB, CD and EF loops, for the corresponding region of the CH3 domain of the anti-hen egg lysozyme antibody HelD1.3. Generation of the HelD1.3 antibody is described in Tello et al. 1993 The heavy and light chain sequences of antibody HelD1.3 are shown in SEQ ID 186 and 173, respectively. The mock $mAb^2$ molecules were produced by transient expression in HEK293-6E cells. To assess the amount of protein produced, IgG protein content was quantified by BioLayer Interferometry using the Octet QKe platform with Protein A quantitation biosensors from PALL (18-5021). Proteins were purified by protein A affinity chromatography using mAb SelectSure columns. 53 phage-derived CD137 $mAb^2$ proteins presented measurements below the detection threshold and therefore determined to be unsuitable for further analysis. 32 $mAb^2$ were purified using mAb Select SuRe protein A columns (GE Healthcare, 11003494): FS22-005, FS22-007, FS22-033, FS22-042, FS22-049, FS22-050, FS22-052, FS22-053, FS22-054, FS22-167, FS22-169, FS22-170, FS22-171, FS22-172, FS22-173, FS22-174, FS22-175, FS22-176, FS22-177, FS22-178, FS22-179, FS22-180, FS22-181, FS22-183, FS22-184, FS22-186, FS22-187, FS22-191, FS22-192, FS22-193, FS22-194, FS22-195.

For the purpose of comparing expression levels, some of the earlier Fcabs were also sub-cloned and expressed as soluble Fcabs (containing a truncated hinge) in HEK293-6E cells and purified using mAb Select SuRe protein A columns. Interestingly, it was found that some of the Fcabs were observed to have significantly better biophysical behaviour and production yields in mock $mAb^2$ format than as soluble Fcabs. Such was the case of naïve clone FS22-053 that was produced in very low yields as soluble Fcab but this improved 25-fold when expressed in a mock $mAb^2$ format, resulting in more clones being available for characterisation.

3.2 Binding to Recombinant Antigen by BLI 31 of the purified mock $mAb^2$ molecules (excluding clone FS22-175) were tested for binding to human recombinant antigen in a single-point binding experiment by BioLayer Interferometry using the Octet QKe platform. Streptavidin BLI biosensors (PALL 18-5021) were used to capture biotinylated hCD137-mFc-Avi antigen at 10 μg/ml in kinetic buffer (PALL). Sensors were then dipped for 240 seconds into a well with purified $mAb^2$ diluted 1:1 in the same kinetic buffer, followed by into a well containing 1× kinetic buffer for 240 seconds. Binding hits were classified in a simple Boolean yes/no criterion as defined by a BLI response above buffer and wild-type IgG1 control HelD1.3 mAb (G1/HelD1.3): 12 $mAb^2$ did not bind and 19 bound CD137-coated sensors (FS22-007, FS22-033, FS22-042, FS22-049, FS22-050, FS22-052, FS22-053, FS22-054, FS22-169, FS22-172, FS22-173, F522-174, FS22-179, FS22-180, FS22-181, FS22-183, FS22-187, FS22-194, FS22-195).

3.3 Activity of Selected Anti-CD137 Mock $mAb^2$ in a Human NF-κB Reporter Assay Multimerisation and clustering is required for TNFR signalling (Bitra et al, 2017). CD137 clusters and activates the NF-κB signalling pathway when it interacts with its cognate ligand, CD137L. Agonist molecules mimic the ligand in driving clustering and activation of CD137, thereby activating the NF-κB signalling pathway. It is known that some agonistic antibodies can inherently cause CD137 clustering upon binding for example, urelumab whereas as others require additional crosslinking of the antibody itself to induce CD137 clustering, such as utomilumab (Fisher et al, 2012). Fc gamma receptors on effector cells are known to induce such crosslinking in vivo, though this is inefficient and may occur away from the site of therapeutic interest. Since dose limiting toxicities have been associated with treatment with some anti-CD137 antibodies, it was decided to select for anti-CD137 binding Fcabs which did not have the ability to inherently agonise, but to select only those that required additional crosslinking in order to induce CD137 clustering. Therefore, an assay that can detect the activation of the NF-κB signalling pathway in a cell upon clustering of CD137 expressed on the cell surface by crosslinked antibodies, but that showed little activity when the antibodies were not crosslinked, was developed. This assay was then used to test the agonistic functional activity of 27 anti-CD137 Fcab clones in mock $mAb^2$ format, and 6 anti-CD137 Fcab clones in anti-CD20 $mAb^2$ format, irrespective of whether the Fcabs were found to bind recombinant antigen by BLI or not.

Protein L was used as a crosslinking agent to drive cross linking of the mock $mAb^2$ via their Fab portions in the assay and NF-κB activation was measured.

cDNA encoding human CD137 (SEQ ID 180) was subcloned into pMSCV-neomycin vector (Takara Clontech, Cat. 634401) using EcoRI-HF and XhoI restriction enzymes. RetroPack PT67 cell line (Clontech, Cat. 631510) was used to produce retroviral particles following the manufacturer's protocol. This retro virus was subsequently used to transduce HEK.FRT.luc cells that were previously generated by transducing a Flp-In T-REx 293 HEK cell line (Life Technologies, R780-07) with Qiagen Cignal Lenti NFkB Reporter (luc) (Qiagen, cat no 336851) lentivirus containing a NF-κB-sensitive promoter controlling the expression of luciferase. These HEK.FRT.luc.hCD137 cells were used to screen the mock $mAb^2$ containing the CD137 binders identified in selections.

A 2 μM dilution of each mock $mAb^2$ was prepared in DPBS (Life Technologies, 14190169) and further diluted 1:3 in reporter cell medium (DMEM (Gibco, Cat. 61965-026); 10% FCS (Gibco, Cat. 10270-106); 1× PennStrep (Gibco, Cat. 15140-122); Blasticidin 15 μg/ml (Melford Laboratories Ltd. Cat. B1105); Puromycin 5 μg/ml (Life technologies, Cat. A11113803); Zeocin 100 μg/ml (InvivGen, Cat. 11006-33-0); Geneticin 500 μg/ml (Life Technologies, Cat. 10131-027). Protein L (Life Technologies, 21189), was used as an artificial crosslinking agent and was mixed with the $mAb^2$ molecules in a 1:4 molar ratio. After a 24-hour incubation, cells were treated with 100 μl Promega Bio-Glo™ luciferase assay reagent (Promega cat no G7941) according to manufacturer's instructions and luminescence was measured with an integration time of 0.5 seconds on a plate reader with the Gen5 Software, BioTek. Luminescence values are a measure of the luciferase produced in response to the activation of the NF-κB signalling pathway by the clustering of CD137 induced by crosslinked Fcabs. The luminescence values were plotted versus the log concentration of Fcab and the resulting curves were fitted using the log (agonist) vs response equation in GraphPad Prism.

Hits were identified by having at least a 10-fold increase in luciferase signal when crosslinked with protein L as compared to when not crosslinked. These clones were determined to be capable of inducing CD137 clustering and subsequent activation of downstream signalling pathways. Of all clones tested, two were able to induce this 10-fold increase in luciferase on crosslinking, FS22-053 and FS22-172, though an $EC_{50}$ could not be determined for either. Both were selected for further characterisation in a DO11.10 T cell activation assay. Surprisingly, activity was not observed for the remaining clones in crosslinked conditions despite binding to CD137 target by BLI, perhaps indicating they were binding at an irrelevant epitope on CD137, or that the affinity of such clones was not sufficient to bind CD137 strongly enough to initiate the NF-κB signalling cascade. Overall, while more than 30 Fcabs were tested, only two Fcabs (FS22-053 and FS22-172) were identified from the naïve selections which exhibited the desired function in the NF-κB reporter assay when crosslinked and had little activity when not crosslinked.

3.4 Activity of the Selected Anti-CD137 Mock $mAb^2$ in a DO11.10 T Cell Activation Assay CD137 clustering via agonist molecules on activated T cells elicits T cell activation and downstream signalling resulting in, but not limited to, IL-2 production. Since FS22-053 and FS22-172 were identified as having activity in the NFKB reporter assay, their ability to activate CD137 was tested in a T cell activation assay. A DO11.10 T cell activation assay using DO11.10 T cells engineered to overexpress human CD137 was developed and T cell activation was assessed by measuring IL-2 release.

DO11.10 T cells (National Jewish Health) were transduced with a lentiviral vector designed to overexpress mouse or human CD137 as described earlier. As well as FS22-053 and FS22-172, the following clones were tested in this DO11.10 T cell activation assay: FS22-007, FS22-033, FS22-042, FS22-049, FS22-050, FS22-052, FS22-054, (all in "mock" HelD1.3 $mAb^2$ format). Dilutions of $mAb^2$ or 20H4.9 positive control mAb either with or without recombinant Protein L (Life Technologies, 21189) crosslinker were prepared and added to DO11.10.hCD137 cells in a 96 well round bottom plate that had been coated overnight with 0.1 μg/ml anti-CD3 antibody (clone 17A2, BioLegend, 100208). After an 18-hour incubation, supernatants were collected and assayed with mouse IL-2 ELISA kit (eBioscience, 88-7024-86) following the manufacturer's instructions. Plates were read at 450 nm using the plate reader with the Gens Software, BioTek. Absorbance values of 570 nm were subtracted from those of 450 nm (Correction). The standard curve for calculation of cytokine concentration was based on four parameter logistic curve fit (Gens Software, BioTek). The concentration of mIL-2 was plotted vs the log concentration of $mAb^2$ or benchmark mAb and the resulting curves were fitted using the log (agonist) vs response equation in GraphPad Prism.

Clones FS22-053 and FS22-172 showed significantly enhanced activity when crosslinked with Protein L in this assay. FS22-053 had an activity of 126 nM when not crosslinked and an activity of 21 nM when crosslinked (an improvement of 6-fold), while FS22-172 had an activity of 950 nM when not crosslinked and an activity of 44 nM when crosslinked (an improvement of 22-fold). As a result, both clones were selected for affinity maturation. In addition, while clone FS22-033 showed no activity in this assay, it was also selected for affinity maturation as it was thought likely to bind recombinant antigen at a different epitope because it did not compete with clones FS22-053 and FS22-172 for binding in the BLI binding assay (data not shown). It was thought that an improvement in binding affinity of the clone to CD137 may also result in improved functional activity (see Example 4.1).

3.5 Preparation of Anti-Human CD137 Fcabs in a CD137/CD20 $mAb^2$ Format

A panel of anti-CD137 Fcabs (FS22-053, FS22-175, FS22-176, FS22-177, FS22-178, FS22-179) were produced to allow characterisation of the Fcabs in a more biologically-relevant $mAb^2$ format. The $mAb^2$ were prepared by substituting part of the CH3 domain Fcabs comprising the AB, CD and EF loops, for the corresponding region of the CH3 domain of the anti-CD20 2F2 clone (from U.S. Pat. No. 8,529,902 B2) to produce $mAb^2$ that bound both CD137 and CD20. These CD137/CD20 $mAb^2$ were produced by transient expression in HEK293-6E cells and purified using mAb Select SuRe protein A columns.

3.6 Activity of Anti-CD137/CD20 $mAb^2$ in a DO11.10 T Cell Activation Assay

Example 3.4 describes a T cell activation assay in which anti-CD137 mock $mAb^2$ were crosslinked using Protein L. That set up provided a reliable and reproducible way to screen a substantial number of molecules, though the higher order structures formed by the antibodies and $mAb^2$ when crosslinked are suboptimal and not representative of the physiological environment. A more biologically relevant setting is one in which the $mAb^2$ molecule is crosslinked through binding of its Fab arms to a target present in the biological system. This cell-based in vitro system optimises presentation of the antibodies and $mAb^2$ via Fab binding to cell membranes, driving clustering of the antibodies which in turn, increases the affinity of the CD137 Fcab arm towards its target on T cells.

$CD20^+$ Daudi cells (ATCC CCL-213) were seeded in 96 well round bottom plate at 1:1 ratio with the DO11.10.hCD137 cells used in Example 3.4. The 6 clones produced in Example 3.5 in CD137/CD20 $mAb^2$ were tested in this DO11.10 T cell activation assay. Dilutions of $mAb^2$ or positive control mAb with or without recombinant Protein L (Life Technologies, 21189) crosslinker were prepared and added to DO11.10.hCD137 and Daudi cells in a 96 well round bottom plate that had been coated overnight with 0.1

μg/ml anti-CD3 antibody (clone 17A2, BioLegend, 100208). After an 18-hour incubation, supernatants were collected and assayed with mouse IL-2 ELISA kit (eBioscience, 88-7024-86) following the manufacturer's instructions. Plates were read at 450 nm using the plate reader with the Gens Software, BioTek. Absorbance values of 570 nm were subtracted from those of 450 nm (Correction). The standard curve for calculation of cytokine concentration was based on four parameter logistic curve fit (Gens Software, BioTek). The concentration of mIL-2 was plotted vs the log concentration of $mAb^2$ or benchmark mAb and the resulting curves were fitted using the log (agonist) vs response equation in Graph Pad Prism. Of all clones tested, FS22-053 was the only one that showed significant IL-2 production in this CD20 cell-based crosslinking setup, with an EC50 of 0.3 nM (and 126 nM in absence of $CD20^+$ cells).

Examples 3.4 and 3.6 show that FS22-053 could drive clustering and activation of CD137 on the surface of DO11.10 T cells when crosslinked by either Protein L or by cell based crosslinking via Fab binding to another target in the $mAb^2$ formats tested (HeID1.3 and CD20).

Example 4: Affinity Maturation of Anti-Human Fcabs

As previously discussed, three clones were selected for affinity maturation based on their functional characteristics in the NF-κB reporter assay, DO11.10 T cell activation assays FS22-053 and FS22-172), or thought to bind to a different area of CD137 (FS22-033).

4.1 Affinity Maturation of FS22-033

Two yeast and two phage displayed libraries were constructed from the FS22-033 clone, one by randomising five residues in the AB loop of the CH3 domain and the other by randomising five residues in the EF loop of the CH3 domain using ELLA primers. ELLA primers specify the codons used for each amino acid and their relative abundance within the mix. Only cysteine was excluded from the mix and no bias was given to any other amino acid.

For the phage FS22-033 AB and FS22-033 EF libraries, two rounds of selections for affinity matured clones were performed using 200 nM hCD137-mFc-Avi in round 1 and 10 nM hCD137-mFc-Avi in round 2. 96 clones from each selection output were screened by phage ELISA. This screening identified 24 unique clones (FS22-033-001 through FS22-033-024), all of which were produced as mock $mAb^2$ containing HeID1.3 and then tested for improved binding kinetics by BLI as described in Example 3.2. None of these 24 affinity-matured clones performed better than the parental FS22-033 clone in this assay and so were not pursued. For the yeast FS22-033 AB and FS22-033 EF libraries, three rounds of selections were performed as follows: rounds 1 and 2 with 300 nM hCD137-mFc-Avi followed by a third round with 300 nM hCD137-mFc-Avi, 300 nM cyno CD137-mFc-Avi, or 300 nM hCD137-Avi-his. 1056 clones from the outputs of rounds 2 and 3 were sequenced, all unique clones identified were screened in an antigen binding flow cytometry assay for improved binding to antigen compared to the parental FS22-033 clone using 30 nM of human dimeric recombinant antigen, and clones were ranked by the percentage of APC+ cells which correlates with binding strength. The best five clones (FS22-033-025, FS22-033-026, FS22-033-027, FS22-033-028, FS22-033-029) were then produced as HeID1.3 $mAb^2$ (as described in example 3.1) and binding to human dimeric recombinant antigen was tested by BLI as described earlier but none of the clones showed improved kinetic profile to the parental FS22-033 clone and so these clones were not pursued further.

4.2 Affinity Maturation of FS22-053 and FS22-172

Four yeast displayed libraries were constructed from the FS22-053 and FS22-172 Fcab clones. Seven residues (at positions 15-16.1 according to IMGT) were randomised using ELLA primers, with the same trinucleotide distribution as that described in Example 4.1, in the AB loop of the CH3 domain of each clone to make libraries FS22-053 AB and FS22-172 AB. Five residues (at positions 92-94 and 97-98 according to IMGT) were randomised using ELLA primers in the EF loop of the CH3 domain resulting in libraries FS22-053 EF and FS22-172 EF.

For libraries FS22-053 AB and FS22-053 EF, and FS22-172 AB and FS22-172 EF, three or four selection rounds were performed on the yeast libraries to select for affinity matured clones using either dimeric hCD137-mFc-Avi antigen or monomeric hCD137-Avi-His antigen. Monomeric antigen was used in alternation with dimeric antigens to ensure clones retained affinity to the antigen and did not bind exclusively through avidity. The use of monomeric or dimeric antigen, as well as the concentration used was determined empirically during each round by flow cytometry, determined by whether enrichment against the monomeric or dimeric antigen was observed in the previous round. Whenever possible, a sorting gate above the parental was used to isolate affinity matured clones compared to the parental molecule. Selection pressure was increased up to 1 nM of dimeric antigen. During each selection round, individual clones were spotted on agar plates to assess the progress of the selection. Each clone was grown and induced individually and next its binding and structural parameters were determined by flow cytometry using biotinylated dimeric antigen as well as anti-CH2 structural markers as described earlier. This screening cascade was followed to allow the determination of selection success based on a sample of clones from the selection output and to allow for early screening of individual clones that could be subsequently produced as soluble proteins.

1152 yeast single clones in total were screened for binding to biotinylated recombinant antigen in an antigen binding flow cytometry as described earlier. Selections on the FS22-053 EF library resulted in enrichment of 138 unique loop sequences. Likewise, 30 unique loop sequences were isolated from the FS22-172 AB library. Libraries FS22-053 AB and FS22-172 EF did not contain any clones which showed any binding improvement over the parental clones. Sequence analysis across the best-binding clones from the FS22-053 EF and FS22-172 AB libraries revealed a conserved PPY sequence pattern in the AB loops. Since this sequence was conserved after affinity maturation, and was independently selected for in two separate lineages of Fcabs, it may be important for epitope binding on CD137. Additionally, a conserved LE or LD sequence pattern in the EF loops of the CH3 domain of the clones of both the FS22-053 and FS22-172 lineages, which suggests this amino acid motif in the EF loop is required for improved binding.

In order to assess the progress of the selections and whether it would be necessary to recombine mutated AB and EF loops between affinity matured clones, the top five unique clones from the FS22-053 EF library (FS22-053-008, FS22-053-009, FS22-053-010, FS22-053-011, FS22-053-012) ranked by presenting specific binding to 10 nM dimeric human antigen (higher than 30% APC positive cells in a flow cytometry binding assay), and the top six unique clones from the FS22-172 AB library (FS22-172-001, FS22-172-002, FS22-172-003, FS22-172-004, FS22-172-005, FS22-172-006, all showing above 10% APC positive cells when screened with 10 nM dimeric human antigen in the same assay) were produced as mock $mAb^2$ (HelD1.3) and model $mAb^2$ (PD-L1) $mAb^2$ to assess functional and kinetic improvement of the randomised loops.

Example 5: Construction, Expression and Characterisation of Affinity-Matured Anti-Human CD137 Fcabs in "Mock" $mAb^2$ Format

5.1 Construction of Anti-Human CD137 Fcabs in "Mock" and Model $mAb^2$ Format 16 affinity matured clones derived from the parental FS22-053 clone (FS22-053-001 to FS22-053-016), and 6 clones derived from the parental FS22-172 clones (FS22-172-001 to FS22-172-006) were prepared in $mAb^2$ format. Clones FS22-053-001 to FS22-053-007 were not further pursued as they did not express in $mAb^2$ format at a level that allowed downstream purification for further testing and characterisation. It was found that the remaining clones had at least 95% sequence identity in their CH3 domain when compared to the CH3 sequence of the parent clone from which it was derived. A percentage sequence similarity matrix was generated by comparing each amino acid position with that of the reference sequence (parental clones FS22-053 or FS22-172). (FIG. 1D shows the percentage sequence identity of the CH3 domain of clones FS22-053-008 to FS22-053-016 and FS22-053-017 (see example 10.1) compared to the parent FS22-053 CH3 domain. FIG. 1E shows the percentage sequence identity of the CH3 domain of clones FS22-172-001 to FS22-172-006 compared to the parent FS22-053 CH3 domain.

"Mock" $mAb^2$ antibodies comprising the anti-human CD137 Fcabs in HelD1.3 were prepared for further characterisation of the affinity matured Fcabs in $mAb^2$ format. These $mAb^2$ were prepared as described in Example 3.1.

Model $mAb^2$ were also produced comprising the anti-human CD137 Fcabs and also a PD-L1 binding Fab region (clone YW243.55.S70 from U.S. Pat. No. 8,217,149 B2). They were prepared similarly to the method described in Example 3.1 by substitution of part of the CH3 of the anti-PD-L1 binding antibody containing the AB, CD and EF loops with the corresponding region of the Fcab. These PD-L1 model $mAb^2$ contain a LALA mutation in the CH2 domain (AA). The introduction of the LALA mutation in the CH2 domain of human IgG1 is known to reduce Fc γ receptor binding (Bruhns, P., et al. (2009) and Hezareh M., et al. (2001)).

The CD137/HelD1.3 and CD137-AA/PD-L1 $mAb^2$ were produced by transient expression in HEK293-6E cells and purified using mAb Select SuRe protein A columns.

5.2 Activity of Human Fcabs in Mock $mAb^2$ Format in Human NF-κB Reporter Cell Assay The functional activity of the affinity-matured anti-human CD137 Fcabs in mock $mAb^2$ (HelD1.3) format listed in Table 3 was tested in the same NF-κB luciferase assay described in Example 3.3. Luminescence was measured with an integration time of 0.5 seconds in a plate reader with the Gen5 Software, BioTek. The results of this assay are shown in Table 3 and in FIG. 2. As expected, none of the Fcabs showed activity without Protein L crosslinking (−XL). All affinity matured CD137 Fcabs showed a vast improvement over parental CD137 Fcabs for which, while positive in this assay, calculation of an $EC_{50}$ value was not possible (see Example 3.3). FS22-053-008 and FS22-172-003 showed the best activity from each family with the lowest $EC_{50}$ when crosslinked with Protein L (+XL).

TABLE 3

| Fcab clone (in HelD1.3 $mAb^2$ format) | NF-kB signalling with or without protein L crosslinking (XL) | |
|---|---|---|
| | −XL | +XL (EC50 nM) |
| FS22-053-008 | N/A | 26.34 |
| FS22-053-009 | N/A | 64.57 |
| FS22-053-010 | N/A | 47.48 |
| FS22-053-011 | N/A | 32.78 |
| FS22-053-012 | N/A | 119.3 |
| FS22-172-002 | N/A | 124.1 |
| FS22-172-003 | N/A | 32.64 |
| FS22-172-004 | N/A | 123.6 |
| FS22-172-005 | N/A | N/A |
| FS22-172-006 | N/A | 382.4 |

N/A—not applicable as low signal did not allow EC50 determination

5.3 Activity of Affinity Matured Human Fcabs in Model $mAb^2$ Format in Human DO11.10 T Cell Activation Assay The functional activity of the affinity-matured human Fcabs in model $mAb^2$ (PD-L1 LALA) format listed in Table 4 was tested in a DO11.10 T cell activation assay, similar to the assay as described in Example 3.6.

HEK.mPD-L1 cells were produced by subcloning cDNA encoding mouse PD-L1 (SEQ ID NO: 188) into pcDNA5FRT vector (Life Technologies) using KpnI and NotI restriction sites and transforming the vectors into the Flp-In T-REx 293 cell line (Life Technologies, R780-07) using Lipofectamine 2000 (Life Technologies, 11668-019). Cells were grown in DMEM containing 10% FBS, 100 μg/ml Hygromycin B (Melford Laboratories Ltd, Z2475) and 15 μg/ml Blasticidin (Melford Laboratories Ltd, B1105) for 3-4 weeks until colonies of stably transformed cells had formed. These colonies were amplified in the presence of 1 μg/ml Doxycyclin (Sigma Aldrich, D9891) and tested for expression of PD-L1 using PE conjugated PE conjugated anti-mouse PD-L1 (MIH5) antibody (BD Biosciences, 558091).

Cells were detached using cell dissociation buffer, washed once with PBS and $2\times10^5$ cells were plated in wells of a 96-well plate and then incubated with antibody diluted 1:20 in PBS for 1 hour at 4° C. Cells were washed once in PBS and then measured on an Accuri C6 cytometer (BD Biosciences) and the data was analysed using FlowJoX. Expression of mouse PD-L1 was again confirmed.

The 15 clones produced in Example 5.1 in CD137/PD-L1 $mAb^2$ were tested in this DO11.10 T cell activation assay. Dilutions of $mAb^2$ or positive control mAb were prepared and added to either DO11.10.hCD137 ($7.5\times10^3$ cells per well) and HEK.mPD-L1 cells ($2\times10^4$ cells per well) or to DO11.10.hCD137 ($7.5\times10^3$ cells per well) and HEK cells that were not transduced to express mPD-L1 ($2\times10^4$ cells per well) in a 96 well flat bottom plate that had been coated overnight with 0.1 μg/ml anti-CD3 antibody (clone 17A2, BioLegend, 100208). After an 18-hour incubation, supernatants were collected and assayed with mouse IL-2 ELISA kit (eBioscience, 88-7024-86) following the manufacturer's instructions. Plates were read at 450 nm using the plate reader with the Gens Software, BioTek. Absorbance values of 570 nm were subtracted from those of 450 nm (Correction). The standard curve for calculation of cytokine concentration was based on four parameter logistic curve fit (Gens Software, BioTek). The concentration of mIL-2 was plotted vs the log concentration of $mAb^2$ or benchmark mAb and the resulting curves were fitted using the log (agonist) vs response equation in GraphPad Prism. T cell activation was detected by measuring the release of IL-2.

Figure 3:
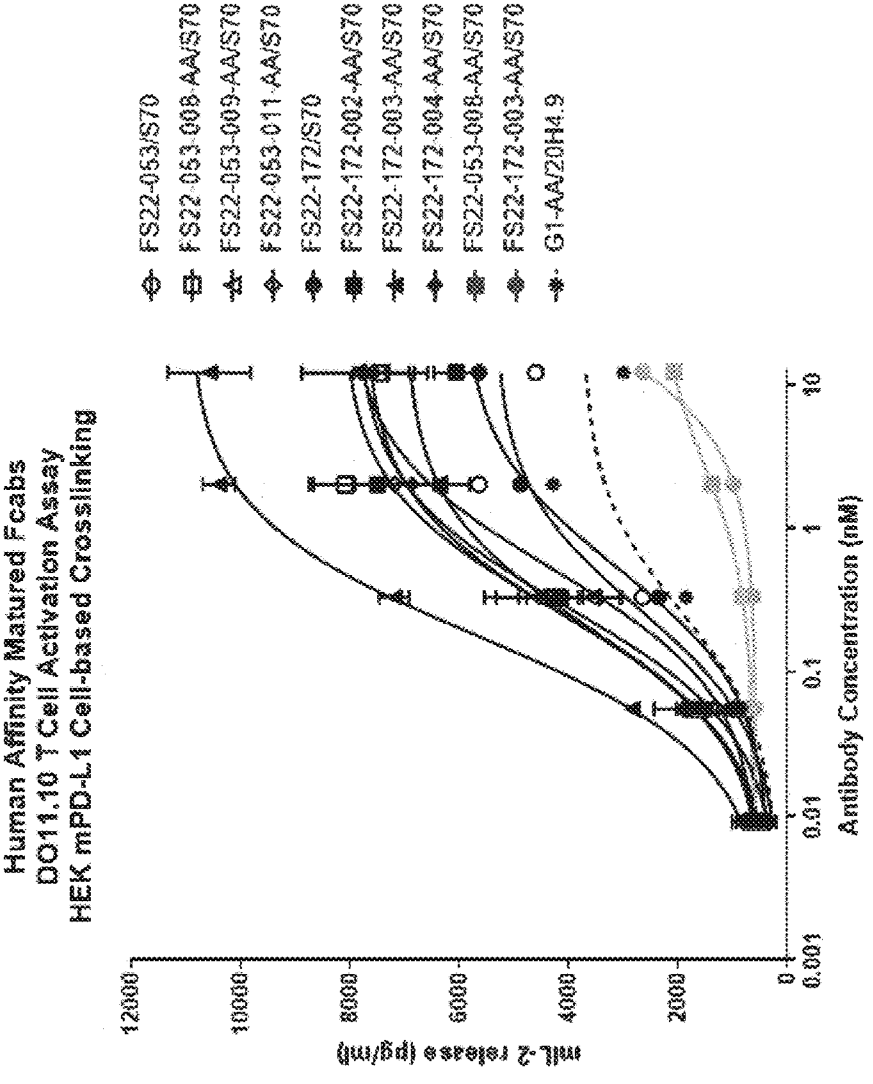
FIG. 3 shows IL-2 release in a T cell activation assay in the presence of anti-human CD137 Fcabs. FS22-053-008, FS22-053-009, FS22-053-011 and FS22-172-002, FS22-172-003, FS22-172-004 in PD-L1 (S70 LALA) mAb$^2$ format drive clustering and activation of CD137 only when crosslinked with HEK cells overexpressing PD-L1 (open and filled black symbols) leading to a release of mouse interleukin-2 (mIL-2) in a DO11.10 T cell activation assay. At increasing concentrations, the positive control anti-human CD137 mAb, 20H4.9, showed an increase in mIL-2 release (dotted line), however the maximal release was significantly less than that of the anti-human CD137 Fcabs. All anti-human CD137 Fcabs in PD-L1 model mAb$^2$ format without HEK cells overexpressing PD-L1 to crosslink (filled grey symbols) show significantly lower mIL-2 release compared to when crosslinked (open and filled black symbols).

The results of this assay are shown in Table 4 and FIG. 3. No T cell activity was observed without crosslinking by binding to PD-L1 expressing cells (No cell-based XL column). Upon crosslinking, all $mAb^2$ had potent T cell activity as seen by the release of high levels of IL-2 and sub-nanmolar $EC_{50}$ values. At increasing concentrations, the positive control anti-human CD137 mAb, G1-AA/20H4.9, shows an increase in mIL-2 release, however the maximal release was significantly less than that of the anti-human CD137 Fcabs. All clones other than FS22-053-009 and FS22-172-005, had an EC50 of less than 0.3 nM so were as good as, if not better than the positive control. The lowest Emax, which is a measure of maximum T cell activation, and might be relevant to greater T cell anti-tumour activity in vivo, observed was 7758 pg/ml which was higher than the positive control.

TABLE 4

| Fcab clone (in PD-L1 model $mAb^2$ format) or mAb | IL-2 release with or without mPD-L1 HEK crosslinking: No Cell-Based XL | +XL Emax (IL-2 pg/ml) | +XL EC50 (nM) |
|---|---|---|---|
| FS22-053 | N/A | 5366 | 0.28 |
| FS22-053-008 | N/A | 8176 | 0.28 |
| FS22-053-009 | N/A | 8083 | 0.52 |
| FS22-053-010 | N/A | 8301 | 0.15 |
| FS22-053-011 | N/A | 7923 | 0.28 |
| FS22-053-012 | N/A | 9808 | 0.20 |
| FS22-053-013 | N/A | 15551 | 0.12 |
| FS22-053-014 | N/A | 12849 | 0.09 |
| FS22-053-015 | N/A | 17079 | 0.18 |
| FS22-053-016 | N/A | 18003 | 0.10 |
| FS22-172 | N/A | 5952 | 0.53 |
| FS22-172-001 | N/A | 10006 | 0.23 |
| FS22-172-002 | N/A | 7001 | 0.20 |
| FS22-172-003 | N/A | 10958 | 0.18 |
| FS22-172-004 | N/A | 7758 | 0.24 |
| FS22-172-005 | N/A | 13021 | 1.27 |
| FS22-172-006 | N/A | 9089 | 0.32 |
| G1-AA/20H4.9 | N/A | 3755 | 0.26 |

N/A—not applicable as low signal did not allow EC50 determination 5.4 Primary Human CD8+ T Cell Activation Assay The activity of the Fcabs to activate CD137 on HEK cells overexpressing CD137 was shown in Example 5.3. To test the activity of the Fcabs on cells which have not been engineered to overexpress CD137, a primary human T cell assay was needed. Activated cytotoxic $CD8^+$ T cells are responsible for directly killing cancer cells and express CD137 on their cell surface (Ye et al, 2014). Clustering of CD137 is known to be essential to induce downstream signalling and further CD8+ T cell activation. A CD8+ T cell activation assay was therefore used to assess the ability of Fcabs (in $mAb^2$ format as detailed below) to drive clustering and subsequent downstream signalling of CD137. CD8+ T cell activation was determined by the release of IL-2.

To isolate T cells, peripheral blood mononuclear cells (PBMCs) were isolated from leucocyte depletion cones, a by-product of platelet donations. Briefly, leucocyte cones contents were flushed with PBS and overlaid on a Ficoll (Sigma-Aldrich, 1440-02) gradient. PBMCs were isolated by centrifugation and the cells that did not cross the Ficoll gradient were recovered. PBMCs were further washed with PBS and remaining red blood cells were lysed through the addition of 10 ml 1× red blood cell lysis buffer (eBioscience, 00-4300-54) according to the manufacturer's instructions. $CD8^+$ T cells were isolated from the PBMCs present in the eluant using the $CD8^+$ T cell isolation kit II (Miltenyi Biotec Ltd, 130-096-495) according to the manufacturer's instructions.

Incubation with an anti-CD3 antibody was used as a first signal to drive initial activation of the T cells. 96-well flat bottom tissue culture plates were coated with 8 μg/ml anti-CD3 antibody (Clone UCHT1, R&D Systems, MAB100-SP) in PBS overnight at 4° C. The plates were then washed 3 times with 200 μl PBS.

For cell-based crosslinking of affinity matured human CD137 Fcabs in PD-L1 model $mAb^2$ format, HEK293 cells overexpressing hPD-L1 (HEK.hPD-L1) were produced essentially as described in example 5.3 but by subcloning cDNA encoding human PD-L1 (SEQ ID NO: 187) instead of mouse PD-L1. HEK.hPD-L1 cells were plated at $2\times10^5$ cells per well on to anti-CD3 antibody-coated (8 μg/ml) 96 well flat bottom plates in 100 μl T cell culture medium (RPMI medium (Life Technologies, 61870-044) with 10% FBS (Life Technologies), 1× Penicillin Streptomycin (Life Technologies, 15140122), 1 mM Sodium Pyruvate (Gibco, 11360-070), 10 mM Hepes (Sigma-Aldrich, H0887), 2 mM L-Glutamine (Sigma-Aldrich, G7513) and 50 μM 2-mercaptoethanol (Gibco, M6250)). Once HEK.hPD-L1 cells or HEK cells that were not transduced to express hPD-L1 had adhered after 4 hours incubation, all T cell culture medium was removed and replaced with 100 μl T cell culture medium containing T cells at a concentration of $5.0\times10^5$ cells/ml resulting in $5.0\times10^4$ cells/well.

$mAb^2$ were diluted in T cell medium at a 2× final concentration starting at 500 nM and a 1:3 titration was carried out. 100 μl of $mAb^2$ titration was added to the cells for a total assay volume of 200 μl and 1× concentration of antibody.

Positive control anti-CD137 antibody (G1-AA/20H4.9) and negative control isotype IgG antibody (G1-AA/HeID1.3) were each diluted in T cell medium at a 2× final concentration starting at 500 nM containing 500 nM crosslinking agent (anti-human CH2, clone MK1A6 (Jefferis et al., 1985 and Jefferis et al., 1992), produced in-house) and a 1:3 titration was carried out. 100 μl of diluted positive control antibody/crosslinker mix or negative control IgG antibody/crosslinker mix was added to the cells for a total of 200 μl assay volume and 1× concentration of antibody.

The assay was incubated at 37° C., 5% $CO_2$ for 72 hours. Supernatants were collected and assayed with human IL-2 ELISA Ready-SET-Go! kit (eBioscience, Cat. 88-7025-88) following the manufacturer's instructions. Plates were read at 450 nm using the plate reader with the Gen5 Software, BioTek. Absorbance values of 630 nm were subtracted from those of 450 nm (Correction). The standard curve for calculation of cytokine concentration was based on a four-parameter logistic curve fit (Gen5 Software, BioTek). The concentration of human IL-2 (hIL-2) was plotted vs the log concentration of antibody and the resulting curves were fitted using the log (agonist) vs response equation in GraphPad Prism.

Table 5 shows the $EC_{50}$ values and maximum response of IL-2 release observed in the T cell activation assay in the presence of the affinity-matured Fcab clones in PD-L1 model $mAb^2$ format tested with cell-based crosslinking. The positive control anti-human CD137 mAb, 20H4.9, shows an increase in hIL-2 release with an EC50 of 0.5 nM when crosslinked with anti-hCH2 antibody. All clones had activity in the assay, the majority displaying good potency with sub-nanomolar $EC_{50}$s. $mAb^2$ containing Fcabs FS22-053-007, FS22-053-008, FS22-053-010, FS22-053-011, FS22-

Figure 4:
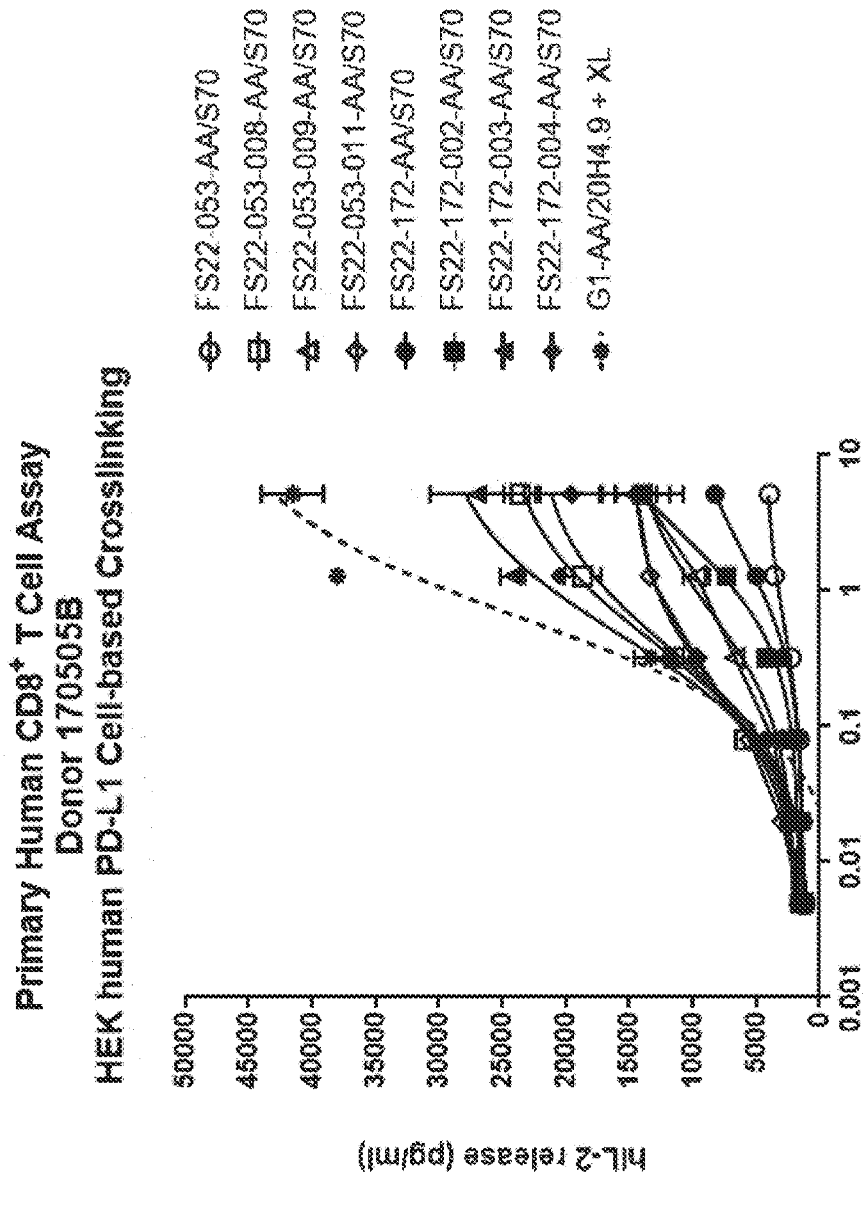
FIG. 4 shows release of human IL-2 (hIL-2) in a human primary CD8$^+$ T cell activation assay. The affinity matured anti-human CD137 Fcabs FS22-053-008, FS22-053-009, FS22-053-011, FS22-172-002, FS22-172-003 and FS22-172-004 in PD-L1 mAb$^2$ format drove CD137 activation of CD8$^+$ T cells when the mAb$^2$ were crosslinked by HEK cells overexpressing PD-L1 leading to release of human IL-2. The activity of the affinity matured Fcabs was better than the activity of the parental Fcabs, FS22-053 (open circles) and FS22-172 (filled circles). The positive control anti-human CD137 mAb, 20H4.9 (dotted line), showed an increase in hIL-2 release and there was a larger release of IL-2 than with the Fcabs, however the EC50 value was larger than that of some anti-human CD137 Fcabs, indicating that better activity was achieved with some anti-human CD137 Fcabs.

053-012, FS22-172-003, FS22-172-004, FS22-172-005 elicited the greatest T cell response with the lowest EC50s in the range of 0.19-to 0.49 nM. A subset of the mAb$^2$ (containing Fcabs FS22-053-008, FS22-053-011, FS22-053-014, FS22-173-003 and FS22-172-004) were also tested without cross-linking by PD-L1 expressed on HEK cells and showed no activity in this assay, as expected. This confirms activity seen in the NF-kB assay and DO11.10 T cell activation assay. FIG. 4 shows representative plots of IL-2 release for the T cell activation assay for FS22-053-007-AA/PD-L1, FS22-053-008-AA/PD-L1 and FS22-172-002-AA/PD-L1, FS22-172-003-AA/PD-L1, FS22-172-004-AA/PD-L1 mAb$^2$.

TABLE 5

| Fcab clone (in PD-L1 model mAb$^2$ format) or mAb | IL-2 release with hPD-L1 HEK crosslinking Donor 170505B Emax | EC50 (nM) |
|---|---|---|
| FS22-053 | 4344 | 0.55 |
| FS22-053-007 | 13119 | 0.22 |
| FS22-053-008 | 25112 | 0.42 |
| FS22-053-009 | 15230 | 0.69 |
| FS22-053-010 | 13978 | 0.37 |
| FS22-053-011 | 14959 | 0.19 |
| FS22-053-012 | 12282 | 0.20 |
| FS22-172 | 10729 | 1.83 |
| FS22-172-001 | 19135 | 0.58 |
| FS22-172-002 | 20615 | 2.69 |
| FS22-172-003 | 30311 | 0.45 |
| FS22-172-004 | 22611 | 0.36 |
| FS22-172-005 | 23626 | 0.49 |
| FS22-172-006 | 27871 | 0.89 |
| 20H4.9 | 14780 | 0.89 |
| 20H4.9 + XL | 44940 | 0.50 |

5.5 Specificity Determination of Anti-Human CD137 Fcabs by Surface Plasmon Resonance (SPR)

The specificity of the anti-human CD137 Fcabs for human CD137 compared to other related TNFSFR family members was tested. 8 of the Fcabs were tested in mock mAb$^2$ (HelD1.3) format and measured by SPR in a Biacore T200 (GE Healthcare) by testing for binding to other human TNFRSF receptors: CD40, OX40 and GITR. Amine coupling (amine coupling kit, GE Healthcare, BR-1000-50) was used to coat human CD40, GITR and OX40 to approximately 1000 RU in Biacore CM5 chips (GE Healthcare, cat no 29149603). Dilutions of anti-human CD137 Fcabs in mock mAb$^2$ format (FS22-053-008/HelD1.3, FS22-053-009/HelD1.3, FS22-053-010/HelD1.3, FS22-053-011/HelD1.3, FS22-053-012/HelD1.3, FS22-053-014/HelD1.3, FS22-172-003/HelD1.3, FS22-172-004/HelD1.3) starting at 1 μM were prepared in HBS-EP+ buffer (BR100669) and injected for 3 min at 30 μl/min and then allowed to dissociate in buffer for 4 min. The chip was regenerated by injection of 10 mM glycine pH 2.5 for 12 s at 30 μl/min. Antibodies specific to the different TNFRSF members were used as positive controls to verify Biacore chip coating. Data was double reference subtracted and analysed using BIAevaluation 3.2 software. The Fcabs did not bid to any of the TNFRSF receptors tested, demonstrating their specificity for CD137. As a result, it is not expected that the Fcabs will elicit off-target binding.

5.6 Binding Affinity of Anti-Human CD137 Fcabs in Mock mAb$^2$ Format for Human, Cynomolgus and Mouse CD137 by SPR The affinity of the anti-human CD137 Fcabs (FS22-053-008, FS22-053-011, FS22-053-014, FS22-172-004, FS22-172-004) for human, cynomolgus (cyno) and mouse CD137 was measured by SPR, to determine whether the Fcabs may be useful for testing in animal studies. An anti-human Fab capture antibody was immobilised on all four flow cells of a CM5 series S chip (GE Healthcare #BR-1005-30) to an average surface density of 6000 RU following the manufacturer's recommendations (GE Healthcare, human Fab capture Kit, #28958325). Each mAb$^2$ was captured to approximately 150 RU by injecting a 3 μg/ml solution of mAb$^2$ diluted in HBS-EP+ buffer (GE Healthcare #BR1006-69) for 60 seconds at 30 μl/min. Then different concentrations of human, cyno or mouse CD137 antigen (unbiotinylated human, cyno or mouse CD137-mFc-Avi or human CD137-Avi-His) in HBS-EP+ buffer were flowed over the chip for 3 min at 60 μl/min and then allowed to dissociate for 10 minutes. After each antigen concentration the chip was regenerated by infecting 10 mM glycine pH 2.1 at a flow rate of 30 μl/min for 30 seconds. Buffer HBS-EP+ was injected before the highest concentration of antigen and after the lowest concentration of antigen for reference subtraction, and one of the concentrations at random was repeated twice. The binding kinetics were fit with a 1:1 Langmuir model to generate equilibrium binding constants ($K_D$) for each sample. Data analysis was performed with BiaEvaluation software version 3.2. The results are shown in Table 6.

Analysis of the results revealed an improved binding for both human and cynomolgus CD137 by all affinity matured clones, compared to the respective parent molecules. The binding affinity for the monomeric human CD137 antigens was weaker (by at least 100-fold) than for the dimeric human and cyno Fc-fusion antigens. As discussed in Example 2, the Fcabs were selected to preferentially bind to dimeric CD137 over monomeric forms of CD137 and this data confirms that the selection strategy was successful. This kinetic behaviour makes them less likely to bind to monomeric CD137 expressed at minimal levels on unstimulated T cells to result in reduced risk of liver or systemic toxicities associated with some anti-CD137 monoclonal antibody therapies.

The data also shows that the anti-human CD137 Fcabs bound to cynomolgus dimeric CD137 with comparable affinity to human dimeric CD137.

The ability of the Fcabs to bind to mouse dimeric CD137 was also tested. None of the clones showed strong binding to the mouse antigen (as shown in Table 6 where N/A indicates that no $K_D$ could be calculated) except for clone FS22-053-014 which was surprisingly found to have a $K_D$ of 24 nM for the mouse antigen. This was unexpected since mouse CD137 and human CD137 share less than 57% sequence homology.

TABLE 6

| Fcab | Human dimeric CD137 $K_D$ (nM) | Cynomolgus dimeric CD137 $K_D$ (nM) | Human monomeric CD137 $K_D$ fold difference relative to human dimeric $K_D$ | Mouse dimeric CD137 $K_D$ (nM) |
|---|---|---|---|---|
| FS22-053 | 38 | 34 | N/A | N/A |
| FS22-053-008 | 4.2 | 0.9 | 170-fold | N/A |
| FS22-053-011 | 5.5 | 1.3 | >200-fold | N/A |
| FS22-053-014 | 3.2 | 0.9 | 100-fold | 24 |
| FS22-172 | 52 | 203 | N/A | N/A |
| FS22-172-003 | 1.5 | 1.3 | >200-fold | N/A |
| FS22-172-004 | 4.3 | 3.5 | >200-fold | N/A |

N/A—not applicable as low signa did not allow $K_D$ determination 5.7 Determination of Fcab Binding Valency Using Heterodimeric and Homodimeric Fcabs Fcabs usually contain two homodimeric Fc chains with antigen binding sites in the CH3 domains. Since these antigen binding sites in the two CH3 domains are in close proximity, the valency of binding of the Fcab was tested to determine whether the CH3 domains could bind to CD137 independently of each another. Heterodimeric Fcabs containing a single antigen binding CH3 domain were constructed by combining one chain of the FS22-172-003 with one chain of a wild-type Fc, using knob-into-hole mutations (Knob: T22W, Hole: T22S L24A Y66V) (Atwell S et al, 1997). Consequently, each heterodimer contained a CH3 from FS22-172-003 (SEQ ID NO: 139) in one chain and a wild-type CH3 (SEQ ID NO: 4) in the other chain. Fcabs were prepared in a $mAb^2$ format.

Figure 14:
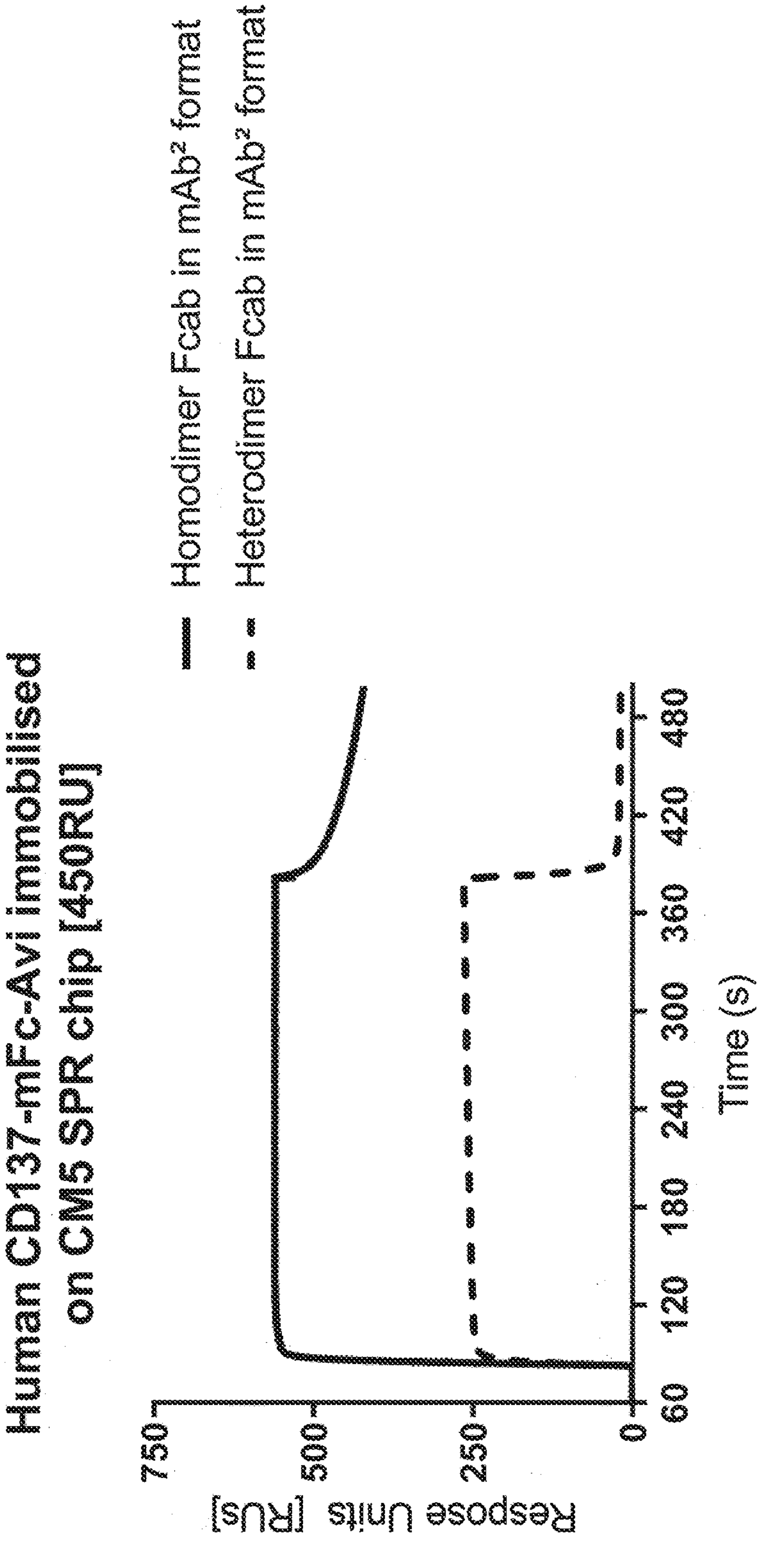
FIG. 14 shows a sensorgram of the binding kinetics of a homodimeric Fcab (FS22-172-003-AA) in $mAb^2$ format (i.e. containing 2 CD137 binding CH3 domains) compared to a heterodimeric Fcab in $mAb^2$ format (containing 1 CD137 binding CH3 domain and one wild type CH3 domain). This sensorgram shows that both molecules bound to CD137, even through only one binding chain. The off-rates were different, with the homodimeric Fcab presenting a much slower dissociation profile, compared to the heterodimeric Fcab. These sensorgrams demonstrate that the anti-CD137 Fcab can bind CD137 bivalently.

The heterodimeric Fcab was compared to the FS22-172-003 homodimer molecule (containing two antigen binding CH3 domains) by SPR binding analysis. For this experiment, monomeric human CD137-mFc-Avi was preferred over dimeric CD137 antigen. To compensate for the weaker binding to monomeric antigen described in Example 5.6, human CD137-mFc-Avi was immobilised on a CM5 chip to a higher density of 450 RU. Hetero- or homodimer Fcabs were injected and flowed over the immobilised antigen. The results in FIG. 14 show that the heterodimeric Fcab, containing only one CD137 binding CH3 domain, was able to bind antigen even in these suboptimal conditions. The off-rate observed for the heterodimeric Fcab was significantly faster than that of the homodimeric Fcab. These results confirm that the FS22-172-003 Fcab was able to bind to CD137 through either or both CH3 domains and confirmed that the selection strategy described in Example 2 was successful since the Fcab was able to engage its target bivalently.

5.8 Binding of Anti-CD137 Fcabs to Cells with Different CD137 Expression Levels

As described in Example 2, the Fcabs were selected to bind CD137 such that they preferentially bound cells with elevated CD137 expression levels. The bivalent and therefor avid binding of FS22-172-003 was confirmed by SPR in Example 5.6: FS22-172-003 exhibited high avidity and stronger binding to dimeric CD137 compared to monomeric CD137.

A range of DO11.10 cells expressing different levels of CD137 were produced as described in Example 3.5. To determine the relative expression of CD137 in each cell line, the antibody binding capacity (ABC) was determined according to manufacturer's protocol (Quantum™ Simply Cellular® #816 Bangs Labs). Each cell line was ranked in order of CD137 expression levels after subtracting background: hCD137 high (ABC: 1,206,283), hCD137 intermediate (ABC: 404,597), hCD137 intermediate/low (ABC: 143,065), hCD137 low (ABC: 14,208), hCD137 negative (ABC: 0).

Binding of anti-human CD137 Fcab in mock $mAb^2$ format (FS22-172-003-AA/HelD1.3), positive control antibody (G1-AA/20H4.9), or isotype control (G1-AA/HelD1.3) to each of the cells described above was tested as follows: DO11.10 cells were harvested from T175 cell culture flasks and centrifuged at 1200 rpm for 3 min and resuspended in ice cold FACS buffer made up of DPBS (Life Technologies, 14190169) and 1% BSA (Sigma-Aldrich, A7906) at $2\times10^6$ cells/ml and 50 μl per well was seeded in a 96-well V-bottom plate (Costar, 3894). All antibodies tested were diluted in FACS buffer in 120 μl. DO11.10 cells were then centrifuged, supernatant removed and cells resuspended in 100 μl of each antibody dilution and incubated at 4° C. for 45 min. Cells were washed twice by centrifugation with 150 μl FACS buffer, resuspended in 100 μl containing goat anti-human IgG (γ-chain specific) F(ab')2 fragment-R-Phycoerythrin antibody (Sigma, P8047) diluted 1:1000 in FACS buffer and incubated at 4° C. for 45 min. The cells were washed once with 150 μl FACS buffer and then with 150 μl DPBS, resuspended in 150 μl DPBS containing DAPI (Biotium, 40043) at 1:10.000 and read on the BDCantoll or iQue (Intellicyt). Data was analysed using FlowJo v10 to determine the signal geometric mean for PE for live cells in each well.

Figure 15:
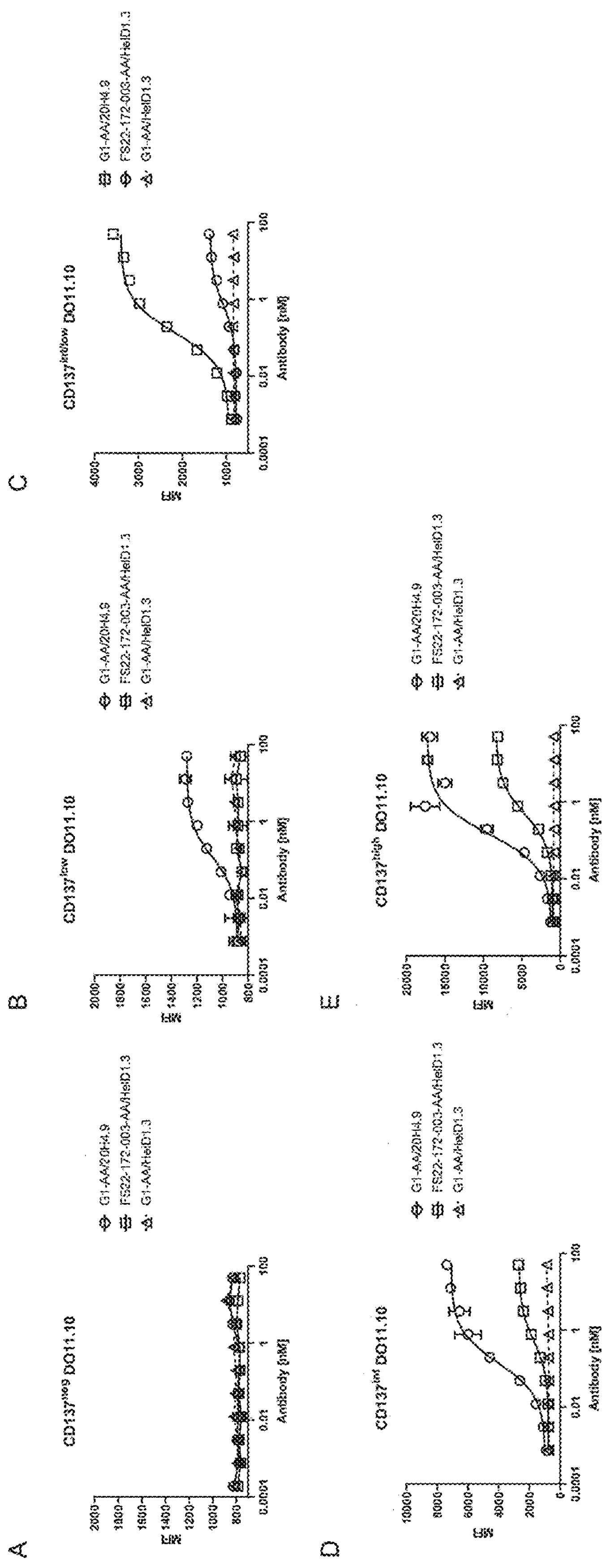
FIG. 15 shows binding of an anti-human CD137 Fcab mock $mAb^2$ format (FS22-172-003-AA/HelD1.3) positive control antibody (G1-AA/20H4.9) and an isotype control antibody (G1-AA/HelD1.3) to cells expressing a range of CD137 levels including a negative control cell line ($hCD137^{neg}$ DO11.10) (A). Binding was determined by flow cytometry. Results showed that while G1-AA/20H4.9 was able to bind all cell lines expressing CD137 (B-E), FS22-172-003-AA/HelD1.3 did not bind the DO11.10 cell line expressing low levels of CD137 (B), and that the fold-difference in binding compared to the positive control was inversely proportional to the amount of CD137 expressed by the cell line.

As shown in FIG. 15, FS22-172-003-AA/HelD1.3 bound stronger to cells with higher CD137 expression (FIG. 15D: CD137int and FIG. 15E: CD137high), and did not bind to cells that expressed very low levels of CD137 (FIG. 15B: CD137low and FIG. 15C: CD137int/low), compared to the positive control G1-AA/20H4.9. Comparatively, the positive control G1-AA/20H4.9 bound better to both dimeric and monomeric antigen, with $K_D$ to dimeric or monomeric antigens within 10-fold of each other, unlike FS22-172-003-AA/HelD1.3 which had at least 200-fold weaker binding to monomeric CD137 antigen than dimeric antigen, as described in Example 5.6.

Example 6: Naïve Selection of Anti-Mouse CD137 Fcabs

To test the activity of anti-CD137 Fcabs in in vivo mouse models, Fcabs which specifically bound to mouse CD137 were generated and characterised.

Phage Display

The six naïve phage libraries displaying the CH3 domain of human IgG1 previously used for selection of Fcabs binding to human CD137 were used for selections of Fcabs binding to mouse CD137, with recombinant mouse dimeric CD137 or cells expressing full-length mouse CD137 used as antigens.

In-house mCD137-mFc-Avi antigen and DO11.10 cells expressing mCD137 (DO11.10.mCD137) were used in selections using the six phage libraries. A simple selection scheme was followed in which all selection rounds (three in total) were performed using 100 nM biotinylated antigen, with a deselection step using 500 nM unlabelled recombinant human Fc fragment. Binders were captured by magnetic beads coated on either streptavidin or neutravidin. Additionally, round 1 outputs which bound to recombinant antigen were also used in selections on DO11.10.mCD137 cells expressing mouse CD137. Briefly, phage outputs were incubated with DO11.10 cells lacking mouse CD137 to discard undesired binders, such as those binding non-specifically to cells. Next, phage were incubated with $1\times10^7$ DO11.10.mCD137 cells. Binders were then eluted by trypsin digestion and then propagated for the second selection round. Round 3 followed a similar process, increasing selection pressure by decreasing the number of DO11.10.mCD137 cells to $5\times10^6$.

All round 3 recombinant antigen outputs (576 clones) and all round 3 cell selection outputs (576 clones) were screened by phage ELISA (as previously described) and for cell binding to DO11.10.mCD137 cells. For ELISA, most clones presented a high signal strength for antigen binding (OD450>1). Therefore, clones that showed less than a 10-fold increase in antigen binding as compared to binding to mouse-Fc were discarded. For cell binding, a FITC MFI higher than $5\times10^5$ was considered positive. Three of the phage libraries performed considerably worse, with many clones exhibiting non-specific binding to the DO11.10.mCD137 cells and recombinant antigens. 34 Fcab clone hits were subcloned and produced as HelD1.3 $mAb^2$ as described in Example 3.1.

Yeast Display

The four naïve yeast libraries displaying CH1 to CH3 domains of human IgG1 previously used for selection of Fcabs binding to human CD137 were used for selections of Fcabs binding to mouse CD137.

A total of 53 separate rounds of selections were performed to identify anti-mouse CD137 binders. In-house-produced, recombinant, dimeric, biotinylated mouse CD137 (mCD137-mFc-Avi) antigen was used to select binders from the yeast naïve libraries. Briefly, round 1 binders were selected by incubating the naïve libraries with 300 nM recombinant antigen and deselected with 2.5 μM unlabelled mouse IgG2a Fc fragment. Outputs were separated using MACS and streptavidin magnetic beads. Three rounds of FACS selections were performed with 300 nM recombinant antigen and 1.5 μM mouse Fc being used for selections and deselections, respectively, as described earlier in Example 2.

Single clones from each of rounds 2, 3 and 4 were spotted on agar plates. To determine output diversity, at least 96 clones from each selection output were sequenced. 126 unique clones (50 clones from round 3 for one of the libraries, 48 clones from round 3 for another of the libraries, and 18 clones from round 4 for the remaining library) were screened for binding to recombinant antigen by flow cytometry. Clones that showed higher than 10% of positive cells in the APC fluorescence channel when incubated with the recombinant antigen and less than 0.2% when incubated with recombinant mFc were considered hits.

Example 7: Characterisation of Anti-Mouse CD137 Fcabs from Naïve Selections 7.1 Specificity Determination of Anti-Mouse CD137 Fcab by BLI The specificity of the anti-mouse CD137 Fcabs for mouse CD137 was tested in HelD1.3 "mock" $mAb^2$ format and measured by BLI in an Octet QKe system by testing for binding of the Fcabs to other mouse TNFRSF receptors (CD40, OX40, GITR). Streptavidin biosensors (PALL ForteBio 18-5021) to coat 10 ng/μl mouse CD40, GITR, OX40 receptors (all obtained from R&D Systems and biotinylated using an EZ-Link Sulfo-NHS-SS-Biotin kit from Thermoscientific #21328). Anti-mouse CD137 Fcabs in mock $mAb^2$ format were diluted 1:1 in kinetic buffer (PALL 18-1092) to a final concentration of at least 1 μM. Antigen-coated sensors were dipped into the $mAb^2$ solutions for 180 seconds followed by 180 seconds in 1× kinetic buffer. Antibodies for each of the TNFRSF receptors were used as positive controls. The Fcab clones FS22m-055, FS22m-063, FS22m-066, FS22m-075, FS22m-135, FS22m-055, FS22m-063, FS22m-066 did not bind to any of the TNFRSF receptors tested, thus demonstrating their specificity for mouse CD137.

Figure 5:
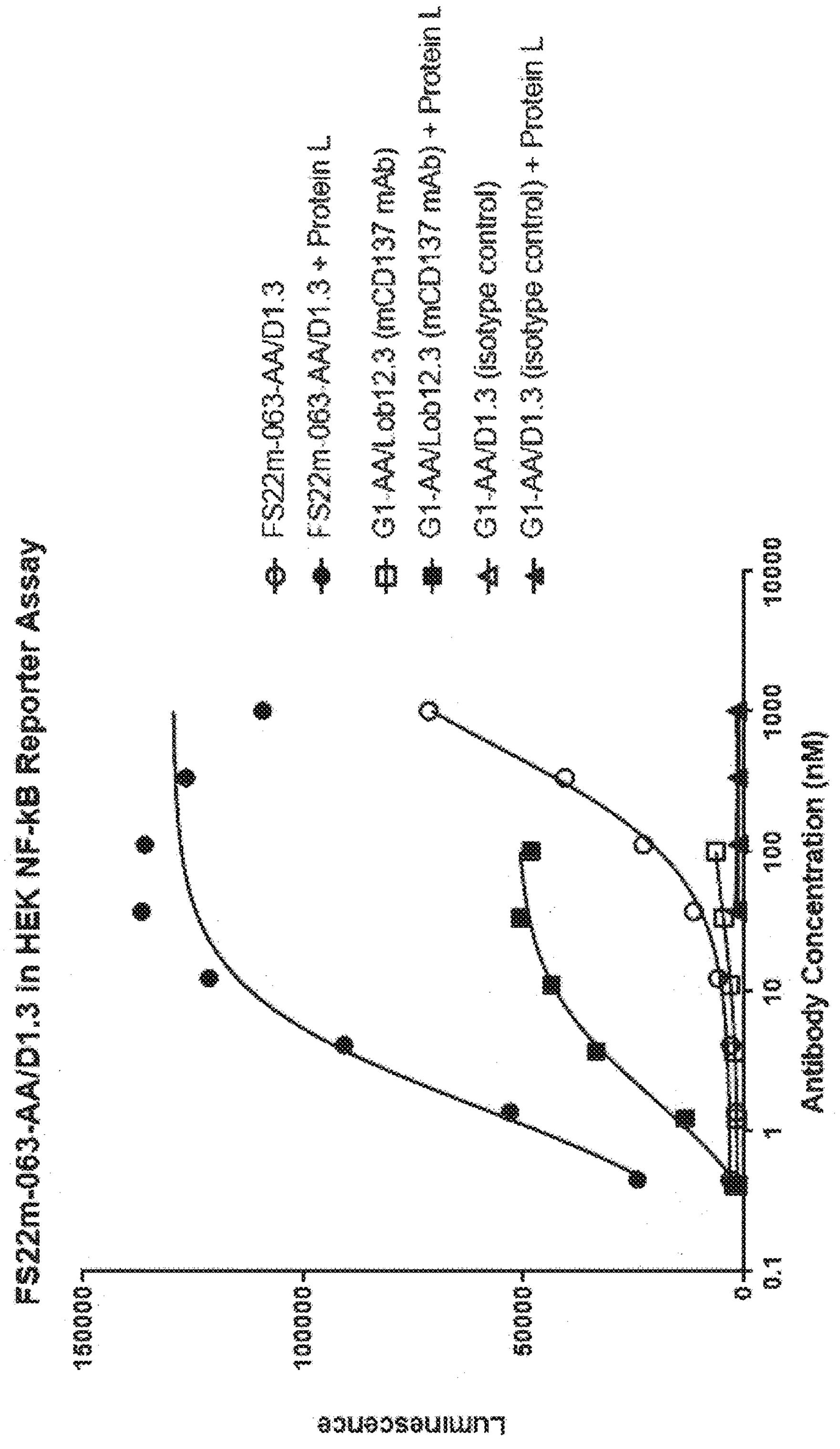
FIG. 5 shows NF-kB signalling determined by luminescence values as a measure of luciferase production caused by CD137 clustering and activation. The anti-mouse CD137 Fcab FS22m-063 in HeID1.3 mock mAb$^2$ format drove CD137 clustering and NF-kB signalling when crosslinked with Protein L in a HEK mCD137 NF-kB reporter assay (filled circles). At concentrations above 100 nM, and when not crosslinked with Protein L, FS22m-063 drove some CD137 clustering and NF-kB signalling but at much lower levels than when crosslinked (open circles). The positive control anti-mouse CD137 mAb, Lob12.3, showed an increase in luminescence when crosslinked with Protein L (filled squares), compared to no crosslinking (open squares), however the maximal response achieved at the highest antibody concentration was significantly less than that of the anti-mouse CD137 Fcab. As expected, the isotype controls showed no activity.

7.2 Activity of Mouse Fcabs in Mock $mAb^2$ Format in a Mouse NF-κB Reporter Cell Assay HEK.FRT.luc cells expressing the mouse CD137 sequence (SEQ ID NO: 184) were produced following the same methodology as previously described in example 3.3. The $mAb^2$ containing the anti-mouse CD137 Fcabs previously selected were screened using this cell line, HEK.FRT.luc.mCD137, according to the method described in example 3.3. 56 $mAb^2$ were tested of which 29 were positive for NF-kB activity. Lob12.3 containing a human IgG1 Fc with a LALA mutation (G1AA/Lob12.3), was used as a positive control anti-mouse CD137 mAb and showed an increase in luminescence confirming the assay's validity. HelD1.3, also containing a human IgG1 Fc with a LALA mutation, was used as a negative control human IgG isotype to rule out interference from the human IgG mock Fab in this assay. EC50s were calculated where possible and $mAb^2$ which did not reach a plateau in activity were disregarded in favour of $mAb^2$ which showed classic sigmoidal activity kinetics. $mAb^2$ were ranked in order of EC50 and fold-change in activity upon Protein L crosslinking. FS22m-063 was selected based on it having the best EC50 upon cross-linking (1.44 nM) and highest fold-change in activity upon crosslinking (27-fold). FIG. 5 shows that the anti-mouse CD137 Fcab FS22m-063 in HelD1.3 mock $mAb^2$ format drives CD137 clustering and NF-kB signalling when cross-linked with Protein L in the HEK mCD137 NF-kB reporter assay.

Example 8: In Vivo Anti-Tumour Activity of FS22m-063 Fcab (in FS22m-063-AA/PD-L1 $mAb^2$)

Having shown that the FS22m-063 Fcab is capable of driving clustering and activation of CD137 in vitro, it was desirable to test their ability to activate CD137 in vivo.

8.1 Preparation of FS22m-063 Fcab in $mAb^2$ Format for In Vivo Testing in Mice

A $mAb^2$ comprising the anti-mouse CD137 Fcab, FS22m-063, and a Fab region specific for PD-L1 using similar methodology to the model $mAb^2$ produced in example 7.1 was prepared and tested for in vivo anti-tumour activity in an MC38 syngeneic mouse tumour model.

Controls: G1-AA/Lob12.3, G1-AA/570, G1-AA/4420.

Control antibodies for the in vivo experiments were produced by joining the variable heavy region of the anti-PD-L1 antibody S70 (clone YW243.55.570 from U.S. Pat. No. 8,217,149 B2) to the human IgG1 (G1m17) constant region containing the LALA mutation, and the variable light region from the S70 antibody was joined to the human constant region (Lm1) via human kappa J– region. The $mAb^2$ was generated by replacing the CH3 domain of the reformatted construct described above with FS22m-063 and was designated 'FS22m-063-AA/S70'.

8.2 Activity of FS22m-063-AA/S70 $mAb^2$ in an MC38 Syngeneic Tumour Model

Syngeneic mouse models are accepted as appropriate murine systems for testing the anti-tumour effect of inhibiting therapeutic targets and have been used extensively to validate development of human therapeutics. The MC38 syngeneic tumour model was used in this experiment as MC38 tumours are known to be highly immunogenic and respond to anti-CD137 antibody monotherapy (Kocak et al, 2006) and express PD-L1 (Juneja et al, 2017).

C57BL/6 female mice (The Jackson Laboratory) aged 9-10 weeks and weighing 17.92 to 23.89 g each were rested for one week prior to the study start. All animals were micro-chipped and given a unique identifier. Each cohort had 12 mice. The MC38 colon carcinoma cell line (National Cancer Institute, USA) was initially expanded, stored, and then pre-screened for pathogens and shown to be pathogen-free. Each animal received $1\times10^6$ cells injected subcutaneously in the right flank in 100 μl in serum-free culture medium (Dulbecco's Modified Eagle Medium). 7 days following tumour cell inoculation, mice which did not have tumours at this point were removed from the study.

The FS22m-063-AA/S70 $mAb^2$ and control antibodies (G1-AA/Lob12.3 (CD137 positive control), G1-AA/S70 (positive control PD-L1), G1-AA/4420 (isotype control))

were injected intraperitoneally into mice at a fixed concentration of 20 μg per dose in DPBS+1 mM arginine+0.05 Tween 80. Each mouse received the $mAb^2$ molecule or the control antibody by 200 μl intraperitoneal (IP) injection on days 7, 9, and 11 following tumour inoculations. Accurate measurements of tumours were taken, any drug dosing due on the day in question was performed, and the mice were put under close observation for the remainder of the study. Tumour volume measurements were taken with callipers to determine the longest axis and the shortest axis of the tumour. The following formula was used to calculate the tumour volume:

$$L \times (S^2)/2$$

Where L=longest axis; S=shortest axis

Figure 6:
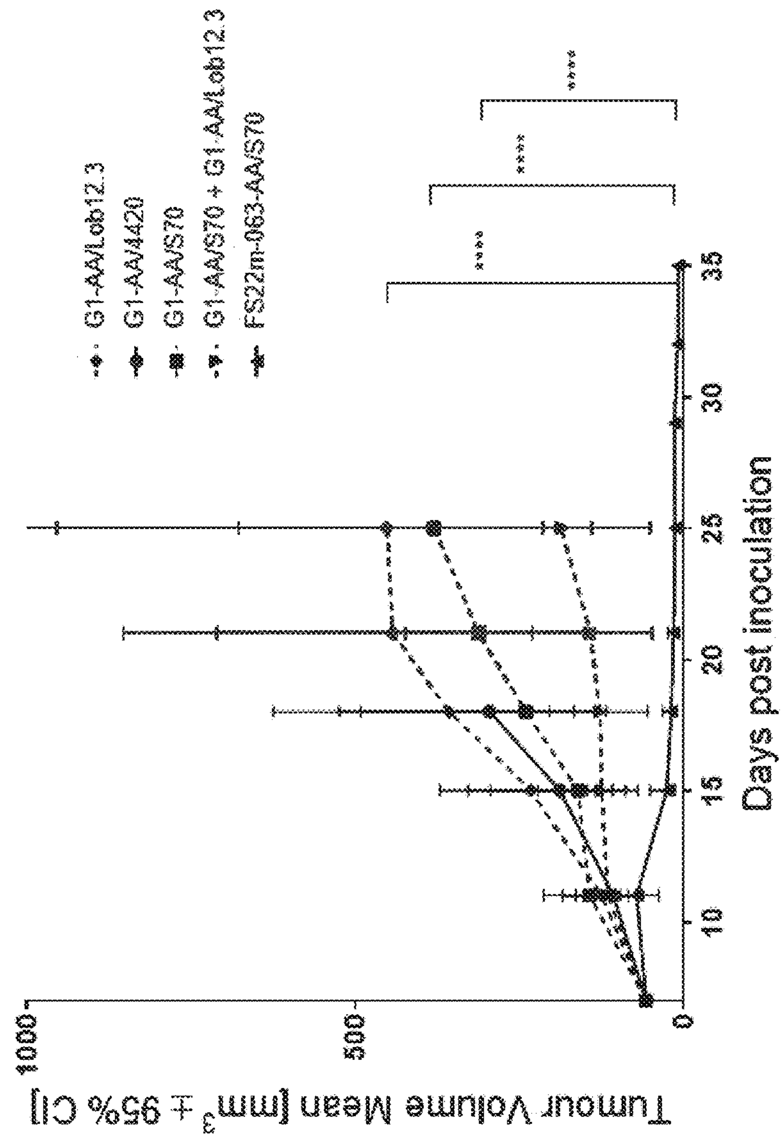
FIG. 6 shows tumour volume measurements of the MC38 syngeneic tumour model grown subcutaneously in C57BL6 mice treated with G1-AA/4420 (IgG control), G1-AA/S70 (PD-L1 positive control), G1-AA/Lob12.3 (CD137 positive control), the combination of G1-AA/S70 plus G1-AA/Lob12.3 and FS22m-063-AA/S70 (the anti-mouse CD137 Fcab FS22m-063 in a PD-L1 mAb$^2$ format). The mean tumour volume [in mm$^3$] plus or minus the 95% Confidence Interval is shown. FS22m-063-AA/S70 was able to significantly reduce tumour growth in a MC38 syngeneic tumour model compared to IgG control treated mice, anti-PD-L1 positive control mAb treated mice, anti-CD137 positive control treated mice. Statistical significance shown pairwise for growth rates over the full time of study using the Mixed Model analysis. **≤0.0001 p-value

As shown in FIG. 6, the FS22m-063-AA/S70 $mAb^2$ showed significant tumour growth inhibition compared to mice treated with any of the control antibodies. Statistical significance was shown pairwise for growth rates over the full time of study using a Mixed Model analysis comparing all groups. As shown in Table 7, unexpectedly all mice treated with FS22m-063-AA/S70 $mAb^2$ were tumour free at the end of the study, compared to only 4 of 12 mice treated with a combination of anti-PD-L1 and anti-CD137 antibodies (G1-AA/S70+G1-AA/Lob12.3) or the PD-L1 or CD137 antibodies alone.

TABLE 7

Tumour free mice per treatment group in an MC38 syngeneic tumour model

| Group | % Tumour Free Mice | Number Tumour Free Mice |
|---|---|---|
| G1-AA/Lob12.3 | 16% | 2/12 |
| G1-AA/4420 | 0% | 0/12 |
| G1-AA/S70 | 16% | 2/12 |
| G1-AA/S70 + G1-AA/Lob12.3 | 33% | 4/12 |
| FS22m-063-AA/S70 | 100% | 12/12 |

The study shows that in mice with a fully functioning immune system, CD137 agonism, presumably as a result of crosslinking via PD-L1, leads to a reduction in tumour growth, presumably through increased cytotoxic activity of CD8+ T cells in the tumour.

Example 9: In Vivo Anti-Tumour Activity of FS22m-063 Fcab (in FS22m-063-AA/PD-1 $mAb^2$)

Having shown that the FS22m-063 Fcab is capable of driving clustering and activation of CD137 in vitro, it was desirable to test their ability to activate CD137 via another Fab target, in this case a target found only on immune cells, PD-1, in vivo.

9.1 Preparation of FS22m-063 Fcab in $mAb^2$ Format for In Vivo Testing in Mice

A $mAb^2$ comprising the anti-mouse CD137 Fcab, FS22m-063, and a Fab region specific for PD-1 was prepared using similar methodology to the model $mAb^2$ produced in example 7.1. and tested for in vivo anti-tumour activity in an MC38 syngeneic mouse tumour model.

Control antibodies (G1/Lob12.3, G1-AA/F2, G1-AA/4420) for the in vivo experiments were produced by joining the variable heavy region of the anti-PD-1 antibody F2 (clone PD1-F2 from WO 2004/056875 A1) to the human IgG1 (G1m17) constant region containing the LALA mutation, and the variable light region from the F2 antibody was joined to the human constant region (Lm1) via human kappa J– region. The $mAb^2$ was generated by replacing the CH3 domain of the reformatted construct described above with FS22m-063 and was designated 'FS22m-063-AA/F2'.

9.2 Activity of FS22m-063-AA/F2 $mAb^2$ in an MC38 Syngeneic Tumour Model

The MC38 syngeneic tumour model was used in this experiment as described in Example 8.2 with the following deviations:

C57BL/6 female mice (Charles River) aged 9-11 weeks were micro-chipped and given a unique identifier. Each cohort had 12 mice. Each animal received $1 \times 10^6$ MC38 colon carcinoma cells injected subcutaneously in the dorsal right flank in 100 μl serum free medium.

The FS22m-063-AA/F2 $mAb^2$ and control antibodies (G1-AA/Lob12.3 (CD137 positive control), G1-AA/F2 (positive control PD-1), G1-AA/4420 (isotype control)) were injected intraperitoneally into mice at a fixed concentration of 20 μg per dose in DPBS+1 mM arginine+0.05 Tween 80. Each mouse received the $mAb^2$ molecule or the control antibody by 200 μl intraperitoneal (IP) injection once tumour volume had reached 50-60 $mm^3$ (Day 0) and on day 2, and 4 following the first dose. Tumours were measured as described in example 8.2.

Figure 7:
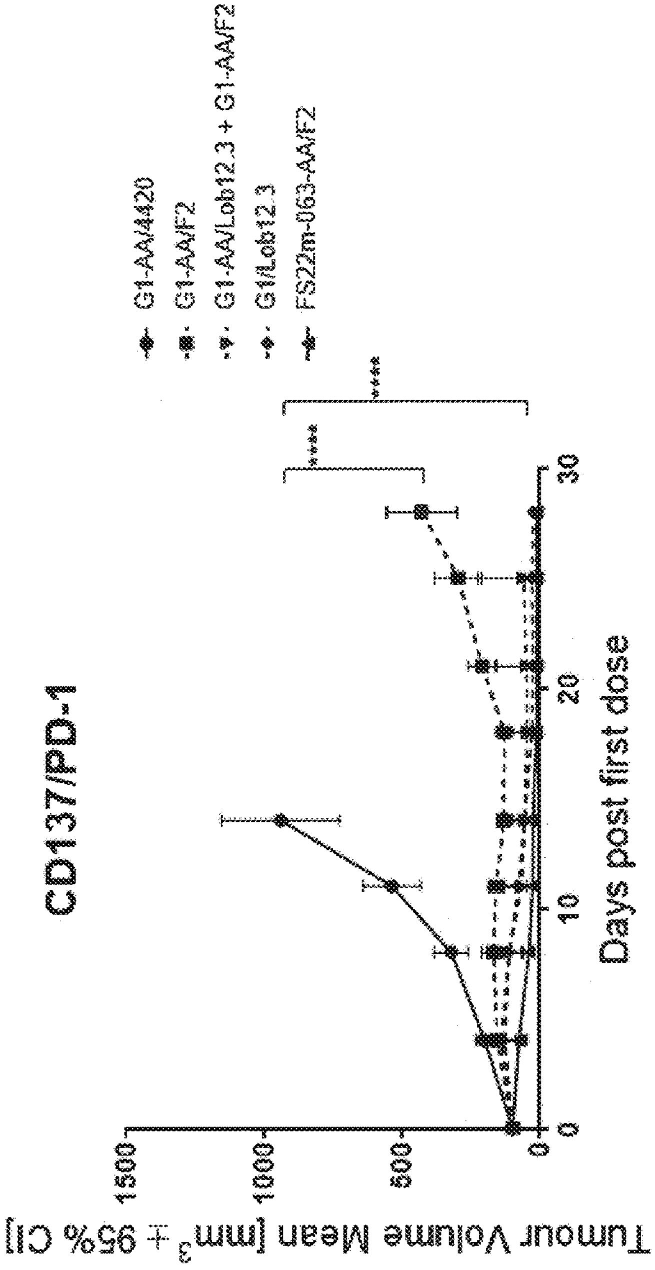
FIG. 7: A shows tumour volume measurements of the MC38 syngeneic tumour model grown subcutaneously in C57BL/6 mice treated with G1-AA/4420 (IgG control), G1-AA/F2 (PD-1 positive control), G1/Lob12.3 (CD137 positive control), the combination of G1-AA/F2 plus G1-AA/Lob12.3 and FS22m-063-AA/F2 (the anti-mouse CD137 Fcab FS22m-063 in a PD-1 mAb$^2$ format). The mean tumour volume [in mm$^3$] plus or minus the 95% Confidence Interval is shown. FS22m-063-AA/F2 was able to significantly reduce tumour growth in a MC38 syngeneic tumour model compared to IgG control treated mice. Statistical significance shown pairwise for growth rates over the full time of study using the Mixed Model analysis. ≤0.0001 p-value. B shows the same data as FIG. 7**A, except that the tumour volume in each mouse treated is shown separately. This highlights that, apart from one mouse, none of the mice treated with FS22m-063-AA/F2 showed any tumour regrowth during the course of the study. In contrast, tumour regrowth was seen in the mice treated with G1-AA/Lob12.3 and G1-AA/F2 towards the end of the study.
Figure 7:
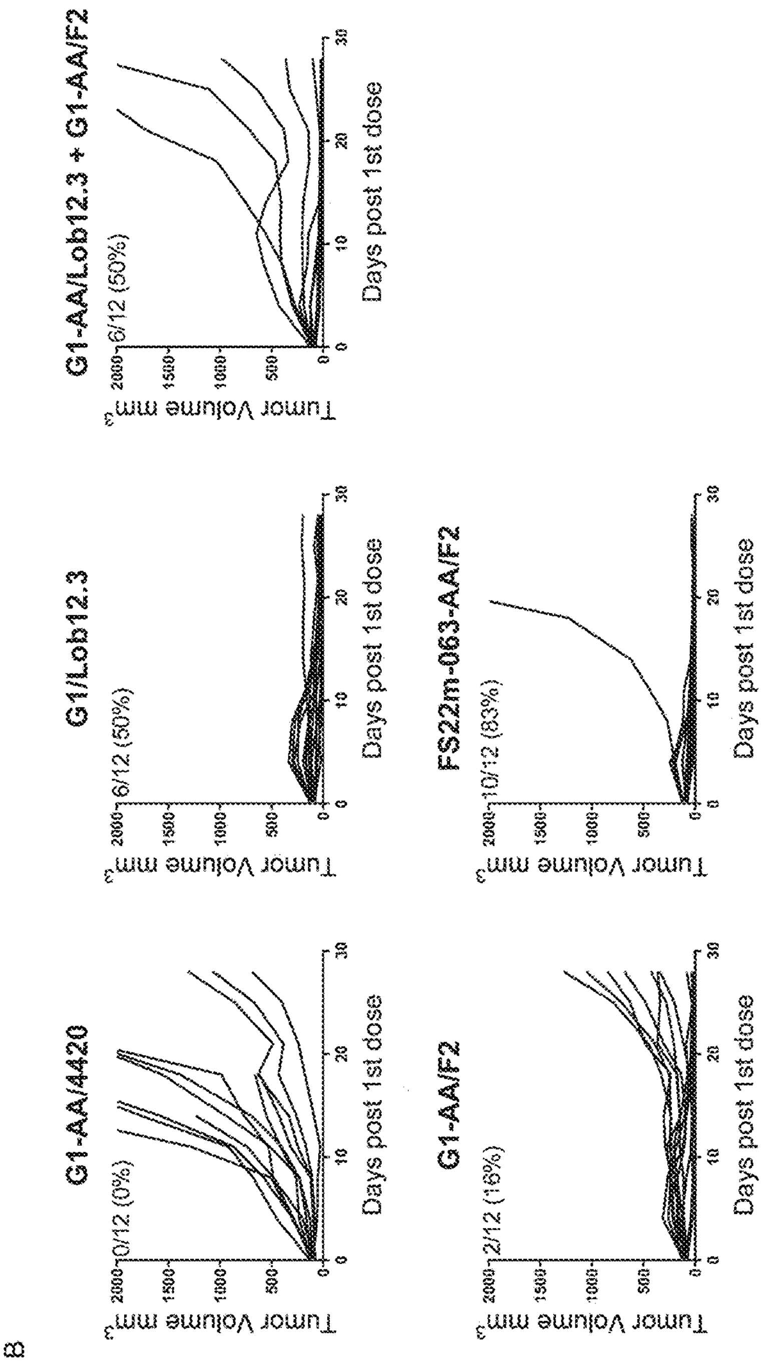
Figure 8:
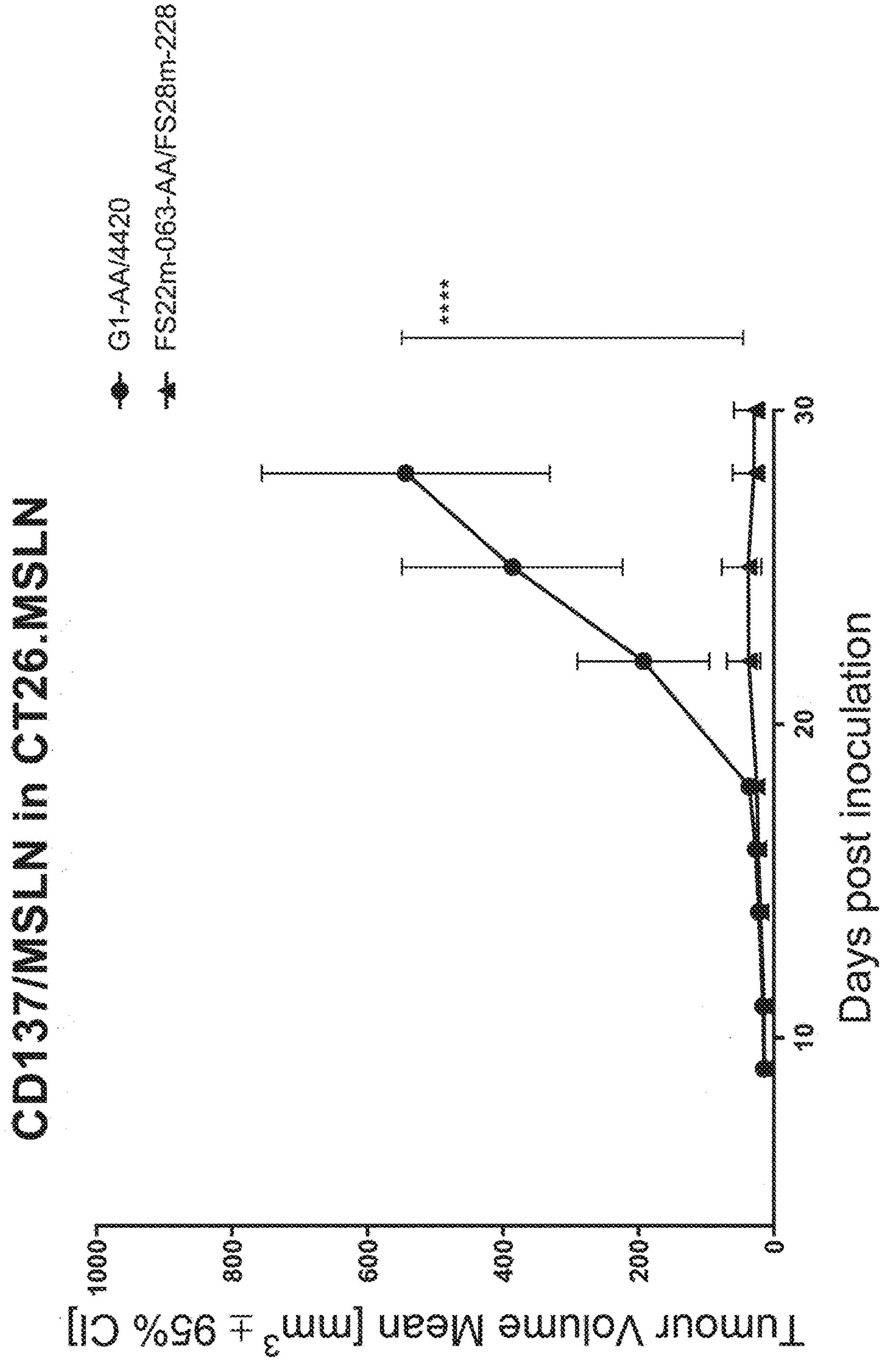
FIG. 8 shows mean tumour volume measurements in a subcutaneous mesothelin positive CT26 syngeneic tumour model (Balb/c). Mice were either treated with G1-AA/4420 (IgG control) or the FS22m-063-AA/FS28m-228 mAb$^2$. Mice treated with FS22m-063-AA/FS28m-228 showed a significant tumour growth inhibition compared to IgG control treated mice. The mean tumour volume [in mm$^3$] plus or minus the 95% Confidence Interval is plotted. Statistical significance shown comparing growth rates over the full time of study pairwise using the Mixed Model analysis. **≤0.0001 p-value

As shown in FIGS. 7 A and B, the FS22m-063-AA/F2 $mAb^2$ showed highly significant tumour growth inhibition compared to mice treated with the isotype control antibody positive control PD-1 antibody. As shown in Table 8, unexpectedly 10 out of 12 mice treated with FS22m-063-AA/F2 $mAb^2$ were tumour free at the end of the study, compared to only 7 of 12 mice treated with a combination of anti-PD-1 and anti-CD137 antibodies (G1-AA/F2+G1-AA/Lob12.3).

TABLE 8

| Group | % Tumour Free Mice | Number Tumour Free Mice |
|---|---|---|
| G1/Lob12.3 | 50% | 6/12 |
| G1-AA/4420 | 0% | 0/12 |
| G1-AA/F2 | 16% | 2/12 |
| G1-AA/F2 + G1-AA/Lob12.3 | 50% | 6/12 |
| FS22m-063-AA/F2 | 83% | 10/12 |

The study shows that in mice with a fully functioning immune system, CD137 agonism, presumably as a result of crosslinking via PD-1 engagement with added PD-1 blockade, leads to a reduction in tumour growth, presumably through increased cytotoxic activity of CD8+ T cells in the tumour.

It also shows that CD137 Fcabs can be crosslinked when in $mAb^2$ format by binding of the Fab arms to an immune cell target, resulting in clustering and activation of CD137.

Example 10: In Vivo Anti-Tumour Activity of a mCD137/MSLN $mAb^2$

Having shown efficacy of a $mAb^2$ comprising the FS22m-063 Fcab and a PD-L1 Fab (Example 8), it was desirable to test the ability of the CD137 Fcabs in a $mAb^2$ format to activate CD137 by crosslinking the mAb2 via binding of its Fab arms to a tumour-specific antigen (TAA), in this case mesothelin (MSLN). Such a tumour-targeted approach is expected to be beneficial in localising the T cell activation to the tumour microenvironment, as crosslinking of the $mAb^2$, and therefore agonism of CD137, will only occur where MSLN is expressed.

A syngeneic mouse tumour model expressing mouse MSLN was constructed. CT26 colon carcinoma cells (ATCC, CRL-2638) expressing full-length mouse mesothelin (SEQ ID NO: 189), were produced by lipofection (Lipofectamine 3000, Thermo Fisher Scientific, catalogue number L3000008) using the pcDNA3.1 vector (+) (Thermo Fisher Scientific, catalogue number V79020). Following the manufacturer's protocol, the CT26 cells were transfected with the pcDNA3.1 vectors containing the mouse MSLN cDNA. A stable transfection was achieved using geneticin as the selection antibiotic (at 600 μg/ml) in complete media (RPMI, 10% FBS).

Expression of mouse MSLN on the CT26 cells was confirmed by flow cytometry by using the positive control antibody MOR6626 (WO 2009/068204 A1). Specifically, cells were incubated with the positive control antibody for 1 hour and then a fluorescently-labelled anti-human IgG detection antibody (Stratech Scientific Ltd, catalogue no. 109-546-098-JIR) was used to detect cell binding. Clonal populations were expanded and subsequently analysed to determine the relative expression levels using the same flow cytometric procedure, after which one clone was selected and denominated CT26.G10.

CT26.G10 tumour growth was confirmed in vivo. Balb/c female mice (Charles River) aged 8-10 weeks were microchipped and given a unique identifier. Each cohort had 17 mice and each animal received $1\times10^5$ cells injected subcutaneously in the dorsal left flank in 100 μl serum free medium. Tumour volume measurements were taken three times per week with callipers as described in Example 8. Study was carried out according to UK Home Office regulations as described in Example 8.

Tissues were collected at the termination of the study, and expression of membrane-bound mesothelin was confirmed by immunohistochemical staining in formalin fixed paraffin embedded (FFPE) tumour tissues as follows: 4 μm FFPE tissue sections were deparaffinised and antigen retrieved using low pH 6.1 at 97° C. (Dako PT Link) followed by a peroxidase block and protein block prior to incubation with a primary anti-mesothelin antibody (LifeSpan Biosciences, catalogue no. LS-C407883) at a concentration of 1 μg/ml. The anti-mesothelin antibody was detected using a labelled polymer-HRP anti-rabbit secondary reagent and a DAB (3,3'-diaminobenzidine) chromogenic endpoint (Dako EnVision+ System).

To assess the efficacy of Fcab FS22m-063, the following molecules or combinations were tested in vivo: the anti-MSLN FS28m-228-010 antibody in human IgG1 isotype with LALA mutations (G1-AA/FS28m-228-010), the Fcab in two "mock" mAb$^2$ formats (FS22m-063-AA/HelD1.3 and FS22m-063-AA/4420), a combination of the FS28m-228-010 antibody with a mock CD137 mAb$^2$ with LALA mutations (G1-AA/FS28m-228-010+FS22m-063-AA/HelD1.3), a human isotype control antibody (G1-AA/HelD1.3), and finally a CD137/MSLN mAb$^2$ (FS22m-063-AA/FS28m-228-010) with LALA mutations.

Balb/c female mice (Charles River) aged 8-10 weeks and weighing 20-25 g each were acclimatised for one week prior to the study start. All animals were micro-chipped and given a unique identified. With the exception of FS22m-063-AA/4420 (n=10 mice), each cohort comprised 20 mice. The CT26.G10 colon carcinoma cell line was expanded and cell banks generated. Each animal received $1\times10^5$ cells injected subcutaneously in the left flank in 100 μl serum free media. Any mice which did not have tumours 12 days following tumour cell inoculation were removed from the study.

200 μg doses of each antibody (~10 mg/kg) were prepared and injected intraperitoneally (IP) into mice. In addition, both FS22m-063-AA/HelD1.3 and G1-AA/FS28m-228-010 were each prepared at 200 μg per dose (~10 mg/kg) for the combination group. 200 μl doses were administered to the mice on days 12, 14 and 16 (q2dx3), following tumour inoculation. Tumour volume measurements were made three times per week using callipers and mice were monitored closely. The study endpoint was determined by humane endpoints based on tumour volume and condition of the mice.

Figure 9:
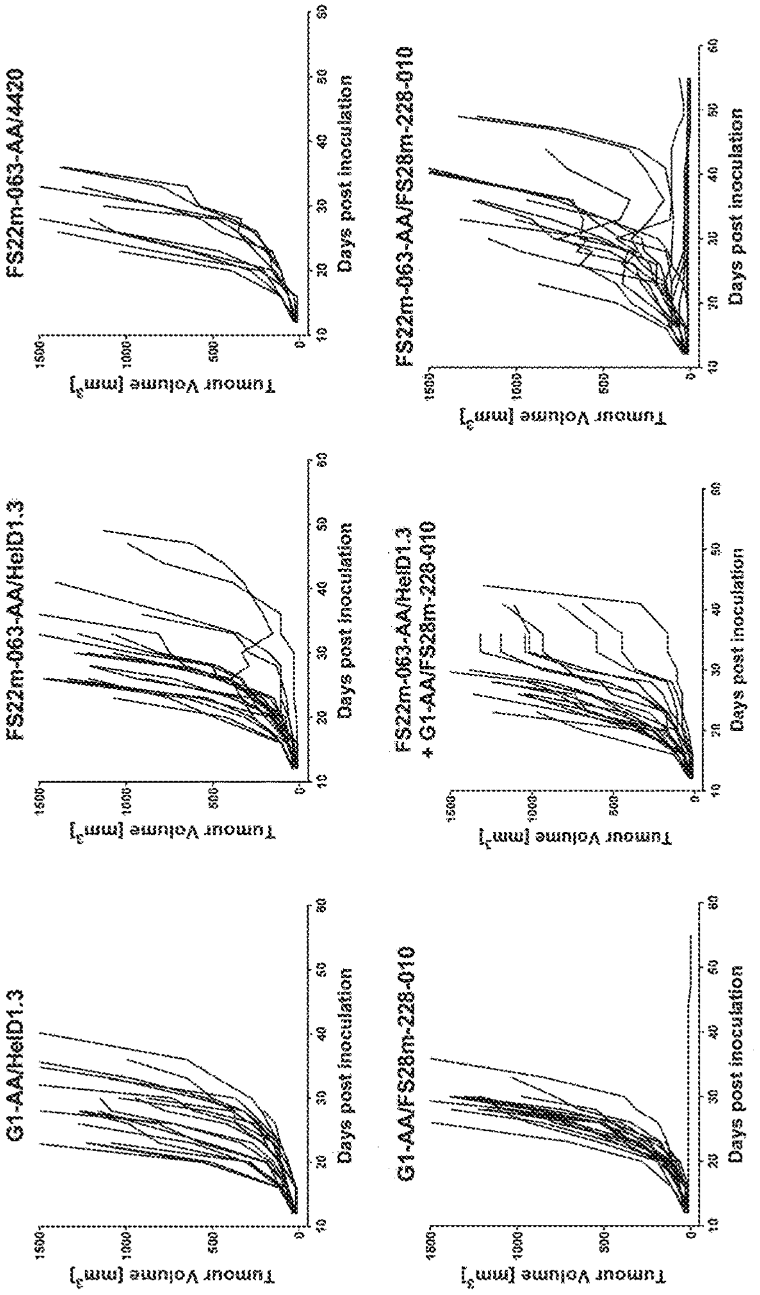
FIG. 9** shows individual tumour volume measurements in the CT26.G10 syngeneic tumour model treated with G1-AA/HeID1.3 (human IgG1 control), FS22m-063-AA/HeID1.3 (anti-mouse CD137 Fcab in mock mAb$^2$ format), FS22m-063-AA/4420 (anti-mouse CD137 Fcab in mock mAb$^2$ format), G1-AA/FS28m-228-010 (anti-mouse MSLN mAb), combination of FS22m-063-AA/HeID1.3 and G1-AA/FS28m-228-010 (anti-mouse CD137 Fcab plus anti-mouse MSLN mAb), and FS22m-063-AA/FS28m-228-010 (anti-mouse CD137/MSLN mAb$^2$). FS22m-063-AA/FS28m-228-010 showed reduced tumour growth compared to the isotype control, as well as other treatment groups.

As shown in FIG. 9, the FS22m-063-AA/FS28m-228-010 mAb$^2$ significantly inhibited tumour growth compared to the G1-AA/HelD1.3 isotype control. Table 9 shows pairwise comparison of the tumour growth rates for all treatment groups over the full course of the study using Mixed Model analysis, comparing all groups to the G1-AA/HelD1.3 isotype control.

TABLE 9

Results of pairwise comparison of the tumour growth using Mixed Model analysis, comparing all groups to the G1-AA/HelD1.3 isotype control.

| Groups | P-values Mixed Model Analysis | |
|---|---|---|
| G1-AA/HelD1.3 10 mg/kg (negative control) | | |
| G1-AA/FS28m-228-010 10 mg/kg | 0.4367 | NS |
| FS22m-063-AA/HelD1.3 10 mg/kg | 0.0017 | *** |
| FS22m-063-AA/4420 10 mg/kg | 0.7067 | NS |
| G1-AA/FS28m-228-010 10 mg/kg + FS22m-063-AA/HelD1.3 10 mg/kg | 0.2093 | NS |
| FS22m-063-AA/FS28m-228-010 10 mg/kg | 0.0000 | **** |

NS p ≥ 0.05;
* p < 0.05;
** p < 0.01;
*** p < 0.001;
**** p < 0.0001

All animals bearing tumours measuring equal or below 62.5 mm$^3$ at the end of the study were counted as fully responding animals (see Table 10). 35% of anti-CD137/MSLN mAb$^2$-treated animals were complete responders to treatment at the end of study, compared to 0% in the G1-AA/HelD1.3 isotype control, FS22m-063-AA/HelD1.3, FS22m-063-AA/4420, and FS22m-063-AA/HelD1.3 and G1-AA/FS28m-228-010 combination groups.

TABLE 10

Number and percentage of tumour-free mice (tumours ≤ 62.mm3) by the end of study in the CT26.G10 syngeneic tumour model.

| Groups | Tumour-free mice at study end |
|---|---|
| G1-AA/HelD1.3 10 mg/kg (negative control) | 0/20 (0%) |
| G1-AA/FS28m-228-010 10 mg/kg | 1/20 (5%) |
| FS22m-063-AA/HelD1.3 10 mg/kg | 0/20 (0%) |
| FS22m-063-AA/4420 10 mg/kg | 0/10 (0%) |
| G1-AA/FS28m-228-010 10 mg/kg + FS22m-063-AA/HelD1.3 10 mg/kg | 0/20 (0%) |
| FS22m-063-AA/FS28m-228-010 10 mg/kg | 7/20 (35%) |

Figure 10:
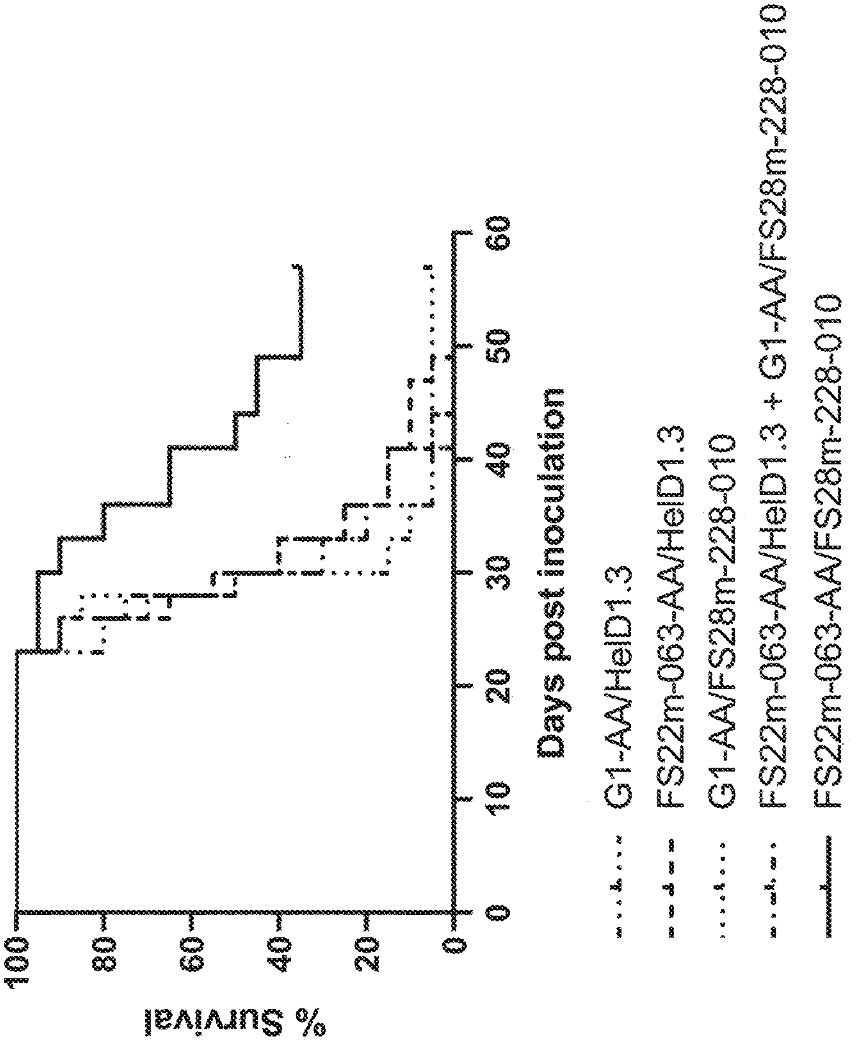
FIG. 10 shows a Kaplan Meier survival curve for the CT26.G10 syngeneic tumour model treated with G1-AA/HeID1.3 (IgG control), FS22m-063-AA/HeID1.3 (anti-mouse CD137 Fcab in mAb$^2$ format), FS22m-063-AA/4420 (anti-mouse CD137 Fcab in mAb$^2$ format), G1-AA/FS28m-228-010 (anti-mouse MSLN Fab), combination of FS22m-063-AA/HeID1.3 and G1-AA/FS28m-228-010 (anti-mouse CD137 Fcab plus anti-mouse MSLN Fab), and FS22m-063-AA/FS28m-228-010 (anti-mouse CD137/MSLN mAb$^2$). The results show that FS22m-063-AA/FS28m-228-010 treatment resulted in significantly improved survival compared to mice treated with the isotype control or other treatment groups.
Figure 11:
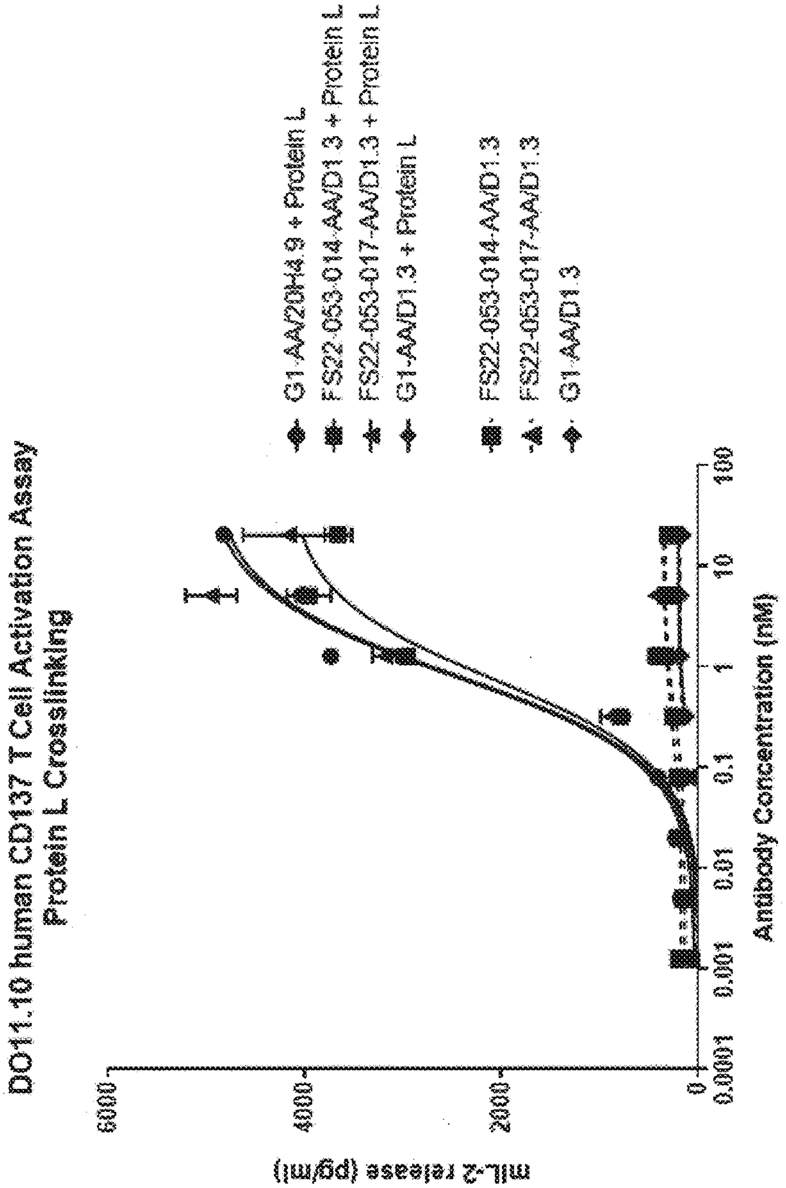
FIG. 11 shows mouse IL-2 release in a DO11.10 human CD137 T cell activation assay testing the mouse and human cross-reactive CD137 Fcabs FS22-053-014 and FS22-053-017 in mock mAb$^2$ format when crosslinked with Protein L. Both Fcabs were able to activate CD137 when crosslinked with Protein L. The positive control anti-human CD137 mAb, 20H4.9, showed an increase in mIL-2 release in line with FS22-053-017 mock mAb$^2$. Both anti-human CD137 Fcabs in mock mAb$^2$ format without Protein L to crosslink (open symbols) showed negligible mIL-2 release compared to when crosslinked (filled symbols).

Survival analysis (FIG. 10 and Table 11) showed that the FS22m-063-AA/FS28m-228-010 mAb$^2$ induced a significant survival benefit compared with the G1-AA/HelD1.3 antibody, whereas the components (G1-AA/FS28m-228-010, FS22m-063-AA/HelD1.3), or G1-AA/FS28m-228-010+FS22m-063-AA/4420 did not demonstrate a survival advantage. In addition, the FS22m-063-AA/FS28m-228-

010 mAb$^2$ resulted in an improved median survival time of 42.5 days compared with G1-AA/HeID1.3 (29 days), FS22m-063-AA/HeID1.3 (30 days), FS22m-063-AA/4420 (29 days), G1-AA/FS28m-228-010 (30 days) and combination of FS22m-063-AA/HeID1.3 with G1-AA/FS28m-228-010 (29 days).

TABLE 11

Median survival times for animals treated with each compound, and results of pairwise statistical analyses (Log-rank) in CT26.G10 syngeneic tumour model.

| Groups | Median Survival (Days) | P-values Log-rank | |
|---|---|---|---|
| G1-AA/HelD1.3 10 mg/kg | 29 | | |
| G1-AA/FS28m-228-010 10 mg/kg | 30 | 0.993 | NS |
| FS22m-063-AA/HelD1.3 10 mg/kg | 30 | 0.3952 | NS |
| FS22m-063-AA/4420 10 mg/kg | 29 | 0.9645 | NS |
| G1-AA/FS28m-228-010 10 mg/kg + FS22m-063-AA/HelD1.3 10 mg/kg | 29 | 0.4706 | NS |
| FS22m-063-AA/FS28m-228-010 10 mg/kg | 42.5 | <0.0001 | **** |

NS p ≥ 0.05;
* p < 0.05;
** p < 0.01;
*** p < 0.001;
**** p < 0.0001

These data suggest that crosslinking of the mAb$^2$ via MSLN is capable of driving CD137 agonism in the tumour; an action of the bispecific antibody which is superior to targeting CD137 and/or MSLN alone (and even in combination), resulting in significantly improved survival of tumour-bearing mice. The Fcab in a mock mAb$^2$ format FS22m-063-AA/HeID1.3 or FS22m-063-AA/4420), without any MSLN targeting Fab, showed no intrinsic activity in this study.

Example 11: Selections to Obtain an Fcab Capable of Binding to Murine and Human CD137

Since it was surprisingly found that some of the Fcabs binding to human CD137 also bound to mouse CD137 (see Example 5.5 for specificity of binding to human, mouse and cynomolgus CD137), it was decided to see if these clones could be improved.

11.1: Site-Directed Modification to Remove a Potential Sequence Liability in FS22-053-014 Clone The mouse-human cross-reactive clone FS22-053-014 was selected because it was shown to be capable of binding to mouse dimeric CD137 antigen by SPR (see example 5.5). However, upon further sequence analysis, it had a potential sequence liability that could result in a post-translational aspartate isomerisation in the EF loop of its CH3 domain as a result of the Q98D mutation together with the wild-type G99 position creating a DG motif. Other affinity-matured clones in the FS22-053 lineage (see Table 12) contained instead a Q98E modification at the same position in the EF loop. The Q98D was mutated to Q98E by site-directed mutagenesis using the QuickChange II mutagenesis kit (Agilent, catalogue no. 200523) according to the manufacturer's recommendations, which yielded clone FS22-053-017. Table 12 below shows a frequently occurring LE motif in the EF loop of the CH3 domains of clones FS22-053-008, FS22-172-003 and FS22-172-004, and the DG motif in the EF loop of the CH3 domain of clone FS22-053-014.

TABLE 12

| | EF loop (92-101) | | | | | | | | | |
|---|---|---|---|---|---|---|---|---|---|---|
| G1 CH3 | D | K | S | R | W | Q | Q | G | N | V |
| FS22-053-008 | D | Y | W | R | W | L | E | G | N | V |
| FS22-053-011 | D | Y | W | R | W | T | D | G | N | V |
| FS22-053-014 | Y | H | W | R | W | L | D | G | N | V |
| FS22-172-003 | G | A | D | R | W | L | E | G | N | V |
| FS22-172-004 | G | A | D | R | W | L | E | G | N | V |
| FS22-053-017 | Y | H | W | R | W | L | E | G | N | V |

Example 12: Characterisation of Mutant FS22-053-017 Fcab Clone 12.1 Activity of FS22-053-017 Fcab in Mock mAb$^2$ Format in Human CD137 DO11.10 T Cell Activation Assay Fcab clone FS22-053-017 was sub-cloned and expressed as a HeID1.3 "mock" mAb$^2$ and then compared to the FS22-053-014 clone, also in HeID1.3 mAb$^2$ format, in a human CD137 DO11.10 T cell activation assay as described in Example 3.4. G1-AA/20H4.9 was used as an anti-CD137 positive control and G1-AA/D1.3 as an IgG control. The mAb$^2$ were tested either without Protein L crosslinking or were crosslinked in a 1:4 ratio with Protein L.

TABLE 13

| Fcab clone (in HeID1.3 mAb$^2$ format) or mAb | IL-2 release with or without Protein L crosslinking No XL | +XL Emax (IL-2 pg/ml) | +XL EC50 (nM) |
|---|---|---|---|
| FS22-053-014 | N/A | 4174 | 0.73 |
| FS22-053-017 | N/A | 4956 | 0.82 |
| G1-AA/20H4.9 | Not measured | 5018 | 0.82 |

N/A—not applicable as low signal did not allow EC50 determination

Figure 12:
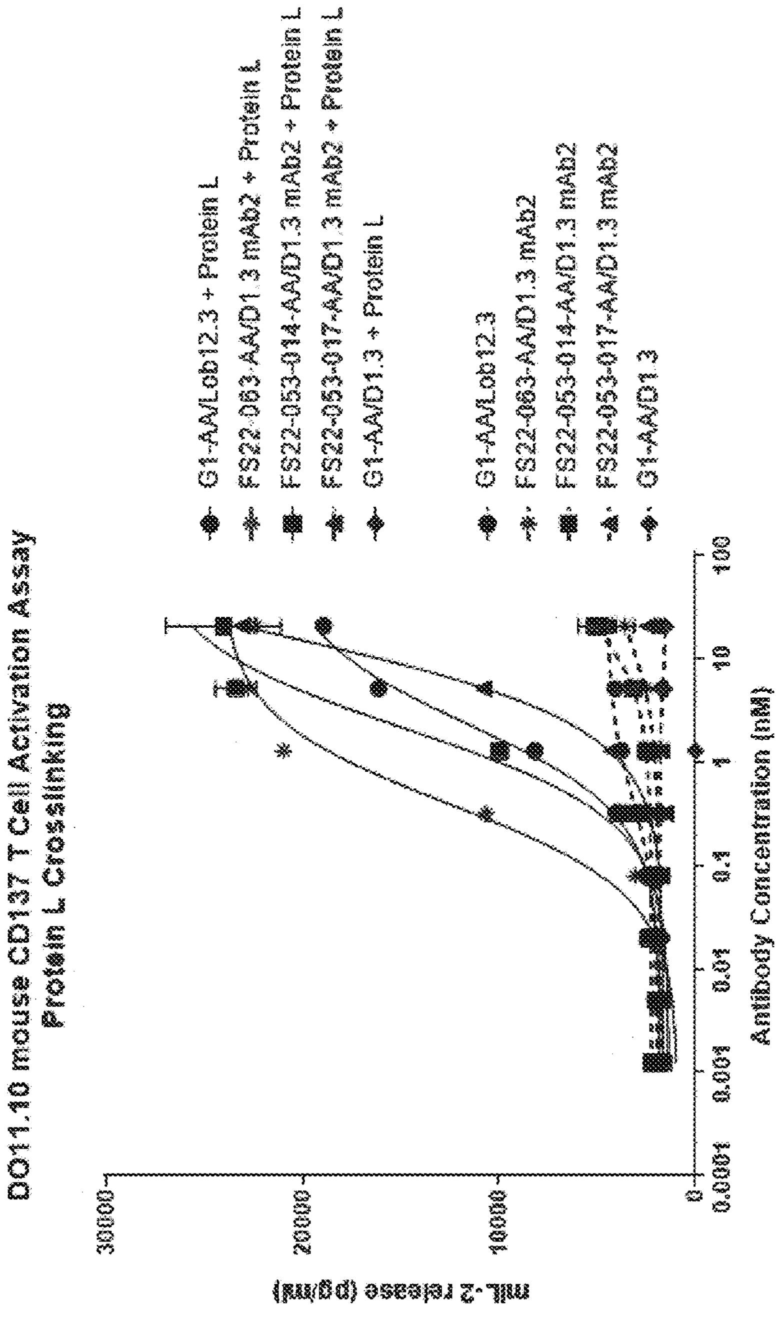
FIG. 12 shows mouse IL-2 release in a DO11.10 mouse CD137 T cell activation assay testing the mouse and human cross-reactive CD137 Fcabs FS22-053-014 and FS22-053-017 in mock mAb$^2$ format when crosslinked with Protein L. FS22-053-014 and FS22-053-017, and anti-mouse CD137 Fcab FS22m-063, all in HeID1.3 mock mAb$^2$ format activated CD137 when crosslinked with Protein L leading to a release of mIL-2. The positive control anti-mouse CD137 mAb, Lob12.3, showed an increase in mIL-2 release as expected. All anti-CD137 Fcabs in mock $mAb^2$ format without Protein L to crosslink (dotted lines) showed greatly reduced mIL-2 release compared to when crosslinked. FS22-053-017 had lower activity in this assay (8-fold worse EC50 compared to FS22-053-014) but still showed activity in the assay.

The results in Table 13 and FIG. 12 show that both FS22-053-17 Fcab in mock mAb$^2$ format FS22-053-014 Fcab in mock mAb$^2$ format had comparable activity when crosslinked by Protein L in the same DO11.10 T cell activation assay. Therefore the mutagenesis carried out did not negatively impact functional activity. Both clones in mock mAb$^2$ format had no activity without crosslinking.

As expected, the positive control anti CD137 had activity only when crosslinked and the IgG control did not have activity, whether or not crosslinked.

12.2 Activity of Mutant FS22-053-017 Fcab in Mock mAb$^2$ Format in Mouse CD137 DO11.10 T Cell Activation Assay The FS22-053-017 clone (in HeID1.3 mock mAb$^2$ format) was also compared against the murine CD137 binding Fcab clone FS22m-063 (also in HeID1.3 mock mAb$^2$ format), as well as the parental FS22-053-014 clone (in HeID1.3 mock mAb$^2$ format), in a mouse CD137 DO11.10 T cell activation assay as described in Example 3.4. The mAb$^2$ molecules were crosslinked with Protein L at a 4:1 molar ratio (mAb$^2$:Protein L).

As expected, all of the molecules tested showed activity as measured by IL-2 release when crosslinked by Protein L but had no activity when not crosslinked. FS22m-063 which was selected to bind to mouse CD137 had the best activity in the assay, with an EC50 of 0.39 nM when crosslinked. Both FS22-053-14 and FS22-053-017 had activity in the assay, indicating that function was not lost due to mutagenesis, though FS22-053-017 had a slight loss in activity with an EC50 which was approximately 8-fold worse than FS22-053-14 when cross linked by Protein L. FIG. 12 shows that the affinity-matured human and murine cross-reactive CD137 Fcabs FS22-053-014 and FS22-053-017, and anti-mouse CD137 Fcab FS22m-063, in HelD1.3 mock $mAb^2$ format activate CD137 when crosslinked with Protein L leading to a release of mIL-2 in a DO11.10 T cell activation assay.

TABLE 14

| Fcab clone (in | IL-2 release with or without Protein L crosslinking | | |
|---|---|---|---|
| HelD1.3 $mAb^2$ format) or mAb | No XL | +XL Emax (IL-2 pg/ml) | +XL EC50 (nM) |
| FS22-053-014 | N/A | 28071 | 2.04 |
| FS22-053-017 | N/A | 41042 | 16.74 |
| FS22m-063 | N/A | 24175 | 0.39 |
| G1-AA/Lob12.3 + Protein L | N/A | 21332 | 2.26 |

N/A—not applicable as low signal did not allow EC50 determination 12.3 Binding Kinetics of FS22-053-017

The equilibrium dissociation constant ($K_D$) of Fcab clone FS22-053-017 was compared to that of clone FS22-053-014 by SPR on a Biacore T200 system. For the hCD137-mFc-Avi antigen the following method was used: an anti-human Fab molecule was immobilised on a CM5 chip to a surface density of between 9,000 and 11,000 response units (RU). The antibodies were diluted to 4 µg/ml in HBS-EP buffer and captured by the anti-Fab molecule with a flow rate of 30 µl/s. Eight different concentrations of hCD137-mFc antigen were used: 200 nM; 66.67 nM; 22.22 nM (included twice), 7.41 nM; 2.47 nM; 0.82 nM, 0.27 nM: 0.091 (diluted in HBS-EP+ buffer) were flowed over the captured $mAb^2$.

For mCD137-mFc-Avi binding kinetic determination, a different approach was used. Mouse PD-L1-mFc-Avi was immobilised on a CM5 chip to a surface density of 200 RUs. $mAb^2$ containing the FS22-053-014 and FS22-053-017 Fcabs in combination with an anti-mouse PD-L1 Fab (S70) were diluted to 7.5 µg/ml in HBS-EP buffer and captured by the immobilised mPD-L1 protein with a flow rate of 60 µl/s. Eight different concentrations of mCD137-mFc antigen were used: 600 nM; 200 nM; 66.67 nM (included twice), 22.2 nM; 7.1 nM; 2.47 nM; 0.82 nM (diluted in HBS-EP+ buffer) were flowed over the captured $mAb^2$. The analysis of the data was done using the Biacore T200 evaluation software. Curves were subtracted against a blank flow cell and fitted using a 1:1 Langmuir binding model with mass transfer, setting RI to zero as constant and $R_{max}$ to local. The results are summarised in Table 15 and show very similar kinetic profiles to human antigen for both Fcab clones, thereby evidencing that there mutating Q98D to Q98E did not have a negative effect on binding to the human antigen. A 2-fold decrease in binding strength to the mouse antigen is also consistent with the functional data shown in Example 11.2.

TABLE 15

| Molecule | $k_a$ (1/Ms) | $k_d$ (1/s) | $K_D$ (nM) |
|---|---|---|---|
| FS22-053-014/HelD1.3 | $8.304 \times 10^4$ | $3.656 \times 10^{-4}$ | 4.403 |
| FS22-053-017/HelD1.3 | $8.853 \times 10^4$ | $4.062 \times 10^{-4}$ | 4.588 |

TABLE 15-continued

| Molecule | $k_a$ (1/Ms) | $k_d$ (1/s) | $K_D$ (nM) |
|---|---|---|---|
| FS22-053-014/mPD-L1 | $1.509 \times 10^5$ | $4.025 \times^{-3}$ | 27 |
| FS22-053-017/mPD-L1 | $1.064 \times 10^5$ | $5.186 \times^{-3}$ | 49 |

Example 13: Involvement of PPY in Antigen Binding (Alanine Scanning of Conserved PPY Motif)

As described in Example 5, a PPY sequence motif was identified in the AB loop of two independently selected Fcabs, and this motif was conserved in all affinity matured clones analysed. It was therefore desirable to comprehend the involvement of this motif in binding to CD137 and overall protein structure. Alanine scanning is a common biological technique used to determine the importance of a specific residues in protein-protein interaction. Briefly, each of the three amino acids in turn and then in unison were substituted with alanine residues. Alanine is considered the most chemically inert, non-bulky residue and is therefore considered unlikely to aid binding.

13.1 Production of Mutant Clones for Alanine Scanning

Mutant clones were produced by site directed mutagenesis on the parental clones (FS22-172-003 and FS22-053-008). The locations of amino acid substitutions within the AB loop are summarised in Table 16, all other residues are conserved to their respective parent. $mAb^2$ variants were then transiently expressed in HEK293-6E cells and purified using mAb Select SuRe protein A columns as described in Example 3. The expression yield of mutants was similar to parental and therefore this suggest the alanine substitutions had no effect on protein production.

TABLE 16

| Parent Clone | Original Sequence of AB Loop | Mutated Sequence of AB Loop | Name of clone |
|---|---|---|---|
| FS22-53-008 | NPPYLFS | NAPYLFS | FS22-053-008_APY |
| | (SEQ ID | NPAYLFS | FS22-053-008_PAY |
| | NO: 19) | NPPALFS | FS22-053-008_PPA |
| | | NAAALFS | FS22-053-008_AAA |
| FS22-172-003 | PYIIPPY | PYIIAPY | FS22-172-003_APY |
| | (SEQ ID | PYIIPAY | FS22-172-003_PAY |
| | NO: 138) | PYIIPPA | FS22-172-003_PPA |
| | | PYIIAAA | FS22-172-003_AAA |

13.2 Binding Kinetics of Mutant Clones

The binding kinetics of the 2 parental clones and 8 mutant clones were compared using an Octet QKe system from ForteBio. Dimeric biotinylated hCD137-mFc-Avi was captured onto streptavidin sensors at 10 µg/ml and then interaction with each $mAb^2$ at a concentration of 200 nM was analysed. Binding of $mAb^2$ to dimeric antigen was impaired for all the FS22-172-003 mutant clones when compared to the parental clone, with clones FS22-172-003 AAA, and FS22-172-003_APY losing all binding, and clones FS22-172-003_PPA, and FS22-172-003_PAY retaining some binding though significantly reduced (5.5- and 4.4-fold lower response units) compared to parental. Binding of FS22-053-008 was also impacted, with variants PAY and AAA losing all binding, and variants APY and PPA showing decreased binding to antigen and slow down of association profile when compared to the parental FS22-053-008 clone.

This data suggests the PPY motif is important for binding of both mAb[2] to CD137 antigen.

13.3 Homology Modelling

Given the involvement of the PPY motif in binding, it was informative to model the Fcabs in silico to evaluate protein structure predictions in the CH3 domain. Structural homology modelling and subsequent conformational searches were performed using the 2019.0101 version of the MOE software suite (Chemical Computing Group ULC). The Fc region in Protein Data Bank [PDB] structure 5JII was used as the structural template for the Fcab region of both FS22-172-003 and FS22-053-008. Since insertions exist in the AB and EF loop regions with respect to the selected structural template, a de novo loop search with residue sidechain optimisation, was applied to generate the AB and EF loop structurers. The resulting homology models were energy minimised and scored according to geometric criteria including backbone bond lengths, angles, dihedral angles and chirality. Structural homology models with scores passing the criteria were used as the basis for conformational sampling using the LowModeMD simulation method, as implemented within MOE.

Figure 13:
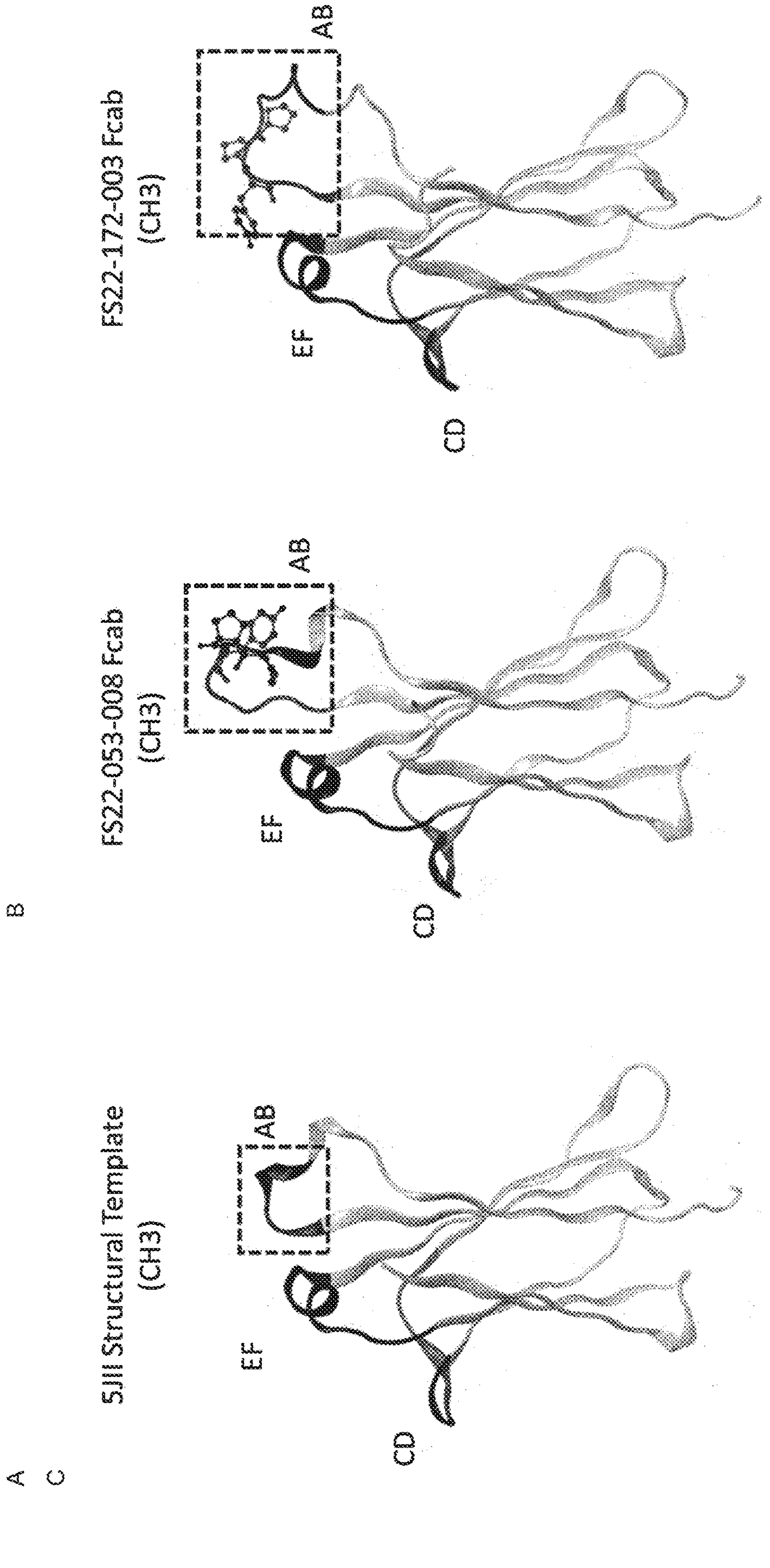
FIG. 13 shows homology models of the FS22 Fcabs compared to the structural template (PDB ID 5JII) containing the wild-type human IgG1 Fc CH3 domain. The images show 5JII Fc (A), and representative structures of the FS22-053-008 (B) and FS-172-003 (C) Fcabs. One CH3 domain of each structure has been rendered using a grey ribbon diagram representation. The AB, CD and EF loops are indicated by black shading of the ribbons and are labelled accordingly. The predicted structure of the AB loop is highlighted in dotted lines for comparison purposes, and shows the protrusion caused by the PPY motif which is likely to play a key role in binding.

The homology models in FIG. 13 show that the AB and EF loops of both Fcabs adopt different conformations compared to the template 5JII, with the PPY motif playing a role in the AB-loops protrusion from the core of the CH3 domain. The PPY motif also mediates interactions that lead to AB loop conformational stabilisation through both interactions within the loop and between the loop and the rest of the structure. Conformational searches performed using LowModeMD simulations also highlighted that the tyrosine residue in the PPY motif interacts with the Q3 (IMGT) and D12 (IMGT) in the CH3 domain of same chain. In the CH3 domain, possibly stabilising the AB loop. Put together with the results shown in Example 13.2, this suggests that the PPY motif is important for binding of both FS22-172-003 and FS22-053-008 to CD137.

Sequence Listing

Amino acid sequences of WT Fcab CH3 domain structural loops
WT Fcab AB loop-RDELTKNQ (SEQ ID NO: 1)
WT Fcab CD loop-SNGQPENNY (SEQ ID NO: 2)
WT Fcab EF loop-DKSRWQQGNV (SEQ ID NO: 3)

Amino acid sequence of WT Fcab CH3 domain (SEQ ID NO: 4)
AB, CD and EF loops underlined
GQPREPQVYTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPG Amino acid sequence of the Fcab CH2 domain with LALA-PA mutation
(SEQ ID NO: 5)
LALA-PA mutation underlined
APEAAGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALAAPIEKTISKAK Amino acid sequence of the Fcab CH2 domain with LALA mutation
(SEQ ID NO: 6)
LALA mutation underlined
APEAAGGPSVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAK Amino acid sequence of the truncated Fcab hinge region (SEQ ID NO: 7)
TCPPCP Amino acid sequence of WT Fcab with LALA mutation (SEQ ID NO: 8)
Hinge region (underlined), CH2 domain (bold), CH3 domain (italics),
LALA mutation (bold and underlined)
TCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELTKNQVSLTCLVKGFYPSDIAVEWESNGQPENNYKTTPPVLDSDGSFFLYSKLTVDKSRWQQGNV*
*FSCSVMHEALHNHYTQKSLSLSPGK*

Amino acid sequence of WT Fcab without LALA mutation (SEQ ID NO: 9)
Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELTKNQVSLTCLVKGFYPSDIAVEWESNGQPENNYKTTPPVLDSDGSFFLYSKLTVDKSRWQQGNV*
*FSCSVMHEALHNHYTQKSLSLSPG*

Amino acid sequence of PPY motif (SEQ ID NO: 10)
PPY

Amino acid sequence of Fcab FS22-033 with LALA mutation (SEQ ID NO: 11)
Hinge region (underlined), CH2 domain (bold), CH3 domain (italics),
LALA mutation (bold and underlined)
TCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*EYFEQEVSLTCLVKGFYPSDIAVEWESNGQPENNYKTTPPVLDSDGSFFLYSKLTVARHRWQLGNVF*
*SCSVMHEALHNHYTQKSLSLSPG*

Amino acid sequence of Fcab FS22-033 without LALA mutation
(SEQ ID NO: 12)
Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK

-continued

Sequence Listing

PREEQYNSTYRVVSVLTVLHQDWLNGKEYKCKVSNKALPAPIEKTISKAK*GQPREPQVYTLPPSRD*
*EYFEQEVSLTCLVKGFYPSDIAVEWESNGQPENNYKTTPPVLDSDGSFFLYSKLTVARHRWQLGNVF*
*SCSVMHEALHNHYTQKSLSLSPG*

Amino acid sequence of the heavy chain of FS22-033/HelD1.3 mock mAb$^2$
with LALA mutation (SEQ ID NO: 13)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDEYFEQEVSLTCLVKGFYPSDIAVEWESNGQPENNYKTTPPVLD
SDGSFFLYSKLTVARHRWQLGNVFSCSVMHEALHNHYTQKSLSLSPG Amino acid sequence of the heavy chain of FS22-033/HelD1.3 mock mAb$^2$
without LALA mutation (SEQ ID NO: 14)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDEYFEQEVSLTCLVKGFYPSDIAVEWESNGQPENNYKTTPPVLD
SDGSFFLYSKLTVARHRWQLGNVFSCSVMHEALHNHYTQKSLSLSPG Amino acid sequence of Fcab FS22-053 with LALA mutation (SEQ ID NO: 15)
Hinge region (underlined), CH2 domain (bold), CH3 domain (italics), LALA
mutation (bold and underlined)
TCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVYYNRWQ*
*DGNVFSCSVMHEALHNHYTQKSLSLSPG*

Amino acid sequence of Fcab FS22-053 without LALA mutation
(SEQ ID NO: 16)
Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVYYNRWQ*
*DGNVFSCSVMHEALHNHYTQKSLSLSPG*

Amino acid sequence of the heavy chain of FS22-053/HelD1.3 mock mAb$^2$
with LALA mutation (SEQ ID NO: 17)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVYYNRWQDGNVFSCSVMHEALHNHYTQKSLSLSPG Amino acid sequence of the heavy chain of FS22-053/HelD1.3 mock mAb$^2$
without LALA mutation (SEQ ID NO: 18)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVYYNRWQDGNVFSCSVMHEALHNHYTQKSLSLSPG Amino acid sequences of Fcab FS22-053-008 CH3 domain structural loop
sequences
FS22-053-008 first sequence-NPPYLFS (SEQ ID NO: 19)
FS22-053-008 second sequence-DYWRWLE (SEQ ID NO: 20)

Amino acid sequence of Fcab FS22-053-008 CH3 domain (SEQ ID NO: 21)
First and second sequences underlined
GQPREPQVYTLPPSRDELNPPYLFSNQVSLTCLVKGFYPSDIAVEWESNGQPENNYKTTPPVLDSDG
SFFLYSKLTVDYWRWLEGNVFSCSVMHEALHNHYTQKSLSLSPG Nucleic acid sequence of Fcab FS22-053-008 CH3 domain (SEQ ID NO: 22)
GGACAGCCTCGAGAACCACAGGTGTACACCCTGCCCCCATCCCGGGATGAGCTGAACCCGCCG
TACCTGTTCTCTAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTACTGG -continued Sequence Listing ACTCCGACGGCTCCTTCTTCCTCTACAGCAAGCTCACCGTGGATTACTGGAGGTGGCTGGAAGG
GAACGTCTTCTCATGCTCCGTGATGCATGAGGCGCTGCACAACCACTACACTCAGAAGAGCTTG
TCCCTGTCGCCCGGT Amino acid sequence of Fcab FS22-053-008 with LALA mutation (SEQ ID NO: 23)
Hinge region (underlined), CH2 domain (bold), CH3 domain (italics), LALA mutation (bold and underlined)
TCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVDYWRWL*
*EGNVFSCSVMHEALHNHYTQKSLSLSPG*

Nucleic acid sequence of Fcab FS22-053-008 with LALA mutation (SEQ ID NO: 24)
ACTTGCCCGCCTTGCCCAGCCCCGGAAGCTGCCGGTGGTCCTTCGGTGTTCCTCTTCCCGCCC
AAGCCGAAGGATACCCTGATGATCTCACGGACCCCCGAAGTGACCTGTGTGGTGGTGGACGTG
TCCCACGAGGACCCGGAAGTGAAATTCAATTGGTACGTGGATGGAGTGGAAGTGCACAACGCCA
AGACCAAGCCACGGGAAGAACAGTACAACTCTACCTACCGCGTGGTGTCCGTGCTCACTGTGCT
GCACCAAGACTGGCTGAACGGGAAGGAGTACAAGTGCAAAGTGTCCAACAAGGCGCTGCCTGC
CCCAATTGAGAAAACTATCTCGAAAGCCAAGGGCCAGCCTCGAGAACCACAGGTGTACACCCTG
CCCCCATCCCGGGATGAGCTGAACCCGCCGTACCTGTTCTCTAACCAGGTCAGCCTGACCTGCC
TGGTCAAAGGCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTACAGCAAGCT
CACCGTGGATTACTGGAGGTGGCTGGAAGGGAACGTCTTCTCATGCTCCGTGATGCATGAGGCT
CTGCACAACCACTACACACAGAAGAGCCTCTCCCTGTCTCCGGGT Amino acid sequence of Fcab FS22-053-008 without LALA mutation (SEQ ID NO: 25)
Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVDYWRWL*
*EGNVFSCSVMHEALHNHYTQKSLSLSPG*

Nucleic acid sequence of Fcab FS22-053-008 without LALA mutation (SEQ ID NO: 26)
ACTTGCCCGCCTTGCCCAGCCCCGGAACTGCTGGGTGGTCCTTCGGTGTTCCTCTTCCCGCCCA
AGCCGAAGGATACCCTGATGATCTCACGGACCCCCGAAGTGACCTGTGTGGTGGTGGACGTGT
CCCACGAGGACCCGGAAGTGAAATTCAATTGGTACGTGGATGGAGTGGAAGTGCACAACGCCAA
GACCAAGCCACGGGAAGAACAGTACAACTCTACCTACCGCGTGGTGTCCGTGCTCACTGTGCTG
CACCAAGACTGGCTGAACGGGAAGGAGTACAAGTGCAAAGTGTCCAACAAGGCGCTGCCTGCC
CCAATTGAGAAAACTATCTCGAAAGCCAAGGGCCAGCCTCGAGAACCACAGGTGTACACCCTGC
CCCCATCCCGGGATGAGCTGAACCCGCCGTACCTGTTCTCTAACCAGGTCAGCCTGACCTGCCT
GGTCAAAGGCTTCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTACAGCAAGCTC
ACCGTGGATTACTGGAGGTGGCTGGAAGGGAACGTCTTCTCATGCTCCGTGATGCATGAGGCTC
TGCACAACCACTACACACAGAAGAGCCTCTCCCTGTCTCCGGGT Amino acid sequence of the heavy chain of FS22-053-008/HelD1.3 mock mAb$^2$ with LALA mutation (SEQ ID NO: 27)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVDYWRWLEGNVFSCSVMHEALHNHYTQKSLSLSPG Amino acid sequence of the heavy chain of FS22-053-008/HelD1.3 mock mAb$^2$ without LALA mutation (SEQ ID NO: 28)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVDYWRWLEGNVFSCSVMHEALHNHYTQKSLSLSPG Amino acid sequences of Fcab FS22-053-009 CH3 domain structural loop sequences
FS22-053-009 first sequence-NPPYLFS (SEQ ID NO: 19)
FS22-053-009 second sequence-EHTRWLD (SEQ ID NO: 29)

Amino acid sequence of Fcab FS22-053-009 CH3 domain (SEQ ID NO: 30)

-continued

| Sequence Listing |
| --- |

First and second sequences underlined
GQPREPQVYTLPPSRDELNPPYLFSNQVSLTCLVKGFYPSDIAVEWESNGQPENNYKTTPPVLDSDG
SFFLYSKLTVEHTRWLDGNVFSCSVMHEALHNHYTQKSLSLSPG Nucleic acid sequence of Fcab FS22-053-009 CH3 domain (SEQ ID NO: 31)
GGCCAGCCTCGAGAACCACAGGTGTACACCCTGCCCCCATCCCGGGATGAGCTGAACCCGCCG
TACCTGTTCTCTAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGAACATACTAGGTGGCTGGATGG
GAACGTCTTCTCATGCTCCGTGATGCATGAGGCTCTGCACAACCACTACACACAGAAGAGCCTC
TCCCTGTCTCCGGGT Amino acid sequence of Fcab FS22-053-009 with LALA mutation
(SEQ ID NO: 32)
Hinge region (underlined), CH2 domain (bold), CH3 domain (italics), LALA
mutation (bold and underlined)
TCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVEHTRWL*
*DGNVFSCSVMHEALHNHYTQKSLSLSPG*

Nucleic acid sequence of Fcab FS22-053-009 with LALA mutation
(SEQ ID NO: 33)
ACTTGCCCGCCTTGCCCAGCCCCGGAAGCTGCCGGTGGTCCTTCGGTGTTCCTCTTCCCGCCC
AAGCCGAAGGATACCCTGATGATCTCACGGACCCCCGAAGTGACCTGTGTGGTGGTGGACGTG
TCCCACGAGGACCCGGAAGTGAAATTCAATTGGTACGTGGATGGAGTGGAAGTGCACAACGCCA
AGACCAAGCCACGGGAAGAACAGTACAACTCTACCTACCGCGTGGTGTCCGTGCTCACTGTGCT
GCACCAAGACTGGCTGAACGGGAAGGAGTACAAGTGCAAAGTGTCCAACAAGGCGCTGCCTGC
CCCAATTGAGAAAACTATCTCGAAAGCCAAGGGCCAGCCTCGAGAACCACAGGTGTACACCCTG
CCCCCATCCCGGGATGAGCTGAACCCGCCGTACCTGTTCTCTAACCAGGTCAGCCTGACCTGCC
TGGTCAAAGGCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTACAGCAAGCT
CACCGTGGAACATACTAGGTGGCTGGATGGGAACGTCTTCTCATGCTCCGTGATGCATGAGGCT
CTGCACAACCACTACACACAGAAGAGCCTCTCCCTGTCTCCGGGT Amino acid sequence of Fcab FS22-053-009 without LALA mutation
(SEQ ID NO: 34)
Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVEHTRWL*
*DGNVFSCSVMHEALHNHYTQKSLSLSPG*

Nucleic acid sequence of Fcab FS22-053-009 without LALA mutation
(SEQ ID NO: 35)
ACTTGCCCGCCTTGCCCAGCCCCGGAACTGCTGGGTGGTCCTTCGGTGTTCCTCTTCCCGCCCA
AGCCGAAGGATACCCTGATGATCTCACGGACCCCCGAAGTGACCTGTGTGGTGGTGGACGTGT
CCCACGAGGACCCGGAAGTGAAATTCAATTGGTACGTGGATGGAGTGGAAGTGCACAACGCCAA
GACCAAGCCACGGGAAGAACAGTACAACTCTACCTACCGCGTGGTGTCCGTGCTCACTGTGCTG
CACCAAGACTGGCTGAACGGGAAGGAGTACAAGTGCAAAGTGTCCAACAAGGCGCTGCCTGCC
CCAATTGAGAAAACTATCTCGAAAGCCAAGGGCCAGCCTCGAGAACCACAGGTGTACACCCTGC
CCCCATCCCGGGATGAGCTGAACCCGCCGTACCTGTTCTCTAACCAGGTCAGCCTGACCTGCCT
GGTCAAAGGCTTCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTACAGCAAGCTC
ACCGTGGAACATACTAGGTGGCTGGATGGGAACGTCTTCTCATGCTCCGTGATGCATGAGGCTC
TGCACAACCACTACACACAGAAGAGCCTCTCCCTGTCTCCGGGT Amino acid sequence of the heavy chain of FS22-053-009/HelD1.3 mock
$mAb^2$ with LALA mutation (SEQ ID NO: 36)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVEHTRWLDGNVFSCSVMHEALHNHYTQKSLSLSPG Amino acid sequence of the heavy chain of FS22-053-009/HelD1.3 mock
$mAb^2$ without LALA mutation (SEQ ID NO: 37)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVEHTRWLDGNVFSCSVMHEALHNHYTQKSLSLSPG -continued Sequence Listing Amino acid sequences of Fcab FS22-053-010 CH3 domain structural loop sequences
FS22-053-010 first sequence-NPPYLFS (SEQ ID NO: 19)
FS22-053-010 second sequence-DYMRWLD (SEQ ID NO: 38)

Amino acid sequence of Fcab FS22-053-010 CH3 domain (SEQ ID NO: 39)
First and second sequences underlined
GQPREPQVYTLPPSRDELNPPYLFSNQVSLTCLVKGFYPSDIAVEWESNGQPENNYKTTPPVLDSDG
SFFLYSKLTVDYMRWLDGNVFSCSVMHEALHNHYTQKSLSLSPG Nucleic acid sequence of Fcab FS22-053-010 CH3 domain (SEQ ID NO: 40)
GGCCAGCCTCGAGAACCACAGGTGTACACCCTGCCCCCATCCCGGGATGAGCTGAACCCGCCG
TACCTGTTCTCTAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGATTACATGAGGTGGCTGGATGG
GAACGTCTTCTCATGCTCCGTGATGCATGAGGCTCTGCACAACCACTACACACAGAAGAGCCTC
TCCCTGTCTCCGGGT Amino acid sequence of Fcab FS22-053-010 with LALA mutation
(SEQ ID NO: 41)
Hinge region (underlined), CH2 domain (bold), CH3 domain (italics), LALA mutation (bold and underlined)
TCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVDYMRWL*
*DGNVFSCSVMHEALHNHYTQKSLSLSPG*

Nucleic acid sequence of Fcab FS22-053-010 with LALA mutation
(SEQ ID NO: 42)
ACTTGCCCGCCTTGCCCAGCCCCGGAAGCTGCCGGTGGTCCTTCGGTGTTCCTCTTCCCGCCC
AAGCCGAAGGATACCCTGATGATCTCACGGACCCCCGAAGTGACCTGTGTGGTGGTGGACGTG
TCCCACGAGGACCCGGAAGTGAAATTCAATTGGTACGTGGATGGAGTGGAAGTGCACAACGCCA
AGACCAAGCCACGGGAAGAACAGTACAACTCTACCTACCGCGTGGTGTCCGTGCTCACTGTGCT
GCACCAAGACTGGCTGAACGGGAAGGAGTACAAGTGCAAAGTGTCCAACAAGGCGCTGCCTGC
CCCAATTGAGAAAACTATCTCGAAAGCCAAGGGCCAGCCTCGAGAACCACAGGTGTACACCCTG
CCCCCATCCCGGGATGAGCTGAACCCGCCGTACCTGTTCTCTAACCAGGTCAGCCTGACCTGCC
TGGTCAAAGGCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTACAGCAAGCT
CACCGTGGATTACATGAGGTGGCTGGATGGGAACGTCTTCTCATGCTCCGTGATGCATGAGGCT
CTGCACAACCACTACACACAGAAGAGCCTCTCCCTGTCTCCGGGT Amino acid sequence of Fcab FS22-053-010 without LALA mutation
(SEQ ID NO: 43)
Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVDYMRWL*
*DGNVFSCSVMHEALHNHYTQKSLSLSPG*

Nucleic acid sequence of Fcab FS22-053-010 without LALA mutation
(SEQ ID NO: 44)
ACTTGCCCGCCTTGCCCAGCCCCGGAACTGCTGGGTGGTCCTTCGGTGTTCCTCTTCCCGCCCA
AGCCGAAGGATACCCTGATGATCTCACGGACCCCCGAAGTGACCTGTGTGGTGGTGGACGTGT
CCCACGAGGACCCGGAAGTGAAATTCAATTGGTACGTGGATGGAGTGGAAGTGCACAACGCCAA
GACCAAGCCACGGGAAGAACAGTACAACTCTACCTACCGCGTGGTGTCCGTGCTCACTGTGCTG
CACCAAGACTGGCTGAACGGGAAGGAGTACAAGTGCAAAGTGTCCAACAAGGCGCTGCCTGCC
CCAATTGAGAAAACTATCTCGAAAGCCAAGGGCCAGCCTCGAGAACCACAGGTGTACACCCTGC
CCCCATCCCGGGATGAGCTGAACCCGCCGTACCTGTTCTCTAACCAGGTCAGCCTGACCTGCCT
GGTCAAAGGCTTCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTACAGCAAGCTC
ACCGTGGATTACATGAGGTGGCTGGATGGGAACGTCTTCTCATGCTCCGTGATGCATGAGGCTC
TGCACAACCACTACACACAGAAGAGCCTCTCCCTGTCTCCGGGT Amino acid sequence of the heavy chain of FS22-053-010/HelD1.3 mock $mAb^2$ with LALA mutation (SEQ ID NO: 45)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVDYMRWLDGNVFSCSVMHEALHNHYTQKSLSLSPG Amino acid sequence of the heavy chain of FS22-053-010/HelD1.3 mock $mAb^2$ without LALA mutation (SEQ ID NO: 46)
VH domain (underlined)

-continued

Sequence Listing

QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVDYMRWLDGNVFSCSVMHEALHNHYTQKSLSLSPG

Amino acid sequences of Fcab FS22-053-011 CH3 domain structural loop sequences
FS22-053-011 first sequence-NPPYLFS (SEQ ID NO: 19)
FS22-053-011 second sequence-DYWRWTD (SEQ ID NO: 47)

Amino acid sequence of Fcab FS22-053-011 CH3 domain (SEQ ID NO: 48)
First and second sequences underlined
GQPREPQVYTLPPSRDELNPPYLFSNQVSLTCLVKGFYPSDIAVEWESNGQPENNYKTTPPVLDSDG
SFFLYSKLTVDYWRWTDGNVFSCSVMHEALHNHYTQKSLSLSPG Nucleic acid sequence of Fcab FS22-053-011 CH3 domain (SEQ ID NO: 49)
GGACAGCCTCGAGAGCCTCAAGTGTACACCCTGCCCCCATCCCGGGATGAGCTGAACCCGCCG
TACCTGTTCTCTAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGATTACTGGAGGTGGACTGATGG
GAACGTCTTCTCATGCTCCGTGATGCATGAGGCGCTGCACAACCACTACACTCAGAAGAGCTTG
TCCCTGTCGCCCGGA Amino acid sequence of Fcab FS22-053-011 with LALA mutation
(SEQ ID NO: 50)
Hinge region (underlined), CH2 domain (bold), CH3 domain (italics),
LALA mutation (bold and underlined)
TCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVDYWRWT*
*DGNVFSCSVMHEALHNHYTQKSLSLSPG*

Nucleic acid sequence of Fcab FS22-053-011 with LALA mutation
(SEQ ID NO: 51)
ACTTGCCCGCCTTGCCCAGCCCCGGAAGCTGCCGGTGGTCCTTCGGTGTTCCTCTTCCCGCCC
AAGCCGAAGGATACCCTGATGATCTCACGGACCCCCGAAGTGACCTGTGTGGTGGTGGACGTG
TCCCACGAGGACCCGGAAGTGAAATTCAATTGGTACGTGGATGGAGTGGAAGTGCACAACGCCA
AGACCAAGCCACGGGAAGAACAGTACAACTCTACCTACCGCGTGGTGTCCGTGCTCACTGTGCT
GCACCAAGACTGGCTGAACGGGAAGGAGTACAAGTGCAAAGTGTCCAACAAGGCGCTGCCTGC
CCCAATTGAGAAAACTATCTCGAAAGCCAAGGGCCAGCCTCGAGAACCACAGGTGTACACCCTG
CCCCCATCCCGGGATGAGCTGAACCCGCCGTACCTGTTCTCTAACCAGGTCAGCCTGACCTGCC
TGGTCAAAGGCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTACAGCAAGCT
CACCGTGGATTACTGGAGGTGGACTGATGGGAACGTCTTCTCATGCTCCGTGATGCATGAGGCT
CTGCACAACCACTACACACAGAAGAGCCTCTCCCTGTCTCCGGGT Amino acid sequence of Fcab FS22-053-011 without LALA mutation
(SEQ ID NO: 52)
Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVDYWRWT*
*DGNVFSCSVMHEALHNHYTQKSLSLSPG*

Nucleic acid sequence of Fcab FS22-053-011 without LALA mutation
(SEQ ID NO: 53)
ACTTGCCCGCCTTGCCCAGCCCCGGAACTGCTGGGTGGTCCTTCGGTGTTCCTCTTCCCGCCCA
AGCCGAAGGATACCCTGATGATCTCACGGACCCCCGAAGTGACCTGTGTGGTGGTGGACGTGT
CCCACGAGGACCCGGAAGTGAAATTCAATTGGTACGTGGATGGAGTGGAAGTGCACAACGCCAA
GACCAAGCCACGGGAAGAACAGTACAACTCTACCTACCGCGTGGTGTCCGTGCTCACTGTGCTG
CACCAAGACTGGCTGAACGGGAAGGAGTACAAGTGCAAAGTGTCCAACAAGGCGCTGCCTGCC
CCAATTGAGAAAACTATCTCGAAAGCCAAGGGCCAGCCTCGAGAACCACAGGTGTACACCCTGC
CCCCATCCCGGGATGAGCTGAACCCGCCGTACCTGTTCTCTAACCAGGTCAGCCTGACCTGCCT
GGTCAAAGGCTTCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTACAGCAAGCTC
ACCGTGGATTACTGGAGGTGGACTGATGGGAACGTCTTCTCATGCTCCGTGATGCATGAGGCTC
TGCACAACCACTACACACAGAAGAGCCTCTCCCTGTCTCCGGGT Amino acid sequence of the heavy chain of FS22-053-011/HelD1.3 mock $mAb^2$ with LALA mutation (SEQ ID NO: 54)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI -continued Sequence Listing CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVDYWRWTDGNVFSCSVMHEALHNHYTQKSLSLSPG Amino acid sequence of the heavy chain of FS22-053-011/HelD1.3 mock $mAb^2$ without LALA mutation (SEQ ID NO: 55)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVDYWRWTDGNVFSCSVMHEALHNHYTQKSLSLSPG Amino acid sequences of Fcab FS22-053-012 CH3 domain structural loop sequences
FS22-053-012 first sequence-NPPYLFS (SEQ ID NO: 19)
FS22-053-012 second sequence-DHMRWLE (SEQ ID NO: 56)

Amino acid sequence of Fcab FS22-053-012 CH3 domain (SEQ ID NO: 57)
First and second sequences underlined
GQPREPQVYTLPPSRDELNPPYLFSNQVSLTCLVKGFYPSDIAVEWESNGQPENNYKTTPPVLDSDG
SFFLYSKLTVDHMRWLEGNVFSCSVMHEALHNHYTQKSLSLSPG Nucleic acid sequence of Fcab FS22-053-012 CH3 domain (SEQ ID NO: 58)
GGCCAGCCTCGAGAACCACAGGTGTACACCCTGCCCCCATCCCGGGATGAGCTGAACCCGCCG
TACCTGTTCTCTAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGATCATATGAGGTGGCTGGAAGG
GAACGTCTTCTCATGCTCCGTGATGCATGAGGCTCTGCACAACCACTACACACAGAAGAGCCTC
TCCCTGTCTCCGGGT Amino acid sequence of Fcab FS22-053-012 with LALA mutation (SEQ ID NO: 59)
Hinge region (underlined), CH2 domain (bold), CH3 domain (italics), LALA mutation (bold and underlined)
TCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVDHMRWL*
*EGNVFSCSVMHEALHNHYTQKSLSLSPG*

Nucleic acid sequence of Fcab FS22-053-012 with LALA mutation (SEQ ID NO: 60)
ACTTGCCCGCCTTGCCCAGCCCCGGAAGCTGCCGGTGGTCCTTCGGTGTTCCTCTTCCCGCCC
AAGCCGAAGGATACCCTGATGATCTCACGGACCCCCGAAGTGACCTGTGTGGTGGTGGACGTG
TCCCACGAGGACCCGGAAGTGAAATTCAATTGGTACGTGGATGGAGTGGAAGTGCACAACGCCA
AGACCAAGCCACGGGAAGAACAGTACAACTCTACCTACCGCGTGGTGTCCGTGCTCACTGTGCT
GCACCAAGACTGGCTGAACGGGAAGGAGTACAAGTGCAAAGTGTCCAACAAGGCGCTGCCTGC
CCCAATTGAGAAAACTATCTCGAAAGCCAAGGGCCAGCCTCGAGAACCACAGGTGTACACCCTG
CCCCCATCCCGGGATGAGCTGAACCCGCCGTACCTGTTCTCTAACCAGGTCAGCCTGACCTGCC
TGGTCAAAGGCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTACAGCAAGCT
CACCGTGGATCATATGAGGTGGCTGGAAGGGAACGTCTTCTCATGCTCCGTGATGCATGAGGCT
CTGCACAACCACTACACACAGAAGAGCCTCTCCCTGTCTCCGGGT Amino acid sequence of Fcab FS22-053-012 without LALA mutation (SEQ ID NO: 61)
Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVDHMRWL*
*EGNVFSCSVMHEALHNHYTQKSLSLSPG*

Nucleic acid sequence of Fcab FS22-053-012 without LALA mutation (SEQ ID NO: 62)
ACTTGCCCGCCTTGCCCAGCCCCGGAACTGCTGGGTGGTCCTTCGGTGTTCCTCTTCCCGCCCA
AGCCGAAGGATACCCTGATGATCTCACGGACCCCCGAAGTGACCTGTGTGGTGGTGGACGTGT
CCCACGAGGACCCGGAAGTGAAATTCAATTGGTACGTGGATGGAGTGGAAGTGCACAACGCCAA
GACCAAGCCACGGGAAGAACAGTACAACTCTACCTACCGCGTGGTGTCCGTGCTCACTGTGCTG
CACCAAGACTGGCTGAACGGGAAGGAGTACAAGTGCAAAGTGTCCAACAAGGCGCTGCCTGCC
CCAATTGAGAAAACTATCTCGAAAGCCAAGGGCCAGCCTCGAGAACCACAGGTGTACACCCTGC
CCCCATCCCGGGATGAGCTGAACCCGCCGTACCTGTTCTCTAACCAGGTCAGCCTGACCTGCCT
GGTCAAAGGCTTCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTACAGCAAGCTC
ACCGTGGATCATATGAGGTGGCTGGAAGGGAACGTCTTCTCATGCTCCGTGATGCATGAGGCTC -continued Sequence Listing

TGCACAACCACTACACACAGAAGAGCCTCTCCCTGTCTCCGGGT

Amino acid sequence of the heavy chain of FS22-053-012/HelD1.3 mock mAb$^2$ with LALA mutation (SEQ ID NO: 63)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVDHMRWLEGNVFSCSVMHEALHNHYTQKSLSLSPG Amino acid sequence of the heavy chain of FS22-053-012/HelD1.3 mock mAb$^2$ without LALA mutation (SEQ ID NO: 64)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVDHMRWLEGNVFSCSVMHEALHNHYTQKSLSLSPG Amino acid sequences of Fcab FS22-053-013 CH3 domain structural loop sequences
FS22-053-013 first sequence-NPPYLFS (SEQ ID NO: 19)
FS22-053-013 second sequence-GYERWLE (SEQ ID NO: 65)

Amino acid sequence of Fcab FS22-053-013 CH3 domain (SEQ ID NO: 66)
First and second sequences underlined
GQPREPQVYTLPPSRDELNPPYLFSNQVSLTCLVKGFYPSDIAVEWESNGQPENNYKTTPPVLDSDG
SFFLYSKLTVGYERWLEGNVFSCSVMHEALHNHYTQKSLSLSPG Nucleic acid sequence of Fcab FS22-053-013 CH3 domain (SEQ ID NO: 67)
GGCCAGCCTCGAGAACCACAGGTGTACACCCTGCCCCCATCCCGGGATGAGCTGAACCCGCCG
TACCTGTTCTCTAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGGTTACGAAAGGTGGCTGGAAGG
GAACGTCTTCTCATGCTCCGTGATGCATGAGGCTCTGCACAACCACTACACACAGAAGAGCCTC
TCCCTGTCTCCGGGT Amino acid sequence of Fcab FS22-053-013 with LALA mutation (SEQ ID NO: 68)
Hinge region (underlined), CH2 domain (bold), CH3 domain (italics), LALA mutation (bold and underlined)
TCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVGYERWL*
*EGNVFSCSVMHEALHNHYTQKSLSLSPG*

Nucleic acid sequence of Fcab FS22-053-013 with LALA mutation (SEQ ID NO: 69)
ACTTGCCCGCCTTGCCCAGCCCCGGAAGCTGCCGGTGGTCCTTCGGTGTTCCTCTTCCCGCCC
AAGCCGAAGGATACCCTGATGATCTCACGGACCCCCGAAGTGACCTGTGTGGTGGTGGACGTG
TCCCACGAGGACCCGGAAGTGAAATTCAATTGGTACGTGGATGGAGTGGAAGTGCACAACGCCA
AGACCAAGCCACGGGAAGAACAGTACAACTCTACCTACCGCGTGGTGTCCGTGCTCACTGTGCT
GCACCAAGACTGGCTGAACGGGAAGGAGTACAAGTGCAAAGTGTCCAACAAGGCGCTGCCTGC
CCCAATTGAGAAAACTATCTCGAAAGCCAAGGGCCAGCCTCGAGAACCACAGGTGTACACCCTG
CCCCCATCCCGGGATGAGCTGAACCCGCCGTACCTGTTCTCTAACCAGGTCAGCCTGACCTGCC
TGGTCAAAGGCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTACAGCAAGCT
CACCGTGGGTTACGAAAGGTGGCTGGAAGGGAACGTCTTCTCATGCTCCGTGATGCATGAGGCT
CTGCACAACCACTACACACAGAAGAGCCTCTCCCTGTCTCCGGGT Amino acid sequence of Fcab FS22-053-013 without LALA mutation (SEQ ID NO: 70)
Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVGYERWL*
*EGNVFSCSVMHEALHNHYTQKSLSLSPG*

Nucleic acid sequence of Fcab FS22-053-013 without LALA mutation (SEQ ID NO: 71)
ACTTGCCCGCCTTGCCCAGCCCCGGAACTGCTGGGTGGTCCTTCGGTGTTCCTCTTCCCGCCCA
AGCCGAAGGATACCCTGATGATCTCACGGACCCCCGAAGTGACCTGTGTGGTGGTGGACGTGT -continued Sequence Listing CCCACGAGGACCCGGAAGTGAAATTCAATTGGTACGTGGATGGAGTGGAAGTGCACAACGCCAA
GACCAAGCCACGGGAAGAACAGTACAACTCTACCTACCGCGTGGTGTCCGTGCTCACTGTGCTG
CACCAAGACTGGCTGAACGGGAAGGAGTACAAGTGCAAAGTGTCCAACAAGGCGCTGCCTGCC
CCAATTGAGAAAACTATCTCGAAAGCCAAGGGCCAGCCTCGAGAACCACAGGTGTACACCCTGC
CCCCATCCCGGGATGAGCTGAACCCGCCGTACCTGTTCTCTAACCAGGTCAGCCTGACCTGCCT
GGTCAAAGGCTTCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTACAGCAAGCTC
ACCGTGGGTTACGAAAGGTGGCTGGAAGGGAACGTCTTCTCATGCTCCGTGATGCATGAGGCTC
TGCACAACCACTACACACAGAAGAGCCTCTCCCTGTCTCCGGGT Amino acid sequence of the heavy chain of FS22-053-013/HelD1.3 mock
mAb$^2$ with LALA mutation (SEQ ID NO: 72)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVGYERWLEGNVFSCSVMHEALHNHYTQKSLSLSPG Amino acid sequence of the heavy chain of FS22-053-013/HelD1.3 mock
mAb$^2$ without LALA mutation (SEQ ID NO: 73)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVGYERWLEGNVFSCSVMHEALHNHYTQKSLSLSPG Amino acid sequences of Fcab FS22-053-014 CH3 domain structural loop
sequences
FS22-053-014 first sequence-NPPYLFS (SEQ ID NO: 19)
FS22-053-014 second sequence-YHWRWLD (SEQ ID NO: 74)

Amino acid sequence of Fcab FS22-053-014 CH3 domain (SEQ ID NO: 75)
First and second sequences underlined
GQPREPQVYTLPPSRDELNPPYLFSNQVSLTCLVKGFYPSDIAVEWESNGQPENNYKTTPPVLDSDG
SFFLYSKLTVYHWRWLDGNVFSCSVMHEALHNHYTQKSLSLSPG Nucleic acid sequence of Fcab FS22-053-014 CH3 domain (SEQ ID NO: 76)
GGACAGCCTCGAGAGCCTCAAGTGTACACCCTGCCCCCATCCCGGGATGAGCTGAACCCGCCG
TACCTGTTCTCTAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGTACCATTGGAGGTGGCTGGATGG
GAACGTCTTCTCATGCTCCGTGATGCATGAGGCGCTGCACAACCACTACACTCAGAAGAGCTTG
TCCCTGTCGCCCGGA Amino acid sequence of Fcab FS22-053-014 with LALA mutation
(SEQ ID NO: 77)
Hinge region (underlined), CH2 domain (bold), CH3 domain (italics),
LALA mutation (bold and underlined)
TCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVYHWRWL*
*DGNVFSCSVMHEALHNHYTQKSLSLSPG*

Nucleic acid sequence of Fcab FS22-053-014 with LALA mutation
(SEQ ID NO: 78)
ACTTGCCCGCCTTGCCCAGCCCCGGAAGCTGCCGGTGGTCCTTCGGTGTTCCTCTTCCCGCCC
AAGCCGAAGGATACCCTGATGATCTCACGGACCCCCGAAGTGACCTGTGTGGTGGTGGACGTG
TCCCACGAGGACCCGGAAGTGAAATTCAATTGGTACGTGGATGGAGTGGAAGTGCACAACGCCA
AGACCAAGCCACGGGAAGAACAGTACAACTCTACCTACCGCGTGGTGTCCGTGCTCACTGTGCT
GCACCAAGACTGGCTGAACGGGAAGGAGTACAAGTGCAAAGTGTCCAACAAGGCGCTGCCTGC
CCCAATTGAGAAAACTATCTCGAAAGCCAAGGGCCAGCCTCGAGAACCACAGGTGTACACCCTG
CCCCCATCCCGGGATGAGCTGAACCCGCCGTACCTGTTCTCTAACCAGGTCAGCCTGACCTGCC
TGGTCAAAGGCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTACAGCAAGCT
CACCGTGTACCATTGGAGGTGGCTGGATGGGAACGTCTTCTCATGCTCCGTGATGCATGAGGCT
CTGCACAACCACTACACACAGAAGAGCCTCTCCCTGTCTCCGGGT Amino acid sequence of Fcab FS22-053-014 without LALA mutation
(SEQ ID NO: 79)
Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK

-continued

Sequence Listing

PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVYHWRWL*
*DGNVFSCSVMHEALHNHYTQKSLSLSPG*

Nucleic acid sequence of Fcab FS22-053-014 without LALA mutation (SEQ ID NO: 80)
ACTTGCCCGCCTTGCCCAGCCCCGGAACTGCTGGGTGGTCCTTCGGTGTTCCTCTTCCCGCCCA
AGCCGAAGGATACCCTGATGATCTCACGGACCCCCGAAGTGACCTGTGTGGTGGTGGACGTGT
CCCACGAGGACCCGGAAGTGAAATTCAATTGGTACGTGGATGGAGTGGAAGTGCACAACGCCAA
GACCAAGCCACGGGAAGAACAGTACAACTCTACCTACCGCGTGGTGTCCGTGCTCACTGTGCTG
CACCAAGACTGGCTGAACGGGAAGGAGTACAAGTGCAAAGTGTCCAACAAGGCGCTGCCTGCC
CCAATTGAGAAAACTATCTCGAAAGCCAAGGGCCAGCCTCGAGAACCACAGGTGTACACCCTGC
CCCCATCCCGGGATGAGCTGAACCCGCCGTACCTGTTCTCTAACCAGGTCAGCCTGACCTGCCT
GGTCAAAGGCTTCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTACAGCAAGCTC
ACCGTGTACCATTGGAGGTGGCTGGATGGGAACGTCTTCTCATGCTCCGTGATGCATGAGGCTC
TGCACAACCACTACACACAGAAGAGCCTCTCCCTGTCTCCGGGT Amino acid sequence of the heavy chain of FS22-053-014/HelD1.3 mock mAb[2] with LALA mutation (SEQ ID NO: 81)
VH domain (underlined)
<u>QVQLQESGPGLVRPSQTLSLTCTVSGSTFSGYGVNWVRQPPGRGLEWIGMIWGDGNTDYNSALKS</u>
<u>RVTMLVDTSKNQFSLRLSSVTAADTAVYYCARERDYRLDYWGQGSLVTVSS</u>ASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVYHWRWLDGNVFSCSVMHEALHNHYTQKSLSLSPG Amino acid sequence of the heavy chain of FS22-053-014/HelD1.3 mock mAb[2] without LALA mutation (SEQ ID NO: 82)
VH domain (underlined)
<u>QVQLQESGPGLVRPSQTLSLTCTVSGSTFSGYGVNWVRQPPGRGLEWIGMIWGDGNTDYNSALKS</u>
<u>RVTMLVDTSKNQFSLRLSSVTAADTAVYYCARERDYRLDYWGQGSLVTVSS</u>ASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVYHWRWLDGNVFSCSVMHEALHNHYTQKSLSLSPG Amino acid sequences of Fcab FS22-053-015 CH3 domain structural loop sequences
FS22-053-015 first sequence-NPPYLFS (SEQ ID NO: 19)
FS22-053-015 second sequence-DHWRWLQ (SEQ ID NO: 83)

Amino acid sequence of Fcab FS22-053-015 CH3 domain (SEQ ID NO: 84)
First and second sequences underlined
GQPREPQVYTLPPSRDEL<u>NPPYLFS</u>NQVSLTCLVKGFYPSDIAVEWESNGQPENNYKTTPPVLDSDG
SFFLYSKLTV<u>DHWRWLQ</u>GNVFSCSVMHEALHNHYTQKSLSLSPG Nucleic acid sequence of Fcab FS22-053-015 CH3 domain (SEQ ID NO: 85)

Amino acid sequence of Fcab FS22-053-015 with LALA mutation (SEQ ID NO: 86)
Hinge region (underlined), CH2 domain (bold), CH3 domain (italics), LALA mutation (bold and underlined)
<u>TCPPCP</u>APEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVDHWRWL*
*QGNVFSCSVMHEALHNHYTQKSLSLSPG*

Nucleic acid sequence of Fcab FS22-053-015 with LALA mutation (SEQ ID NO: 87)
ACTTGCCCGCCTTGCCCAGCCCCGGAAGCTGCCGGTGGTCCTTCGGTGTTCCTCTTCCCGCCC
AAGCCGAAGGATACCCTGATGATCTCACGGACCCCCGAAGTGACCTGTGTGGTGGTGGACGTG
TCCCACGAGGACCCGGAAGTGAAATTCAATTGGTACGTGGATGGAGTGGAAGTGCACAACGCCA
AGACCAAGCCACGGGAAGAACAGTACAACTCTACCTACCGCGTGGTGTCCGTGCTCACTGTGCT
GCACCAAGACTGGCTGAACGGGAAGGAGTACAAGTGCAAAGTGTCCAACAAGGCGCTGCCTGC
CCCAATTGAGAAAACTATCTCGAAAGCCAAGGGCCAGCCTCGAGAACCACAGGTGTACACCCTG
CCCCCATCCCGGGATGAGCTGAACCCGCCGTACCTGTTCTCTAACCAGGTCAGCCTGACCTGCC
TGGTCAAAGGCTTCTATCCCAGCGACATCGCCGTGGAGTGGGAGAGCAATGGGCAGCCGGAGA
ACAACTACAAGACCACGCCTCCCGTGTTGGACTCCGACGGCTCCTTCTTCCTCTACAGCAAGCT
CACCGTGGATCATTGGAGGTGGCTGCAGGGGAACGTCTTCTCATGCTCCGTGATGCATGAGGCT
CTGCACAACCACTACACACAGAAGAGCCTCTCCCTGTCTCCGGGT Amino acid sequence of Fcab FS22-053-015 without LALA mutation (SEQ ID NO: 88)

-continued

| Sequence Listing |
|---|

Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVDHWRWL*
*QGNVFSCSVMHEALHNHYTQKSLSLSPG*

Nucleic acid sequence of Fcab FS22-053-015 without LALA mutation
(SEQ ID NO: 89)
ACTTGCCCGCCTTGCCCAGCCCCGGAACTGCTGGGTGGTCCTTCGGTGTTCCTCTTCCCGCCCA
AGCCGAAGGATACCCTGATGATCTCACGGACCCCCGAAGTGACCTGTGTGGTGGTGGACGTGT
CCCACGAGGACCCGGAAGTGAAATTCAATTGGTACGTGGATGGAGTGGAAGTGCACAACGCCAA
GACCAAGCCACGGGAAGAACAGTACAACTCTACCTACCGCGTGGTGTCCGTGCTCACTGTGCTG
CACCAAGACTGGCTGAACGGGAAGGAGTACAAGTGCAAAGTGTCCAACAAGGCGCTGCCTGCC
CCAATTGAGAAAACTATCTCGAAAGCCAAGGGCCAGCCTCGAGAACCACAGGTGTACACCCTGC
CCCCATCCCGGGATGAGCTGAACCCGCCGTACCTGTTCTCTAACCAGGTCAGCCTGACCTGCCT
GGTCAAAGGCTTCTATCCCAGCGACATCGCCGTGGAGTGGGAGAGCAATGGGCAGCCGGAGAA
CAACTACAAGACCACGCCTCCCGTGTTGGACTCCGACGGCTCCTTCTTCCTCTACAGCAAGCTC
ACCGTGGATCATTGGAGGTGGCTGCAGGGGAACGTCTTCTCATGCTCCGTGATGCATGAGGCTC
TGCACAACCACTACACACAGAAGAGCCTCTCCCTGTCTCCGGGT Amino acid sequence of the heavy chain of FS22-053-015/HelD1.3 mock
mAb[2] with LALA mutation (SEQ ID NO: 90)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVDHWRWLQGNVFSCSVMHEALHNHYTQKSLSLSPG Amino acid sequence of the heavy chain of FS22-053-015/HelD1.3 mock
mAb[2] without LALA mutation (SEQ ID NO: 91)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVDHWRWLQGNVFSCSVMHEALHNHYTQKSLSLSPG Amino acid sequences of Fcab FS22-053-016 CH3 domain structural loop
sequences
FS22-053-016 first sequence-NPPYLFS (SEQ ID NO: 19)
FS22-053-016 second sequence-DYIRWLN (SEQ ID NO: 92)

Amino acid sequence of Fcab FS22-053-016 CH3 domain (SEQ ID NO: 93)
First and second sequences underlined
GQPREPQVYTLPPSRDELNPPYLFSNQVSLTCLVKGFYPSDIAVEWESNGQPENNYKTTPPVLDSDG
SFFLYSKLTVDYIRWLNGNVFSCSVMHEALHNHYTQKSLSLSPG Nucleic acid sequence of Fcab FS22-053-016 CH3 domain (SEQ ID NO: 94)
GGCCAGCCTCGAGAACCACAGGTGTACACCCTGCCCCCATCCCGGGATGAGCTGAACCCGCCG
TACCTGTTCTCTAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGATTACATCAGGTGGCTGAACGG
GAACGTCTTCTCATGCTCCGTGATGCATGAGGCTCTGCACAACCACTACACACAGAAGAGCCTC
TCCCTGTCTCCGGGT Amino acid sequence of Fcab FS22-053-016 with LALA mutation
(SEQ ID NO: 95)
Hinge region (underlined), CH2 domain (bold), CH3 domain (italics),
LALA mutation (bold and underlined)
TCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVDYIRWLN*
*GNVFSCSVMHEALHNHYTQKSLSLSPG*

Nucleic acid sequence of Fcab FS22-053-016 with LALA mutation
(SEQ ID NO: 96)
ACTTGCCCGCCTTGCCCAGCCCCGGAAGCTGCCGGTGGTCCTTCGGTGTTCCTCTTCCCGCCC
AAGCCGAAGGATACCCTGATGATCTCACGGACCCCCGAAGTGACCTGTGTGGTGGTGGACGTG
TCCCACGAGGACCCGGAAGTGAAATTCAATTGGTACGTGGATGGAGTGGAAGTGCACAACGCCA
AGACCAAGCCACGGGAAGAACAGTACAACTCTACCTACCGCGTGGTGTCCGTGCTCACTGTGCT
GCACCAAGACTGGCTGAACGGGAAGGAGTACAAGTGCAAAGTGTCCAACAAGGCGCTGCCTGC
CCCAATTGAGAAAACTATCTCGAAAGCCAAGGGCCAGCCTCGAGAACCACAGGTGTACACCCTG -continued Sequence Listing CCCCCATCCCGGGATGAGCTGAACCCGCCGTACCTGTTCTCTAACCAGGTCAGCCTGACCTGCC
TGGTCAAAGGCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTACAGCAAGCT
CACCGTGGATTACATCAGGTGGCTGAACGGGAACGTCTTCTCATGCTCCGTGATGCATGAGGCT
CTGCACAACCACTACACACAGAAGAGCCTCTCCCTGTCTCCGGGT Amino acid sequence of Fcab FS22-053-016 without LALA mutation
(SEQ ID NO: 97)
Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVDYIRWLN*
*GNVFSCSVMHEALHNHYTQKSLSLSPG*

Nucleic acid sequence of Fcab FS22-053-016 without LALA mutation
(SEQ ID NO: 98)
ACTTGCCCGCCTTGCCCAGCCCCGGAACTGCTGGGTGGTCCTTCGGTGTTCCTCTTCCCGCCCA
AGCCGAAGGATACCCTGATGATCTCACGGACCCCCGAAGTGACCTGTGTGGTGGTGGACGTGT
CCCACGAGGACCCGGAAGTGAAATTCAATTGGTACGTGGATGGAGTGGAAGTGCACAACGCCAA
GACCAAGCCACGGGAAGAACAGTACAACTCTACCTACCGCGTGGTGTCCGTGCTCACTGTGCTG
CACCAAGACTGGCTGAACGGGAAGGAGTACAAGTGCAAAGTGTCCAACAAGGCGCTGCCTGCC
CCAATTGAGAAAACTATCTCGAAAGCCAAGGGCCAGCCTCGAGAACCACAGGTGTACACCCTGC
CCCCATCCCGGGATGAGCTGAACCCGCCGTACCTGTTCTCTAACCAGGTCAGCCTGACCTGCCT
GGTCAAAGGCTTCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTACAGCAAGCTC
ACCGTGGATTACATCAGGTGGCTGAACGGGAACGTCTTCTCATGCTCCGTGATGCATGAGGCTC
TGCACAACCACTACACACAGAAGAGCCTCTCCCTGTCTCCGGGT Amino acid sequence of the heavy chain of FS22-053-016/HelD1.3 mock
mAb[2] with LALA mutation (SEQ ID NO: 99)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVDYIRWLNGNVFSCSVMHEALHNHYTQKSLSLSPG Amino acid sequence of the heavy chain of FS22-053-016/HelD1.3 mock
mAb[2] without LALA mutation (SEQ ID NO: 100)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVDYIRWLNGNVFSCSVMHEALHNHYTQKSLSLSPG Amino acid sequences of Fcab FS22-053-017 CH3 domain structural loop
sequences
FS22-053-017 first sequence-NPPYLFS (SEQ ID NO: 19)
FS22-053-017 second sequence-YHWRWLE (SEQ ID NO: 101)

Amino acid sequence of Fcab FS22-053-017 CH3 domain (SEQ ID NO: 102)
First and second sequences underlined
GQPREPQVYTLPPSRDELNPPYLFSNQVSLTCLVKGFYPSDIAVEWESNGQPENNYKTTPPVLDSDG
SFFLYSKLTVYHWRWLEGNVFSCSVMHEALHNHYTQKSLSLSPG Nucleic acid sequence of Fcab FS22-053-017 CH3 domain (SEQ ID NO: 103)
GGACAGCCTCGAGAACCACAGGTGTACACTCTGCCCCCTTCACGCGACGAACTCAATCCGCCCT
ACCTGTTCTCCAACCAAGTCTCCCTGACCTGTCTTGTGAAGGGTTTCTACCCATCCGATATCGCC
GTGGAGTGGGAGAGCAACGGACAGCCGGAGAACAACTATAAGACTACCCCGCCTGTGCTGGAC
TCGGACGGCAGCTTCTTCTTGTACTCCAAACTGACCGTGTACCACTGGCGGTGGCTGGAAGGGA
ACGTGTTTAGCTGCTCCGTCATGCATGAAGCCCTGCACAACCACTACACCCAGAAGTCCCTCTC
GCTCTCTCCGGGT Amino acid sequence of Fcab FS22-053-017 with LALA mutation
(SEQ ID NO: 104)
Hinge region (underlined), CH2 domain (bold), CH3 domain (italics),
LALA mutation (bold and underlined)
TCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVYHWRWL*
*EGNVFSCSVMHEALHNHYTQKSLSLSPG*

-continued

Sequence Listing

Nucleic acid sequence of Fcab FS22-053-017 with LALA mutation
(SEQ ID NO: 105)
ACTTGCCCGCCTTGCCCAGCCCCGGAAGCTGCCGGTGGTCCTTCGGTGTTCCTCTTCCCGCCC
AAGCCGAAGGATACCCTGATGATCTCACGGACCCCCGAAGTGACCTGTGTGGTGGTGGACGTG
TCCCACGAGGACCCGGAAGTGAAATTCAATTGGTACGTGGATGGAGTGGAAGTGCACAACGCCA
AGACCAAGCCACGGGAAGAACAGTACAACTCTACCTACCGCGTGGTGTCCGTGCTCACTGTGCT
GCACCAAGACTGGCTGAACGGGAAGGAGTACAAGTGCAAAGTGTCCAACAAGGCGCTGCCTGC
CCCAATTGAGAAAACTATCTCGAAAGCCAAGGGACAGCCTCGAGAACCACAGGTGTACACTCTG
CCCCCTTCACGCGACGAACTCAATCCGCCCTACCTGTTCTCCAACCAAGTCTCCCTGACCTGTCT
TGTGAAGGGTTTCTACCCATCCGATATCGCCGTGGAGTGGGAGAGCAACGGACAGCCGGAGAA
CAACTATAAGACTACCCCGCCTGTGCTGGACTCGGACGGCAGCTTCTTCTTGTACTCCAAACTGA
CCGTGTACCACTGGCGGTGGCTGGAAGGGAACGTGTTTAGCTGCTCCGTCATGCATGAAGCCCT
GCACAACCACTACACCCAGAAGTCCCTCTCGCTCTCTCCGGGT Amino acid sequence of Fcab FS22-053-017 without LALA mutation
(SEQ ID NO: 106)
Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNPPYLFSNQVSLTCLVKGFYPSDIAVEWESNGQPENNYKTTPPVLDSDGSFFLYSKLTVYHWRWL*
*EGNVFSCSVMHEALHNHYTQKSLSLSPG*

Nucleic acid sequence of Fcab FS22-053-017 without LALA mutation
(SEQ ID NO: 107)
ACTTGCCCGCCTTGCCCAGCCCCGGAACTGCTGGGTGGTCCTTCGGTGTTCCTCTTCCCGCCCA
AGCCGAAGGATACCCTGATGATCTCACGGACCCCCGAAGTGACCTGTGTGGTGGTGGACGTGT
CCCACGAGGACCCGGAAGTGAAATTCAATTGGTACGTGGATGGAGTGGAAGTGCACAACGCCAA
GACCAAGCCACGGGAAGAACAGTACAACTCTACCTACCGCGTGGTGTCCGTGCTCACTGTGCTG
CACCAAGACTGGCTGAACGGGAAGGAGTACAAGTGCAAAGTGTCCAACAAGGCGCTGCCTGCC
CCAATTGAGAAAACTATCTCGAAAGCCAAGGGACAGCCTCGAGAACCACAGGTGTACACTCTGC
CCCCTTCACGCGACGAACTCAATCCGCCCTACCTGTTCTCCAACCAAGTCTCCCTGACCTGTCTT
GTGAAGGGTTTCTACCCATCCGATATCGCCGTGGAGTGGGAGAGCAACGGACAGCCGGAGAAC
AACTATAAGACTACCCCGCCTGTGCTGGACTCGGACGGCAGCTTCTTCTTGTACTCCAAACTGAC
CGTGTACCACTGGCGGTGGCTGGAAGGGAACGTGTTTAGCTGCTCCGTCATGCATGAAGCCCT
GCACAACCACTACACCCAGAAGTCCCTCTCGCTCTCTCCGGGT Amino acid sequence of the heavy chain of FS22-053-017/HelD1.3 mock
mAb$^2$ with LALA mutation (SEQ ID NO: 108)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVYHWRWLEGNVFSCSVMHEALHNHYTQKSLSLSPG Amino acid sequence of the heavy chain of FS22-053-017/HelD1.3 mock
mAb$^2$ without LALA mutation (SEQ ID NO: 109)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNPPYLFSNQVSLTCLVKGFYPSDIAVEWESNGQPENNYKTT
PPVLDSDGSFFLYSKLTVYHWRWLEGNVFSCSVMHEALHNHYTQKSLSLSPG Amino acid sequences of Fcab FS22-172 CH3 domain structural loop
sequences
FS22-172 first sequence-RKYYPPY (SEQ ID NO: 110)
FS22-172 second sequence-GADRWLE (SEQ ID NO: 111)

Amino acid sequence of Fcab FS22-172 CH3 domain (SEQ ID NO: 112)
First and second sequences underlined
GQPREPQVYTLPPSRDELRKYYPPYNQVSLTCLVKGFYPSDIAVEWESNGQPENNYKTTPPVLDSD
GSFFLYSKLTVGADRWLEGNVFSCSVMHEALHNHYTQKSLSLSPG Nucleic acid sequence of Fcab FS22-172 CH3 domain (SEQ ID NO: 113)
GGCCAGCCTCGAGAACCACAGGTGTACACCCTGCCCCCATCCCGGGATGAGCTGCGTAAATAC
TACCCGCCGTACAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGGCGCAGATAGGTGGCTGGAAG
GGAACGTCTTCTCATGCTCCGTGATGCATGAGGCTCTGCACAACCACTACACACAGAAGAGCCT
CTCCCTGTCTCCGGGT Amino acid sequence of Fcab FS22-172 with LALA mutation (SEQ ID NO: 114)

-continued

| Sequence Listing |
|---|

Hinge region (underlined), CH2 domain (bold), CH3 domain (italics),
LALA mutation (bold and underlined)
TCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQVYTLPPSRD
ELRKYYPPYNQVSLTCLVKGFYPSDIAVEWESNGQPENNYKTTPPVLDSDGSFFLYSKLTVGADRWL
EGNVFSCSVMHEALHNHYTQKSLSLSPG Nucleic acid sequence of Fcab FS22-172 with LALA mutation
(SEQ ID NO: 115)
ACTTGCCCGCCTTGCCCAGCCCCGGAAGCTGCCGGTGGTCCTTCGGTGTTCCTCTTCCCGCCC
AAGCCGAAGGATACCCTGATGATCTCACGGACCCCCGAAGTGACCTGTGTGGTGGTGGACGTG
TCCCACGAGGACCCGGAAGTGAAATTCAATTGGTACGTGGATGGAGTGGAAGTGCACAACGCCA
AGACCAAGCCACGGGAAGAACAGTACAACTCTACCTACCGCGTGGTGTCCGTGCTCACTGTGCT
GCACCAAGACTGGCTGAACGGGAAGGAGTACAAGTGCAAAGTGTCCAACAAGGCGCTGCCTGC
CCCAATTGAGAAAACTATCTCGAAAGCCAAGGGCCAGCCTCGAGAACCACAGGTGTACACCCTG
CCCCCATCCCGGGATGAGCTGCGTAAATACTACCCGCCGTACAACCAGGTCAGCCTGACCTGCC
TGGTCAAAGGCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTACAGCAAGCT
CACCGTGGGCGCAGATAGGTGGCTGGAAGGGAACGTCTTCTCATGCTCCGTGATGCATGAGGC
TCTGCACAACCACTACACACAGAAGAGCCTCTCCCTGTCTCCGGGT Amino acid sequence of Fcab FS22-172 without LALA mutation
(SEQ ID NO: 116)
Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAKGQPREPQVYTLPPSRD
ELRKYYPPYNQVSLTCLVKGFYPSDIAVEWESNGQPENNYKTTPPVLDSDGSFFLYSKLTVGADRWL
EGNVFSCSVMHEALHNHYTQKSLSLSPG Nucleic acid sequence of Fcab FS22-172 without LALA mutation
(SEQ ID NO: 117)
ACTTGCCCGCCTTGCCCAGCCCCGGAACTGCTGGGTGGTCCTTCGGTGTTCCTCTTCCCGCCCA
AGCCGAAGGATACCCTGATGATCTCACGGACCCCCGAAGTGACCTGTGTGGTGGTGGACGTGT
CCCACGAGGACCCGGAAGTGAAATTCAATTGGTACGTGGATGGAGTGGAAGTGCACAACGCCAA
GACCAAGCCACGGGAAGAACAGTACAACTCTACCTACCGCGTGGTGTCCGTGCTCACTGTGCTG
CACCAAGACTGGCTGAACGGGAAGGAGTACAAGTGCAAAGTGTCCAACAAGGCGCTGCCTGCC
CCAATTGAGAAAACTATCTCGAAAGCCAAGGGCCAGCCTCGAGAACCACAGGTGTACACCCTGC
CCCCATCCCGGGATGAGCTGCGTAAATACTACCCGCCGTACAACCAGGTCAGCCTGACCTGCCT
GGTCAAAGGCTTCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTACAGCAAGCTC
ACCGTGGGCGCAGATAGGTGGCTGGAAGGGAACGTCTTCTCATGCTCCGTGATGCATGAGGCT
CTGCACAACCACTACACACAGAAGAGCCTCTCCCTGTCTCCGGGT Amino acid sequence of the heavy chain of FS22-172/HelD1.3 mock mAb[2]
with LALA mutation (SEC) ID NO: 118)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELRKYYPPYNQVSLTCLVKGFYPSDIAVEWESNGQPENNYKTT
PPVLDSDGSFFLYSKLTVGADRWLEGNVFSCSVMHEALHNHYTQKSLSLSPG Amino acid sequence of the heavy chain of FS22-172/HelD1.3 mock mAb[2]
without LALA mutation (SEQ ID NO: 119)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELRKYYPPYNQVSLTCLVKGFYPSDIAVEWESNGQPENNYKTT
PPVLDSDGSFFLYSKLTVGADRWLEGNVFSCSVMHEALHNHYTQKSLSLSPG Amino acid sequences of Fcab FS22-172-001 CH3 domain structural loop
sequences
FS22-172-001 first sequence-PFVMPPY (SEQ ID NO: 120)
FS22-172-001 second sequence-GADRWLE (SEQ ID NO: 111)

Amino acid sequence of Fcab FS22-172-001 CH3 domain (SEQ ID NO: 121)
First and second sequences underlined
GQPREPQVYTLPPSRDELPFVMPPYNQVSLTCLVKGFYPSDIAVEWESNGQPENNYKTTPPVLDSD
GSFFLYSKLTVGADRWLEGNVFSCSVMHEALHNHYTQKSLSLSPG Nucleic acid sequence of Fcab FS22-172-001 CH3 domain (SEQ ID NO: 122)
GGCCAGCCTCGAGAACCACAGGTGTACACCCTGCCCCCATCCCGGGATGAGCTGCCATTCGTT -continued

| Sequence Listing |
|---|

ATGCCACCATACAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGGCGCAGATAGGTGGCTGGAAG
GGAACGTCTTCTCATGCTCCGTGATGCATGAGGCTCTGCACAACCACTACACACAGAAGAGCCT
CTCCCTGTCTCCGGGT

Amino acid sequence of Fcab FS22-172-001 with LALA mutation
(SEQ ID NO: 123)
Hinge region (underlined), CH2 domain (bold), CH3 domain (italics),
LALA mutation (bold and underlined)
TCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELPFVMPPYNQVSLTCLVKGFYPSDIAVEWESNGQPENNYKTTPPVLDSDGSFFLYSKLTVGADRWL*
*EGNVFSCSVMHEALHNHYTQKSLSLSPG*

Nucleic acid sequence of Fcab FS22-172-001 with LALA mutation
(SEQ ID NO: 124)
ACTTGCCCGCCTTGCCCAGCCCCGGAAGCTGCCGGTGGTCCTTCGGTGTTCCTCTTCCCGCCC
AAGCCGAAGGATACCCTGATGATCTCACGGACCCCCGAAGTGACCTGTGTGGTGGTGGACGTG
TCCCACGAGGACCCGGAAGTGAAATTCAATTGGTACGTGGATGGAGTGGAAGTGCACAACGCCA
AGACCAAGCCACGGGAAGAACAGTACAACTCTACCTACCGCGTGGTGTCCGTGCTCACTGTGCT
GCACCAAGACTGGCTGAACGGGAAGGAGTACAAGTGCAAAGTGTCCAACAAGGCGCTGCCTGC
CCCAATTGAGAAAACTATCTCGAAAGCCAAGGGCCAGCCTCGAGAACCACAGGTGTACACCCTG
CCCCCATCCCGGGATGAGCTGCCATTCGTTATGCCACCATACAACCAGGTCAGCCTGACCTGCC
TGGTCAAAGGCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTACAGCAAGCT
CACCGTGGGCGCAGATAGGTGGCTGGAAGGGAACGTCTTCTCATGCTCCGTGATGCATGAGGC
TCTGCACAACCACTACACACAGAAGAGCCTCTCCCTGTCTCCGGGT Amino acid sequence of Fcab FS22-172-001 without LALA mutation
(SEQ ID NO: 125)
Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELPFVMPPYNQVSLTCLVKGFYPSDIAVEWESNGQPENNYKTTPPVLDSDGSFFLYSKLTVGADRWL*
*EGNVFSCSVMHEALHNHYTQKSLSLSPG*

Nucleic acid sequence of Fcab FS22-172-001 without LALA mutation
(SEQ ID NO: 126)
ACTTGCCCGCCTTGCCCAGCCCCGGAACTGCTGGGTGGTCCTTCGGTGTTCCTCTTCCCGCCCA
AGCCGAAGGATACCCTGATGATCTCACGGACCCCCGAAGTGACCTGTGTGGTGGTGGACGTGT
CCCACGAGGACCCGGAAGTGAAATTCAATTGGTACGTGGATGGAGTGGAAGTGCACAACGCCAA
GACCAAGCCACGGGAAGAACAGTACAACTCTACCTACCGCGTGGTGTCCGTGCTCACTGTGCTG
CACCAAGACTGGCTGAACGGGAAGGAGTACAAGTGCAAAGTGTCCAACAAGGCGCTGCCTGCC
CCAATTGAGAAAACTATCTCGAAAGCCAAGGGCCAGCCTCGAGAACCACAGGTGTACACCCTGC
CCCCATCCCGGGATGAGCTGCCATTCGTTATGCCACCATACAACCAGGTCAGCCTGACCTGCCT
GGTCAAAGGCTTCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTACAGCAAGCTC
ACCGTGGGCGCAGATAGGTGGCTGGAAGGGAACGTCTTCTCATGCTCCGTGATGCATGAGGCT
CTGCACAACCACTACACACAGAAGAGCCTCTCCCTGTCTCCGGGT Amino acid sequence of the heavy chain of FS22-172-001/HelD1.3 mock
mAb$^2$ with LALA mutation (SEQ ID NO: 127)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELPFVMPPYNQVSLTCLVKGFYPSDIAVEWESNGQPENNYKTT
PPVLDSDGSFFLYSKLTVGADRWLEGNVFSCSVMHEALHNHYTQKSLSLSPG Amino acid sequence of the heavy chain of FS22-172-001/HelD1.3 mock
mAb$^2$ without LALA mutation (SEQ ID NO: 128)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELPFVMPPYNQVSLTCLVKGFYPSDIAVEWESNGQPENNYKTT
PPVLDSDGSFFLYSKLTVGADRWLEGNVFSCSVMHEALHNHYTQKSLSLSPG Amino acid sequences of Fcab FS22-172-002 CH3 domain structural loop
sequences
FS22-172-002 first sequence-PFQMPPY (SEQ ID NO: 129)
FS22-172-002 second sequence-GADRWLE (SEQ ID NO: 111)

-continued

| Sequence Listing |
|---|

Amino acid sequence of Fcab FS22-172-002 CH3 domain (SEQ ID NO: 130)
First and second sequences underlined
GQPREPQVYTLPPSRDELPFQMPPYNQVSLTCLVKGFYPSDIAVEWESNGQPENNYKTTPPVLDSD
GSFFLYSKLTVGADRWLEGNVFSCSVMHEALHNHYTQKSLSLSPG Nucleic acid sequence of Fcab FS22-172-002 CH3 domain (SEQ ID NO: 131)
GGCCAGCCTCGAGAACCACAGGTGTACACCCTGCCCCCATCCCGGGATGAGCTGCCATTCCAG
ATGCCACCATACAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGGCGCAGATAGGTGGCTGGAAG
GGAACGTCTTCTCATGCTCCGTGATGCATGAGGCTCTGCACAACCACTACACACAGAAGAGCCT
CTCCCTGTCTCCGGGT Amino acid sequence of Fcab FS22-172-002 with LALA mutation
(SEQ ID NO: 132)
Hinge region (underlined), CH2 domain (bold), CH3 domain (italics),
LALA mutation (bold and underlined)
TCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELPFQMPPYNQVSLTCLVKGFYPSDIAVEWESNGQPENNYKTTPPVLDSDGSFFLYSKLTVGADRWL*
*EGNVFSCSVMHEALHNHYTQKSLSLSPG*

Nucleic acid sequence of Fcab FS22-172-002 with LALA mutation
(SEQ ID NO: 133)
ACTTGCCCGCCTTGCCCAGCCCCGGAAGCTGCCGGTGGTCCTTCGGTGTTCCTCTTCCCGCCC
AAGCCGAAGGATACCCTGATGATCTCACGGACCCCCGAAGTGACCTGTGTGGTGGTGGACGTG
TCCCACGAGGACCCGGAAGTGAAATTCAATTGGTACGTGGATGGAGTGGAAGTGCACAACGCCA
AGACCAAGCCACGGGAAGAACAGTACAACTCTACCTACCGCGTGGTGTCCGTGCTCACTGTGCT
GCACCAAGACTGGCTGAACGGGAAGGAGTACAAGTGCAAAGTGTCCAACAAGGCGCTGCCTGC
CCCAATTGAGAAAACTATCTCGAAAGCCAAGGGCCAGCCTCGAGAACCACAGGTGTACACCCTG
CCCCCATCCCGGGATGAGCTGCCATTCCAGATGCCACCATACAACCAGGTCAGCCTGACCTGCC
TGGTCAAAGGCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTACAGCAAGCT
CACCGTGGGCGCAGATAGGTGGCTGGAAGGGAACGTCTTCTCATGCTCCGTGATGCATGAGGC
TCTGCACAACCACTACACACAGAAGAGCCTCTCCCTGTCTCCGGGT Amino acid sequence of Fcab FS22-172-002 without LALA mutation
(SEQ ID NO: 134)
Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELPFQMPPYNQVSLTCLVKGFYPSDIAVEWESNGQPENNYKTTPPVLDSDGSFFLYSKLTVGADRWL*
*EGNVFSCSVMHEALHNHYTQKSLSLSPG*

Nucleic acid sequence of Fcab FS22-172-002 without LALA mutation
(SEQ ID NO: 135)
ACTTGCCCGCCTTGCCCAGCCCCGGAACTGCTGGGTGGTCCTTCGGTGTTCCTCTTCCCGCCCA
AGCCGAAGGATACCCTGATGATCTCACGGACCCCCGAAGTGACCTGTGTGGTGGTGGACGTGT
CCCACGAGGACCCGGAAGTGAAATTCAATTGGTACGTGGATGGAGTGGAAGTGCACAACGCCAA
GACCAAGCCACGGGAAGAACAGTACAACTCTACCTACCGCGTGGTGTCCGTGCTCACTGTGCTG
CACCAAGACTGGCTGAACGGGAAGGAGTACAAGTGCAAAGTGTCCAACAAGGCGCTGCCTGCC
CCAATTGAGAAAACTATCTCGAAAGCCAAGGGCCAGCCTCGAGAACCACAGGTGTACACCCTGC
CCCCATCCCGGGATGAGCTGCCATTCCAGATGCCACCATACAACCAGGTCAGCCTGACCTGCCT
GGTCAAAGGCTTCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTACAGCAAGCTC
ACCGTGGGCGCAGATAGGTGGCTGGAAGGGAACGTCTTCTCATGCTCCGTGATGCATGAGGCT
CTGCACAACCACTACACACAGAAGAGCCTCTCCCTGTCTCCGGGT Amino acid sequence of the heavy chain of FS22-172-002/HelD1.3 mock
$mAb^2$ with LALA mutation (SEQ ID NO: 136)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELPFQMPPYNQVSLTCLVKGFYPSDIAVEWESNGQPENNYKTT
PPVLDSDGSFFLYSKLTVGADRWLEGNVFSCSVMHEALHNHYTQKSLSLSPG Amino acid sequence of the heavy chain of FS22-172-002/HelD1.3 mock
$mAb^2$ without LALA mutation (SEQ ID NO: 137)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV -continued Sequence Listing SHEDPEVKFNWYVDGVEVHNAKTKPREEQYNSTYRVVSVLTVLHQDWLNGKEYKCKVSNKALPAPI
EKTISKAKGQPREPQVYTLPPSRDELPFQMPPYNQVSLTCLVKGFYPSDIAVEWESNGQPENNYKTT
PPVLDSDGSFFLYSKLTVGADRWLEGNVFSCSVMHEALHNHYTQKSLSLSPG Amino acid sequences of Fcab FS22-172-003 CH3 domain structural loop sequences
FS22-172-003 first sequence-PYIIPPY (SEQ ID NO: 138)
FS22-172-003 second sequence-GADRWLE (SEQ ID NO: 111)

Amino acid sequence of Fcab FS22-172-003 CH3 domain (SEQ ID NO: 139)
First and second sequences underlined
GQPREPQVYTLPPSRDELPYIIPPYNQVSLTCLVKGFYPSDIAVEWESNGQPENNYKTTPPVLDSDGS
FFLYSKLTVGADRWLEGNVFSCSVMHEALHNHYTQKSLSLSPG Nucleic acid sequence of Fcab FS22-172-003 CH3 domain (SEQ ID NO: 140)
GGACAGCCTCGAGAACCACAGGTGTACACCCTGCCCCCATCCCGGGATGAGCTGCCATACATC
ATCCCACCATACAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGGCGCAGATAGGTGGCTGGAAG
GGAACGTCTTCTCATGCTCCGTGATGCATGAGGCGCTGCACAACCACTACACTCAGAAGAGCTT
GTCCCTGTCGCCCGGT Amino acid sequence of Fcab FS22-172-003 with LALA mutation
(SEQ ID NO: 141)
Hinge region (underlined), CH2 domain (bold), CH3 domain (italics),
LALA mutation (bold and underlined)
TCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELPYIIPPYNQVSLTCLVKGFYPSDIAVEWESNGQPENNYKTTPPVLDSDGSFFLYSKLTVGADRWLE*
*GNVFSCSVMHEALHNHYTQKSLSLSPG*

Nucleic acid sequence of Fcab FS22-172-003 with LALA mutation
(SEQ ID NO: 142)
ACTTGCCCGCCTTGCCCAGCCCCGGAAGCTGCCGGTGGTCCTTCGGTGTTCCTCTTCCCGCCCAAGCC
GAAGGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAGCC
ACGGGAAGAACAGTACAACTCTACCTACCGCGTGGTGTCCGTGCTCACTGTGCTGCACCAAGACTGG
CTGAACGGGAAGGAGTACAAGTGCAAAGTGTCCAACAAGGCGCTGCCTGCCCCAATTGAGAAAACT
ATCTCGAAAGCCAAGGGACAGCCTCGAGAACCACAGGTGTACACCCTGCCCCCATCCCGGGATGAGC
TGCCATACATCATCCCACCATACAACCAGGTCAGCCTGACCTGCCTGGTCAAAGGCTTCTATCCCAGC
GACATCGCCGTGGAGTGGGAGAGCAATGGGCAGCCGGAGAACAACTACAAGACCACGCCTCCCGTG
CTGGACTCCGACGGCTCCTTCTTCCTCTACAGCAAGCTCACCGTGGGCGCAGATAGGTGGCTGGAAG
GGAACGTCTTCTCATGCTCCGTGATGCATGAGGCGCTGCACAACCACTACACTCAGAAGAGCTTGTCC
CTGTCGCCCGGT Amino acid sequence of Fcab FS22-172-003 without LALA mutation
(SEQ ID NO: 143)
Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELPYIIPPYNQVSLTCLVKGFYPSDIAVEWESNGQPENNYKTTPPVLDSDGSFFLYSKLTVGADRWLE*
*GNVFSCSVMHEALHNHYTQKSLSLSPG*

Nucleic acid sequence of Fcab FS22-172-003 without LALA mutation
(SEQ ID NO: 144)
ACTTGCCCGCCTTGCCCAGCCCCGGAACTGCTGGGTGGTCCTTCGGTGTTCCTCTTCCCGCCCAAGCC
GAAGGATACCCTGATGATCTCACGGACCCCCGAAGTGACCTGTGTGGTGGTGGACGTGTCCCACGA
GGACCCGGAAGTGAAATTCAATTGGTACGTGGATGGAGTGGAAGTGCACAACGCCAAGACCAAGCC
ACGGGAAGAACAGTACAACTCTACCTACCGCGTGGTGTCCGTGCTCACTGTGCTGCACCAAGACTGG
CTGAACGGGAAGGAGTACAAGTGCAAAGTGTCCAACAAGGCGCTGCCTGCCCCAATTGAGAAAACT
ATCTCGAAAGCCAAGGGACAGCCTCGAGAACCACAGGTGTACACCCTGCCCCCATCCCGGGATGAGC
TGCCATACATCATCCCACCATACAACCAGGTCAGCCTGACCTGCCTGGTCAAAGGCTTCTATCCCAGC
GACATCGCCGTGGAGTGGGAGAGCAATGGGCAGCCGGAGAACAACTACAAGACCACGCCTCCCGTG
CTGGACTCCGACGGCTCCTTCTTCCTCTACAGCAAGCTCACCGTGGGCGCAGATAGGTGGCTGGAAG
GGAACGTCTTCTCATGCTCCGTGATGCATGAGGCGCTGCACAACCACTACACTCAGAAGAGCTTGTCC
CTGTCGCCCGGT Amino acid sequence of the heavy chain of FS22-172-003/HelD1.3 mock
mAb$^2$ with LALA mutation (SEQ ID NO: 145)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELPYIIPPYNQVSLTCLVKGFYPSDIAVEWESNGQPENNYKTTP
PVLDSDGSFFLYSKLTVGADRWLEGNVFSCSVMHEALHNHYTQKSLSLSPG -continued Sequence Listing Amino acid sequence of the heavy chain of FS22-172-003/HelD1.3 mock mAb[2] without LALA mutation (SEQ ID NO: 146)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELPYIIPPYNQVSLTCLVKGFYPSDIAVEWESNGQPENNYKTTP
PVLDSDGSFFLYSKLTVGADRWLEGNVFSCSVMHEALHNHYTQKSLSLSPG Amino acid sequences of Fcab FS22-172-004 CH3 domain structural loop sequences
FS22-172-004 first sequence-NYIYPPY (SEQ ID NO: 147)
FS22-172-004 second sequence-GADRWLE (SEQ ID NO: 111)

Amino acid sequence of Fcab FS22-172-004 CH3 domain (SEQ ID NO: 148)
First and second sequences underlined
GQPREPQVYTLPPSRDELNYIYPPYNQVSLTCLVKGFYPSDIAVEWESNGQPENNYKTTPPVLDSDG
SFFLYSKLTVGADRWLEGNVFSCSVMHEALHNHYTQKSLSLSPG Nucleic acid sequence of Fcab FS22-172-004 CH3 domain (SEQ ID NO: 149)
GGACAGCCTCGAGAGCCTCAAGTGTACACCCTGCCCCCATCCCGGGATGAGCTGAACTACATCT
ACCCACCATACAACCAGGTCAGCCTGACCTGCCTGGTCAAAGGCTTCTATCCCAGCGACATCGC
CGTGGAGTGGGAGAGCAATGGGCAGCCGGAGAACAACTACAAGACCACGCCTCCCGTGCTGGA
CTCCGACGGCTCCTTCTTCCTCTACAGCAAGCTCACCGTGGGCGCAGATAGGTGGCTGGAAGG
GAACGTCTTCTCATGCTCCGTGATGCATGAGGCGCTGCACAACCACTACACTCAGAAGAGCTTG
TCCCTGTCGCCCGGA Amino acid sequence of Fcab FS22-172-004 with LALA mutation
(SEQ ID NO: 150)
Hinge region (underlined), CH2 domain (bold), CH3 domain (italics), LALA mutation (bold and underlined)
TCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNYIYPPYNQVSLTCLVKGFYPSDIAVEWESNGQPENNYKTTPPVLDSDGSFFLYSKLTVGADRWL*
*EGNVFSCSVMHEALHNHYTQKSLSLSPG*

Nucleic acid sequence of Fcab FS22-172-004 with LALA mutation
(SEQ ID NO: 151)
ACTTGCCCGCCTTGCCCAGCCCCGGAAGCTGCCGGTGGTCCTTCGGTGTTCCTCTTCCCGCCC
AAGCCGAAGGATACCCTGATGATCTCACGGACCCCCGAAGTGACCTGTGTGGTGGTGGACGTG
TCCCACGAGGACCCGGAAGTGAAATTCAATTGGTACGTGGATGGAGTGGAAGTGCACAACGCCA
AGACCAAGCCACGGGAAGAACAGTACAACTCTACCTACCGCGTGGTGTCCGTGCTCACTGTGCT
GCACCAAGACTGGCTGAACGGGAAGGAGTACAAGTGCAAAGTGTCCAACAAGGCGCTGCCTGC
CCCAATTGAGAAAACTATCTCGAAAGCCAAGGGCCAGCCTCGAGAACCACAGGTGTACACCCTG
CCCCCATCCCGGGATGAGCTGAACTACATCTACCCACCATACAACCAGGTCAGCCTGACCTGCC
TGGTCAAAGGCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTACAGCAAGCT
CACCGTGGGCGCAGATAGGTGGCTGGAAGGGAACGTCTTCTCATGCTCCGTGATGCATGAGGC
TCTGCACAACCACTACACACAGAAGAGCCTCTCCCTGTCTCCGGGT Amino acid sequence of Fcab FS22-172-004 without LALA mutation
(SEQ ID NO: 152)
Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELNYIYPPYNQVSLTCLVKGFYPSDIAVEWESNGQPENNYKTTPPVLDSDGSFFLYSKLTVGADRWL*
*EGNVFSCSVMHEALHNHYTQKSLSLSPG*

Nucleic acid sequence of Fcab FS22-172-004 without LALA mutation
(SEQ ID NO: 153)
ACTTGCCCGCCTTGCCCAGCCCCGGAACTGCTGGGTGGTCCTTCGGTGTTCCTCTTCCCGCCCA
AGCCGAAGGATACCCTGATGATCTCACGGACCCCCGAAGTGACCTGTGTGGTGGTGGACGTGT
CCCACGAGGACCCGGAAGTGAAATTCAATTGGTACGTGGATGGAGTGGAAGTGCACAACGCCAA
GACCAAGCCACGGGAAGAACAGTACAACTCTACCTACCGCGTGGTGTCCGTGCTCACTGTGCTG
CACCAAGACTGGCTGAACGGGAAGGAGTACAAGTGCAAAGTGTCCAACAAGGCGCTGCCTGCC
CCAATTGAGAAAACTATCTCGAAAGCCAAGGGCCAGCCTCGAGAACCACAGGTGTACACCCTGC
CCCCATCCCGGGATGAGCTGAACTACATCTACCCACCATACAACCAGGTCAGCCTGACCTGCCT
GGTCAAAGGCTTCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTACAGCAAGCTC
ACCGTGGGCGCAGATAGGTGGCTGGAAGGGAACGTCTTCTCATGCTCCGTGATGCATGAGGCT
CTGCACAACCACTACACACAGAAGAGCCTCTCCCTGTCTCCGGGT Amino acid sequence of the heavy chain of FS22-172-004/HelD1.3 mock mAb[2] with LALA mutation (SEQ ID NO: 154)

-continued

| Sequence Listing |
|---|

VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNYIYPPYNQVSLTCLVKGFYPSDIAVEWESNGQPENNYKTTP
PVLDSDGSFFLYSKLTVGADRWLEGNVFSCSVMHEALHNHYTQKSLSLSPG Amino acid sequence of the heavy chain of FS22-172-004/HelD1.3 mock
mAb[2] without LALA mutation (SEQ ID NO: 155)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELNYIYPPYNQVSLTCLVKGYPSDIAVEWESNGQPENNYKTTP
PVLDSDGSFFLYSKLTVGADRWLEGNVFSCSVMHEALHNHYTQKSLSLSPG Amino acid sequences of Fcab FS22-172-005 CH3 domain structural loop
sequences
FS22-172-005 first sequence-QQVYPPY (SEQ ID NO: 156)
FS22-172-005 second sequence-GADRWLE (SEQ ID NO: 111)

Amino acid sequence of Fcab FS22-172-005 CH3 domain (SEQ ID NO: 157)
First and second sequences underlined
GQPREPQVYTLPPSRDELQQVYPPYNQVSLTCLVKGFYPSDIAVEWESNGQPENNYKTTPPVLDSD
GSFFLYSKLTVGADRWLEGNVFSCSVMHEALHNHYTQKSLSLSPG Nucleic acid sequence of Fcab FS22-172-005 CH3 domain (SEQ ID NO: 158)
GGCCAGCCTCGAGAACCACAGGTGTACACCCTGCCCCCATCCCGGGATGAGCTGCAGCAGGTT
TACCCACCATACAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGGCGCAGATAGGTGGCTGGAAG
GGAACGTCTTCTCATGCTCCGTGATGCATGAGGCTCTGCACAACCACTACACACAGAAGAGCCT
CTCCCTGTCTCCGGGT Amino acid sequence of Fcab FS22-172-005 with LALA mutation
(SEQ ID NO: 159)
Hinge region (underlined), CH2 domain (bold), CH3 domain (italics),
LALA mutation (bold and underlined)
TCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELQQVYPPYNQVSLTCLVKGFYPSDIAVEWESNGQPENNYKTTPPVLDSDGSFFLYSKLTVGADRWL*
*EGNVFSCSVMHEALHNHYTQKSLSLSPG*

Nucleic acid sequence of Fcab FS22-172-005 with LALA mutation
(SEQ ID NO: 160)
ACTTGCCCGCCTTGCCCAGCCCCGGAAGCTGCCGGTGGTCCTTCGGTGTTCCTCTTCCCGCCC
AAGCCGAAGGATACCCTGATGATCTCACGGACCCCCGAAGTGACCTGTGTGGTGGTGGACGTG
TCCCACGAGGACCCGGAAGTGAAATTCAATTGGTACGTGGATGGAGTGGAAGTGCACAACGCCA
AGACCAAGCCACGGGAAGAACAGTACAACTCTACCTACCGCGTGGTGTCCGTGCTCACTGTGCT
GCACCAAGACTGGCTGAACGGGAAGGAGTACAAGTGCAAAGTGTCCAACAAGGCGCTGCCTGC
CCCAATTGAGAAAACTATCTCGAAAGCCAAGGGCCAGCCTCGAGAACCACAGGTGTACACCCTG
CCCCCATCCCGGGATGAGCTGCAGCAGGTTTACCCACCATACAACCAGGTCAGCCTGACCTGCC
TGGTCAAAGGCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTACAGCAAGCT
CACCGTGGGCGCAGATAGGTGGCTGGAAGGGAACGTCTTCTCATGCTCCGTGATGCATGAGGC
TCTGCACAACCACTACACACAGAAGAGCCTCTCCCTGTCTCCGGGT Amino acid sequence of Fcab FS22-172-005 without LALA mutation
(SEQ ID NO: 161)
Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELQQVYPPYNQVSLTCLVKGFYPSDIAVEWESNGQPENNYKTTPPVLDSDGSFFLYSKLTVGADRWL*
*EGNVFSCSVMHEALHNHYTQKSLSLSPG*

Nucleic acid sequence of Fcab FS22-172-005 without LALA mutation
(SEQ ID NO: 162)
ACTTGCCCGCCTTGCCCAGCCCCGGAACTGCTGGGTGGTCCTTCGGTGTTCCTCTTCCCGCCCA
AGCCGAAGGATACCCTGATGATCTCACGGACCCCCGAAGTGACCTGTGTGGTGGTGGACGTGT
CCCACGAGGACCCGGAAGTGAAATTCAATTGGTACGTGGATGGAGTGGAAGTGCACAACGCCAA
GACCAAGCCACGGGAAGAACAGTACAACTCTACCTACCGCGTGGTGTCCGTGCTCACTGTGCTG
CACCAAGACTGGCTGAACGGGAAGGAGTACAAGTGCAAAGTGTCCAACAAGGCGCTGCCTGCC
CCAATTGAGAAAACTATCTCGAAAGCCAAGGGCCAGCCTCGAGAACCACAGGTGTACACCCTGC -continued Sequence Listing CCCCATCCCGGGATGAGCTGCAGCAGGTTTACCCACCATACAACCAGGTCAGCCTGACCTGCCT
GGTCAAAGGCTTCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTACAGCAAGCTC
ACCGTGGGCGCAGATAGGTGGCTGGAAGGGAACGTCTTCTCATGCTCCGTGATGCATGAGGCT
CTGCACAACCACTACACACAGAAGAGCCTCTCCCTGTCTCCGGGT Amino acid sequence of the heavy chain of FS22-172-005/HelD1.3 mock mAb$^2$ with LALA mutation (SEQ ID NO: 163)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELQQVYPPYNQVSLTCLVKGFYPSDIAVEWESNGQPENNYKTT
PPVLDSDGSFFLYSKLTVGADRWLEGNVFSCSVMHEALHNHYTQKSLSLSPG Amino acid sequence of the heavy chain of FS22-172-005/HelD1.3 mock mAb$^2$ without LALA mutation (SEQ ID NO: 164)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELQQVYPPYNQVSLTCLVKGFYPSDIAVEWESNGQPENNYKTT
PPVLDSDGSFFLYSKLTVGADRWLEGNVFSCSVMHEALHNHYTQKSLSLSPG Amino acid sequences of Fcab FS22-172-006 CH3 domain structural loop sequences
FS22-172-006 first sequence-RKYYPPY (SEQ ID NO: 110)
FS22-172-006 second sequence-GADRWLE (SEQ ID NO: 111)

Amino acid sequence of Fcab FS22-172-006 CH3 domain (SEQ ID NO: 165)
First and second sequences underlined
GQPREPQVYTLPPSRDELRKYYPPYNQLSLTCLVKGFYPSDIAVEWESNGQPENNYKTTPPVLDSD
GSFFLYSKLTVGADRWLEGNVFSCSVMHEALHNHYTQKSLSLSPG Nucleic acid sequence of Fcab FS22-172-006 CH3 domain (SEQ ID NO: 166)
GGCCAGCCTCGAGAACCACAGGTGTACACCCTGCCCCCATCCCGGGATGAGCTGCGTAAATAC
TACCCGCCGTACAACCAGCTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGGGCGCAGATAGGTGGCTGGAAG
GGAACGTCTTCTCATGCTCCGTGATGCATGAGGCTCTGCACAACCACTACACACAGAAGAGCCT
CTCCCTGTCTCCGGGT Amino acid sequence of Fcab FS22-172-006 with LALA mutation (SEQ ID NO: 167)
Hinge region (underlined), CH2 domain (bold), CH3 domain (italics), LALA mutation (bold and underlined)
TCPPCPAPEAAGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELRKYYPPYNQLSLTCLVKGFYPSDIAVEWESNGQPENNYKTTPPVLDSDGSFFLYSKLTVGADRWL*
*EGNVFSCSVMHEALHNHYTQKSLSLSPG*

Nucleic acid sequence of Fcab FS22-172-006 with LALA mutation (SEQ ID NO: 168)
ACTTGCCCGCCTTGCCCAGCCCCGGAAGCTGCCGGTGGTCCTTCGGTGTTCCTCTTCCCGCCC
AAGCCGAAGGATACCCTGATGATCTCACGGACCCCCGAAGTGACCTGTGTGGTGGTGGACGTG
TCCCACGAGGACCCGGAAGTGAAATTCAATTGGTACGTGGATGGAGTGGAAGTGCACAACGCCA
AGACCAAGCCACGGGAAGAACAGTACAACTCTACCTACCGCGTGGTGTCCGTGCTCACTGTGCT
GCACCAAGACTGGCTGAACGGGAAGGAGTACAAGTGCAAAGTGTCCAACAAGGCGCTGCCTGC
CCCAATTGAGAAAACTATCTCGAAAGCCAAGGGCCAGCCTCGAGAACCACAGGTGTACACCCTG
CCCCCATCCCGGGATGAGCTGCGTAAATACTACCCGCCGTACAACCAGCTCAGCCTGACCTGCC
TGGTCAAAGGCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTACAGCAAGCT
CACCGTGGGCGCAGATAGGTGGCTGGAAGGGAACGTCTTCTCATGCTCCGTGATGCATGAGGC
TCTGCACAACCACTACACACAGAAGAGCCTCTCCCTGTCTCCGGGT Amino acid sequence of Fcab FS22-172-006 without LALA mutation (SEQ ID NO: 169)
Hinge region (underlined), CH2 domain (bold) and CH3 domain (italics)
TCPPCPAPELLGGPSVFLFPPKPKDTLMISRTPEVTCVVVDVSHEDPEVKFNWYVDGVEVHNAKTK
PREEQYNSTYRVVSVLTVLHQDWLNGKEYKCKVSNKALPAPIEKTISKAK*GQPREPQVYTLPPSRD*
*ELRKYYPPYNQLSLTCLVKGFYPSDIAVEWESNGQPENNYKTTPPVLDSDGSFFLYSKLTVGADRWL*
*EGNVFSCSVMHEALHNHYTQKSLSLSPG*

-continued

Sequence Listing

Nucleic acid sequence of Fcab FS22-172-006 without LALA mutation
(SEQ ID NO: 170)
ACTTGCCCGCCTTGCCCAGCCCCGGAACTGCTGGGTGGTCCTTCGGTGTTCCTCTTCCCGCCCA
AGCCGAAGGATACCCTGATGATCTCACGGACCCCCGAAGTGACCTGTGTGGTGGTGGACGTGT
CCCACGAGGACCCGGAAGTGAAATTCAATTGGTACGTGGATGGAGTGGAAGTGCACAACGCCAA
GACCAAGCCACGGGAAGAACAGTACAACTCTACCTACCGCGTGGTGTCCGTGCTCACTGTGCTG
CACCAAGACTGGCTGAACGGGAAGGAGTACAAGTGCAAAGTGTCCAACAAGGCGCTGCCTGCC
CCAATTGAGAAAACTATCTCGAAAGCCAAGGGCCAGCCTCGAGAACCACAGGTGTACACCCTGC
CCCCATCCCGGGATGAGCTGCGTAAATACTACCCGCCGTACAACCAGCTCAGCCTGACCTGCCT
GGTCAAAGGCTTCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTACAGCAAGCTC
ACCGTGGGCGCAGATAGGTGGCTGGAAGGGAACGTCTTCTCATGCTCCGTGATGCATGAGGCT
CTGCACAACCACTACACACAGAAGAGCCTCTCCCTGTCTCCGGGT Amino acid sequence of the heavy chain of FS22-172-006/HelD1.3 mock
$mAb^2$ with LALA mutation (SEQ ID NO: 171)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELRKYYPPYNQLSLTCLVKGFYPSDIAVEWESNGQPENNYKTT
PPVLDSDGSFFLYSKLTVGADRWLEGNVFSCSVMHEALHNHYTQKSLSLSPG Amino acid sequence of the heavy chain of FS22-172-006/HelD1.3 mock
$mAb^2$ without LALA mutation (SEQ ID NO: 172)
VH domain (underlined)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELRKYYPPYNQLSLTCLVKGFYPSDIAVEWESNGQPENNYKTT
PPVLDSDGSFFLYSKLTVGADRWLEGNVFSCSVMHEALHNHYTQKSLSLSPG Amino acid sequence of the light chain of HelD1.3 mock $mAb^2$
(SEQ ID NO: 173)
VL domain (underlined)
DIQMTQSPASLSASVGETVTITCRASGNIHNYLAWYQQKQGKSPQLLVYNAKTLADGVPSRFSGSGS
GTQYSLKINSLQPEDFGSYYCQHFWSTPRTFGGGTKLEIKRTVAAPSVFIFPPSDEQLKSGTASVVCL
LNNFYPREAKVQWKVDNALQSGNSQESVTEQDSKDSTYSLSSTLTLSKADYEKHKVYACEVTHQGL
SSPVTKSFNRGEC Amino acid sequences of Fcab FS22-053 CH3 domain structural loop
sequences
FS22-053 First sequence-NPPYLFS (SEQ ID NO: 19)
FS22-053 Second sequence-YYNRWQD (SEQ ID NO: 174)

Amino acid sequence of Fcab FS22-053 CH3 domain (SEQ ID NO: 175)
(First and second sequences are underlined).
GQPREPQVYTLPPSRDELNPPYLFSNQVSLTCLVKGFYPSDIAVEWESNGQPENNYKTTPPVLDSDG
SFFLYSKLTVYYNRWQDGNVFSCSVMHEALHNHYTQKSLSLSPG Nucleic acid sequence of Fcab FS22-053 CH3 domain (SEQ ID NO: 176)
GGCCAGCCTCGAGAACCACAGGTGTACACCCTGCCCCCATCCCGGGATGAGCTGAACCCGCCG
TACCTGTTCTCTAACCAGGTCAGCCTGACCTGCCTGGTCAAAGGCTTCTATCCCAGCGACATCG
CCGTGGAGTGGGAGAGCAATGGGCAGCCGGAGAACAACTACAAGACCACGCCTCCCGTGCTGG
ACTCCGACGGCTCCTTCTTCCTCTACAGCAAGCTCACCGTGTATTATAACAGGTGGCAGGATGG
GAACGTCTTCTCATGCTCCGTGATGCATGAGGCTCTGCACAACCACTACACACAGAAGAGCCTC
TCCCTGTCTCCGGGT Nucleic acid sequence of Fcab FS22-053 Fcab with LALA (SEQ ID NO: 177)
ACTTGCCCGCCTTGCCCAGCCCCGGAAGCTGCCGGTGGTCCTTCGGTGTTCCTCTTCCCGCCC
AAGCCGAAGGATACCCTGATGATCTCACGGACCCCCGAAGTGACCTGTGTGGTGGTGGACGTG
TCCCACGAGGACCCGGAAGTGAAATTCAATTGGTACGTGGATGGAGTGGAAGTGCACAACGCCA
AGACCAAGCCACGGGAAGAACAGTACAACTCTACCTACCGCGTGGTGTCCGTGCTCACTGTGCT
GCACCAAGACTGGCTGAACGGGAAGGAGTACAAGTGCAAAGTGTCCAACAAGGCGCTGCCTGC
CCCAATTGAGAAAACTATCTCGAAAGCCAAGGGCCAGCCTCGAGAACCACAGGTGTACACCCTG
CCCCCATCCCGGGATGAGCTGAACCCGCCGTACCTGTTCTCTAACCAGGTCAGCCTGACCTGCC
TGGTCAAAGGCTTCTATCCCAGCGACATCGCCGTGGAGTGGGAGAGCAATGGGCAGCCGGAGA
ACAACTACAAGACCACGCCTCCCGTGCTGGACTCCGACGGCTCCTTCTTCCTCTACAGCAAGCT
CACCGTGTATTATAACAGGTGGCAGGATGGGAACGTCTTCTCATGCTCCGTGATGCATGAGGCT
CTGCACAACCACTACACACAGAAGAGCCTCTCCCTGTCTCCGGGT Nucleic acid sequence of Fcab FS22-053 Fcab without LALA (SEQ ID NO: 178)
ACTTGCCCGCCTTGCCCAGCCCCGGAACTGCTGGGTGGTCCTTCGGTGTTCCTCTTCCCGCCCA -continued

| Sequence Listing |
|---|

AGCCGAAGGATACCCTGATGATCTCACGGACCCCCGAAGTGACCTGTGTGGTGGTGGACGTGT
CCCACGAGGACCCGGAAGTGAAATTCAATTGGTACGTGGATGGAGTGGAAGTGCACAACGCCAA
GACCAAGCCACGGGAAGAACAGTACAACTCTACCTACCGCGTGGTGTCCGTGCTCACTGTGCTG
CACCAAGACTGGCTGAACGGGAAGGAGTACAAGTGCAAAGTGTCCAACAAGGCGCTGCCTGCC
CCAATTGAGAAAACTATCTCGAAAGCCAAGGGCCAGCCTCGAGAACCACAGGTGTACACCCTGC
CCCCATCCCGGGATGAGCTGAACCCGCCGTACCTGTTCTCTAACCAGGTCAGCCTGACCTGCCT
GGTCAAAGGCTTCTATCCCAGCGACATCGCCGTGGAGTGGGAGAGCAATGGGCAGCCGGAGAA
CAACTACAAGACCACGCCTCCCGTGCTGGACTCCGACGGCTCCTTCTTCCTCTACAGCAAGCTC
ACCGTGTATTATAACAGGTGGCAGGATGGGAACGTCTTCTCATGCTCCGTGATGCATGAGGCTC
TGCACAACCACTACACACAGAAGAGCCTCTCCCTGTCTCCGGGT

Amino acid sequences of full-length immunoglobulin hinge region
(SEQ ID NO: 179)
EPKSCDKTHTCPPCP Amino acid sequence of human CD137 (SEQ ID NO: 180)
Extracellular domain (italics); transmembrane and intracellular
domains (bold)
*LQDPCSNCPAGTFCDNNRNQICSPCPPNSFSSAGGQRTCDICRQCKGVFRTRKECSSTSNAECDCT*
*PGFHCLGAGCSMCEQDCKQGQELTKKGCKDCCFGTFNDQKRGICRPWTNCSLDGKSVLVNGTKER*
*DVVCGPSPADLSPGASSVTPPAPAREPGHSPQ*IISFFLALTSTALLFLLFFLTLRFSVVKRGRKKLLYI
FKQPFMRPVQTTQEEDGCSCRFPEEEEGGCEL

Amino acid sequence of human CD137 extracellular domain (SEQ ID NO: 181)
LQDPCSNCPAGTFCDNNRNQICSPCPPNSFSSAGGQRTCDICRQCKGVFRTRKECSSTSNAECDCT
PGFHCLGAGCSMCEQDCKQGQELTKKGCKDCCFGTFNDQKRGICRPWTNCSLDGKSVLVNGTKER
DVVCGPSPADLSPGASSVTPPAPAREPGHSPQ Amino acid sequence of cynomolqus CD137 (SEQ ID NO: 182)
Extracellular domain (italics); transmembrane and intracellular
domains (bold)
*LQDLCSNCPAGTFCDNNRSQICSPCPPNSFSSAGGQRTCDICRQCKGVFKTRKECSSTSNAECDCIS*
*GYHCLGAECSMCEQDCKQGQELTKKGCKDCCFGTFNDQKRGICRPWTNCSLDGKSVLVNGTKERD*
*VVCGPSPADLSPGASSATPPAPAREPGHSPQ**IIFFLALTSTVVLFLLFFLVLRFSVVKRSRKKLLYIFK*
*QPFMRPVQTTQEEDGCSCRFPEEEEGGCEL*

Amino acid sequence of cynomolgus CD137 extracellular domain
(SEQ ID NO: 183)
LQDLCSNCPAGTFCDNNRSQICSPCPPNSFSSAGGQRTCDICRQCKGVFKTRKECSSTSNAECDCIS
GYHCLGAECSMCEQDCKQGQELTKKGCKDCCFGTFNDQKRGICRPWTNCSLDGKSVLVNGTKERD
VVCGPSPADLSPGASSATPPAPAREPGHSPQ Amino acid sequence of mouse CD137 (SEQ ID NO: 184)
Extracellular domain (italics); transmembrane and intracellular
domains (bold)
*VQNSCDNCQPGTFCRKYNPVCKSCPPSTFSSIGGQPNCNICRVCAGYFRFKKFCSSTHNAECECIE*
*GFHCLGPQCTRCEKDCRPGQELTKQGCKTCSLGTFNDQNGTGVCRPWTNCSLDGRSVLKTGTTEK*
*DVVCGPPVVSFSPSTTISVTPEGGPGGHSLQVL*TLFLALTSALLLALIFITLLFSVLKWIRKKFPHIFKQ
PFKKTTGAAQEEDACSCRCPQEEEGGGGGYEL

Amino acid sequence of mouse CD137 extracellular domain (SEQ ID NO: 185)
VQNSCDNCQPGTFCRKYNPVCKSCPPSTFSSIGGQPNCNICRVCAGYFRFKKFCSSTHNAECECIE
GFHCLGPQCTRCEKDCRPGQELTKQGCKTCSLGTFNDQNGTGVCRPWTNCSLDGRSVLKTGTTEK
DVVCGPPVVSFSPSTTISVTPEGGPGGHSLQVL Amino acid sequence of heavy chain of G1/HelD1.3 mAb (SEQ ID NO: 186)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG Amino acid sequence of human PD-L1 (SEQ ID NO: 187)
MRIFAVFIFMTYWHLLNAFTVTVPKDLYVVEYGSNMTIECKFPVEKQLDLAALIVYWEMEDKNIIQFV
HGEEDLKVQHSSYRQRARLLKDQLSLGNAALQITDVKLQDAGVYRCMISYGGADYKRITVKVNAPY
NKINQRILVVDPVTSEHELTCQAEGYPKAEVIWTSSDHQVLSGKTTTTNSKREEKLFNVTSTLRINTT
TNEIFYCTFRRLDPEENHTAELVIPELPLAHPPNERTHLVILGAILLCLGVALTFIFRLRKGRMMDVKK
CGIQDTNSKKQSDTHLEET Amino acid sequence of murine PD-L1 (SEQ ID NO: 188)
MRIFAGIIFTACCHLLRAFTITAPKDLYVVEYGSNVTMECRFPVERELDLLALVVYWEKEDEQVIQFVA
GEEDLKPQHSNFRGRASLPKDQLLKGNAALQITDVKLQDAGVYCCIISYGGADYKRITLKVNAPYRKIN
QRISVDPATSEHELICQAEGYPEAEVIWTNSDHQPVSGKRSVTTSRTEGMLLNVTSSLRVNATANDV
FYCTFWRSQPGQNHTAELIIPELPATHPPQNRTHWVLLGSILLFLIVVSTVLLFLRKQVRMLDVEKCGV
EDTSSKNRNDTQFEET -continued

| Sequence Listing |
| --- |

Amino acid sequence of mouse mesothelin (SEQ ID NO: 189)
DAEQKACPPGKEPYKVDEDLIFYQNWELEACVDGTMLARQMDLVNEIPFTYEQLSIFKHKLDKTYPQ
GYPESLIQQLGHFFRYVSPEDIHQWNVTSPDTVKTLLKVSKGQKMNAQAIALVACYLRGGGQLDEDM
VKALGDIPLSYLCDFSPQDLHSVPSSVMWLVGPQDLDKCSQRHLGLLYQKACSAFQNVSGLEYFEKI
KTFLGGASVKDLRALSQHNVSMDIATFKRLQVDSLVGLSVAEVQKLLGPNIVDLKTEEDKSPVRDWLF
RQHQKDLDRLGLGLQGGIPNGYLVLDFNVREAFS Amino acid sequence of heavy chain of FS22m-063-AA/FS28m-228 $mAb^2$
(SEQ ID NO: 190)
EVQLLESGGGLVQPGGSLRLSCAASGFTFSTYFMVWVRQAPGKGLEWVSMISPKSSNTYYADSVKG
RFTISRDNSKNTLYLQMNSLRAEDTAVYYCARWFTPARFDYWGQGTLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDEPYWSYVSLTCLVKGFYPSDIAVEWESNGQPENNYKTTPPVLD
SDGSFFLYSKLTVMNYRWELGNVFSCSVMHEALHNHYTQKSLSLSPG Amino acid sequence of light chain of FS22m-063-AA/FS28m-228 $mAb^2$
(SEQ ID NO: 191)
EIVLTQSPGTLSLSPGERATLSCRASQSVSSSYLAWYQQKPGQAPRLLIYGASSRATGIPDRFSGSGS
GTDFTLTISRLEPEDFAVYYCQQPFPSFTFGQGTKVEIKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLS
SPVTKSFNRGEC Amino acid sequence of heavy chain of G1AA/HelD1.3 mAb (with LALA)
(SEQ ID NO: 192)
QVQLQESGPGLVRPSQTLSLTCTVSGSTFSGYGVNWVRQPPGRGLEWIGMIWGDGNTDYNSALKS
RVTMLVDTSKNQFSLRLSSVTAADTAVYYCARERDYRLDYWGQGSLVTVSSASTKGPSVFPLAPSS
KSTSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPEAAGGPSVFLFPPKPKDTLMISRTPEVTCVVVDV
SHEDPEVKFNWYVDGVEVHNAKTKPREEQYNSTYRVVSVLTVLHQDWLNGKEYKCKVSNKALPAPI
EKTISKAKGQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPG Amino acid sequence of heavy chain of FS22-172-004-AA/S70 (with LALA)
(SEQ ID NO: 193)
EVQLVESGGGLVQPGGSLRLSCAASGFTFSDSWIHWVRQAPGKGLEWVAWISPYGGSTYYADSVK
GRFTISADTSKNTAYLQMNSLRAEDTAVYYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSRDELNYIYPPYNQVSLTCLVKGFYPSDIAVEWESNGQPENNYK
TTPPVLDSDGSFFLYSKLTVGADRWLEGNVFSCSVMHEALHNHYTQKSLSLSPG Amino acid sequence of heavy chain of FS22-172-004-AA/S70 (without LALA)
(SEQ ID NO: 194)
EVQLVESGGGLVQPGGSLRLSCAASGFTFSDSWIHWVRQAPGKGLEWVAWISPYGGSTYYADSVK
GRFTISADTSKNTAYLQMNSLRAEDTAVYYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELNYIYPPYNQVSLTCLVKGFYPSDIAVEWESNGQPENNYKTT
PPVLDSDGSFFLYSKLTVGADRWLEGNVFSCSVMHEALHNHYTQKSLSLSPG Amino acid sequence of light chain of FS22-172-004-AA/S70
(SEQ ID NO: 194)
DIQMTQSPSSLSASVGDRVTITCRASQDVSTAVAWYQQKPGKAPKLLIYSASFLYSGVPSRFSGSGS
GTDFTLTISSLQPEDFATYYCQQYLYHPATFGQGTKVEIKRTVAAPSVFIFPPSDEQLKSGTASVVCLL
NNFYPREAKVQWKVDNALQSGNSQESVTEQDSKDSTYSLSSTLTLSKADYEKHKVYACEVTHQGLS
SPVTKSFNRGEC Amino acid sequence of heavy chain of FS22-172-003-AA/S70 (with LALA)
(SEQ ID NO: 195)
EVQLVESGGGLVQPGGSLRLSCAASGFTFSDSWIHWVRQAPGKGLEWVAWISPYGGSTYYADSVK
GRFTISADTSKNTAYLQMNSLRAEDTAVYYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSRDELPYIIPPYNQVSLTCLVKGFYPSDIAVEWESNGQPENNYKT
TPPVLDSDGSFFLYSKLTVGADRWLEGNVFSCSVMHEALHNHYTQKSLSLSPG Amino acid sequence of heavy chain of FS22-172-003-AA/S70 (without LALA)
(SEQ ID NO: 196)
EVQLVESGGGLVQPGGSLRLSCAASGFTFSDSWIHWVRQAPGKGLEWVAWISPYGGSTYYADSVK
GRFTISADTSKNTAYLQMNSLRAEDTAVYYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD -continued Sequence Listing VSHEDPEVKFNWYVDGVEVHNAKTKPREEQYNSTYRVVSVLTVLHQDWLNGKEYKCKVSNKALPAP
IEKTISKAKGQPREPQVYTLPPSRDELPYIIPPYNQVSLTCLVKGFYPSDIAVEWESNGQPENNYKTTP
PVLDSDGSFFLYSKLTVGADRWLEGNVFSCSVMHEALHNHYTQKSLSLSPG Amino acid sequence of heavy chain of FS22-172-002-AA/S70 (with LALA)
(SEQ ID NO: 197)
EVQLVESGGGLVQPGGSLRLSCAASGFTFSDSWIHWVRQAPGKGLEWVAWISPYGGSTYYADSVK
GRFTISADTSKNTAYLQMNSLRAEDTAVYYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVV
DVSHEDPEVKFNWYVDGVEVHNAKTKPREEQYNSTYRVVSVLTVLHQDWLNGKEYKCKVSNKALP
APIEKTISKAKGQPREPQVYTLPPSRDELPFQMPPYNQVSLTCLVKGFYPSDIAVEWESNGQPENNY
KTTPPVLDSDGSFFLYSKLTVGADRWLEGNVFSCSVMHEALHNHYTQKSLSLSPG Amino acid sequence of heavy chain of FS22-172-002-AA/S70 (without LALA)
(SEQ ID NO: 198)
EVQLVESGGGLVQPGGSLRLSCAASGFTFSDSWIHWVRQAPGKGLEWVAWISPYGGSTYYADSVK
GRFTISADTSKNTAYLQMNSLRAEDTAVYYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELPFQMPPYNQVSLTCLVKGFYPSDIAVEWESNGQPENNYKT
TPPVLDSDGSFFLYSKLTVGADRWLEGNVFSCSVMHEALHNHYTQKSLSLSPG FS22-172-002-AA/S70 Heavy chain (without LALA) (SEQ ID NO: 199)
EVQLVESGGGLVQPGGSLRLSCAASGFTFSDSWIHWVRQAPGKGLEWVAWISPYGGSTYYADSVK
GRFTISADTSKNTAYLQMNSLRAEDTAVYYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELPFQMPPYNQVSLTCLVKGFYPSDIAVEWESNGQPENNYKT
TPPVLDSDGSFFLYSKLTVGADRWLEGNVFSCSVMHEALHNHYTQKSLSLSPG FS22-172-002-AA/S70 Heavy chain (with LALA) (SEQ ID NO 200)
EVQLVESGGGLVQPGGSLRLSCAASGFTFSDSWIHWVRQAPGKGLEWVAWISPYGGSTYYADSVK
GRFTISADTSKNTAYLQMNSLRAEDTAVYYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELPFQMPPYNQVSLTCLVKGFYPSDIAVEWESNGQPENNYKT
TPPVLDSDGSFFLYSKLTVGADRWLEGNVFSCSVMHEALHNHYTQKSLSLSPG FS22-053-011-AA/S70 Heavy chain (without LALA) (SEQ ID NO: 201)
EVQLVESGGGLVQPGGSLRLSCAASGFTFSDSWIHWVRQAPGKGLEWVAWISPYGGSTYYADSVK
GRFTISADTSKNTAYLQMNSLRAEDTAVYYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELNPPYLFSNQVSLTCLVKGFYPSDIAVEWESNGQPENNYKTT
PPVLDSDGSFFLYSKLTVDYWRWTDGNVFSCSVMHEALHNHYTQKSLSLSPG FS22-053-011-AA/S70 Heavy chain (with LALA) (SEQ ID NO: 202)
EVQLVESGGGLVQPGGSLRLSCAASGFTFSDSWIHWVRQAPGKGLEWVAWISPYGGSTYYADSVK
GRFTISADTSKNTAYLQMNSLRAEDTAVYYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELNPPYLFSNQVSLTCLVKGFYPSDIAVEWESNGQPENNYKTT
PPVLDSDGSFFLYSKLTVDYWRWTDGNVFSCSVMHEALHNHYTQKSLSLSPG FS22-053-008-AA/S70 Heavy chain (with LALA) (SEQ ID NO: 203)
EVQLVESGGGLVQPGGSLRLSCAASGFTFSDSWIHWVRQAPGKGLEWVAWISPYGGSTYYADSVK
GRFTISADTSKNTAYLQMNSLRAEDTAVYYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELNPPYLFSNQVSLTCLVKGFYPSDIAVEWESNGQPENNYKTT
PPVLDSDGSFFLYSKLTVEHTRWLDGNVFSCSVMHEALHNHYTQKSLSLSPG FS22-053-008-AA/S70 Heavy chain (without LALA) (SEQ ID NO: 204)
EVQLVESGGGLVQPGGSLRLSCAASGFTFSDSWIHWVRQAPGKGLEWVAWISPYGGSTYYADSVK
GRFTISADTSKNTAYLQMNSLRAEDTAVYYCARRHWPGGFDYWGQGTLVTVSAASTKGPSVFPLAP
SSKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPEAAGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSRDELNPPYLFSNQVSLTCLVKGFYPSDIAVEWESNGQPENNYKTT
PPVLDSDGSFFLYSKLTVEHTRWLDGNVFSCSVMHEALHNHYTQKSLSLSPG -continued

| Sequence Listing |
|---|
| FS22m-063-AA/F2 Heavy chain (without LALA) (SEQ ID NO: 205)<br>EVQLVQSGGGVVQPGRSLRLSCAASGFTFSSYWMSWVRQAPGKGLEWVSAISGSGGSTYYADSVK<br>GRFTISRDNSKNTLYLQMNSLRAEDTAVYYCAKENWGSYFDLWGQGTTVTVSSASTKGPSVFPLAP<br>SSKSTSGGTAALGCLVKDYFPEPVTVSWNSGALTSGVHTFPAVLQSSGLYSLSSVVTVPSSSLGTQT<br>YICNVNHKPSNTKVDKKVEPKSCDKTHTCPPCPAPELLGGPSVFLFPPKPKDTLMISRTPEVTCVVVD<br>VSHEDPEVKFNWYVDGVEVHNAKTKPREEQYNSTYRVVSVLTVLHQDWLNGKEYKCKVSNKALPAP<br>IEKTISKAKGQPREPQVYTLPPSRDEPYWSYVSLTCLVKGFYPSDIAVEWESNGQPENNYKTTPPVLD<br>SDGSFFLYSKLTVMNYRWELGNVFSCSVMHEALHNHYTQKSLSLSPG |
| FS22m-063-AA/F2 Heavy chain (without LALA) (SEQ ID NO: 206)<br>EVQLVQSGGGVVQPGRSLRLSCAASGFTFSSYWMSWVRQAPGKGLEWVSAISGSGGSTYYADSVK<br>GRFTISRDNSKNTLYLQMNSLRAEDTAVYYCAKENWGSYFDLWGQGTTVTVSSASTKGPSVFPLAP<br>SSKSTSGGTAALGCLVKDYFPEPVTVSWNSGALTSGVHTFPAVLQSSGLYSLSSVVTVPSSSLGTQT<br>YICNVNHKPSNTKVDKKVEPKSCDKTHTCPPCPAPEAAGGPSVFLFPPKPKDTLMISRTPEVTCVVVD<br>VSHEDPEVKFNWYVDGVEVHNAKTKPREEQYNSTYRVVSVLTVLHQDWLNGKEYKCKVSNKALPAP<br>IEKTISKAKGQPREPQVYTLPPSRDEPYWSYVSLTCLVKGFYPSDIAVEWESNGQPENNYKTTPPVLD<br>SDGSFFLYSKLTVMNYRWELGNVFSCSVMHEALHNHYTQKSLSLSPG |
| FS22m-063-AA/F2 Light chain (SEQ ID NO: 207)<br>DIVMTQSPSTLSASVGDRVTITCRASQGISSWLAWYQQKPGRAPKVLIYKASTLESGVPSRFSGSGS<br>GTDFTLTISSLQPEDFATYYCQQSYSTPWTFGQGTKLEIKRTVAAPSVFIFPPSDEQLKSGTASVVCLL<br>NNFYPREAKVQWKVDNALQSGNSQESVTEQDSKDSTYSLSSTLTLSKADYEKHKVYACEVTHQGLS<br>SPVTKSFNRGEC |
| FS22m-063/FS28m-228 Heavy chain (without LALA) (SEQ ID NO: 208)<br>EVQLLESGGGLVQPGGSLRLSCAASGFTFSTYFMVWVRQAPGKGLEWVSMISPKSSNTYYADSVKG<br>RFTISRDNSKNTLYLQMNSLRAEDTAVYYCARWFTPARFDYWGQGTLVTVSSASTKGPSVFPLAPSS<br>KSTSGGTAALGCLVKDYFPEPVTVSWNSGALTSGVHTFPAVLQSSGLYSLSSVVTVPSSSLGTQTYI<br>CNVNHKPSNTKVDKKVEPKSCDKTHTCPPCPAPELLGGPSVFLFPPKPKDTLMISRTPEVTCVVVDV<br>SHEDPEVKFNWYVDGVEVHNAKTKPREEQYNSTYRVVSVLTVLHQDWLNGKEYKCKVSNKALPAPI<br>EKTISKAKGQPREPQVYTLPPSRDEPYWSYVSLTCLVKGFYPSDIAVEWESNGQPENNYKTTPPVLD<br>SDGSFFLYSKLTVMNYRWELGNVFSCSVMHEALHNHYTQKSLSLSPG |

REFERENCES

All documents mentioned in this specification are incorporated herein by reference in their entirety.

Altschul S F, Gish W, Miller W, Myers E W, Lipman D J. Basic local alignment search tool. J. Mol. Biol. 215(3), 403-10 (1990).

Altschul S F, Madden T L, Schaffer A A, Zhang J, Zhang Z, Miller W, Lipman D J. Gapped BLAST and PSI-BLAST: a new generation of protein database search programs. Nucleic Acids Res. 25(17), 3389-402 (1997).

Andrade V C, Vettore A L, Felix R S, Almeida M S, Carvalho F, Oliveira J S, Chauffaille M L, Andriolo A, Caballero O L, Zago M A, Colleoni G W. Prognostic impact of cancer/testis antigen expression in advanced stage multiple myeloma patients. Cancer Immun. 8, 2 (2008).

Atwell S, Ridgway J B, Wells J A, Carter P. Stable heterodimers from remodelling the domain interface of a homodimer using a phage display library. J. Mol. Biol. 270(1), 26-35 (1997)

Bagshawe K D, Sharma S K, Springer C J, Antoniw P, Rogers G T, Burke P J, Melton R. Antibody-enzyme conjugates can generate cytotoxic drugs from inactive precursors at tumor sites. Antibody, Immunoconjugates and Radiopharmaceuticals 4, 915-922 (1991).

Bartkowiak, T. & Curran, M. A., 2015. 4-1BB Agonists: Multi-Potent Potentiators of Tumor Immunity. Frontiers in Oncology, 5:117, p. 1-17.

Bhome R, Bullock M D, Al Saihati H A, Goh R W, Primrose J N, Sayan A E, Mirnezami A H. A top-down view of the tumor microenvironment: structure, cells and signaling. Front. Cel. Dev. Biol. 3, 33 (2015).

Bitra A, Tzanko D, Wang J, Picarda G, Benedict C, Croft M, Zajonc D. 2017. Crystal structure of murine 4-1BB and its interaction with 4-1BBL support a role for galectin-9 in 4-1BB signalling. Journal of Biological Chemistry.

Bruhns P, Iannascoli B, England P, Mancardi D A, Fernandez N, Jorieux S, Daëron M. 2009. Specificity and affinity of human Fcgamma receptors and their polymorphic variants for human IgG subclasses. Blood 113(16), 3716-25.

Carter P, Smith L, Ryan M. Identification and validation of cell surface antigens for antibody targeting in oncology. Endocr. Relat. Cancer 11(4), 659-87 (2004).

Cheever M A, Allison J P, Ferris A S, Finn O J, Hastings B M, Hecht T T, Mellman I, Prindiville S A, Viner J L, Weiner L M, Matrisian L M. Clin. Cancer Res. 15(17), 5323-37 (2009).

Chen D S, Mellman I. Oncology meets immunology: the cancer-immunity cycle. Immunity 39(1), 1-10 (2013).

Chester, C. et al., 2015. Dual antibody therapy to harness the innate anti-tumor immune response to enhance antibody targeting of tumors. Current Opinion in Immunology, 33, pp. 1-8.

Chester, C. et al., 2018. Immunotherapy targeting 4-1BB: mechanistic rationale, clinical results, and future strategies. Blood, 131(1), pp. 49-57.

Chester, C., Ambulkar, S. & Kohrt, H. E., 2016. 4-1BB agonism: adding the accelerator to cancer immunotherapy. Cancer Immunology, 65(10): 1243-1248

Croft, M., 2003. Co-stimulatory members of the TNFR family: keys to effective T-cell immunity? Nat. Rev. Immunol. 3:609-620.

Dubrot J, Milheiro F, Alfaro C, Palazón A, Martinez-Forero I, Perez-Gracia J L, Morales-Kastresana A, Romero-Trevejo J L, Ochoa M C, Hervás-Stubbs S, Prieto J, Jure-Kunkel M, Chen L, Melero I. Treatment with anti-CD137 mAbs causes intense accumulations of liver T cells without selective antitumor immunotherapeutic effects in this organ. Cancer Immunol. Immunother. 59(8), 1223-33 (2010).

Fisher T, Kamperschroer C, Oliphant T, Love V, Lira P, Doyonnas R, Bergqvist S, Baxi S, Rohner A, Shen A, Huang C, Sokolowski S, Sharp L. 2012. Targeting of 4-1BB by monoclonal antibody PF-05082566 enhances T-cell function and promotes anti-tumour activity. Cancer Immunol Immunother 61:1721-1733.

Gubin M M, Artyomov M N, Mardis E R, Schreiber R D. Tumor neoantigens: building a framework for personalized cancer immunotherapy. J. Clin. Invest. 125(9), 3413-21 (2015).

Gure A O, Chua R, Williamson B, Gonen M, Ferrera C A, Gnjatic S, Ritter G, Simpson A J, Chen Y T, Old L J, Altorki N K. Cancer-testis genes are coordinately expressed and are markers of poor outcome in non-small cell lung cancer. Clin. Cancer Res. 11(22), 8055-62 (2005).

Hasenhindl C, Traxlmayr M W, Wozniak-Knopp G, Jones P C, Stadlmayr G, Raker F, Obinger C. Stability assessment on a library scale: a rapid method for the evaluation of the commutability and insertion of residues in C-terminal loops of the CH3 domains of IgG1-Fc. Protein Eng. Des. Sel., 26(10), 675-82 (2013).

Hezareh M, Hessell A J, Jensen R C, van de Winkel J G, Parren P W. 2001. Effector function activities of a panel of mutants of a broadly neutralizing antibody against human immunodeficiency virus type 1. J. Virol. 75(24), 12161-8.

Hinner et al., "Costimulatory T-cell engagement by PRS-343, a CD137 (4-1BB)/HER2 bispecific, leads to tumour growth inhibition and TIL expansion in humanized mouse model", poster presentation at the CRI-CIMT-AACR International Cancer Immunotherapy Conference: Translating Science into Survival; 25-28 Sep. 2016; New York, NY Hu S, Shively L, Raubitschek A, Sherman M, Williams L E, Wong J Y, Shively J E, Wu A M. Minibody: A novel engineered anti-carcinoembryonic antigen antibody fragment (single-chain Fv-CH3) which exhibits rapid, high-level targeting of xenografts. Cancer Res. 56(13), 3055-61 (1996).

Hurtado, J. C., Kim, Y. J. & Kwon, B. S., 1997. Signals through 4-1BB are costimulatory to previously activated splenic T cells and inhibit activation-induced cell death. Journal of immunology (Baltimore, Md.: 1950), 158(6), pp. 2600-2609.

Idusogie E E, Presta L G, Gazzano-Santoro H, Totpal K, Wong P Y, Ultsch M, Meng Y G, Mulkerrin M G. Mapping of the Clq binding site on rituxan, a chimeric antibody with a human IgG1 Fc. J. Immunol. 164(8), 4178-84 (2000).

Jefferis R, Reimer C B, Skvaril F, de Lange G, Ling N R, Lowe J, Walker M R, Phillips D J, Aloisio C H, Wells T W. Evaluation of monoclonal antibodies having specificity for human IgG sub-classes: results of an IUIS/WHO collaborative study. Immunol. Lett. 1, 223-52 (1985).

Jefferis R, Reimer C B, Skvaril F, de Lange G G, Goodall D M, Bentley T L, Phillips D J, Vlug A, Harada S, Radl J. Evaluation of monoclonal antibodies having specificity for human IgG subclasses: results of the 2nd IUIS/WHO collaborative study. Immunol. Lett. 31(2), 143-68 (1992).

Juneja V, McGuire K, Manguso R, LaFleur M, Collins N, Haining N, Freeman G, Sharpe A. 2017. PD-L1 on tumor cells is sufficient for immune evasion in immunogenic tumors and inhibits CD8 T cell cytotoxicity. JEM 214 (4):895.

Kabat E A, Wu T T, Perry H M, Gottesman K S, Foeller C. Sequences of Proteins of Immunological Interest, 5th ed. NIH Publication No. 91-3242. Washington, D.C.: U.S. Department of Health and Human Services (1991).

Klein C, Schaefer W, Regula J T. The use of CrossMAb technology for the generation of bi- and multispecific antibodies. MAbs. 8(6), 1010-20 (2016).

Kocak E, Lute K, Chang X, May K F Jr, Exten K R, Zhang H, Abdessalam S F, Lehman A M, Jarjoura D, Zheng P, Liu Y. 2006. Combination therapy with anti-CTL antigen-4 and anti-4-1BB antibodies enhances cancer immunity and reduces autoimmunity. Cancer Res 66(14):7276-84.

Kohrt, H. E. et al., 2010. CD137 stimulation enhances the antilymphoma activity of anti-CD20 antibodies. Blood, 117(8), pp. 2423-2432.

Kohrt, H. E. et al., 2014. Targeting CD137 enhances the efficacy of cetuximab. The Journal of clinical investigation, 124(6), pp. 2668-2682.

Kohrt, H. E., Houot, R., Weiskopf, K., et al., 2012b. Stimulation of natural killer cells with a CD137-specific antibody enhances trastuzumab efficacy in xenotransplant models of breast cancer. The Journal of clinical investigation, 122(3), pp. 1066-1075.

Kontermann (2012). Dual targeting strategies with bispecific antibodies. MAbs 4(2):182-97.

Ledermann J A, Begent R H, Massof C, Kelly A M, Adam T, Bagshawe K D. A phase-I study of repeated therapy with radiolabelled antibody to carcinoembryonic antigen using intermittent or continuous administration of cyclosporin A to supress the immune response. Int. J. Cancer 47(5), 659-64 (1991).

Lefranc M P, Giudicelli V, Duroux P, Jabado-Michaloud J, Folch G, Aouinti S, Carillon E, Duvergey H, Houles A, Paysan-Lafosse T, Hadi-Saljoqi S, Sasorith S, Lefranc G, Kossida S. IMGT®, the international ImMunoGeneTics information system® 25 years on. Nucleic Acids Res. 43(Database issue), D413-22 (2015).

Lefranc M P, Pommié C, Kaas Q, Duprat E, Bosc N, Guiraudou D, Jean C, Ruiz M, Da Piédade I, Rouard M, Foulquier E, Thouvenin V, Lefranc G. IMGT unique numbering for immunoglobulin and T cell receptor constant domains and Ig superfamily C-like domains. Dev. Comp. Immunol. 29(3), 185-203 (2005).

Lin W. et al, 2008. Fc-dependent expression of CD137 on human NK cells: insights into 'agonistic' effects of anti-CD137 monoclonal antibodies, 112(3)699-707

Link et al. 2018. Preclinical pharmacology of MP0310: A 4-1BB/FAP bispecific DARPin drug candidate promoting tumor-restricted T-cell costimulation [abstract]. Annual Meeting of the American Association for Cancer Research; 2018 Apr. 14-18; Chicago: AACR; 8. Abstract nr 3752.

Liu et al. 2017. Tumor Antigen Expression-dependent Activation of the CD137 Costimulatory Pathway by Bispecific DART® Proteins. Annual Meeting of the American Association for Cancer Research 2017, Apr. 1-5, Washington, D.C. Abstract nr 3642.

Makkouk, A., Chester, C. & Kohrt, H. E., 2016. Rationale for anti-CD137 cancer immunotherapy. European journal of cancer (Oxford, England: 1990), 54, pp. 112-119.

Malarkannan S, Horng T, Shih P P, Schwab S, Shastri N. Presentation of out-of-frame peptide/MHC class I complexes by a novel translation initiation mechanism. Immunity 10(6), 681-90 (1999).

Napoletano C, Bellati F, Tarquini E, Tomao F, Taurino F, Spagnoli G, Rughetti A, Muzii L, Nuti M, Benedetti Panici P. MAGE-A and NY-ESO-1 expression in cervical cancer: prognostic factors and effects of chemotherapy. Am. J. Obstet. Gynecol. 198(1), 99.e1-99.e7 (2008).

Pearson W R, Lipman D J. Improved tools for biological sequence comparison. Proc. Natl. Acad. Sci. U.S.A. 85(8), 2444-8 (1988).

Podojil J R, Miller S D. Potential targeting of B7-H4 for the treatment of cancer. Immunol. Rev. 276(1), 40-51 (2017).

Reichen et al. 2018. FAP-mediated tumor accumulation of a T-cell agonistic FAP/4-1BB DARPin drug candidate analyzed by SPECT/CT and quantitative biodistribution [abstract]. Annual Meeting of the American Association for Cancer Research; 2018 Apr. 14-18; Chicago: AACR. Abstract nr 3029.

Ridgway J. B. B, Presta L. G, Carter P. ‘Knobs-into-holes’ engineering of antibody CH3 domains for heavy chain heterodimerization. Protein Engineering 9(7), 617-621 (1996).

Rosenberg S. Development of Cancer Vaccines. ASCO Educational Book Spring: 60-62 (2000). Scott A M, Renner C. Tumour Antigens Recognized by Antibodies. eLS (2001).

Segal, N. H. et al., 2018. Phase I Study of Single-Agent Utomilumab (PF-05082566), a 4-1BB/CD137 Agonist, in Patients with Advanced Cancer. Clinical Cancer Research, 24(8):1816-1823.

Shuford, W. W., Klussman, K. & Tritchler, D. D., 1997. 4-1BB costimulatory signals preferentially induce $CD8^+$ T cell proliferation and lead to the amplification in vivo of cytotoxic T cell responses. J Exp Med, 186(1):47-55.

Simpson A J, Cabellero O L, Jungbluth O L, Chen Y T, Old L J. Cancer/testis antigens, gametogenesis and cancer. Nat. Rev. Cancer 5(8), 615-25 (2005).

Smith T F, Waterman M S. Identification of common molecular subsequences. J. Mol. Biol. 147(1), 195-7 (1981).

Spiess, Zhai, Carter (2015). Alternative molecular formats and therapeutic applications for bispecific antibodies. Molecular Immunology. 67:95-106.

Tai Y T, Anderson K C. Targeting B-cell maturation antigen in multiple myeloma. Immunotherapy 7(11), 1187-99 (2015).

Tello et al., 1993. Three-dimensional structure and thermodynamics of antigen binding by anti-lysozyme antibodies, Biochem Soc. Trans., 21(4):943-6.

Tinguely M, Jenni B, Knights A, Lopes B, Korol D, Rousson V, Curioni Fontecedro A, Cogliatti Bittermann A G, Schmid U, Dommann-Scherrer C, Maurer R, Renner C, Probst-Hensch N M, Moch H, Knuth A, Zippelius A. MAGE-C1/CT-7 expression in plasma cell myeloma: sub-cellular localization impacts on clinical outcome. Cancer Sci. 99(4), 720-5 (2008).

Velazquez E F, Jungbluth A A, Yancovitz M, Gnjatic S, Adams S, O'Neill D, Zavilevich K, Albukh T, Christos P, Mazumdar M, Pavlick A, Polsky D, Shapiro R, Berman R, Spira J, Busam K, Osman I, Bhardwaj N. Expression of the cancer/testis antigen NY-ESO-1 in primary and metastatic malignant melanoma (MM)—correlation with prognostic factors. Cancer Immun. 7, 11 (2007).

Vinay, D. S., and Kwon, B. S., 2011. 4-1BB signalling beyond T cells. Cell Mol Immunol. 8(4): 284-284

Wang X, Mathieu M, Brerski R J. IgG Fc engineering to modulate antibody effector functions. Protein Cell. 9(1), 63-73 (2018).

Wen T, Bukczynski J, Watts T H., 2002. 4-1BB Ligand-Mediated Costimulation of Human T Cells Induces CD4 and CD8 T Cell Expansion, Cytokine Production, and the Development of Cytolytic Effector Function. The Journal of Immunology, 168(10):4897-906.

Wesche-Soldato D E, Chung C S, Gregory S H, Salazar-Mather T P, Ayala C A, Ayala A. $CD8^+$ T cells promote inflammation and apoptosis in the liver after sepsis: role of Fas-FasL. Am. J. Pathol. 171(1), 87-96 (2007).

Westwood, J. A. et al., 2014. Combination anti-CD137 and anti-CD40 antibody therapy in murine myc-driven hematological cancers. Leukemia Research, 38(8), pp. 948-954.

Won, E.-Y. et al., 2009. The structure of the trimer of human 4-1BB ligand is unique among members of the tumor necrosis factor superfamily. The Journal of biological chemistry, 285(12), pp. 9202-9210.

Wozniak-Knopp G, Bartl S, Bauer A, Mostageer M, Woisetschläger M, Antes B, Ettl K, Kainer M, Weberhofer G, Wiederkum S, Himmler G, Mudde G C, Rüker F. Introducing antigen-binding sites in structural loops of immunoglobulin constant domains: Fc fragments with engineered HER2/neu-binding sites and antibody properties. Protein Eng. Des. Sel. 23(4), 289-97 (2010).

Ye Q, Song D, Poussin M, Yamamoto T, Best A, Li C, Coukos G, Powell Jr D. 2014. CD137 accurately identifies and enriches for naturally-occurring tumor-reactive T cells in tumor. Clin Cancer Res 20(1):44-55.

The invention claimed is:

1. A specific binding member that binds CD137 and comprises a CD137 antigen-binding site located in a CH3 domain of the specific binding member, the CD137 antigen-binding site comprising a first sequence located in the AB structural loop of the CH3 domain, wherein said first sequence comprises the sequence PPY (SEQ ID NO: 10), and wherein:

(i) when the specific binding member comprises the sequences set forth in SEQ ID NO: 138 and SEQ ID NO: 111 [FS22-172-003] in the AB and EF structural loops of the CH3 domain, respectively, the specific binding member does not comprise a CDR-based antigen-binding site that binds PD-L1 or MSLN, and (ii) when the specific binding member comprises the sequences set forth in SEQ ID NO: 19 and SEQ ID NO: 20 [FS22-053-008] in the AB and EF structural loops of the CH3 domain, respectively, the specific binding member does not comprise a CDR-based antigen-binding site that binds PD-L1.

2. The specific binding member according to claim 1, wherein the specific binding member comprises an insertion in the AB structural loop.

3. The specific binding member according to claim 2, wherein said insertion is 5 amino acids in length.

4. The specific binding member according to claim 1, wherein the first sequence is the first sequence of specific binding member:

(i) FS22-172-003 set forth in SEQ ID NO: 138;
(ii) FS22-172-002 set forth in SEQ ID NO: 129;
(iii) FS22-172-004 set forth in SEQ ID NO: 147;
(iv) FS22-172-001 set forth in SEQ ID NO: 120;
(v) FS22-172-005 set forth in SEQ ID NO: 156;
(vi) FS22-172-006 set forth in SEQ ID NO: 110; or
(vii) FS22-172 set forth in SEQ ID NO: 110.

5. The specific binding member according to claim 4, wherein the specific binding member further comprises a second sequence located in the EF structural loop of the CH3 domain, and wherein the second sequence is the second sequence of specific binding member FS22-172-003, FS22-172-002, FS22-172-004, FS22-172-001, FS22-172-005, FS22-172-006, or FS22-172 set forth in SEQ ID NO: 111.

6. The specific binding member according to claim 1, wherein the specific binding member comprises the CH3 domain sequence of specific binding member:

(i) FS22-172-003 set forth in SEQ ID NO: 139;
(ii) FS22-172-002 set forth in SEQ ID NO: 130;
(iii) FS22-172-004 set forth in SEQ ID NO: 148;
(iv) FS22-172-001 set forth in SEQ ID NO: 121;
(v) FS22-172-005 set forth in SEQ ID NO: 157;
(vi) FS22-172-006 set forth in SEQ ID NO: 165; or
(vii) FS22-172 set forth in SEQ ID NO: 112.

7. The specific binding member according to claim 1, wherein the specific binding member comprises the sequence of specific binding member FS22-172-003, FS22-172-002, FS22-172-004, FS22-172-001, FS22-172-005, FS22-172-006, or FS22-172 set forth in SEQ ID NO: 141, 132, 150, 123, 159, 167, and 114, respectively.

8. The specific binding member according to claim 1, wherein the first sequence is the first sequence of specific binding member FS22-053-008, FS22-053-009, FS22-053-011, FS22-053-017, FS22-053-014, FS22-053-010, FS22-053-012, FS22-053-013, FS22-053-015, FS22-053-016, and/or FS22-053 set forth in SEQ ID NO: 19.

9. The specific binding member according to claim 8, wherein the specific binding member further comprises a second sequence located in the EF structural loop of the CH3 domain, and wherein the second sequence is the second sequence of specific binding member:

(i) FS22-053-008 set forth in SEQ ID NO: 20;
(ii) FS22-053-009 set forth in SEQ ID NO: 29;
(iii) FS22-053-011 set forth in SEQ ID NO: 47;
(iv) FS22-053-017 set forth in SEQ ID NO: 101;
(v) FS22-053-014 set forth in SEQ ID NO: 74;
(vi) FS22-053-010 set forth in SEQ ID NO: 38;
(vii) FS22-053-012 set forth in SEQ ID NO: 56;
(viii) FS22-053-013 set forth in SEQ ID NO: 65;
(ix) FS22-053-015 set forth in SEQ ID NO: 83;
(x) FS22-053-016 set forth in SEQ ID NO: 92; or
(xi) FS22-053 set forth in SEQ ID NO: 174.

10. The specific binding member according to claim 1, wherein the specific binding member comprises the CH3 domain sequence of specific binding member:

(i) FS22-053-008 set forth in SEQ ID NO: 21;
(ii) FS22-053-009 set forth in SEQ ID NO: 30;
(iii) FS22-053-011 set forth in SEQ ID NO: 48;
(iv) FS22-053-017 set forth in SEQ ID NO: 102;
(v) FS22-053-014 set forth in SEQ ID NO: 75;
(vi) FS22-053-010 set forth in SEQ ID NO: 39;
(vii) FS22-053-012 set forth in SEQ ID NO: 57;
(viii) FS22-053-013 set forth in SEQ ID NO: 66;
(ix) FS22-053-015 set forth in SEQ ID NO: 84;
(x) FS22-053-016 set forth in SEQ ID NO: 93; or
(xi) FS22-053 set forth in SEQ ID NO: 175.

11. The specific binding member according to claim 1, wherein the specific binding member comprises the sequence of: specific binding member FS22-053-008, FS22-053-009, FS22-053-011, FS22-053-017, FS22-053-014, FS22-053-010, FS22-053-012, FS22-053-013, FS22-053-015, FS22-053-016, or FS22-053 set forth in SEQ ID NO: 23, 32, 50, 104, 77, 41, 59, 68, 86, 95, and 15, respectively.

12. The specific binding member according to claim 1, wherein the specific binding member comprises the first sequence, first and second sequence, CH3 domain sequence, or sequence of specific binding member FS22-172-003 or FS22-053-008, preferably FS22-172-003.

13. The specific binding member according to claim 1, wherein the specific binding member further comprises a CDR-based antigen-binding site.

14. The specific binding member according to claim 13, wherein the specific binding member is an antibody molecule.

15. The antibody molecule according to claim 14, wherein the CDR-based antigen-binding site binds a second antigen selected from the group consisting of: an immune cell antigen, a tumour antigen, and a pathogenic antigen.

16. The specific binding member according to claim 1, wherein the specific binding member has been modified to reduce or abrogate binding of the specific binding member to one or more Fcγ receptors.

17. A nucleic acid molecule encoding the specific binding member according to claim 1.

18. A method of producing a specific binding member according to claim 1, comprising culturing a recombinant host cell comprising a nucleic acid encoding the specific binding member of claim 1 under conditions for production of the specific binding member.

19. The specific binding member according to claim 1, wherein the specific binding member is conjugated to a bioactive molecule.

20. A pharmaceutical composition comprising the antibody molecule according to claim 14 and a pharmaceutically acceptable excipient.

21. A method of treating a disease or disorder in an individual comprising administering to the individual a therapeutically effective amount of the antibody molecule according to claim 14.

22. A method according to claim 21, wherein the treatment is the treatment of cancer or an infectious disease in an individual.

* * * * *